United States Patent [19]

Harada et al.

[11] Patent Number: 4,906,659
[45] Date of Patent: Mar. 6, 1990

[54] ANTIBIOTIC TAN-749, ITS DERIVATIVES, PRODUCTION AND USE THEREOF

[75] Inventors: Setsuo Harada, Kawanishi; Hideo Ono, Kobe; Hirotomo Masuya, Kawabe; Hideaki Natsugari, Ashiya, all of Japan

[73] Assignee: Takeda Chemical Industries, Ltd., Osaka, Japan

[21] Appl. No.: 129,737

[22] Filed: Dec. 7, 1987

Related U.S. Application Data

[63] Continuation-in-part of Ser. No. 868,739, May 30, 1986, abandoned, and a continuation-in-part of Ser. No. 941,208, Dec. 12, 1986, abandoned.

[30] Foreign Application Priority Data

Jun. 18, 1985 [JP] Japan .................. 60-133491
Jun. 18, 1985 [JP] Japan .................. 60-143711
Dec. 23, 1985 [JP] Japan .................. 60-291055
Dec. 27, 1985 [JP] Japan .................. 60-289671
Dec. 10, 1986 [JP] Japan .................. 61-293879
Dec. 26, 1986 [JP] Japan .................. 61-311586

[51] Int. Cl.$^4$ .................. C07C 123/00; A61K 35/00
[52] U.S. Cl. .................. 514/478; 424/116; 514/564; 514/626; 514/631; 560/159; 560/160; 560/169; 562/561; 562/564; 564/197; 564/225
[58] Field of Search .............. 564/197, 225; 562/561, 562/564; 560/159, 160, 169; 514/478, 564, 626, 631; 424/16

[56] References Cited

U.S. PATENT DOCUMENTS 3,743,580 7/1973 Umezawa et al. .................. 514/564

FOREIGN PATENT DOCUMENTS 0206068 12/1986 European Pat. Off. .
0229313 7/1987 European Pat. Off. .

OTHER PUBLICATIONS

Shibihara et al., J. Am. Chem. Soc., vol. 94, No. 12, pp. 4353–4354, 1972.
Kondo et al., The Journal of Antibiotics, vol. 24, No. 10, pp. 732–734 (1971).
Kondo et al., Journal of the American Chemical Society, vol. 93, pp. 6305–6306 (1971).
Uehara et al., The Journal of Antibiotics, vol. 29, No. 9, pp. 937–942 (1976).
Pierdet et al., Tetrahedron, vol. 36, pp. 1763–1772 (1980).
Streicher et al., the Journal of Antibiotics, vol. 31, No. 7, pp. 725–728 (1978).
Kondo et al., The Journal of Antibiotics, vol. 29, No. 2, pp. 208–210 (1976).

*Primary Examiner*—Robert A. Wax
*Attorney, Agent, or Firm*—Wenderoth, Lind & Ponack

[57] ABSTRACT

A compound of the formula

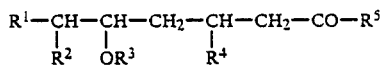

wherein $R^1$ and $R^4$ are independently amino or an organic residue bonded through nitrogen, $R^2$ is hydrogen or alkyl which may be substituted, $R^3$ is hydrogen or a protecting group and $R^5$ is hydroxyl which may be substituted or amino which may be substituted or salts thereof; with the proviso that when $R^1$ is amino, leucylamino, acetylamino or benzyloxycarbonylamino, $R^3$ is hydrogen, methyl or 2-tettrahydropyranyl, $R^4$ is amino, acetylamino or benzyloxycarbonylamino and $R^5$ is hydroxyl which may be substituted or amino which may be substituted, $R^2$ is alkyl which may be substituted, has antibacterial activities against drug-resistant bacteria and therefore can be useful as a chemotherapeutic drug for bacterial infections in mammals.

50 Claims, 10 Drawing Sheets

ANTIBIOTIC TAN-749, ITS DERIVATIVES, PRODUCTION AND USE THEREOF

This is a continuation-in-part of Ser. Nos. 868,739 and 941,208 filed on May 30, 1986 and Dec. 12, 1986, respectively, both now abandoned.

The present invention relates to a novel antibiotic TAN-749 (abbreviated TAN-749 in some cases hereinafter) and derivatives thereof, which can be used favorably as a therapeutic drug for bacterial infection, compounds related to TAN-749, which can be used as raw materials for production of TAN-749 and derivatives thereof, production and use thereof.

TAN-749A and C and TAN-749B and D are expressed by the formulas, $C_{15}H_{27}N_5O_3$, respectively, and have δ-hydroxy-β-lysine as a constituent amino acid.

As antibiotics having δ-hydroxy-β-lysine as a constituent amino acid there have heretofore been known negamycin[2-(3R,5R)-3,6-diamino-5-hydroxyhexanoyl-1-methylhydrazinoacetic acid] [cf. H. Umezawa et al., The Journal of the American Chemical Society, 93, 6305 (1971)] (±)-negamycin (A. Pierdet et al., Tetrahedron, 36, 1763 (1980)], its 6-N-leucyl derivatives [cf. H. Umezawa et al., The Journal of Antibiotics, 24, 732 (1971)], and its carboxamide derivatives [cf. W. Streicher et al., The Journal of Antibiotics, 31, 725 (1978)], but no improvement is recognized in the antibiotics activity in these derivatives as compared with negamycin.

Due to the development of the therapeutics using antibiotics, diseases caused by bacteria have been overcome to a considerable extent. However, increase of diseases due to changes in the flora of disease-causative bacteria (replacement of bacteria) or the advent of drug-resistant bacteria (acquisition of drug-resistance) resulting from long-term or high-dose medication with conventional antibiotics is still a serious problem in the field of medication of infectious diseases. For overcoming this problem, antibiotics having a novel structure and thus novel biological activities are always sought for in this field.

The present inventors isolated a great number of bacterial species from the soil in search for new antibiotics and then separated and investigated antibiotics produced by those species, finding that some microbes produce a new antibiotic. These microbes belong to the genus Pseudomonas and are capable of producing an antibiotic possessing antibacterial activity against both gram-positive and gram-negative bacteria including drug-resistant ones. The antibiotics can be accumulated in a medium by incubating said microbes in the medium. The inventors then separated this antibiotic and on the basis of its physical, chemical and biological properties, proved that it was a new antibiotic; it was named antibiotic TAN-749. TAN-749 is composed of 4 constituents; these were named TAN-749A, B, C and D, respectively.

In the present specification, antibiotics TAN-749A, B, C and D, or each of them, is generally called antibiotic TAN-749 or simply TAN-749 in some cases. As the results of further investigation, each TAN-749 component was found to be expressed by the following structures:

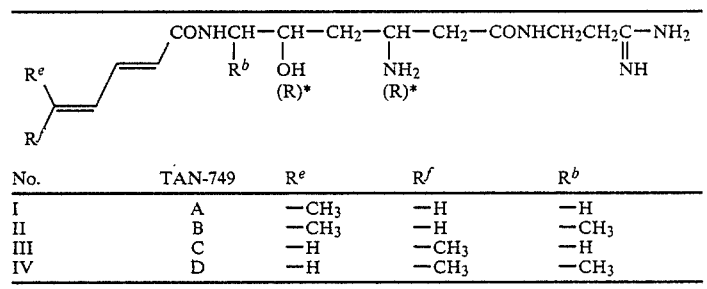

| No. | TAN-749 | $R^e$ | $R^f$ | $R^b$ |
|---|---|---|---|---|
| I | A | —CH₃ | —H | —H |
| II | B | —CH₃ | —H | —CH₃ |
| III | C | —H | —CH₃ | —H |
| IV | D | —H | —CH₃ | —CH₃ |

The present inventors, noting that compounds having δ-hydroxy-β-lysine as the constituent amino acid have antibiotic activities, attempted chemical modification in a broader extent and found that some of the derivatives showed excellent antibiotic activities, thus accomplishing the present invention.

More specifically, the present invention relates to
(1) A compound of the formula (I)

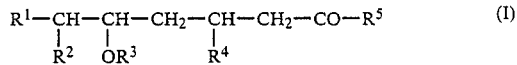

wherein $R^1$ and $R^4$ are independently amino group or an organic residue bonded to the carbon to which it is attached through nitrogen, $R^2$ is hydrogen or an alkyl group which may be substituted, $R^3$ is hydrogen or a protecting group, and $R^5$ is a hydroxyl group which may be substituted or an amino group which may be substituted, or salts thereof;
with the proviso that when $R^1$ is amino group, leucylamino group, acetylamino group or benzyloxycarbonylamino group, $R^3$ is hydrogen, methyl group or 2-tetrahydropyranyl group, $R^4$ is amino group, acetylamino group or benzyloxycarbonylamino group and $R^5$ is a hydroxyl group which may be substituted or an amino group which may be substituted, $R^2$ is an alkyl group which may be substituted.

(2) a method of preparing a compound of the formula (III)

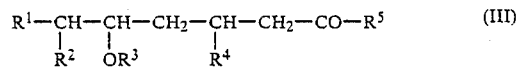

wherein $R^1$, $R^2$, $R^3$, $R^4$ and $R^5$ are of the same meaning as defined above, or salts thereof;
with the proviso that when $R^1$ is amino group, leucylamino group, acetylamino or benzyloxycarbonylamino group, $R^3$ is hydrogen, methyl group or 2-tetrahydropyranyl group, $R^4$ is amino group, acetylamino group or benzyloxycarbonylamino group and $R^5$ is a hydroxyl group which may be substituted or an amino group which may be substituted, $R^2$ is an alkyl group which may be substituted, which comprises allowing a compound of the formula (II)

$$R^{1'}-CH-CH-CH_2-CH-CH_2-CO-R^{5'} \quad (II)$$
$$\phantom{R^{1'}-}\underset{R^{2'}}{|}\phantom{-CH-}\underset{OR^{3'}}{|}\phantom{-CH_2-}\underset{R^{4'}}{|}$$

wherein $R^{1'}$ and $R^{4'}$ are independently amino group or an organic residue bonded to the carbon to which it is attached through nitrogen, $R^{2'}$ is hydrogen or an alkyl group which may be substituted, $R^{3'}$ is hydrogen or a protecting group and $R^{5'}$ is a hydroxyl group which may be substituted or an amino group which may be substituted, (a) to react with a compound capable of introducing an organic residue into a compound wherein at least one of $R^{1'}$ and $R^{4'}$ is amino group, or (b) to react with a compound capable of introducing an amino group which may be substituted, or a substituted hydroxyl group into a compound wherein $R^{5'}$ is hydroxyl group or a reactive derivatives thereof at the carboxyl group, or (c) to react with a compound capable of introducing a protecting group into a compound wherein $R^{3'}$ is hydrogen, followed by, upon necessity, subjecting the resultant compound to deprotection reaction, and (3) a method of preparing a compound of the formula (VI)

$$R^{1'}-CH-CH-CH_2-CH-CH_2-CO-R^{5''} \quad (VI)$$
$$\phantom{R^{1'}-}\underset{R^{2'}}{|}\phantom{-CH-}\underset{OR^{3'}}{|}\phantom{-CH_2-}\underset{R^{4'}}{|}$$

wherein $R^{1'}$, $R^{2'}$, $R^{3'}$ and $R^{4'}$ are of the same meaning as defined above, $R^{5''}$ is a substituted hydroxyl group, and $R^{3'}$ may form together with $R^{5''}$ a lactone compound of the formula (VI-1)

$$R^{1'}-CH-CH-CH_2-\underset{|}{C}-CH_2 \quad (VI\text{-}1)$$
$$\phantom{R^{1'}-}\underset{R^{2'}}{|}\phantom{-CH-}\underset{O}{|}\phantom{-CH_2-}\underset{C=O}{}$$

wherein $R^{1'}$, $R^{2'}$ and $R^{4'}$ are of the same meaning as defined above, or a salt thereof, which comprises allowing a compound of the formula (IV)

$$R^{1'''}-CH-CH-CH_2-\underset{\|}{C}-CH_2-CO-R^{5''} \quad (IV)$$
$$\phantom{R^{1'''}-}\underset{R^{2'}}{|}\phantom{-CH-}\underset{OR^{3'}}{|}\phantom{-CH_2-}\underset{O}{}$$

wherein $R^{1'''}$ is an organic residue bonded to the carbon to which it is attached through nitrogen, $R^{2'}$ and $R^{3'}$ are of the same meaning as defined above and $R^{5''}$ is a substituted hydroxyl group, and $R^{3'}$ may form together with $R^{5''}$ a lactone compound of the formula (IV-1)

$$R^{1'''}-CH-CH-CH_2-\underset{\|}{\overset{O}{C}}-CH_2 \quad (IV\text{-}1)$$
$$\phantom{R^{1'''}-}\underset{R^{2'}}{|}\phantom{-CH-}\underset{O}{|}\phantom{-CH_2-}\underset{C=O}{}$$

wherein $R^{1'''}$ and $R^{2'}$ are of the same meaning as defined above to react with a compound of the formula (V)

$$H_2N\text{-}A \quad (V)$$

wherein A is hydrogen, an alkyl group which may be substituted or an hydroxyl group which may be substituted, or a salt thereof, followed by, upon necessity, subjecting the resultant compound to deprotection reaction.

(4) a method of preparing a compound representable by the formula $$R^{a}-NH-CH-CH-CH_2-CH-CH_2-COOH \quad (A)$$
$$\phantom{R^{a}-NH-}\underset{R^{b}}{|}\phantom{-CH-}\underset{OH}{|}\phantom{-CH_2-}\underset{R^{c}}{|}$$

wherein $R^{a}$ is hydrogen, hexanoyl, or sorbyl, $R^{b}$ is hydrogen or methyl and $R^{c}$ is amino which may optionally be protected; with the proviso that when both $R^{a}$ and $R^{b}$ are hydrogen, $R^{c}$ is a protected amino, or salts thereof, which comprises subjecting a compound representable by the formula $$R^{a'}-NH-CH-CH-CH_2-CH-CH_2-CONHCH_2CH_2C\underset{\|}{N}H_2 \quad (B)$$
$$\phantom{R^{a'}-NH-}\underset{R^{b}}{|}\phantom{-CH-}\underset{OH}{|}\phantom{-CH_2-}\underset{R^{c}}{|}\phantom{-CH_2-CONHCH_2CH_2C}\underset{NH}{}$$

wherein $R^{a'}$ is hexanoyl or sorbyl, $R^{b}$ and $R^{c}$ are of the same meaning as defined above, or salts thereof, to hydrolysis, (5) a method of preparing a compound representable by the formula $$R^{a''}-NH-CH-CH-CH_2-CH-CH_2-COR^{d} \quad (C)$$
$$\phantom{R^{a''}-NH-}\underset{R^{b}}{|}\phantom{-CH-}\underset{OH}{|}\phantom{-CH_2-}\underset{R^{c}}{|}$$

wherein $R^{a''}$ is hydrogen or hexanoyl, $R^{b}$, $R^{c}$ and $R^{d}$ are of the same meaning as defined above with the proviso that when both $R^{a''}$ and $R^{b}$ are hydrogen and $R^{c}$ is amino, $R^{d}$ is 2-amidino-ethylamino, or salts thereof, which comprises subjecting a compound representable by the formula $$R^{e}\diagdown\diagup\diagdown\diagup CONH-CH-CH-CH_2-CH-CH_2-COR^{d} \quad (D)$$
$$R^{f}\diagup\phantom{\diagdown\diagup\diagdown\diagup CONH-}\underset{R^{b}}{|}\phantom{-CH-}\underset{OH}{|}\phantom{-CH_2-}\underset{R^{c}}{|}$$

wherein $R^{b}$, $R^{c}$ and $R^{d}$ are of the same meaning as defined above and $R^{e}$ and $R^{f}$ each is hydrogen or methyl, with the proviso that $R^{e}$ and $R^{f}$ are not simultaneously hydrogen or methyl, or salts thereof, to catalytic reduction, and when necessary, further to deacylation, (6) a method of producing antibiotics TAN-749A, B, C and D, or their salts, characterized in that microbes belonging to the genus Pseudomonas capable of producing one or more of antibiotics TAN-749A, B, C and D are incubated in a medium to produce and accumulate one or more of antibiotics TAN-479A, B, C and D in the culture broth and then to collect it (them) and (7) a pharmaceutical composition for treating bacterial infection, which contains an effective amount of one or more of antibiotics TAN-749 A, B, C and D or their derivatives, and a carrier.

Figure 1:
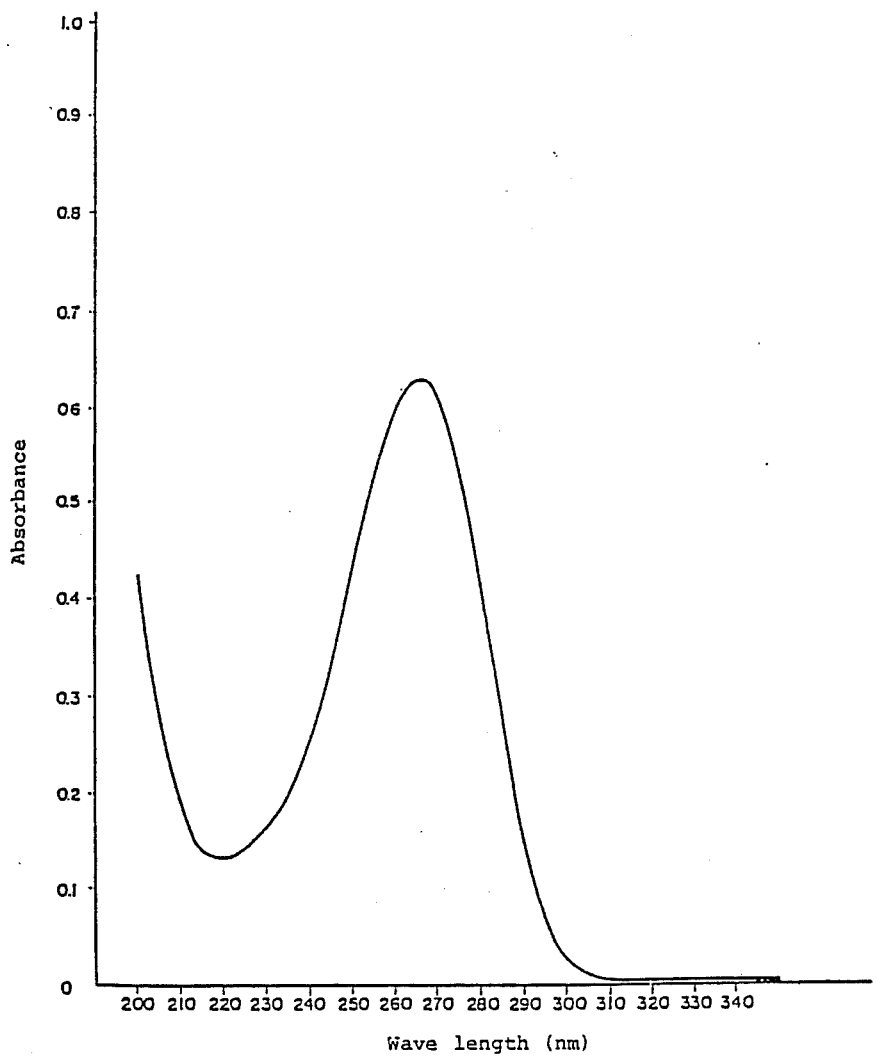
FIG. 1 is an ultraviolet (UV) absorption spectrum (in water) of TAN-749A dihydrochloride.

Bacterial which can be used in the present method as microbes producing antibiotic TAN-749 include all microbes belonging to the genus Pseudomonas capable of producing antibiotic TAN-749, e.g. *Pseudomonas fluorescens*. To speak more concretely, included is *Pseudomonas fluorescens* YK-437 (abbreviated "strain YK-437" in some cases hereinafter), which was isolated from a plant collected at Mt. Shirouma, Nagano Prefecture, Japan.

Strain YK-437 has the following bacteriological characteristics:

(a) Morphology

Morphological characteristics were observed after incubation on a nutrient agar slant medium at 24° C. for 5 days.

| Cell shape and size | Rod, 0.5 ~ 1.0 μm × 1.5 ~ 4 μm |
|---|---|
| Motility | Yes (flagellatory) |
| Sporulation | No |
| Gram-stain | Negative |
| Acid fastness | Non-acid-fast |

(b) Growth states on various media

Growth states were observed on various media at 24° C. for 1 to 14 days.

① Nutrient agar plate culture:

Colonies are colorless, transparent and circular. The colony surface is head-like to convex spherical. The colony margin is sinuous. No diffusible pigment is produced.

② Nutrient agar slant culture:

Colonies are cloth-like, highly lustrous, opaque and colorless.

③ Nutrient broth culture:

Grows in turbid suspension. Forms a thin pellicle. No precipitation appears.

④ Nutrient gelatin stab culture:

Grows well mainly on upper portion. Liquefies with high liquefication activity.

⑤ Litmus milk:

Litmus-reduction activity is not observed. Peptonization activity is observed but coagulation is not.

(c) Physiological characteristics

① Nitrate reduction: −
② Denitrification: −
③ MR (methyl red) test: −
④ VP (Voges-Proskauer) test: −
⑤ Indole production: −
⑥ Hydrogen sulfide production (lead acetate paper): −
⑦ Starch hydrolysis: −

⑧ Citric acid utilization (Kosel's citrate medium, Christensen's citrate medium, Simmons' citrate medium): +

⑨ Inorganic nitrogen source utilization:
(I) Potassium nitrate: +
(II) Ammonium sulfate: +

⑩ Pigment production (King's A medium, King's B medium, Mannitol yeast extract agar medium): Lemon-color intracellular pigment production and lemon-color water-soluble pigment production are both observed in King's B medium.

King's A medium: Glycerol 10 g, Peptone 20 g, Magnesium chloride 1.4 g, Ammonium sulfate 10 g, Agar 15 g, Distilled water 1,000 ml, pH 7.2

King's B medium: Glycerol 10 g, Peptone 20 g, Potassium monohydrogen phosphate 1.5 g, Magnesium sulfate 1.5 g, Agar 15 g, pH 7.2

⑪ Urease: +
⑫ Oxidase: +
⑬ Catalase: +
⑭ Growing conditions:
(I) pH: Grows in a pH range of 4.1 to 8.5. Optimum pH ranges from 6.3 to 8.2.
(II) Temperature: Grows in a range of 8° to 36° C. Optimum temperature ranges from 11° to 24° C.

⑮ Oxygen demand: Aerobic
⑯ O-F (oxidative-fermentative) test [Hugh.Leifson method]: Oxidative
⑰ Acid and gas production from sugars and their utilization:

| | Acid (Peptone Water) | Gas (Peptone Water) | Utilization (Davis' Medium) |
|---|---|---|---|
| L-arabinose | + | − | + |
| D-xylose | + | − | + |
| D-glucose | + | − | + |
| D-mannose | + | − | + |
| D-fructose | − | − | + |
| D-galactose | + | − | + |
| Maltose | − | − | + |
| Sucrose | ± | − | + |
| Lactose | − | − | + |
| Trehalose | − | − | + |
| D-sorbitol | − | − | + |
| D-mannitol | − | − | + |
| Inositol | − | − | + |
| Glycerol | − | − | + |
| Starch | − | − | + |

+: Positive, ±: Pseudopositive, −: Negative

⑱ G+C (guanine-cytosine) content of DNA: 66.4±1.5 mole % (Tm method)
⑲ Sodium chloride tolerance: 0~5%
⑳ Decomposing activity for carboxymethyl cellulose or colloidal chitin: −
㉑ Decomposing activity for agar or arginate: −
㉒ Decomposing activity for Tween 80: +

Strain YK-437 was collated with bacterial species described in Bergey's Manual of Determinative Bacteriology, 8th edition, or the International Journal of Systematic Bacteriology, Vol. 30, pp. 225~420 (1980) and validation lists shown in the journal; this strain was thought of as belonging to the genus Pseudomonas, based on the following facts, i.e. it is an aerobic gram-negative rod possessing flagellatory motility, it is positive in both catalase and oxidase activities, and the G+C content of its DNA is 66.4±1.0 mole %.

According to said Bergey's Manual of Determinative Bacteriorogy, the genus Pseudomonas is divided into four sections, i.e. Section I, II, III and IV, by its characteristics concerning requirement of growth factors, intracellular accumulation of poly-β-hydroxy butyrate, utilization of DL-arginine and growth at 40° C.

Table A shows the characteristics of the strain YK-437 as obtained by further experiments.

TABLE A

Characteristics of strain YK-437

| Test sort | Result* |
|---|---|
| Poly-β-hydroxybutyrate accumulation | − |
| Arginine dihydrolase | + |
| Pigment production | |
| King's A medium | − |
| King's B medium | + |
| Denitrification | − |
| Lipase (Tween 80) activity | − |
| Gelatin hydrolysis | + |
| Poly-β-hydroxybutyrate hydrolysis | − |
| Utilization of carbon sources** | |
| Trehalose | + |
| Sucrose | + |
| L-Arabinose | + |
| Propionate*** | − |
| Butyrate**** | − |
| Sorbitol | + |
| Adonitol | + |
| Propylene glycol | − |
| Ethanol | − |

*+: Positive, −: Negative
**Stanier's medium (Journal of General Microbiology Vol. 43, pp. 159-271 (1966)) was used.
***Sodium propionate
****Sodium butyrate It was considered appropriate that the strain YK-437 belongs to the Section I on the basis of the facts that the strain has no auxotrophy and doesn't accumulate poly-β-hydroxybutyrate as an intracellular carbon reserve.

Ten species are included in Section I. As the strain YK-437 produces fluorochrome and possesses argininedihydrolase, the strain YK-437 was thought of as belonging to any of *Pseudomonas aeruginosa, Pseudomonas putida, Pseudomonas fluorescens, Pseudomonas chlororaphis* and *Pseudomonas aureofaciens*.

The strain YK-437 is different from *Pseudomonas aeruginosa* at the point of denitrification and utilization of trehalose and geraniol, and from *Pseudomonas putida* at the point of hydrolysis of gelatin and utilization of trehalose. The strain YK-437 is different from *Pseudomonas chlororaphis* at the point of denitrification, lipase-activity and utilization of carbon sources, and from *Pseudomonas aureofaciens* at the point of utilization of sorbitol and adonitol.

The above-described characteristics of the strain YK-437 are in good agreement with those of *Pseudomonas fluorescens*. Therefore, the strain YK-437 was identified with *Pseudomonas fluorescens* and was designated *Pseudomonas fluorescens* YK-437.

*Pseudomonas fluorescens* YK-437 has been deposited under the accession number of IFO 14446 at the Institute for Fermentation, Osaka (IFO), since June 7, 1985.

This microbe, which was deposited on June 15, 1985 at Fermentation Research Institute, Agency of Industrial Science and Technology, Ministry of International Trade and Industry, Japan (FRI) under the accession number of FERM P-8312, the deposit being converted to a deposit under the Budapest Treaty, has been stored at FRI under the accession number of FERM BP-1005.

Bacteria belonging to the genus Pseudomonas used in the method in this invention, in general, are very susceptible to mutagens, e.g., it can be varied easily by artificial variation using ultraviolet, X-rays, chemicals such as nitrosoguanidine and ethyl methanesulfonate, etc.; however, strains which can be used in the present invention include all variants capable of producing TAN-749.

In the incubation of TAN-749-producing bacteria, substances which can be assimilated by the bacteria are used properly as carbon sources: glucose, maltose, lactose, blackstrap molasses, oil and fats (soybean oil, olive oil, etc.), and organic acids (citric acid, succinic acid, gluconic acid, etc.). As nitrogen sources, various organic or inorganic nitrogen compounds can be used: soybean flour, cotton seed powder, corn steep liquor, dried yeast, yeast extract, meat extract, peptone, urea, ammonium sulfate, ammonium nitrate, ammonium chloride, and ammonium phosphate. Inorganic salts such as sodium chloride, potassium chloride, calcium carbonate, magnesium sulfate, potassium primary phosphate and potassium secondary phosphate, which are essential to ordinary bacterial cultures, can be properly used singly or in combination.

Heavy metals such as ferrous sulfate and copper sulfate, and vitamins such as vitamin $B_1$ and biotin, are added if required. Antifoaming agents such as silicon oil and polyalkylene glycol ether, and surface active agents, can also be added to the medium. Other organic or inorganic substances which facilitate bacterial growth and thus promote TAN-749 production can also be added.

As for culture methods, ordinary production methods for antibiotics can be applied; solid and liquid cultures are both applicable. In the case of liquid cultures, any of standing cultures, shaking cultures, submerged culture, aeration cultures, etc. can be conducted; the aeration submerged culture is especially preferable. Culture temperature can be chosen in a range of approx. 10° C. to 30° C.; it is recommended that the incubation be conducted between approx. 17° C. and 24° C. A medium pH can be chosen in a range of approx. 4 to 8; recommended pH ranges from approx. 6 to 7. The culture should be performed for approx. 8 to 168 hours, preferably approx. 24 to 144 hours.

In collecting TAN-749, the purposed product, from cultures, separation methods which are usually employed to collect metabolites produced by microbes from their cultures can properly be used. For example, TAN-749, which behaves as a water-soluble alkaline substance, and is thus contained mainly in culture filtrate, can be collected by performing the following procedures. That is, the culture liquid, after addition of a filter aid, is subjected to filtration or centrifugation to remove bacterial cells. The resulting culture filtrate is put in contact with a proper carrier to adsorb biologically active components in the filtrate, and the active components are then desorbed using an appropriate solvent to separate and recover the purposed products. Chromatographic carriers which can be used favorably include compounds with which adsorbability difference is applied, such as activated charcoal, powdered cellulose and adsorptive resins, those with which functional group difference is applied, such as cation exchange resins, cation exchange cellulose and cation exchange dextran gel, and those with which a molecular weight difference is applied, such as dextran gel. Eluents which can be used in proper combination to elute purposed compounds from these carriers include hydrated solutions of water-soluble organic solvents, such as hydrated acetone and hydrated alcohols, and aqueous solutions containing acids, alkalis, buffer solutions, organic salts or inorganic salts, though combination varies with carrier types and qualities.

In some cases, crude products containing antibiotics, obtained using these chromatographic methods, are subjected to HPLC for separation to obtain purified products.

Methods for recovering TAN-749 are described in more detail hereinafter. Antibacterial substances contained in the filtrate can be adsorbed using cation-exchange resins such as Amberlite IRC-50 and CG-50 (Rohm & Haas Co., U.S.A.) and then eluted using aqueous solutions or buffer solutions containing salts or acids. Antibiotics can be adsorbed also using cation-exchange dextran gels such as CM-Sephadex (Pharmacia Fine Chemicals, Sweden) and then eluted using aqueous or buffer solutions containing salts or acids. It is recommended that activated charcoal for chromatography (Takeda Chemical Industries Co., Ltd., Japan) or adsorptive resins such as Diaion HP-20 and SP-207 (Mitsubishi Chemical Industries Co., Ltd., Japan) and Amberlite XAD-II (Rohm & Haas Co., U.S.A.) be used to remove salts and coloring substances, etc. from resulting eluates. Eluted fractions are powdered via processes including concentration and lyophilization. When the resulting powder is low in purity, the use of HPLC is recommended for further purification. Carriers which can be used in such HPLC include TSK gel (Toyo Soda Manufacturing Co., Ltd., Japan) and YMC gel (Yamamura Chemical Laboratories, Japan). As for mobile phase, mixed solutions of methanol, acetonitrile, etc. and an aqueous or buffer solutions containing inorganic salts, can be used. TAN-749 is separated in the form of a salt of mineral acids such as hydrochloric acid, sulfuric acid and phosphoric acid, or of organic acids such as formic acid, acetic acid and oxalic acid.

TAN-749 salts separated in the processes shown above can be converted into free TAN-749 compounds using conventional methods, and said free compounds can be converted into the same salts as above using conventional methods.

Dihydrochlorides of TAN-749A, B, C and D, which were obtained in Example 1 (shown later), possess the following physical and chemical properties:

[1] TAN-749A dihydrochloride
  (1) Appearance: Colorless solid
  (2) Specific rotation:
    $[\alpha]_D^{25} -11° \pm 5°$ (c=1.06, H$_2$O)
  (3) pKa' value: 8.0
  (4) Molecular weight: 326 (M+H)$^+$, 348 (M+Na)$^+$ (SI-MS method, M represents the molecular weight of the free compound.)
  (5) Molecular formula: C$_{15}$H$_{27}$N$_5$O$_3$.2HCl
  (6) Elemental analysis:
    Samples were analyzed after being dried on phosphorous pentoxide under reduced pressure at 40° C. for 6 hours. (Calculation was conducted on the condition that one mole of water contained in the sample.)

| | Found | Calculated | |
|---|---|---|---|
| C | 43.6 ± 2.0 | C 43.27 | |
| H | 7.4 ± 1.0 | H 7.50 | |
| N | 17.0 ± 1.5 | N 16.82 | |
| O | | O 15.37 | |
| Cl | 16.4 ± 1.5 | Cl 17.03 | (%) |

Figure 2:
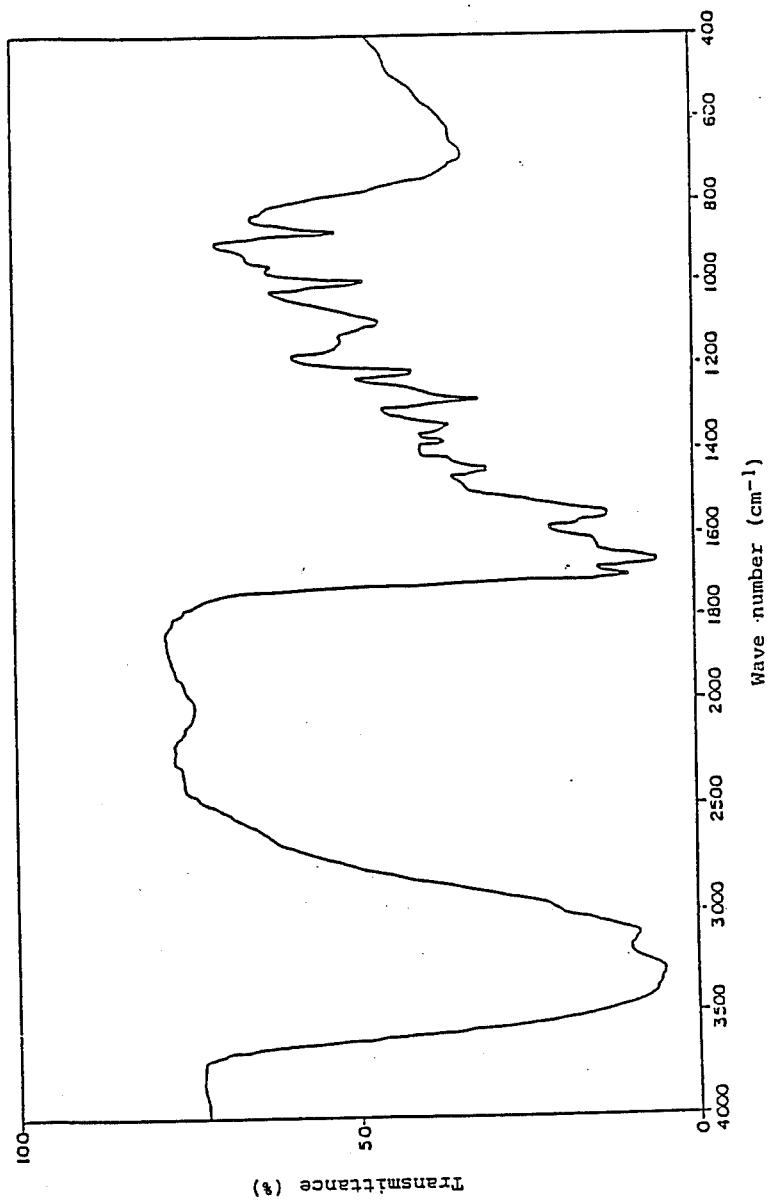
FIG. 2 is an infrared (IR) absorption spectrum (kBr method) of TAN-749A dihydrochloride.
Figure 3:
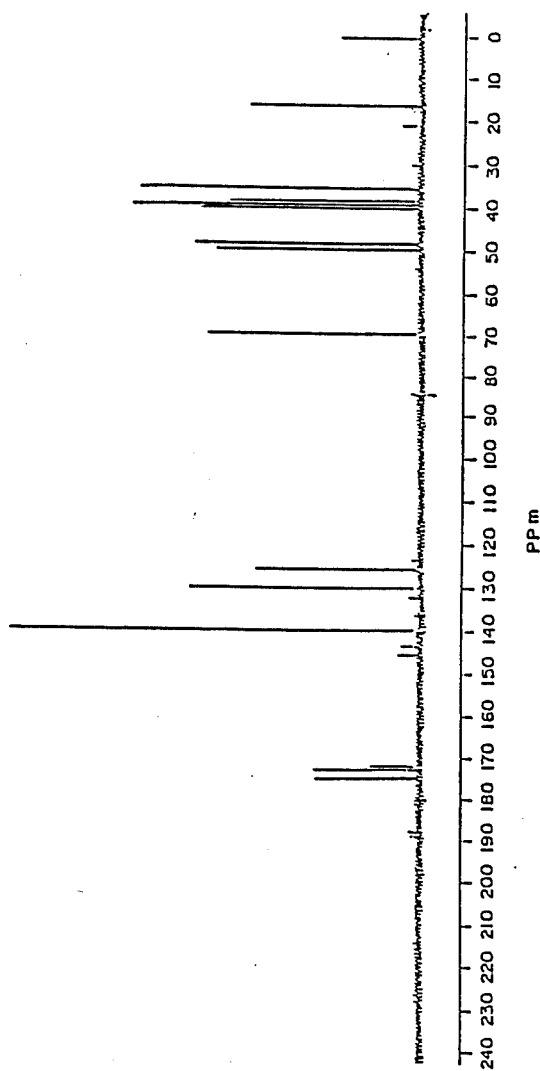
FIG. 3 is a $^{13}C$ nuclear magnetic resonance (NMR) spectrum of TAN-749A dihydrochloride.

(7) Ultraviolet (UV) absorption spectrum (in water):
    Refer to FIG. 1.
    $\lambda_{max}$ 266±3 nm (E$_1$ $_{cm}$$^{1\%}$ =658±100)
  (8) Infrared (IR) absorption spectrum (KBr method):
    Refer to FIG. 2. Main absorption wavenumbers are as follows:
    3400, 3100, 1700, 1670, 1550, 1440, 1380, 1340, 1280,
    1220, 1150, 1100, 1000, 960, 870, 680 (cm$^{-1}$)
  (9) $^{13}$C nuclear magnetic resonance (NMR) spectrum:
    The following signals are measured in deuterium oxide at 100 MHz.
    Refer to FIG. 3.
    174.7(s), 172.3(s), 171.7(s), 139.3(d), 139.3(d),
    129.6(d), 125.3(d) 69.2(d), 49.2(d), 47.8(t),
    39.8(t), 39.1(t), 38.1(t), 35.2(t), 16.0(q) (ppm)
    (Symbols shown above represent signal types, i.e. s: singlet, d: doublet, t: triplet q: quartet.)
  (10) High performance liquid chromatography (HPLC);
    Retention time: R$_t$=4.4 (min)
    Column: YMC-PAK A312 (Yamamura Chemical Laboratories)
    Mobile phase: 12% methanol/0.01M phosphoric acid solution (pH 3)
    Flow rate: 2 ml/min
  (11) Color reaction:
    Positive: Ehrlich's reaction, Dimethylbenzaldehyde, Potassium permanganate
    Negative: Ninhydrin, Greig-Leaback's, Sakaguchi's, Dragendorff's reactions
  (12) Solubility:
    Soluble: Water, Dimethyl sulfoxide, Methanol
    Sparingly soluble: Acetone, Ethyl acetate, Diethyl ether
  (13) Acidity or basicity:
    Neutral (Free compound is basic.)

[2] TAN-749B dihydrochloride
  (1) Appearance: Colorless solid
  (2) Specific rotation:
    $[\alpha]_D^{25} +56° \pm 20°$ (c=1.0, H$_2$O)
  (3) pKa' value: 8.05
  (4) Molecular weight: 340 (M+H)$^+$, 362 (M+Na)$^+$ (SI-MS method)
  (5) Molecular formula: C$_{16}$H$_{29}$N$_5$O$_3$.2HCl
  (6) Elemental analysis
    Analysis was conducted under the same conditions with TAN-749A dihydrochloride. (Calculated as 1.5 mole of water was contained in the sample.)

| | Found | Calculated | |
|---|---|---|---|
| C | 43.62 | C 43.94 | |
| H | 7.53 | H 7.37 | |
| N | 16.06 | N 16.01 | |
| O | | O 16.46 | |
| Cl | 16.31 | Cl 16.21 | (%) |

Figure 4:
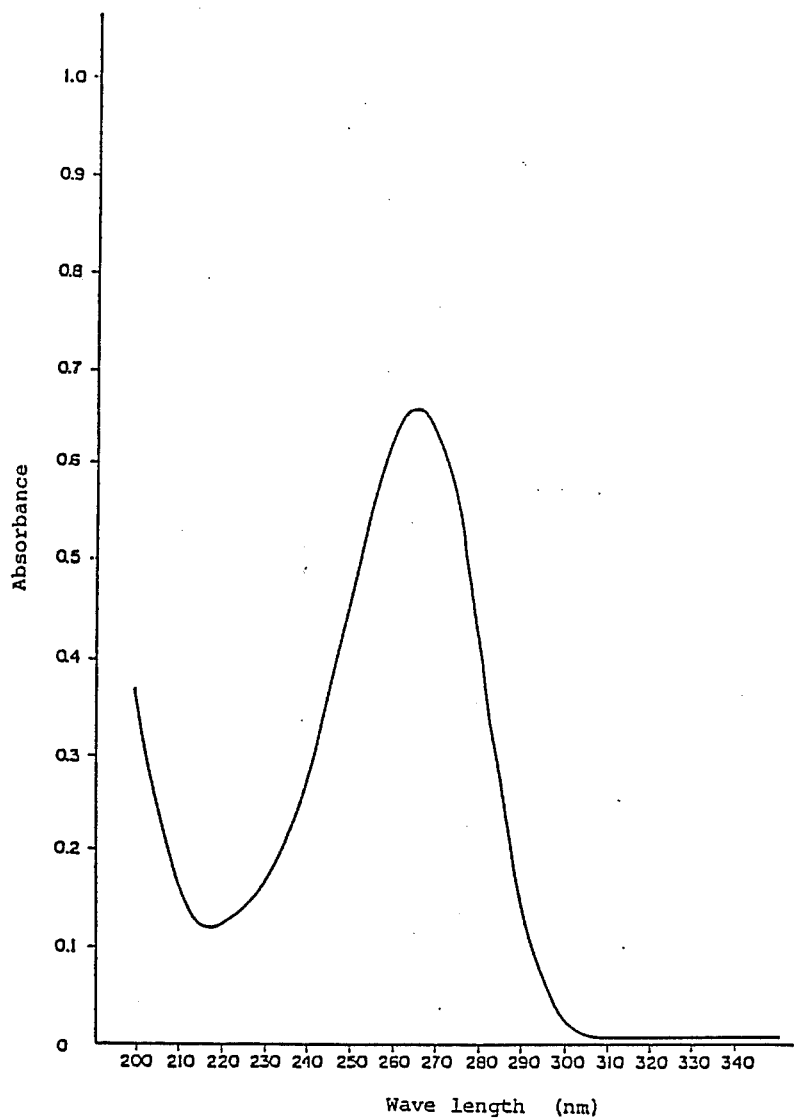
FIG. 4 is a UV spectrum (in water) of TAN-749B dihydrochloride.
Figure 5:
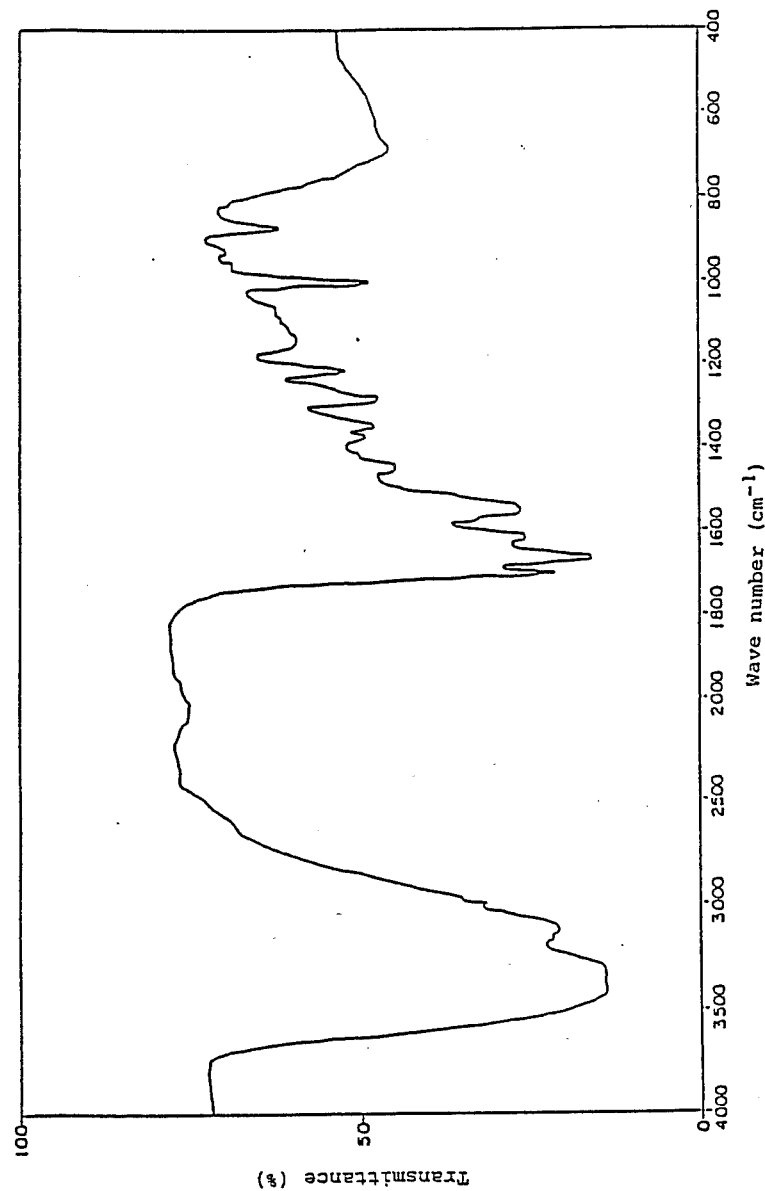
FIG. 5 is an IR spectrum (kBr method) of TAN-749B dihydrochloride.

(7) UV spectrum (in water):
    Refer to FIG. 4.
    $\lambda_{max}$ 264±3 nm (E$_1$ $_{cm}$$^{1\%}$ =660±100)
  (8) IR spectrum (KBr method):
    Refer to FIG. 5.
    3300, 3100, 1700, 1660, 1610, 1550, 1450, 1420, 1380,
    1350, 1280, 1220, 1150, 1070, 1000, 960, 930, 870, 690 (cm$^{-1}$)

Figure 6:
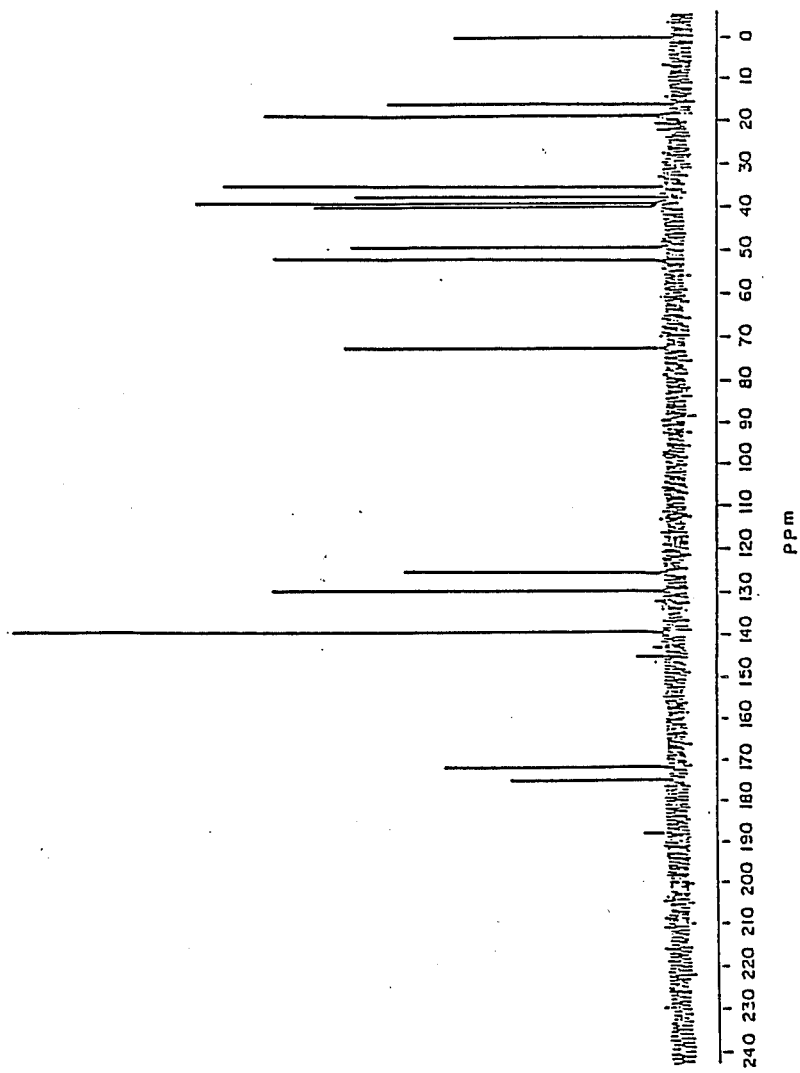
FIG. 6 is a $^{13}C$ NMR spectrum of TAN-749B dihydrochloride.

(9) $^{13}C$ NMR spectrum:
  The following signals are measured in deutrium oxide at 100 MHz.
  Refer to FIG. 6.
  174.7(s), 171.6(s), 139.3(d), 139.2(d), 129.6(d), 125.5(d), 72.6(d), 52.3(d), 49.3(d), 39.9(t), 39.1(t), 37.5(t), 35.2(t), 18.8(q), 16.0(q) (ppm)
(10) HPLC:
  Retention time: $R_t = 7.2$ (min)
  (Same conditions with TAN-749A)
(11) Color reaction:
  Same with TAN-749A dihydrochloride
(12) Solubility:
  Same with TAN-749A dihydrochloride
(13) Acidity or basicity:
  Neutral (Free compound is basic.)

[3] TAN-749C dihydrochloride
  (1) Appearance: Colorless solid
  (2) Specific rotation:
    $[\alpha]_D^{23} - 11° \pm 5°$ (c=0.68, $H_2O$)
  (3) Molecular weight: 326 $(M+H)^+$, 348 $(M+Na)^+$ (SI-MS method)
  (4) Molecular formula: $C_{15}H_{27}N_5O_3 \cdot 2HCl$
  (5) Elemental analysis:
    (Calculated as 0.5 mole of water was contained in the sample.)

|   | Found |   | Calculated |   |
|---|---|---|---|---|
| C | 44.35 | C | 44.23 |   |
| H | 7.83  | H | 7.42  |   |
| N | 17.28 | N | 17.19 |   |
| O |       | O | 13.75 |   |
| Cl| 17.59 | Cl| 17.41 | (%) |

Figure 7:
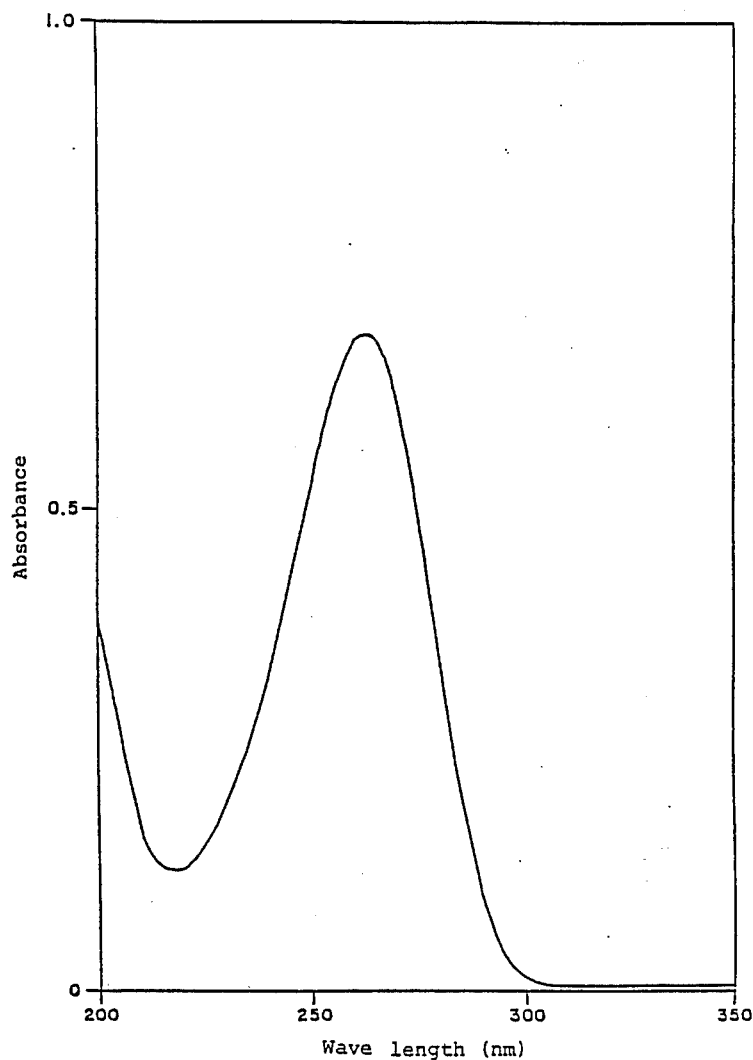
FIG. 7 is a UV spectrum (in water) of TAN-749C dihydrochloride.
Figure 8:
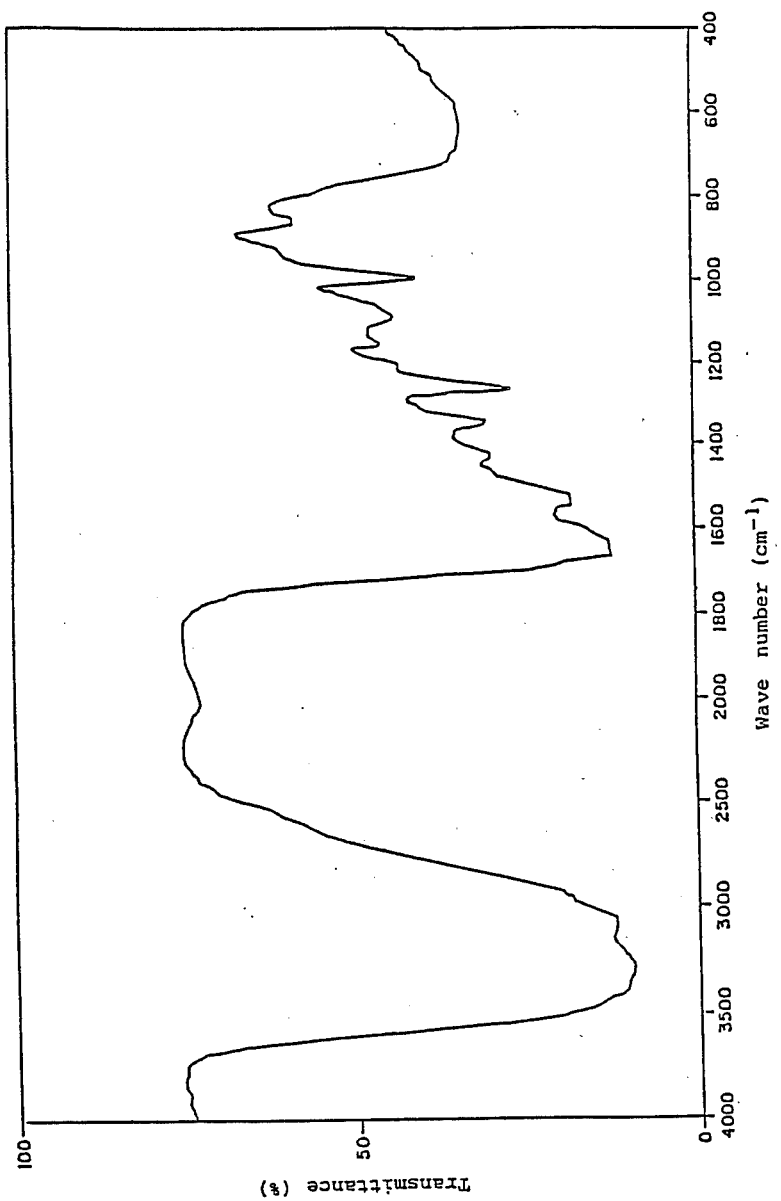
FIG. 8 is an IR spectrum (kBr method) of TAN-749C dihydrochloride.

(6) UV spectrum (in water):
  Refer to FIG. 7.
  $\lambda_{max}\ 262 \pm 3$ nm ($E_{1\ cm}^{1\%} = 680 \pm 100$)
(7) IR spectrum (KBr method):
  Refer to FIG. 8.
  3250, 3070, 1660, 1630, 1540, 1430, 1340, 1260, 1200,
  1150, 1085, 995, 860, 650 (cm$^{-1}$)
(8) $^{13}C$ NMR spectrum:
  At 100 MHz in deuterium oxide
  174.7(s), 172.3(s), 171.6(s), 145.1(d), 143.0(d), 132.0(d), 123.1(d), 69.2(d), 49.2(d), 47.7(t), 39.7(t), 39.1(t), 38.0(t), 35.2(t), 20.6(q) (ppm)
(9) Color reaction:
  Same with TAN-749A dihydrochloride
(10) HPLC:
  Retention time: $R_t = 5.7$ (min) [A:$R_t = 5.3$ (min)]
  Column: YMC-PAK A312
  Mobile phase: 30% acetonitrile/0.01M octane sulfonate/0.02M phosphoric acid solution (pH 3.0)
  Flow rate: 2 ml/min
(11) Solubility:
  Same with TAN-749A dihydrochloride
(12) Acidity or basicity:
  Neutral (Free compound is basic.)

[4] TAN-749D dihydrochloride
  (1) Appearance: Colorless solid
  (2) Specific rotation:
    $[\alpha]_D^{24} + 30° \pm 10°$ (c=0.5, $H_2O$)
  (3) Molecular weight: 340 $(M+H)^+$, 362 $(M+Na)^+$ (SI-MS method)
  (4) Molecular formula: $C_{16}H_{29}N_5O_3 \cdot 2HCl$
  (5) Elemental analysis
    (Calculated as 0.5 mole of water was contained in the sample.)

|   | Found |   | Calculated |   |
|---|---|---|---|---|
| C | 45.15 | C | 45.61 |   |
| H | 7.98  | H | 7.65  |   |
| N | 16.44 | N | 16.62 |   |
| O |       | O | 13.29 |   |
| Cl| 16.59 | Cl| 16.83 | (%) |

Figure 9:
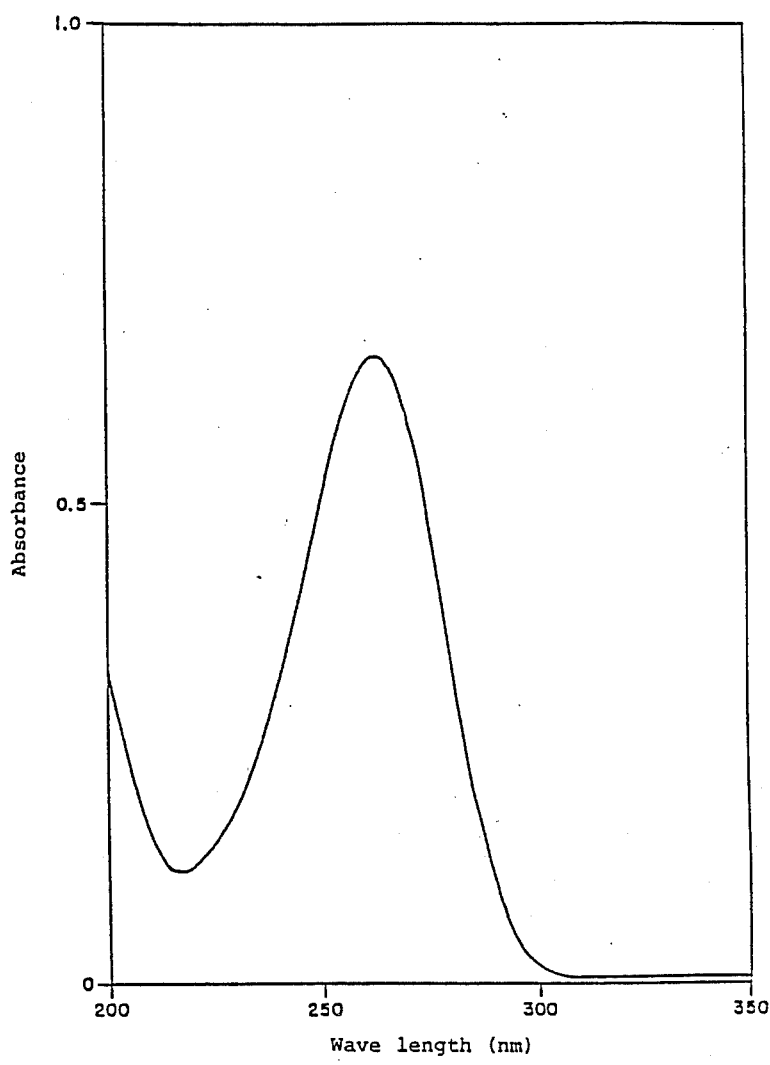
FIG. 9 is a UV spectrum (in water) of TAN-749D dihydrochloride.
Figure 10:
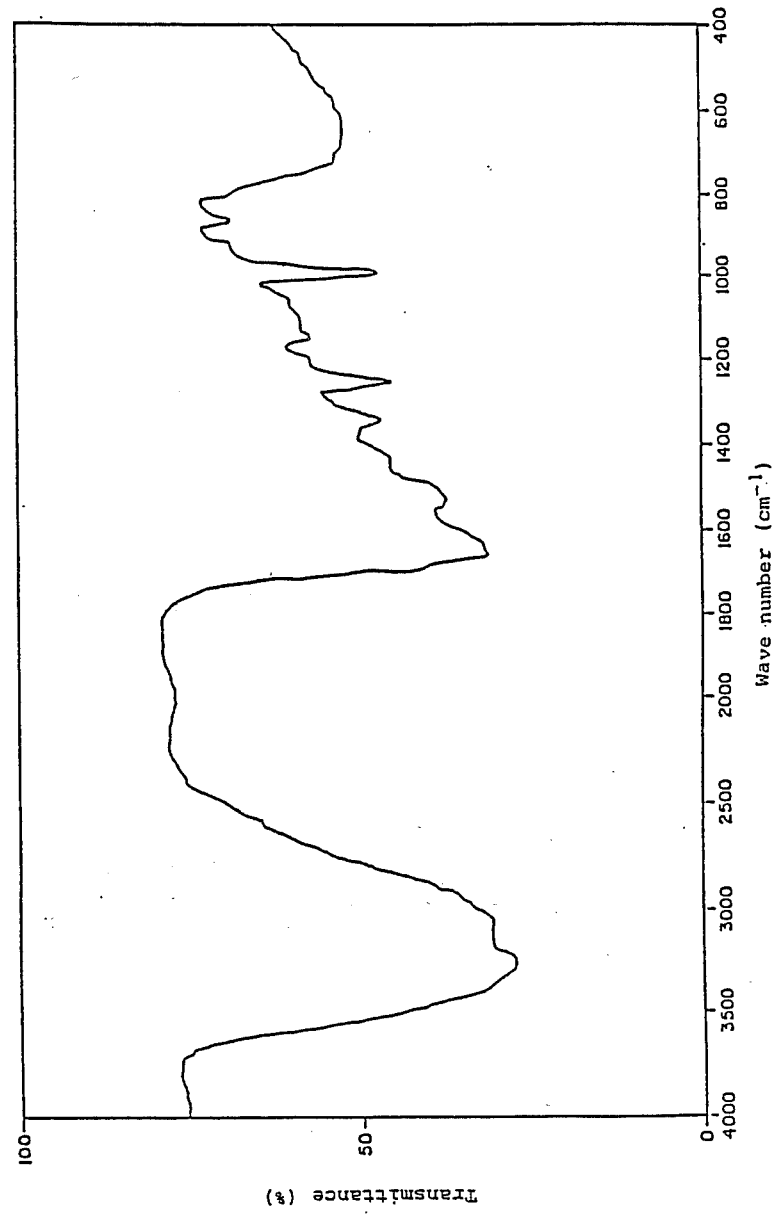
FIG. 10 is an IR spectrum (kBr method) of TAN-749D dihydrochloride.

(6) UV spectrum (in water):
  Refer to FIG. 9.
  $\lambda_{max}\ 262 \pm 3$ nm ($E_{1\ cm}^{1\%} = 655 \pm 100$)
(7) IR spectrum (KBr method):
  Refer to FIG. 10.
  3250, 3050, 1660, 1635, 1530, 1435, 1345, 1260, 1200,
  1150, 995, 860, 650 (cm$^{-1}$)
(8) $^{13}C$ NMR spectrum:
  At 100 MHz in deuterium oxide
  174.7(s), 171.7(s), 171.6(s), 145.3(d), 143.0(d), 132.0(d), 123.2(d), 72.5(d), 52.2(d), 49.3(t), 39.9(t), 39.2(t), 37.5(t), 35.3(t), 20.7(q), 18.8(q) (ppm)
(9) Color reaction:
  Same with TAN-749A dihydrochloride
(10) HPLC:
  Retention time: $R_t = 6.2$ (min) [B:$R_t = 5.8$ (min)]
  (Same conditions with TAN-749C dihydrochloride)
(11) Solubility:
  Same with TAN-749A dihydrochloride
(12) Acidity or basicity:
  Neutral (Free compound is basic.)

Examples of the organic residue bonded to the carbon to which it is attached through nitrogen shown by $R^1$, $R^{1'}$, $R^{1''}$, $R^4$ or $R^{4'}$ in the above general formula include acylamino group, amino group substituted through carbon, alkenylamino group, thioamino group, phosphorylamino group, etc. The organic residue bonded to the carbon to which it is attached through nitrogen shown by $R^{1''}$ is preferably a protected amino.

As the acyl group in the above-mentioned acylamino, the acyl group derivable from an organic carboxylic acid is mentioned.

Examples of the acylamino group include groups representable by the formula

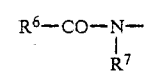

wherein $R^6$ is hydrogen, alkyl* (in the explanation of each group in this specification, groups bearing the mark "*" are those which may be substituted), alkenyl*, cycloalkyl*, aryl*, heterocyclic ring*, alkoxy*, aryloxy* or alkynyl*, $R^7$ is hydrogen, alkyl* or acyl*, and $R^6$ and $R^7$ may form a ring, groups representable by the formula

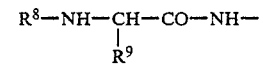

wherein $R^8$ is hydrogen, amino acid residue*, an amino-protecting group or groups representable by the formula $R^{10}$—$(CH_2)_n$—$C(=Z)$— {wherein $R^{10}$ is heterocyclic ring*, alkoxy* or amino*, n is an integer of 0 to 2 and Z is O or S, respectively}, $R^9$ is hydrogen, alkyl*, aryl*, cycloalkenyl or heterocyclic ring*, respectively, groups representable by the formula $R^{11}-R^{12}-CO-NH-$ wherein $R^{11}$ is groups representable by the formula

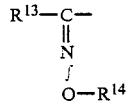

{$R^{13}$ is alkyl*, heterocyclic ring* or aryl*, $R^{14}$ is hydrogen, alkyl*, alkenyl*, arylcarbonyl*, cycloalkyl*, heterocyclic ring* or groups representable by the formula $-R^{15}-R^{16}$ (wherein $R^{15}$ is alkylene*, cycloalkylene or alkenylene, $R^{16}$ is aryl*, carboxyl* or its ester or mono- or di-alkylamide, respectively), respectively} and $R^{12}$ is a chemical bond or groups representable by the formula

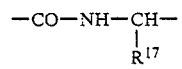

(wherein $R^{17}$ is alkyl*, aryl* or heterocyclic ring*), respectively, groups representable by the formula

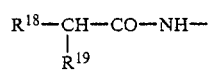

wherein $R^{18}$ is aryl*, heterocyclic ring* or cycloalkenyl and $R^{19}$ is hydroxy, carboxy*, sulfamoyl, sulfo, sulfoxy, aryloxycarbonyl* or acyloxy*, respectively, groups representable by the formula $R^{20}-R^{21}-CH_2-CO-NH-$ wherein $R^{20}$ is alkyl*, alkynyl*, cyano, aryl*, aryloxy*, alkenylene*, heterocyclic ring*, amino* or groups representable by the formula $R^{20'}-C(=S)-$ (wherein $R^{20'}$ is alkoxy) and $R^{21}$ is a chemical bond or $-S-$, respectively, groups representable by the formula $R^{22}-CO-CO-NH-$ wherein $R^{22}$ is hydrogen, alkyl*, alkoxy*, aryl*, aryloxy* heterocyclic ring* or amino*, and groups representable by the formula

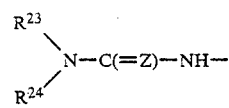

wherein $R^{23}$ and $R^{24}$ independently are hydrogen, alkyl*, aryl*, heterocyclic ring* or cycloalkyl, and Z is O, S or NH, respectively.

The formula

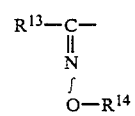

in $R^{11}$ stands for syn-isomers representable by the formula

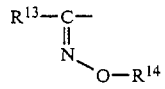

and anti-isomers presentable by the formula

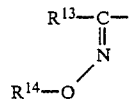

or a mixture thereof.

Examples of the amino groups substituted through carbon mentioned as examples of the organic residue bonded to the carbon to which it is attached through nitrogen shown by the afore-mentioned $R^1$, $R^{1'}$, $R^{1''}$, $R^4$ or $R^{4'}$ include groups representable by the formula $R^{25}-NH-$ wherein $R^{25}$ is alkyl* or alkenyl*, groups representable by the formula

wherein $R^{26}$ and $R^{27}$ are independently alkyl*, aryl* or alkenyl*, respectively, including the case where $R^{26}$ and $R^{27}$ form heterocyclic ring* together with the adjacent nitrogen atom and groups representable by the formula

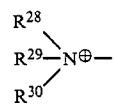

wherein $R^{28}$, $R^{29}$ and $R^{30}$ are independently alkyl*, aryl* or alkenyl*, respectively, including the case where $R^{28}$ and $R^{29}$ or $R^{30}$ form a heterocyclic ring* together with the adjacent nitrogen atom Examples of the alkenylamino as examples of the organic residue bonded to the carbon to which it is attached through nitrogen shown by the afore-mentioned $R^1$, $R^{1'}$, $R^{1''}$, $R^4$ or $R^{4'}$ include groups representable by the formula

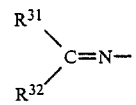

wherein $R^{31}$ and $R^{32}$ are independently hydrogen, alkyl*, aryl*, cycloalkyl*, amino* or heterocyclic ring*, including the case where $R^{31}$ and $R^{32}$ form cycloalkyl* or heterocyclic ring* together with the adjacent carbon atom.

Examples of the thioamino as examples of the organic residue bonded to the carbon to which it is attached through nitrogen shown by the afore-mentioned $R^1$, $R^{1'}$, $R^{1''}$, $R^4$ or $R^{4'}$ include groups representable by the formula $R^{33}-SO_n-NH-$ wherein $R^{33}$ is alkyl* or aryl* and n is an integer of 0 to 2.

Examples of the phosphorylamino as examples of the organic residue bonded to the carbon to which it is attached through nitrogen shown by the afore-mentioned $R^1$, $R^{1'}$, $R^{1''}$, $R^4$ or $R^{4'}$ include groups representable by the formula

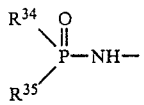

wherein $R^{34}$ and $R^{35}$ are independently alkyl*, aryl*, alkoxy* or aryloxy*, including the case where $R^{34}$ and $R^{35}$ form heterocyclic ring*.

In the above formulae, the organic residue bonded to the carbon to which it is attached through nitrogen shown by $R^1$, $R^{1'}$, $R^{1''}$, $R^4$ or $R^{4'}$ is preferably of a molecular weight of 500 or less.

In the above formulae, the alkyl which may be substituted, shown by $R^2$ or $R^{2'}$ is preferably a $C_{1-10}$ alkyl which may have substituents shown below. And $R^2$ or $R^{2'}$ may bond with the nitrogen atom of the adjacent $R^1$, $R^{1'}$ or $R^{1''}$ to form a cyclic ring.

As the hydroxyl-protecting group shown by $R^3$ or $R^{3'}$ in the above-mentioned general formula, use is made of, for example, ester residues including alkyl groups having 1 to 20 carbon atoms to be described later, acetyl, chloroacetyl, etc., esterified carboxyl groups including $\beta,\beta,\beta$-trichloroethoxycarbonyl, $\beta$-trimethylsilylethoxycarbonyl, etc., ether residues including benzyl, p-nitrobenzyl, allyl, trityl, methoxymethyl, methylthiomethyl, $\beta$-methoxyethoxymethyl, etc., silylether residues including trimethylsilyl, triethylsilyl, tert-butyldimethylsilyl, etc., acetal residues including 2-tetrahydropyranyl, 4-methoxy-4-tetrahydropyranyl, etc., etc.

These hydroxyl-protecting groups are not limited to only $R^3$ and $R^{3'}$, but can also be conveniently used as protecting hydroxyl groups when existing in any other substituents. Further, $R^3$ or $R^{3'}$ may form, together with a group shown by the above-mentioned $R^7$, cyclic structure as in, for example, 2,2-dimethylthioxazolidine or 2,2-dimethyltetrahydro-1,3-oxazine. $R^3$ or $R^{3'}$ may form, together with $R^4$ or $R^{4'}$, 2-oxo-1,3-oxazine, etc.

As the amino group which may be substituted shown by $R^5$ or $R^{5'}$ in the afore-mentioned general formula, use is made of, for example, groups representable by the formula $R^{36}$—NH— wherein $R^{36}$ is hydrogen, alkyl*, cycloalkyl*, aryl*, alkenyl*, heterocyclic ring*, hydroxy, alkoxy* or amino*] or groups representable by the formula

wherein $R^{37}$ and $R^{38}$ are independently alkyl*, aryl* or alkenyl*, including the case where $R^{37}$ and $R^{38}$ form heterocyclic ring* together with the adjacent nitrogen atom.

As the substituents in the hydroxyl group which may be substituted shown by $R^5$ or $R^{5'}$ are exemplified by alkyl*, cycloalkyl*, aryl*, alkenyl*, etc.

As the substituent in the substituted hydroxyl group shown by $R^{5''}$ are exemplified by the groups which are used as the protecting groups of the carboxyl groups shown below.

As the alkyl which may be substituted, shown by A in the above-mentioned formula, those having 1 to 10 carbon atoms and optionally having the substituents shown below are preferable.

As the substituent of the hydroxyl group which may be substituted shown by A are exemplified by a $C_{1-6}$ alkyl such as methyl, ethyl, propyl, etc. an aralkyl such as benzyl, etc.

As the alkyl in the groups in the above-mentioned formulae, those having 1 to 20 carbon atoms for example are preferable, which are exemplified by methyl, ethyl, n-propyl, isopropyl, sec-butyl, t-butyl, 1,1-dimethylpropyl, n-pentyl, isopentyl, n-hexyl, isohexyl, heptyl, octyl, nonanyl, decanyl, undecanyl, dodecanyl, tridecanyl, tetradecanyl, pentadecanyl, hexadecanyl, heptadecanyl, octadecanyl, nonadecanyl, eicosanyl, etc.

Substituents which said alkyl groups may optionally have are exemplified by halogen, nitro, amino (which may be substituted with acyl, alkyl, iminomethyl, imino(aryl-substituted)methyl, amidino, alkenyl, cycloalkyl or aryl), sulfo, cyano, hydroxy, carboxy, mercapto, cycloalkyl, alkoxy (which may be substituted with amino, hydroxy, carboxy, halogen, aryl, cycloalkyl or alkoxy), aryl (which may be substituted with halogen, alkyl, alkoxy, alkylamine, amino, carbamoyl, sulfo, alkylsulfonyl, cyano, hydroxy, carboxy, nitro, acyloxy, aralkyloxy or sulfoxy), aryl carbonyl optionally having such substituents as in the aryl mentioned above, aryloxy optionally having such substituents as the aryl mentioned above, heterocyclic ring (which may be substituted with nitro, oxo, aryl, alkenylene, halogenoalkyl, alkylsulfonyl, alkyl, alkoxy, alkylamino, amino, halogen, carbamoyl, hydroxy, cyano, carboxy or sulfo), acyl, acyloxy, carbamoyloxy, alkoxycarbonyloxy, acyloxy-ethoxy, aralkyl (which may be substituted with alkyl, alkoxy, halogen, amino, hydroxy, nitro, cyano, carbamoyl or sulfamoyl), aralkyloxy (which may be substituted with acyloxy, alkyl, alkoxy, halogen, amino, hydroxy, nitro, cyano, carbamoyl or sulfamoyl), aminoxy, iminoxy, alkylsulfonyl, aminosulfonyl, arylsulfonyl, alkylsulfinyl, alkylthio (which may be substituted with cyano, halogen, carboxy, alkylamino, imino, carbamoyl or acylamino), arylthio, heterocyclic ring-thio (which may be substituted with cyano, hydroxy, amino, alkylamino, alkyl, halogen or oxo), heterocyclic ring (which may be substituted with cyano, hydroxy, amino, alkyl, halogen or oxo) alkylthio, iminomethyl amino, iminoethylamino, silyl (which may be substituted with alkyl or aryl), alkyloxycarbonyl, arylcarbonyl (which may be substituted with acyloxy, halogen, amino, hydroxy, alkoxy or sulfamoyl), phthalimido, succinimido, aminocarbonyl, mono- and dialkylaminocarbonyl, phosphoryl (which may be substituted with alkyl or aryl), etc.

Preferable examples of cycloalkyl optionally forming a ring in the groups of the above-mentioned formulae are those having 3 to 8 carbon atoms, which include cyclopropyl, cyclobutyl, cyclopentyl, cyclohexyl, cycloheptyl, cycloocty, etc.

Substituents which said cycloalkyl group may optionally have are exemplified by halogen, nitro, amino (which may be substituted with acyl, amidino or iminomethyl), hydroxy, sulfo, cyano, carboxy, oxo, etc.

As the cycloalkylene in the groups of the afore-mentioned formulae, are mentioned the above-mentioned cycloalkyl having one more chemical bond.

Examples of aryl and the aryl in arylcarbonyl, aryloxycarbonyl, aryloxy or arylthio include phenyl, naphthyl, biphenyl, anthryl, indenyl, etc.

Examples of substituents which said aryl group may optionally have include halogen, nitro, cyano, amino (which may be substituted with alkyl, alkenyl, cycloalkyl or aryl), sulfo, hydroxy, sulfoxy, sulfamoyl, alkyl (which may be substituted with amino, halogen, hydroxy or cyano), alkoxy, aralkyloxy, alkylsulfonamide, methylenedioxy, alkylsulfonyl, alkylsulfonylamino, etc., and these aryl groups may form, a condensed ring (e.g. tetrahydronaphthyl, indanyl, acenaphthyl, etc.) together with the cycloalkyl.

Preferable examples of the alkoxy in the groups of the above-mentioned formulae are those having 1 to 6 carbon atoms, which include methoxy, ethoxy, n-propoxy, i-propoxy, n-butoxy, i-butoxy, t-butoxy, n-pentyloxy, n-hexyloxy, etc.

Substituents which the alkoxy group may optionally have are exemplified by halogen, nitro, amino, hydroxy, sulfo, cyano, carboxy, aryl (which may be substituted with nitro, amino, hydroxy, alkyl or alkoxy), silyl (which may be substituted with alkyl, aryl or aralkyl), etc.

Preferable examples of the alkynyl in the groups of the above-mentioned formulae are those having 2 to 6 carbon atoms, which include ethynyl, 1-propinyl, 1-pentynyl, etc. As the substituents which said alkynyl group may optionally have are exemplified by alkyl, alkenyl, aryl, etc.

Preferable alkenyl or alkenylene in the groups of the afore-mentioned formulae are those having 1 to 10 carbon atoms, which are exemplified by methylene, allyl, 1,3-butadienyl, 2,4-pentadienyl, 1,3,5-hexatrienyl, 1,3,5,7-octatetraenyl, 1,3,5,7,9-decapentaenyl, etc.

Examples of substituents which said alkenyl or alkenylene may optionally have include alkyl having 1 to 6 carbon atoms (optionally having the same substituent as those which said alkyl may optionally have), halogen, nitro, amino (which may be substituted with acyl, iminomethylene, amidine, alkyl or aryl), sulfo, cyano, hydroxy, carboxyalkyloxycarbonyl, carbamoyl, alkylthio, allylthio, alkylsulfinyl, arylsulfinyl, alkylsulfonyl, arylsulfonyl, sulfamoyl, aryl, acyl, etc. The alkenyl or alkenylene include isomers (E, Z compounds) relative to the double bond.

Heterocyclic rings in the groups of the afore-mentioned formulae or heterocyclic rings formed by these groups are exemplified by 5- to 7-membered heterocyclic ring containing one sulfur atom, nitrogen atom or oxygen atom, 5- to 6-membered heterocyclic ring containing 2 to 4 nitrogen atoms, and 5- to 6-membered heterocyclic ring containing 1 to 2 nitrogen atoms and one sulfur atom or oxygen atom, and these heterocyclic rings may optionally be condensed with a 6-membered ring containing nitrogen atoms of not more than 2, benzene ring or a 5-membered ring containing one sulfur atom.

Specific examples of the above-mentioned heterocycles include 2-pyridyl, 3-pyridyl, 4-pyridyl, pyrimidinyl, pyrazinyl, pyridazinyl, piperazinyl, pyrazolyl, imidazolyl, thiazolyl, isothiazolyl, oxazolyl, isoxazolyl, pyrido[2,3-d]pyrimidyl, benzopyranyl, 1,8-naphthyridyl, 1,5-naphthyridyl, 1,6-naphthyridyl, 1,7-naphthyridyl, 2,7-naphthyridyl, 2,6-naphthyridyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, pyranyl, hexahydro-1H-azepinyl, indolyl, isoindolizinyl, chromanyl, etc.

Examples of substituents which these heterocycle groups may optionally have include amino (which may be substituted with acyl, halogen-substituted alkylacyl, phenyl or alkyl), halogen, nitro, sulfo, cyano, hydroxy, carboxy, oxo, thioxo, $C_{1-10}$ alkyl [which may be substituted with aryl, halogen, amino, hydroxy, carboxy, alkoxy, alkylsulfonyl, dialkylamino, phosphoric acid (which may be substituted with alkyl), cycloalkyl, alkoxy (which may be substituted with halogen, hydroxy), acyl having 1 to 4 carbon atoms, aryl (which may be substituted with halogen, nitro, alkyl, alkoxy, amino, sulfo, hydroxy, cyano), oxo, thioxo, amino acid residue - thio (examples of the amino acid residue are those as set forth later), $C_{1-10}$ alkylthio [which may be substituted with aryl, halogen, amino, hydroxy, carboxy, alkoxy, alkylsulfonyl, dialkylamino, phosphoric acid (which may be substituted with alkyl)], heterocyclic ring (which may be substituted with alkyl, alkoxy, halogen, nitro, cyano, carboxy, formyl, alkylsulfonyl), groups of the formula $R^{39}$—CH=N— wherein $R^{39}$ is heterocyclic ring (which may be substituted with alkyl, alkoxy, halogen, nitro, cyano, hydroxy, carboxy, formyl, alkylsulfonyl), etc.

Examples of the acyl shown by $R^7$ include phthaloyl, succinyl, maleoyl, citraconoyl, glutaryl, adipoyl, etc., forming a ring together with $R^6$. Examples of substituents which said acyl group may optionally have include halogen, nitro, amino, hydroxy, sulfo, cyano, carboxy, etc.

Examples of the acyl in the acyloxy in the above-mentioned formulae are preferably those having 1 to 4 carbon atoms, which include formyl, acetyl, propionyl, butyryl, isobutyryl, etc., which may be substituted with, for example, alkyl (which may be substituted with amino, halogen, cyano, alkoxy, carboxy, hydroxy), etc.

Examples of the amino acid residue shown by $R^8$ in the afore-mentioned formula include glycyl, alanyl, valyl, leucyl, isoleucyl, seryl, threonyl, cysteinyl, cystyl, methionyl, α- or β-asparagyl, α- or γ-glutamyl, lysyl, arginyl, phenylalanyl, phenylglycyl, tyrosyl, histidyl, triptophanyl, prolyl, etc. The above-mentioned amino acid residue includes D-compounds and L-compounds, when it has both of them.

Examples of substituents which said amino acid residue may optionally have include halogen, hydroxy, sulfo, carboxy, cyano, alkylamino, aralkyloxycarbonyl, aralkyloxy, guanidino, etc.

As the amino-protecting group shown by $R^8$ in the afore-mentioned formulae, use is conveniently made of, for example, those usable for this purpose in the field of peptide synthesis. More specifically, they are, for example, aromatic acyl groups including phthaloyl, 4-nitrobenzoyl, 4-tert-butylbenzoyl, 4-tert-butylbenzenesulfonyl, benzenesulfonyl, toluenesulfonyl, etc., aliphatic acyl groups including formyl, acetyl, propionyl, monochloroacetyl, dichloroacetyl, trichloroacetyl, methanesulfonyl, ethanesulfonyl, trifluoroacetyl, malonyl, succinyl, etc., esterified carboxyl groups including methoxycarbonyl, ethoxycarbonyl, t-butoxycarbonyl, isopropoxycarbonyl, 2-cyanoethoxycarbonyl, 2,2,2-trichloroethoxycarbonyl, benzyloxycarbonyl, 4-nitrobenzyloxycarbonyl, 4-methoxybenzyloxycarbonyl, diphenylmethyloxycarbonyl, methoxymethyloxycarbonyl, acetylmethyloxycarbonyl, isobornyloxycarbonyl, phenyloxycarbonyl, etc., methylene group such as (hexahydro-1H-azepin-1-yl)methylene, etc., sulfonyl group such as 2-amino-2-carboxyethylsulfonyl, etc., and further, amino-protecting groups, other than acyl group, such as trityl, 2-nitrophenylthio, benzylidene, 4-nitrobenzylidene, di- or tri-alkylsilyl, benzyl, 4-nitrobenzyl, etc. Selection of the above-mentioned protecting groups is not specifically limitative in the present invention, and specifically preferable ones being monochloroacetyl, benzyloxycarbonyl, 4-methoxybenzyloxycarbonyl, 4-nitrobenzyloxycarbonyl. These amino-protecting groups are not limited only to those shown by $R^8$, and they can conveniently be used as protecting groups of amino groups in any other substituents as well.

The cycloalkenyl shown by $R^9$ and $R^{18}$ in the above formulae is exemplified by cyclohexene, cyclohexadiene, cycloheptene, cyclopentene, cyclooctene, etc.

Examples of the substituents of carboxy groups which may be substituted in the above-mentioned formulae include alkyl (which may be substituted with halogen, cyano, hydroxy), aryl (which may be substituted with alkyl, alkoxy, halogen, hydroxy, acyloxy, sulfo, cyano, sulfamoyl), silyl (which may be substituted with alkyl, aryl, aralkyl), heterocyclic ring (which may be substituted with amino, alkylamino, sulfamoyl, carbamoyl, halogen, cyano, nitro), amino (which may be substituted with alkyl, aryl, cycloalkyl, sulfo or aralkyl, and 5- to 6-membered heterocyclic ring may be formed together with the nitrogen in the amino group), etc. These substituents may, in some cases, be used as carboxyl-protecting groups, and are exemplified by ester residues of methyl, ethyl, n-propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, β-trimehtylsilylethyl, methylthiomethyl, trityl, β,β,β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di tert-butyl-4-hydroxybenzyl, mesylmethyl, benzenesulfonylmethyl, phenylthiomethyl, dimethylaminoethyl, pyridine-1-oxide-2-methyl, methylsulfinylmethyl, bis(p-methoxyphenyl)-methyl, 2-cyano-1,1-dimethylethyl, etc., silyl group, etc.

Examples of the substituents in the amino which may be substituted in the afore-mentioned formulae include amidine, iminomethyl, imino(aryl-substituted)methyl, guanidinocarbonyl, heterocyclic ring* (which may be substituted with the same substituents as those of the afore-mentioned heterocyclic ring), imino (substituted with heterocyclic ring)methyl, alkylcarbonyl, arylcarbonyl, hydroxyalkyl, alkyl, cycloalkyl, alkenyl, cycloalkenyl, aryl, amino, etc.

Examples of groups when the above-mentioned $R^6$ and $R^7$ form a cyclic group include 2,2-dimethyl-5-oxo-4-phenylimidazolidine, etc.

The halogen in the description of the afore-mentioned substituents is exemplified by chlorine, bromine, fluorine and iodine.

Preferable alkyls in the above description of substituents are those having 1 to 10 carbon atoms, more preferably those having 1 to 6 or 1 to 4 carbon atoms, which are exemplified by methyl, ethyl, n-propyl, i-propyl, n-butyl, i-butyl, t-butyl, sec-butyl, n-pentyl, isopentyl, n-hexyl, isohexyl, heptyl, octyl, nonyl, decyl, etc.

Preferable cycloalkyls as the afore-mentioned substituents are those having 3 to 6 carbon atoms, which are exemplified by cyclopropyl, cyclobutyl, cyclopentyl, cyclohexyl, etc.

Preferable examples of the alkoxy as the above-mentioned substituents include those having 1 to 4 carbon atoms, more specifically, methoxy, ethoxy, n-propoxy, i-propoxy, n-butoxy, i-butoxy, t-butoxy, etc.

Examples of the aryl as the above-mentioned substituents include phenyl, naphthyl, etc.

Examples of the heterocyclic ring as the above-mentioned substituents include the same ones as those of the above-mentioned heterocyclic ring.

Preferable examples of the acyl as the above-mentioned substituents include those having 1 to 6 carbon atoms, more preferably 1 to 4 carbon atoms, such as formyl, acetyl, propionyl, butyryl, isobutyryl, valeryl, isovaleryl, pivaloyl, hexanoyl, etc.

Examples of the aralkyl as the above-mentioned substituents include benzyl, phenethyl, phenylpropyl.

Examples of the alkenyl or alkenylene as the above-mentioned substituents include the same ones as those of the above-mentioned alkenyl.

Examples of the amino acid residue as the above-mentioned substituents include the same ones as shown by $R^8$ mentioned above.

Examples of the 5- to 6-membered ring formed together with nitrogen in the amino group as the above-mentioned substituents include piperidine, pyrrolidine, imidazolidine, morpholine, piperazine, etc.

The number of substituents in each of the above-mentioned groups is preferably 1 to 3.

In the above-mentioned organic residues bonded through nitrogen, specific examples of acylamino groups shown by the formula

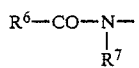

include 3-(2,6-dichlorophenyl)-5-methylisoxazol-4-yl-carbonylamino, 4-ethyl-2,3-dioxo-1-piperazinocarbonylamino, 3-phenyl-5-methylisoxazol-4-yl-carbonylamino, 3-(2-chlorophenyl)-5-methylisoxazol-4-yl-carbonylamino, 3-(2-chloro-6-fluorophenyl)-5-methylisoxazol-4-yl-carbonylamino, nicotinylamino, benzoylamino, 4-bromobenzoylamino, 4-dimethylaminobenzoylamino, 2,6-dimethyoxybenzoylamino, formylamino, acetylamino, propionylamino, butyrylamino, isobutyrylamino, pivaloylamino, valerylamino, isovalerylamino, hexanoylamino, heptanoylamino, octanoylamino, nonanoylamino, decanoylamino, undecanoylamino, lauroyl, myristoyl, palmitoyl, stearoyl, methoxycarbonylamino, benzyloxycarbonylamino, 4-nitrobenzyloxycarbonylamino, 1-amino-cyclohexylcarbonylamino, t-butoxycarbonylamino, 2-aminocyclohexylcarbonylamino, 3-ethoxynaphthoylamino, 2-(2-amino-4-thiazolyl)-2-ethylideneacetylamino, 2-(2-amino-4-thiazolyl)-2-chloromethyleneacetylamino, phthalimido, succinimido, 1,2-cyclohexanedicarboxyimido, 2-(trimethylsilyl)ethoxycarbonylamino, 2,2-dimethyl-5-oxo-4-phenyl-imidazolidine, 4-(carbamoylcarboxymethylene)-1,3-dithiethan-2-yl-carbonylamino, acrylamino, 2-butenoylamino, 3-methylbutenoylamino, cinnamoylamino, 3-carboxybutenylamino, 3-diphenylmethyloxycarbonylbutenylamino, 2,4-pentadienoylamino, 5-carboxy-2,4-pentadienoylamino, 5-methoxycarbonyl-2,4-pentadienoyl, 5-diphenylmethyloxycarbonyl-2,4-pentadienoylamino, 5-benzyloxycarbonyl-2,4-pentadienoylamino, 5-octyloxycarbonyl-2,4-pentadienoylamino, 5-phenyl-2,4-pentadienoylamino, 2,4-hexadienoylamino(sorbylamino), 5-benzyloxycarbonyl-2,4-hexadienoylamino, 5-methyl-2,4-hexadienoylamino, 3-methyl-2,4-hexadienoylamino, 2-methyl-2,4-hexadienoylamino, 4-bromo-2,4-hexadienoylamino, 4-chloro-2,4-hexadienoylamino, 6-methylthio-2,4-hexadienoylamino, 6-methylsulfonyl-2,4-hexadienoylamino, 6-methyl-2,4-heptadienoylamino, 2,4,6-octatrienoylamino, 2-phenyl-2,4-hexadienoylamino, 2-hexene-4-ynoylamino, 2-methyl-2-hexene-4-ynoylamino, 4-methyl-2,4-hexadienoylamino, 4-hexene-2-ynoylamino, 2-cyclohexenylideneacetylamino, β-(2-furyl)acryloylamino, 4-oxo-thiopyranyl-3-carbonylamino, 2-cyclopentenylideneacetylamino, 5-(1,2-dithiolan-3-yl)valerylamino, β-methylthioacryloylamino, β-ethoxyacryloylamino, 2-methyl-2,4-pentadienoylamino, 3,4,5-trimethoxybenzoylamino, phenylacetylamino, diphenylacetylamino, naphthoylamino, 5-trifluoromethyl-2,4-pentadienoylamino, 2-ethyl-2,4-hexadienoylamino, 6-fluoro-2,4-hexadienoylamino, 5-chloro-2,4-pentadienoylamino, 4-pyridylmethylamino, 2-aminomethylbenzylamino, 4-[(3-amino-n-propyl)amino]-n-butylamino, 2-amidinopropylamino, 2-amidinoisopropylamino, 2-amidino-2-phenetylamino, N'-amidinomethyl-N'-methylhydrazino, 2-amidrazonoethylamino, amidinomethoxyamino, 2-methoxyethylamino, 2-guanidinomethylbenzylamino (the above-mentioned alkenoylamino groups include all the E,Z isomers relative to the double bond), etc.

Specific examples of the acylamino group shown by the formula

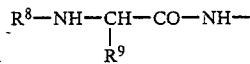

include glycylamino, alanylamino serylamino, glutamylamino, 2-amino-pimelylamino, 2-amino-O-methylpimelylamino, phenylalanylamino, valylamino, leucylamino, arginylamino, lysylamino, benzyl N$^\alpha$-carbobenzoxy-γ-glutamylalanylamino, phenylglycylalanylamino, N-carbobenzoxyalanylamino, N-carbobenzoxyphenylglycylamino, alanylphenylglycylamino, γ-glutamylalanylamino, 2-(4-ethyl-2,3-dioxo-1-piperazinocarboxamido)-2-phenylacetylamino, 2-(4-cyclohexyl-2,3-dioxo-1-piperazinocarboxamido)-2-phenylacetylamino, 2-(4-ethyl-2,3-dioxo-1-piperazinocarboxamido)-2-(4-sulfoxyphenyl)acetylamino, N-(4-ethyl-2,3-dioxo-1-piperazinocarbonyl)alanylamino, N-(4-ethyl-2,3-dioxo-1-piperazinocarbonyl)phenylglycylamino, 2-(2-amino-4-thiazolyl-2-(4-ethyl-2,3-dioxo-1-piparazinocarboxamido)acetylamino, 2-(4-hydroxy-6-methylnicotinamido)-2-phenylacetylamino, 2-(4-hydroxy-6-methylnicotinamido)-2-(4-hydroxyphenyl)acetylamino, 2-{5,8-dihydro-2-(4-formyl-1-piperazinyl)-5-oxopyrido[2,3-d]pyrimidine-6-carboxamido}-2-phenylacetylamino, 2-(3,5-dioxo-1,2,4-triazine-6-carboxamido)-2-(4-hydroxyphenyl)acetylamino, 2-(3-furfurylideneamino-2-oxoimidazolidine-1-carboxamido)-2-phenylacetylamino, 2-(coumarin-3-carboxamido)-2-phenylacetylamino, 2-(4-hydroxy-7-methyl-1,8-naphthyridene-3-carboxamido)-2-phenylacetylamino, 2-(4-hydroxy-7-trifluoromethylquinoline-3-carboxamido)-2-phenylacetylamino, N-[2-(2-amino-4-thiazolyl)acetyl]-phenylglycylamino, 2-(6-bromo-1-ethyl-1,4-dihydro-4-oxothieno[2,3-b]pyridine-3-carboxamido)-2-phenylacetylamino, 2-(4-ethyl-2,3-dioxo-1-piperazinocarboxamido)-2-thienylacetylamino, 2-(4-n-pentyl-2,3-dioxo-1-piperazinocarboxamido)-2-thienylacetylamino, 2-(4-n-octyl-2,3-dioxo-1-piperazinocarboxamido)-2-thienylacetylamino, 2-(4-cyclohexyl-2,3-dioxo-1-piperazinocarboxamido)-2-thienylacetylamino, 2-[4-(2-phenylethyl)-2,3-dioxo-1-piperazinocarboxamido]-2-thienylacetylamino, 2-(3-methylsulfonyl-2-oxoimidazolidine-1-carboxamido)-2-phenylacetylamino, 2-(3-furfurydeneamino-2-oxoimidazolidine-1-carboxamido)-2-(4-hydroxyphenyl)acetylamino, 2-(4-ethyl-2,3-dioxo-1-piperazinocarboxamido)-2-(4-benzyloxyphenyl)acetylamino, 2-(4-ethyl-2,3-dioxo-1-piperazinocarboxamido)-2-(4-methoxyphenyl)acetylamino, 2-(8-hydroxy-1,5-naphthyridine-7-carboxamido)-2-phenylacetylamino, 2-(2-amino-4-thiazolyl)-2-formamidoacetylamino, 2-(2-amino-4-thiazolyl)-2-acetamidoacetylamino, 2-phenyl-2-ureidoacetylamino, 2-phenyl-2-sulfoureidoamino, 2-thienyl-2-ureidoacetylamino, 2-amino-3-sulfamoylpropionylamino, 2-amino-2-(1H-indole-3-yl)acetylamino, 2-amino-2-(3-benzo[b]thienyl)acetylamino, 2-amino-2-(2-naphthyl)acetylamino, phenylglycyl, 2-amino-(4-hydroxyphenyl)acetylamino, 2-amino-2-(1,4-cyclohexadienyl)acetylamino, 2-amino-2-(1-cyclohexenyl)acetylamino, 2-amino-2-(3-chloro-4-hydroxyphenyl)acetylamino, 2-hydroxymethylamino-2-phenylacetylamino, 2-(1-cyclohexenyl)-2-(4-ethyl-2,3-dioxo-1-piperazinocarboxamido)acetylamino, N-[2-(4-ethyl-2,3-dioxo-1-piperazinocarbonyl)]-threonylamino, 2-guanylcarboxamido-2-phenylacetylamino, 2-(4-ethyl-2,3-dioxo-1-piperazinocarboxamido-2-(3,4-dihydroxyphenyl)acetylamino, 2-(4-carboxy-5-imidazolylcarboxamido)-2-phenylacetylamino, 2-amino-2-(3-methylsulfonamidophenyl)acetylamino, 2-amino-3-chloropropionylamino, 2-amino-3-sulfamoylpropionylamino, 2-amino-3-isopropylideneaminooxypropionylamino, 2-amino-3-aminooxypropionylamino, 2-amino-3-carbamoyloxypropionylamino, 2-amino-3-chloroacetamidocarbonyloxypropionylamino, cerylamino, 2-(4-ethyl-2,3-dioxo-1-piperazinocarbonylamino)-3-hdyroxybutyrylamino (in the above specific examples, when the substituents contain asymmetric carbon atoms, all the isomers are also contained in these examples), etc.

Specific examples of the acylamino group shown by the formula R$^{11}$—R$^{12}$—CO—NH— include N-[2-(2-amino-4-thiazolyl)-2-methoxyiminoacetyl]alanylamino, N-[2-(2-amino-4-thiazolyl)-2-methoxyiminoacetyl]-phenylglycylamino, 2-(2-amino-4-thiazolyl)-2-[2-amino-4-thiazolyl)-2-methoxyiminoacetamido]acetylamino, 2-(2-chloroacetamido-4-thiazolyl)-2-methoxyiminoacetylamino, 2-(2-amino-4-thiazolyl)-2-methoxyiminoacetylamino, 2-(2-amino-4-thiazolyl)-2-[(1-methyl-1-carboxyethyl)oxyimino]acetylamino, 2-(2-amino-4-thiazolyl)-2-[(1-methyl-1-methoxycarbonylethyl)oxyimino]acetylamino, 2-(2-amino-4-thiazolyl)-2-carboxylmethyloxyiminoacetylamino, 2-(2-amino-4-thiazolyl)-2-carboxyvinyloxyiminoacetylamino, 2-(2-amino-4-thiazolyl)-2-carboxyethyloxyiminoacetylamino, 2-(2-amino-4-thiazolyl)-2-methoxycarbonylethyloxyiminoacetylamino, 2-(2-amino-5-chloro-4-thiazolyl)-2-methoxyiminoacetylamino, 2-(2-amino-4-thiazolyl)-2-oxyiminoacetylamino, 2-thienyl-2-methoxyiminoacetylamino, 2-furyl-2-methoxyiminoacetylamino, 2-(1,2,4-thiadiazol-3-yl)-2-methoxyiminoacetylamino, 2-(1,2,4-thiadiazol-5-yl)-2-methoxyiminoacetylamino, 2-(1,3,4-thiadiazolyl)-2-methoxyiminoacetylamino, 2-(4-hydroxyphenyl)-2-methoxyiminoacetylamino, 2-phenyl-2-methoxyiminoacetylamino, 2-phenyl-2-oxyiminoacetylamino, 2-[4-(γ-glutamyloxy)phenyl]-2-oxyiminoacetylamino, 2-[4-(3-amino-3-carboxypropoxy)phenyl]-2-oxyiminoacetylamino, 2-thienyl-2-oxyiminoacetylamino, 2-(5-amino-1,2,4-thiadiazol-3-yl)-2-methoxyiminoacetylamino, 2-(5-amino-1,2,4-thiadiazol-3-yl)-2-carboxymethyloxyiminoacetylamino, 2-(5-amino-1,2,4-thiadiazol-3-yl)-2-[(1-methyl-1-carboxyethyl)oxyimino]acetylamino, 2-(2-amino-4-thiazolyl)-2-(1-carboxy-cyclopropyloxyimino)acetylamino, 2-(2-amino-4-thiazolyl)-2-(1-carboxy-cyclobutyloxyimino)acetylamino, 2-(2-amino-4-thiazolyl)-2-(2-imidazolylmethyloxyimino)acetylamino, 2-(2-amino-4-thiazolyl)-2-(2-methyl-4-nitro-1-imidazolylethyloxyimino)acetylamino, 2-(2-amino-4-thiazolyl)-2-(3-pyrazolylmethyloxyimino)acetylamino, 2-(2-amino-4-thiazolyl)-2-(1H-tetrazol-5-yl-methyloxyimino)acetylamino, 2-(2-amino-4-thiazolyl)-2-(2-oxo-3-pyrrolidinyloxyimino)acetylamino, 2-[2-(2-amino-2-carboxyethylthio)]-4-thiazolyl-2-methoxyiminoacetylamino, 2-(2-thioxo-4-thiazolidinyl)-2-methoxyacetylamino (in the above specific examples, when the substituents contain asymmetric carbon atoms, all the isomers derived therefrom are included in these examples), etc.

Specific examples of the acylamino group shown by the formula

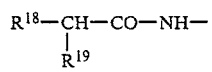
$$R^{18}-CH-CO-NH-$$
$$\phantom{R^{18}-CH}\mid$$
$$\phantom{R^{18}-CH-}R^{19}$$

include 2-phenyl-2-sulfoacetylamino, 2-hydroxy-2-phenylacetylamino, 2-phenyl-2-sulfamoylacetylamino, 2-carboxy-2-phenylacetylamino, 2-(4-hydroxyphenyl)-2-carboxyacetylamino, 2-formyloxy-2-phenylacetylamino, 2-alanyloxy-2-phenylacetylamino, 2-carboxy-2-thienylacetylamino, 2-(2-amino-4-thiazolyl)-2-hydroxyacetylamino, etc.

Specific examples of the acylamino group shown by the formula $R^{20}-R^{21}-CH_2-CO-NH-$ include cyanoacetylamino, phenylacetylamino, phenoxyacetylamino, trifluoromethylthioacetylamino, cyanomethylthioacetylamino, difluoromethylthioacetylamino, 1H-tetrazolyl-1-acetylamino, thienylacetylamino, 2-(2-amino-4-thiazolyl)acetylamino, 4-pyridylthioacetylamino, 2-thienylthioacetylamino, 3,5-dichloro-1,4-dihydro-4-oxopyridine-1-acetylamino, β-carboxyvinylthioacetylamino, 2-(2-aminomethylphenyl)acetylamino, 2-chloroacetylamino, 3-aminopropionylamino, (2-amino-2-carboxy)ethylthioacetylamino, 4-amino-3-hydroxybutyrylamino, 2-carboxyethylthioacetylamino, 2-benzyloxycarbonylaminoacetylamino, β-carbamoyl-β-fluorovinylthioacetylamino, 2-(1-isopropylamino-1-isopropyliminomethylthio)acetylamino, 2-[1-(2-dimethylaminoethyl)-1H-tetrazol-5-yl-thio]acetylamino, 2-(1-methyl-1,3,5-triazol-2-yl)acetylamino, 2-(4-cyano-3-hydroxy-5-isothiazolylthio)acetylamino, hydrazinoacetylamino, 1-methylhydrazinoacetylamino, 2-methylhydrazinoacetyl, 2,2-dimethylhydrazinoacetyl, etc.

Specific examples of the group shown by the formula $R^{22}-CO-CO-NH-$ include methoxalylamino, ethoxalylamino, phenoxalylamino, benzyloxalylamino, pyruvoylamino, ethyloxalylamino, oxamoylamino, benzylaminooxalylamino, thienyloxalylamino, 2-amino-4-thiazolyloxalylamino, ethylaminoxalylamino, etc.

Specific examples of the group shown by the formula

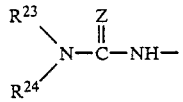
$$R^{23}\phantom{N}\overset{Z}{\underset{\|}{\phantom{C}}}$$
$$\phantom{RR}N-C-NH-$$
$$R^{24}$$

include guanidino, carbamoylamino, methylaminocarbonylamino, ethylaminocarbonylamino, t-butylaminocarbonylamino, isobutylaminocarbonylamino, dimethylaminocarbonylamino, 2-methylphenylaminocarbonylamino, phenylaminocarbonylamino, 3-chlorophenylaminocarbonylamino, 4-nitrophenylaminocarbonylamino, 4-bromophenylaminocarbonylamino, thiocarbamoylamino, methylaminothiocarbonylamino, ethylaminothiocarbonylamino, phenylaminothiocarbonylamino, dimethylaminocarbonylamino, 3-fluorophenylaminocarbonylamino, etc.

In the above-mentioned amino substituted through carbon, specific examples of the group shown by the formula $R^{25}-NH-$ include methylamino, ethylamino, allylamino, cyclohexylamino, cyclohexylmethylamino, benzylamino, 4-chlorobenzylamino, 2-acetyl-1-methylvinylamino, iminomethylamino, 3,4,5-trimethylbenzylamino, etc.

Specific examples of the group shown by the formula

$$R^{26}\phantom{N}$$
$$\phantom{RR}N-$$
$$R^{27}$$

include dimethylamino, diethylamino, dipropylamino, dibenzylamino, dicyclohexylamino, N-benzyl-N-methylamino, diallylamino, N-phenyl-N-methylamino, pyrrolidinyl, piperidinyl, piperazinyl, morpholinyl, etc.

Specific examples of the group shown by the formula

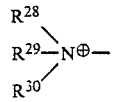
$$R^{28}\phantom{N}$$
$$R^{29}-N^{\oplus}-$$
$$R^{30}$$

include trimethylammonium, triethylammonium, tribenzylammonium, benzyldimethylammonium, methylpyrrolidinium, methylpiperidinium, etc.

Specific examples of the alkenylamino group shown by the formula

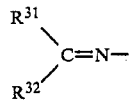
$$R^{31}\phantom{N}$$
$$\phantom{RR}C=N-$$
$$R^{32}$$

include dimethylaminomethyleneamino, 1-dimethylaminoethylideneamino, hexahydro-1H-azepin-1-ylmethyleneamino, 1-(N-benzyl-N-methylamino)-ethylideneamino, 4-dimethylaminobenzylideneamino, (P-nitro)-benzylideneamino, benzylideneamino, etc.

Specific examples of the above-mentioned thioamino group shown by the formula $R^{33}-SO_n-NH-$ include benzenesulfonylamino, 4-methylbenzenesulfonylamino, 4-methoxybenzenesulfonylamino, 2,4,6-trimethylbenzenesulfonylamino, benzylsulfonylamino, 4-methylbenzylsulfonylamino, trifluoromethylsulfonylamino, phenacylsulfonylamino, methylsulfonylamino, ethylsulfonylamino, 4-fluorobenzenesulfonylamino, benzenesulfinylamino, 2-nitrobenzenesulfinylamino, 2,4-dimethylbenzenesulfinylamino, 4-chlorobenzenesulfinylamino, 4-methoxybenzenesulfinylamino, phenylthioamino, 2,4-dinitrophenylthioamino, triphenylmethylthioamino, 2-nitro-4-methoxyphenylthioamino, etc.

Specific examples of the above-mentioned phosphorylamino group shown by the formula

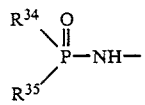

include dimethylphorphorylamino, diethylphosphorylamino, diphenylphosphorylamino, dibenzylphosphorylamino, di-4-chlorophenylphosphorylamino, etc.

It is more preferable that $R^1$ is a $C_{5-10}$ dienoylamino which may be substituted with a $C_{1-5}$ alkyl or a halogen, such as 2,4-pentadienoyl-amino, 2,4-hexadienoylamino, 2-methyl-2,4-hexadienoylamino, 2-methyl-2,4-pentadienoylamino, 6-fluoro-2,4-hexadienoylamino, 5-chloro-2,4-pentadienoylamino, etc.

It is more preferable that $R^4$ is an amino which may be substituted with a $C_{1-5}$ alkyl, such as amino, methylamino, ethylamino, etc., or an amino which is substituted with an amino acid having 2 to 10 carbon atoms, such as glycylamino, serylamino, alanylamino, 2-amino-0-methylpimelylamino, etc.

Specific examples of the alkyl group which may be substituted, shown by $R^2$ or $R^{2'}$, include methyl, ethyl, propyl, isopropyl, butyl, isobutyl, cyclohexylmethyl, benzyl, p-hydroxybenzyl, hydroxymethyl, mercaptomethyl, 1-hydroxyethyl, 2-methylthioethyl, carboxymethyl, 2-carboxyethyl, 3-guanidinopropyl, 4-aminobutyl, 4-imidazolylmethyl, etc.

The amino, hydroxy, mercapto or carboxyl group existing in the above groups may be substituted by the known method in the field of the peptide chemisty.

Specific examples of the cyclic ring which $R^2$ or $R^{2'}$ forms with the nitrogen atom of the adjacent $R^1$, $R^{1'}$ or $R^{1''}$, include pyrrolidine, pyrrolidinone, etc.

Still, it is more preferable that $R^2$ is hydrogen or a $C_{1-6}$ alkyl such as methyl, isopropyl, isobutyl, etc.

Specific examples of the amino group which may be substituted, of the formula $R^{36}-NH-$, as shown by $R^5$ or $R^{5'}$, include, besides those mentioned above as specific examples of the groups shown by $R^{25}-NH-$, 2-aminoethylamino, 2-aminopropylamino, 3-aminopropylamino, 4-aminobutylamino, 2-morpholinoethylamino, 2-(N,N-dimethylamino)ethylamino, 2-N,N,N-trimethylammoniumethylamino, 2-amino-2-carboxyethylamino, 3-amino-3-carboxypropylamino, 2-amino-1-carboxyethylamino, 2-hydroxyethylamino, 2-mercaptoethylamino, carboxymethylamino, 2-carbamoylethylamino, 2-cyanoethylamino, 1,4-dicarboxybutylamino, 1,4-dimethoxycarbonylbutylamino, amidinomethylamino, 2-amidinoethylamino, 3-piperidino-3-iminopropylamino, 3-morpholino-3-iminopropylamino, 2-(N-methyl)amidinoethylamino, 2-(N-methyl-N'-methyl)amidinoethylamino, 2-(N,N-dimethyl)amidinoethylamino, 2-amidinoethyleneamino, 2-diaminomethyleneaminoethylamino, 2-aminomethyleneaminoethylamino, 2-(2-imidazolidino)ethylamino, 2-(4-imidazolyl)ethylamino, 2-(2-imidazolyl)ethylamino, 2-(3-triazolyl)ethylamino, 2-(2-thiazolyl)ethylamino, 1-phosphorylethylamino, 1-(1-phosphorylethylaminocarbonyl)ethylamino, phenylamino, 4-dimethylaminophenylamino, 4-amidinophenylamino, 2-imidazolylamino, 2-pyridylamino, 3-pyridylamino, 4-pyridylamino, 2-pyrimidinylamino, 3-pyridazinylamino, 2-thiazolylamino, hydroxyamino, methoxyamino, ethoxyamino, benzyloxyamino, allyloxyamino, hydrazino, $N^2$-carboxymethyl-$N^2$-methylhydrazino, $N^2,N^2$-dimethylhydrazino, morpholinoamino, piperidinoamino, etc.

Specific examples of the groups representable by the formula

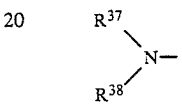

include the same groups as those exemplified as ones representable by the formula

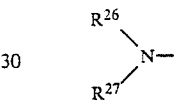

or groups exemplified as those representable by the above-mentioned formula $R^{36}NH-$, in which hydrogen of the amino group is substituted with methyl, ethyl, benzyl, etc.

Specific examples of the hydroxyl group which may be substituted, shown by $R^5$ or $R^{5'}$, include methoxy, ethoxy, allyloxy, benzyloxy, 2-aminoethoxy, 2-aminopropoxy, 3-aminopropoxy, 4-aminobutoxy, 2-(N,N-dimethylamino)ethoxy, 2-N,N,N-trimethylammoniumethoxy, 2-amino-2-carboxyethoxy, 3-amino-3-carboxypropoxy, 2-amino-1-carboxyethoxy, 2-hydroxyethoxy, 2-mercaptoethoxy, 2-carbamoylethoxy, 2-cyanoethoxy, 1,4-dicarboxybutoxy, 1,4-dimethoxycarbonylbutoxy, amidinomethoxy, 2-amidinoethoxy, 3-piperidino-3-iminopropoxy, 3-morpholino-3-iminopropoxy, 2-(N-methyl)amidinoethoxy, 2-(N-methyl-N'-methyl)amidinoethoxy, 2-(N,N-dimethyl)amidinoethoxy, 2-amidinoethyleneoxy, 2-diaminomethyleneaminoethoxy, 2-aminomethyleneaminoethoxy, 2-(2-imidazolidino)ethoxy, 2-(4-imidazolyl)ethoxy, 2-(2-imidazolyl)ethoxy, 2-(3-triazolyl)ethoxy, 2-(2-thiazolyl)ethoxy, 1-phosphorylethoxy, 1-(1-phosphorylethylaminocarbonyl)ethoxy, phenoxy, 4-dimethylaminophenoxy, 4-amidinophenoxy, 4-guanidinophenoxy, 6-amidino-2-naphthyloxy, etc.

Specific examples of the substituent in the substituted hydroxyl group shown by $R^{5''}$ include the above-mentioned protecting groups of the carboxy groups.

Specific examples of the alkyl which may be substituted, shown by A, include methyl, ethyl, propyl, isopropyl, butyl, isobutyl, t-butyl, benzyl, etc.

Still, it is more preferable that $R^5$ is an amidino-$C_{1-5}$ alkylamino which may be substituted by a $C_{1-5}$ alkyl, such as 2-amidinoethylamino, 2-amidinopropylamino, 2-(N-methyl)amidinoethylamino, etc.

A compound representable by the above general formula, in case of its containing an acid group such as carboxylic group, phosphoric acid, etc., may form a salt with an inorganic base such as sodium, potassium, lithium, calcium, magnesium, ammonium, etc. or an organic base such as pyridine, collidine, triethylamine, triethanolamine, etc. Further, a compound representable by the above general formula, in case of its containing a basic group such as amino group, may form a salt with an organic acid such as acetic acid, tartaric acid, methanesulfonic acid, etc., with an inorganic acid such as hydrochloric acid, hydrobromic acid, sulfuric acid, phosphoric acid, etc. or with an acidic amino acid such as aspartic acid, glutamic acid, etc.

Additionally stating, a compound (I), in which $R^3$ is hydrogen and $R^5$ is hydroxyl group, may, sometimes, form a lactone ring as shown below.

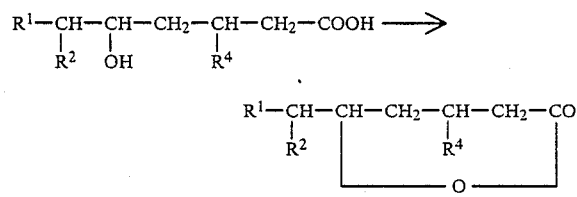

Compounds having a lactone ring as above are all included in the concept of this invention.

Next, the production method of the compound of this invention is described below.

The compound (III-1), which is a compound (III) wherein $R^1$ is an organic residue bonded to the carbon to which it is attached through nitrogen, can be obtained by allowing the compound (II-1), which is a compound (II) wherein $R^{1'}$ is amino group, to react with a compound capable of forming an organic residue bonded to the carbon to which it is attached through nitrogen. The said reaction is exemplified by acylation, carbamoylation (thiocarbamoylation), alkylation, alkenylation, thionation, phosphorylation. Descriptions on the respective reactions are given below.

Acylation

The acylation of amino group can be achieved by allowing the starting compound to react with an acylating agent containing an acyl group in the group $R^{1'}$, for example a reactive derivative of carboxylic acid, in a solvent. As the reactive derivatives of carboxylic acid, use is made of, for example, acid halides, acid anhydrides, amido compounds, active esters, active thioesters, etc. These reactive derivatives are specifically described in the following.

(1) Acid halides:

Acid halides usable herein include, for example, acid chlorides and acid bromides, etc.

(2) Acid anhydrides:

As acid anhydrides, use is made of, for example, monoalkyl carbonic acid mixed anhydrides, mixed acid anhydrides composed of aliphatic carboxylic acid (e.g. acetic acid, pivalic acid, valeric acid, isovaleric acid, trichloroacetic acid, etc.), mixed acid anhydrides composed of aromatic carboxylic acid (e.g. benzoic acid, etc.), symmetrictype acid anhydrides. etc.

(3) Amido compounds:

As amido compounds, use is made of, for example, compounds having an acyl group bonded to the nitrogen in the ring, such as pyrazole, imidazole, 4-substituted imidazole, dimethylpyrazole, benzotriazole, etc.

(4) Active esters:

As active esters, use is made of, for example, esters such as methyl esters, ethyl esters, methoxymethyl esters, propargyl esters, 4-nitrophenyl esters, 2,4-dinitrophenyl esters, trichlorophenyl esters, pentachlorophenyl esters, mesylphenyl esters, etc., as well as esters formed with 1-hydroxy-1H-2-pyridone, N-hydroxysuccinimide, N-hydroxyphthalimide, N-hydroxybenzotriazole, etc.

(5) Active thio esters:

As active thio esters, use is made of, for example, thioesters formed with a heterocyclic thiol such as 2-pyridylthiol, 2-benzthiazolylthiol, etc.

Various reactive derivatives as described above can be properly selected depending on the type of the carboxylic acid.

This reaction may be, in some cases, carried out in the presence of a base. Bases which can be used for this purpose include tertiary amines such as aliphatic tertiary amines (e.g. trimethylamine, triethylamine, tripropylamine, tri-n-butylamine, etc.), N-methylpiperidine, N-methylpyrrolidine, cyclohexyldimethylamine, N-methylmorpholine, etc., dialkylamine such as di-n-butylamine, diisobutylamine, dicyclohexylamine, etc., aromatic amines such as pyridine, lutidine, γ-collidine, etc., hydroxides or carbonates of an alkali metal such as lithium, sodium, potassium, etc., or an alkaline earth metal such as calcium, magnesium etc.

In this method, the reactive derivative of carboxylic acid is employed usually in about equivalent relative to the compound (II-1), but it may also be used in excess, as long as it does not interfere with the reaction. When a base is employed, the amount of the base is usually in an amount of about 1 to 30 equivalents, preferably about 1 to 10 equivalents relative to the compound (II-1), though it varies with the types of the starting compound (II-1), the kinds of the reactive derivatives of carboxylic acid and other reaction conditions then employed. This reaction is usually carried out in a solvent. As the solvent, use is made of, for example, ethers such as dioxane, tetrahydrofuran, diethylether, diisopropylether, propylene oxide, butylene oxide, etc., esters such as ethyl acetate, ethyl formate, etc., halogenated hydrocarbons such as chloroform, dichloromethane, 1,2-dichloroethane, 1,1,1-trichloroethane, etc., hydrocarbons such as benzene, toluene, n-hexane, etc., amides such as N,N-dimethylformamide, N,N-dimethylacetamide, etc., nitriles such as acetonitrile, etc., etc., and these organic solvents are used singly or in combination.

Of the above-mentioned bases, liquid ones can also be used for the dual purposes of base and solvent. Reaction temperature is not specifically limited, as long as the reaction proceeds, but the reaction is carried out usually within the range of from about −50° C. to 150° C., preferably from about −30° C. to 80° C. The reaction usually completes within several ten minutes to several ten hours, though the reaction time varies with the types of the stating compound, the base, the reaction temperature and the solvent then employed, but, in some cases, it requires several ten days.

Carbamoylation (thiocarbamoylation)

The conversion of the amino group to a ureido or thioureido group can be achieved by allowing the starting compound to react with a substituted isocyanate or a substituted isothiocyanate containing a group representable by the above-mentioned formula

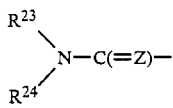

wherein $R^{23}$ and $R^{24}$ are of the same meaning as defined above, in the presence of a solvent. As the substituted isocyanate, use is made of, for example, methyl isocyanate, ethyl isocyanate, phenyl isocyanate, p-bromophenyl isocyanate, etc., and, as the substituted isothiocyanate, use is made of, for example, methyl isothiocyanate, phenyl isothiocyanate, etc. In this reaction, the substituted isocyanate or substituted isothiocyanate is usually employed in an equivalent to Compound (II-1), but it may be used in an excess amount, as long as it does not interfere with the reaction. As the solvent, use is made of, for example, tetrahydrofuran, diethyl ether, ethyl acetate, chloroform, dichloromethane, toluene, etc. The reaction temperature ranges from about $-20°$ C. to about $50°$ C., and the reaction time is usually within a range of from about 10 minutes to about 5 hours.

Alkylation

The reaction for allowing a group bonded through carbon to be bonded to the amino group of Compound (II-1) is described hereafter as alkylation.

The alkylation of Compound (II-1) can be conducted by allowing Compound (II-1) to react with an alkylating agent containing a group bonded to the nitrogen of the group $R^{1'}$ through carbon. Examples of the alkylating agent include halogenated alkyl compounds such as propyl chloride, butyl chloride, benzyl chloride, butyl bromide, benzyl bromide, allyl bromide, methyl iodide, ethyl iodide, propyl iodide, etc., dialkylsulfates such as dimethyl sulfate, diethyl sulfate, etc., substituted sulfonic acid esters such as methyl mesylate, ethyl mesylate, methyl tosylate, ethyl tosylate, etc., dihalogenated alkyl compounds (e.g. 1,5-dichloropentane, 1,4-dichlorobutane, etc.), etc. This reaction is usually conducted in a solvent such as water, methanol, ethanol, benzyl alcohol, benzene, N,N-dimethylformamide, tetrahydrofuran, acetonitrile, etc. The reaction temperature ranges from about 20° C. to 200° C. and the reaction time ranges from about 30 minutes to 50 hours. This reaction, by changing reaction conditions such as the molar ratio of the alkylating agent to Compound (II-1), permits the selective production of a secondary amine compound, a tertiary amine compound or a quaternary amine compound. Introduction of a different substituent into the relevant nitrogen is also possible by conducting the reaction stepwise. The reaction of introducing a group bonded through carbon, other than alkyl, can also be carried out in the same manner as described above.

The said alkylation can also be achieved by allowing Compound (II-1) to be bonded to a carbonyl compound in the presence of a reducing agent. As the reducing agent, use is made of lithium aluminium hydride, sodium cyanoborohydride, sodium borohydride, sodium, sodium amalgam and combinations of zinc and acid. This reaction can also be achieved by catalytic reduction using, for example, palladium, platinum, rhodium or the like as the catalyst.

The reaction of converting the amino group to a compound represented by the formula $R^{25}$—NH—(an imino-substituted alkylamino group, alkylimino-substituted alkylamino group or substituted guanidino group):

The reaction of converting the amino group to an imino-substituted alkylamino group or alkylimino-substituted alkylamino group can be achieved by allowing the starting compound to react with, for example, an imide ester in a solvent such as dioxane, tetrahydrofuran, N,N-dimethylformamide, chloroform, acetone, acetonitrile, water, etc. As proper imide esters, use is made of, for example, methyl formimidate, ethyl formimidate, benzyl formimidate, methyl acetoimidate, methylphenyl acetoimidate, ethyl N-methylformimidate, methyl N-ethylformimidate, methyl N-isopropylformimidate, etc. The reaction temperature ranges from about 0° C. to about 25° C., and the reaction time usually ranges from one hour to 6 hours.

The reaction of converting the amino group to a guanidino group can be achieved by allowing the starting compound to react with, for example, O-alkyl or O-aryl pseudourea or S-alkyl or S-aryl pseudothio urea in a solvent such as water, N,N-dimethylformamide, hexamethyelnephosphoramide, etc. As the above-mentioned pseudourea, use is made of O-methyl pseudourea, S-methyl pseudourea, O-2,4-dichlorophenyl pseudourea, O-N,N-trimethyl pseudourea, etc., and as the above-mentioned pseudothiourea, use is made of S-p-nitrophenyl pseudothiourea, etc. The reaction temperature ranges from about 0° C. to about 40° C., and the reaction time ranges usually from about one hour to 24 hours.

Alkenylation (shiff base formation)

The alkenylation (shiff base formation) of Compound (II-1) can be achieved by subjecting Compound (II-1) to dehydrative condensation with a carbonyl compound. This reaction proceeds even in the absence of solvent, but it can also be carried out in a solvent. As the case may be, an acid or a base is used as a catalyst. The desired compound can also be produced by subjecting Compound (II-1) and a carbonyl compound to heating under reflux in the presence of a dehydrating agent or using a dehydrating apparatus such as Dean and Stark apparatus. As the solvent which can be used for this reaction, use is made of, for example, benzene, toluene, dichloromethane, ethanol, etc. The reaction temperature ranges from about 0° C. to about 200° C., and the reaction time ranges from about one hour to about 20 hours. Acids which can be used as catalysts include, for example, benzensulfonic acid, methanesulfonic acid, sulfuric acid, boron trifluoride, zinc chloride, etc., and bases which can be used as catalysts include, for example, potassium hydroxide, sodium carbonate, etc. Substances which can be used as dehydrating agents for this reaction include molecular sieves, silica gel, anhydrous magnesium sulfate, anhydrous sodium sulfate, etc.

Thionation

The thionation of Compound (II-1) is normally achieved by allowing Compound (II-1) to react with a thiohalide containing a group represented by the formula $R^{33}$—SOn— wherein $R^{33}$ and n are of the same meaning as defined above, (e.g. sulfonyl halide, sulfinyl halide, sulfenyl halide) in a solvent in the presence of a base. As the solvent, use is made of, for example, water, acetone, dioxane, N,N-dimethylformamide, benzene, tetrahydrofuran, dichloromethane or a mixture of them, etc. As the base, use is made of, for example, organic bases such as pyridine, picoline, triethylamine, diisopropylethylamine, N-methylmorpholine, etc. or inorganic bases such as sodium hydroxide, potassium hydroxide, sodium carbonate, sodium hydrogencarbonate, potassium carbonate, etc. In this reaction, the thiohalide is usually employed in an amount of about 1 equivalent relative to Compound (II-1) and the base is usually employed in an amount of about 1 to 10 equivalents relative to Compound (II-1). The reaction temperature ranges from about −20° C. to 80° C., and the reaction time ranges from 15 minutes to 10 hours.

This reaction can also be conducted using, in place of the thiohalide mentioned above, a thio acid anhydride (e.g. toluenesulfonic anhydride, trifluoromethanesulfonic anhydride, etc.). This reaction can also be achieved by allowing the starting compound to react with a thionating agent such as N-sulfonyl-N-methylpyrrolidinium, N-sulfonylimidaolide, N-sulfonyl-1H-1,2,4-triazolide, etc.

Phosphorylation

The phosphorylation of Compound (II-1) can normally be achieved by allowing Compound (II-1) to react with about equivalent phosphoryl chloride containing a group represented by the formula

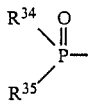

wherein $R^{34}$ and $R^{35}$ are of the same meaning as defined above, (e.g. dimethylphosphoryl chloride, diethylphosphoryl chloride, diphenylphosphoryl chloride, dibenzylphosphoryl chloride, etc.) in a solvent in the presence of about an equal to excess amount of a base. As the base, use is made of an organic base such as pyridine, picoline, triethylamine, N-methylmorpholine, etc., an inorganic base such as sodium hydroxide, potassium hydroxide, sodium hydrogencarbonate, sodium carbonate, etc. As the solvent, use is made of, for example, water, acetone, acetonitrile, dioxane, N,N-dimethylformamide, tetrahydrofuran, dichlormethane, etc., or their mixtures. The reaction temperature ranges from about −20° C. to 80° C., and the reaction time ranges from 15 minutes to 15 hours.

Compound (II-2), which is Compound (II) wherein $R^{1'}$ is an organic residue bonded to the carbon to which it is attached through nitrogen and $R^{4'}$ is amino group, can be converted to Compound (III-2), which is Compound (III) wherein $R^{4'}$ is an organic residue bonded to the carbon through nitrogen, by subjecting the former to reactions, for example, acylation, carbamoylation(-thiocarbamoylation), alkylation, alkenylation, thionation, phosphorylation, etc. The conversion reaction can be carried out in the same manner as that for converting Compound (II-1) to Compound (III-1).

Conversion of Compound (II-3), which is a compound (II) wherein $R^{1'}$ and $R^{4'}$ are organic residues bonded to the carbon to which it is attached through nitrogen and $R^{5'}$ is hydroxyl group, to Compound (III-3), which is a compound (III) wherein $R^5$ is an amino group which may be substituted, by allowing the former to react with an amino group which may be substituted, is carried out by allowing (II-3) or its reactive derivative at its carboxyl group[acid anhydride of the starting compound is synthesized from, for example, acid chloride (such as ethyl chlorocarbonate, benzyl chlorocarbonate), or acid anhydride (acetic anhydride, anhydrous trifluoroacetic acid, etc.] to react with amines containing the above-mentioned amino group which may be substituted. Alternatively, the above conversion can be achieved by allowing (II-3) to react with the above-mentioned amines in the presence of a dehydrative condensing agent such as dicyclohexylcarbodiimide, N-3-dimethylaminopropyl-N-ethylcarbodiimide, N-ethoxycarbonyl-2-ethoxy-1,2-dihydroquinoline, etc. The above-mentioned reaction is conducted by allowing the reaction to proceed in a solvent (e.g. dichloromethane, tetrahydrofuran, N,N-dimethylformamide, etc.) at temperatures ranging from about 0° C. to the refluxing temperature for about 15 minutes to 16 hours, and the amount of amines is usually in excess relative to (II-3), i.e. about 1 to 5 equivalents. For carrying out the above-mentioned reaction, $R^{1'}$ and $R^{4'}$ of Compound (II-3) are preferably organic residues bonded to the carbons through a protected nitrogen, and, as protecting groups for this purpose, such groups mentioned in respect of the above-mentioned $R^{15}$ are sutiably employed. Further, for this reaction, $R^{3'}$ is in some cases desirably a hydroxyl-protecting groups as mentioned above. When $R^{3'}$ of Compound (II-3) is hydrogen, (III-2) can be obtained by converting (II-3) to Compound (VII) represented by the formula

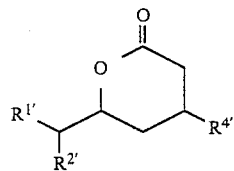 (VII)

wherein $R^{1'}$, $R^{2'}$, $R^{4'}$ are of the same meaning as defined above followed by allowing (VII) to react with amines. The conversion of (II-3) to (IV) can be conducted by allowing (II-3) to react with acid chloride, acid anhdyride or a dehydrative condensing agent as mentioned above. The reaction is conducted in a solvent such as dichloromethane, tetrahydrofuran, N,N-dimethylformamide, etc. at temepratures ranging from about 0° C. to the refluxing temperature for about 15 minutes to 16 hours. The reaction of (VII) with amines is conducted in a solvent such as methanol, ethanol, dichloromethane, chloroform or N,N-dimethylformamide at a molar ratio of (VII) to amines being 1 to excess (about 1 to 5 mol.) for about 15 minutes to 16 hours.

The reaction of Compound (II-3) with alcohols to obtain Compound (III-4) of which $R^5$ is the substituted hydroxyl is conducted using the corresponding alcohols instead of the amines as the same manner as the reaction of Compound (II-3) with the amines to obtain Compound (III-3).

Compound (III-5), which is a compound (III) wherein $R^{3'}$ is a protecting group, can be obtained by subjecting Compound (IV) to a reaction of introducing the protecting group. In this reaction, (IV) is allowed to react with an alkylating agent in a solvent in the presence of a base. As the alkylating agent, use is made of, for example, methyl iodide, dimethyl sulfate, ethyl iodide, allyl bromide, benzyl bromide, etc. As the base, use is made of, for example, an alkali metal such as lithium, sodium, potassium, cesium, etc., an alkaline earth metal such as magnesium, calcium, etc., or their hydrides, hydroxides, carbonates, or alcoholates. As the solvent, use is made of, for example, conventional ones such as dichloromethane, chloroform, tetrahydrofuran, dioxane, benzene, toluene, acetonitrile, N,N-dimethylacetamide, N,N-dimethylformamide, etc. The reaction temperature usually ranges from about −20° C. to 100° C., and the reaction time usually ranges from about 5 minutes to 30 hours. In this reaction, the alkylating agent and the base are used in excess amount relative to Compound (II-4), usually 2–10 equivalents. And, in this reaction, when organic residues bonded through nitrogen shown by $R^{1'}$ and $R^{4'}$ of (II-4) have liberated —NH— group, the hydrogen atom of the group may in some cases, be substituted with an alkyl group.

Thus-obtained Compounds (III-1), (III-2), (III-3), (III-4) and (III-5) are included in the object compound (III), and, when they have protecting groups, those protecting groups can be removed upon necessity. The deprotection reaction can be carried out according to the conventional manner, and it can be achieved using a suitable method selected from routine methods such as those using an acid, those using a base, those using hydrazine, those by reduction, etc., according to the type of the protective group or with the other conditions. In the case of the method using acid, examples of the acid include inorganic acids such as hydrochloric acid, sulfuric acid, phosphoric acid, etc., organic acids such as formic acid, acetic acid, trifluoroacetic acid, propionic acid, etc. and, besides, acidic ion-exchange resin, etc., while their selection varies with the type of the protective group and with the other conditions. In the case of the methods using a base, bases which can be used include inorganic bases such as hydroxides and carbonates of alkali metals (e.g. sodium potassium, etc.) or alkaline earth metals (e.g. calcium, magnesium etc.) and organic bases such as metal alkoxides, organic amines and quaternary ammonium salts and, besides, basic ion-exchange resin, etc., while their selection varies with the type of the protective group and the other factors. When a solvent is used in the case of the above-mentioned methods using an acid or a base, hydrophlic organic solvents, water or mixed solvents are frequently employed.

In the case of the methods by reduction, procedures which can be employed include the procedure using either a metal such as tin or zinc or a metal compound such as chrominum dichloride, chromium acetate, etc. in combination with an organic or inorganic acid such as acetic acid, propionic acid or hydrochloric acid and the procedure of reduction in the presence of a metal catalyst for catalytic reduction, while their selection varies with the type of the protective group and the other factors. Examples of the catalyst for catalytic reduction include platinum catalysts such as platinum wire, platinum sponge, platinum black, platinum oxide, colloidal platinum, etc., palladium catalysts such as palladium sponge, palladium black, palladium oxide, palladium barium sulfate, palladium barium carbonate, palladium carbon, palladium silica gel, colloidal palladium, etc., reduced nickel, nickel oxide, Raney nickel, Urushibara nickel, etc. In the case of the reduction methods using a metal and an acid in combination, metals which can be used include iron, chromium, etc. and acids which can be used include inorganic acids such as hydrochloric acid etc., organic acids such as formic acid, acetic acid, propionic acid, etc. The method by reduction is usually carried out in a solvent, for example, in catalytic reduction, alcohols such as methanol, ethanol, propyl alcohol, isopropyl alcohol, etc. and ethyl acetate, etc. are frequently employed. In the procedure of reduction using a metal and an acid in combination, water, acetone etc. are frequently used, and when the acid is in a liquid state, the acid itself can be used as a solvent.

Reaction temperatures in the respective methods of using an acid or a base or by reduction range usually from those under cooling to those under warming.

Elimination of the protective group from each group of the compound obtained can be conducted in the same manner as described above.

Next, some compounds of this invention are described in detail.

Protective groups for the amino group represented by $R^c$ in these formulas include aromatic acyl groups such as phthaloyl, benzoyl, p-nitrobenzoyl, p-tert-butylbenzoyl, p-tert-butylbenzenesulfonyl, benzenesulfonyl and toluenesulfonyl; aliphatic acyl groups such as formyl, acetyl, propionyl, monochloroacetyl, dichloroacetyl, trichloroacetyl, methanesulfonyl, ethanesulfonyl, trifluoroacetyl, maleyl and succinyl; esterified carbonyl groups such as methoxycarbonyl, ethoxycarbonyl, t-butoxycarbonyl, isopropoxycarbonyl, 2-cyanoethoxycarbonyl, $\beta,\beta,\beta$-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl and phenyloxycarbonyl; methylene groups such as (hexahydro-1H-azepin-1-yl)methylene; sulfonyl groups such as 2-amino-2-carboxyethylsulfonyl; and other groups other than acyl groups, such as trityl, 2-nitrophenylthio, benzylidene, 4-nitrobenzylidene, di- or trialkylsilyl, benzyl and p-nitrobenzyl. Although there are no special limitations in choosing the above mentioned protective groups, it is particularly preferable that p-nitrobenzoyl, acetyl, t-butoxycarbonyl, benzyloxycarbonyl, etc. is used.

Compounds having a hydroxyl group for $R^d$ in the previous formulas sometimes form a lactone ring as follows:

$$R^a-NH-CH-CH-CH_2-CH-CH_2-COOH \longrightarrow$$
$$\phantom{R^a-NH-}\;\;|\;\;\;\;\;|\;\;\;\;\;\;\;\;\;\;\;|$$
$$\phantom{R^a-NH-}R^b\;\;OH\;\;\;\;\;\;R^c$$

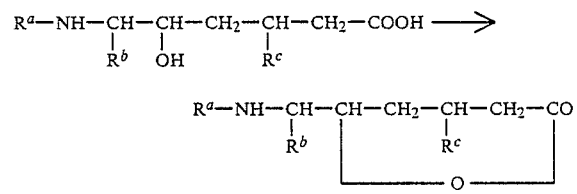

Compounds having a lactone ring as shown above are involved in the present invention.

The methods for preparing compounds involved in the present invention are hereinafter described.

The conventional acid hydrolysis method is used to eliminate the 2-amidino-ethylamino group from Compound (B) or its salts. That is, Compound (B) is dissolved in 2N hydrochloric acid to a concentration of 5 to 20 mg/ml and then refluxed for 5 minutes to 1 hour, preferably 15 to 40 minutes, while being heated (outside temperature: approx. 120° C.) (Method I).

After the neutralization of the reaction liquid, the reaction product is purified by column chromatography using Diaion HP-20 (Mitsubishi Kasei) etc. as the packing. When the reflux is continued for 2 to 10 hours, preferably 4 to 8 hours, under the same conditions, the sorbyl or hexanoyl group is also eliminated from Compound (B), yielding a compound having no groups of 2-amidino-ethylamino, sorbyl and hexanoyl (Method II). The reaction product is purified by column chromatography using Dowex 50W (Dow Chemical, U.S.A.) etc. as the column.

When Compound (D) or its salt is subjected to catalytic reduction, a compound having a sorbyl group whose 2 double bonds are saturated is obtained. This catalytic reduction is carried out using conventional reactions. That is, Compound (D) is dissolved in a polar solvent such as water or acetic acid; a catalyst for catalytic reduction such as platinum oxide, palladium-carbon, or Raney nickel is added, after which the solution is stirred in a hydrogen gas flow. The reaction takes several hours to complete at normal temperature under normal pressure; it can be carried out under increased pressure to decrease reaction time.

It is recommended that both Compound (D) and compounds obtained by either the acid hydrolysis method (Method I) or the catalytic reduction method is treated so that their amino groups are protected by a protective group before being used for the next reaction. A common method of introducing a protective group to an amino group is described in detail by T. W. Greene in "Protective Groups in Organic Synthesis", p.218 (1981), John Wiley & Sons. Typical cases of the introduction of an N-protective group are as follows: In the case of t-butoxycarbonylation, the sample is dissolved in a polar solvent such as a mixture of 50% dioxane and water and approx. 1~4 equivalent triethylamine and approx. 1~3 equivalent 2-(t-butoxycarbonyloxyimino)-2-phenylacetonitrile (hereinafter abbreviated to BOC—ON in some cases) are added; the reaction is carried out by stirring the solution at normal temperature for 0.5 to 8 hours, preferably 3 to 6 hours. In the case of either benzoylation or benzyloxycarbonylation, the sample is dissolved in dilute sodium bicarbonate water and approx. 1~3 equivalent benzoyl chloride or benzyloxycarbonyl chloride is added; the reaction is carried out at normal temperature for some 2 to 8 hours while stirring the solution.

Either Compound (E) representable by the formula (D) wherein $R^c$ is amino group and $R^d$ is 2-amidino-ethylamino, or the catalytic reduction product from the acid hydrolysate (by Method I) described above, is treated so that the fatty acid group is eliminated either as it is or after the introduction of an N-protective group. The elimination is carried out using an enzyme, i.e. deacylase. Deacylases which can be used include deacylase contained in the bacterial cells of *Pseudomonas acidovorans* IFO 13582. When the said deacylase is used for the reaction, the bacterial cells are supplied either as they are or in the form of crude powder, previously treated with acetone etc. The sample is dissolved in a buffer solution such as a phosphoric acid or acetic acid buffer solution (pH: 5 to 9, preferably 6 to 7.5; ion concentration: 0.01 to 0.3M, preferably 0.02 to 0.2M), after which either the bacterial cells or the crude powder is added so that its concentration to 1 mg of the sample is 5 to 500 mg/ml, preferably 20 to 100 mg/ml. Reaction temperature is 30° to 45° C., preferably 34° to 38° C.; reaction time is 10 to 48 hours, preferably 15 to 24 hours. This reaction is generally carried out under aeration while stirring. The reaction liquid is then subjected to centrifugation etc. to remove bacterial cells, after which it is purified by the ion exchange resin method etc.

Compound (B) produces Compound (A) via alkali hydrolysis. This reaction goes in two steps. That is, antibiotic TAN-749, catalytic reduction products from it, or their N-protective group introduction products are first treated under mild conditions so that the 2-amidino-ethylamide group is eliminated. The treating conditions are as follows: for example, Compound (B) is dissolved in a solution of sodium hydroxide; the solution is stirred. Sodium hydroxide concentration is 0.5 to 2 normal, preferably 1 to 1.5 normal. Reaction time is 1 day to 2 weeks, preferably 2 to 8 days when reaction temperature is 20° to 40° C., or 1 to 15 hours, preferably 2 to 8 hours when reaction temperature is 50° to 70° C., preferably 55° to 65° C. (Method III). When more severe reaction conditions are used, not only the 2-amidinoethylamino group but also either the sorbyl group or the hexanoyl group are eliminated from Compound (B), yielding a compound having neither 2-amidino-ethylamino group, nor sorbyl group, nor hexanoyl group (Compound A having a hydrogen atom for $R^a$). In this case, the reaction is carried out by maintaining the same alkaline reaction liquid as that described above at a reaction temperature of 50° to 70° C., preferably 55° to 65° C. for 8 hours to 3 days, preferably 10 to 24 hours (Method IV).

Tables B and C show the main reaction processes described above and the structural formulas of various compounds obtained via those processes, respectively.

TABLE B

| Reaction Process | Starting Material | Reaction Product |
|---|---|---|
| (1) Acid hydrolysis (Method I) | I | XV |
| | II | XVI |
| | VIII | XVIII |
| | IX | XIX |
| (2) Acid hydrolysis (Method II) | I | XXIII |
| | XVI | XXIV |
| (3) Catalytic reduction | I or III | VIII |
| | II or IV | IX |
| | XV | XVIII |
| | XVI | XIX |
| | XVII | XX |
| (4) Deacylation | VIII | XII |
| | X | XIII |
| | XI | XIV |
| | XVIII | XXIII |
| | XIX | XXIV |
| | XX | XXV |
| | XXI | XXVI |
| (5) Introduction of N—protective group | I | V |
| | I | VI |
| | I | VII |
| | VIII | X |
| | IX | XI |
| | XV | XVII |
| | XVIII | XX |
| | XVIII | XXII |
| | XIX | XXI |
| (6) Alkali hydrolysis (Method III) | VI | XVII |
| | X | XX |
| | XI | XXI |
| (7) Alkali hydrolysis (Method IV) | X | XXV |
| | XXI | XXVI |

TABLE C $$R^a-NH-\underset{R^b}{CH}-\underset{OH}{CH}-CH_2-\underset{R^c}{CH}-CH_2-COR^d$$

| Compound | $R^a$ | $R^b$ | $R^c$ | $R^d$ |
|---|---|---|---|---|
| V | $CH_3CH=CH-CH=CH-CO-$ | H— | $C_6H_5CONH-$ | $-NHCH_2CH_2C(=NH)NH_2$ |

TABLE C-continued $$R^a-NH-CH(R^b)-CH(OH)-CH_2-CH(R^c)-CH_2-COR^d$$

| Compound | $R^a$ | $R^b$ | $R^c$ | $R^d$ |
|---|---|---|---|---|
| VI | " | " | CH₃C(CH₃)₂OCONH— | " |
| VII | " | " | C₆H₅CH₂OCONH— | " |
| VIII | CH₃(CH₂)₄CO— | H— | —NH₂ | " |
| IX | " | CH₃— | " | " |
| X | " | H— | CH₃C(CH₃)₂OCONH— | " |
| XI | " | CH₃— | " | " |
| XII | H— | H— | —NH₂ | " |
| XIII | " | " | CH₃C(CH₃)₂OCONH— | " |
| XIV | " | CH₃— | " | " |
| XV | CH₃CH=CH—CH=CH—CO— | H— | —NH₂ | —OH |
| XVI | " | " | " | " |
| XVII | " | H— | CH₃C(CH₃)₂OCONH— | " |
| XVIII | CH₃(CH₂)₄CO— | H— | —NH₂ | " |
| XIX | " | CH₃— | " | " |
| XX | " | H— | CH₃C(CH₃)₂OCONH— | " |
| XXI | " | CH₃— | " | " |
| XXII | " | H— | C₆H₅CH₂OCONH— | " |
| XXIII | H— | H— | —NH₂ | —OH |
| XXIV | " | CH₃— | " | " |
| XXV | " | H— | CH₃C(CH₃)₂OCONH— | " |
| XXVI | " | CH₃— | " | " |

In this invention, the starting compound (II) or (VI) may also be produced by subjecting the compound (IV) and the compound (V) to reduction reaction, and the production method constitutes a part of this invention.

The reduction reaction proceeds by way of the compound represented by the formula (VIII) which is the dehydrated-condensate of (IV) and (V).

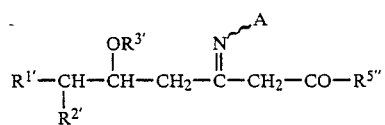

(VIII)

wherein $R^{1'}$, $R^{2'}$, $R^{3'}$, $R^{5''}$ and A are of the same meaning as defined above, $R^{3'}$ may form together with $R^{5''}$ a lactone compound of the formula (VIII-1)

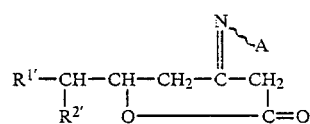

(VIII-1)

or the formula (VIII-2)

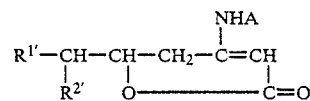

(VIII-2)

wherein $R^{1'}$, $R^{2'}$ and A are of the same meaning as defined above. Therefore, in some cases, it is advantageous to conduct the reduction reaction after isolating the dehydrated-condensate. The condensation reaction is usually conducted using the organic solvents such as methanol, ethanol, ethylether, tetrahydrofuran, dioxane, methylenechloride, chloroform, benzene, toluene, acetic acid, dimethylformamide, dimethylacetamide, etc. The reaction temperature is preferably about −20° C. to 100° C.

The compound (V) may be used in the free form and also in the form of salt of acid such as acetic acid, phosphoric acid, hydrochloric acid, sulfuric acid, etc. in the reaction.

The compound (V) is usually used in the amount of 1 to 50 mol. relative to one mol. of the compound (IV).

In some cases, the reaction advantageously proceeds in the presence of the dehydrating agent such as molecular sieves, phosphorus pentoxide, etc., the abse such as pyridine, triethylamine, diisopropylethylamine, sodium hydrogencarbonate, potassium hydrogencarbonate, sodium cazrbonate, potassium carbonate, etc.

As the reaction conditions for the readuction of the compound (IV) with the compound (V) or the reduction of the compound (VIII), (VIII-1) or (VIII-2) with the compound (V), those of the catalytic reduction using the metals such as platinum, palladium, rhodium, Raney nickel, etc. or the mixture of the above-mentioned metals and the optional carrier such as carbon, barium sulfate, calcium sulfate, barium carbonate, calcium carbonate, etc. those of the reduction using the metal hydride such as lithium alminum hydride, lithium borohydride, lithium cyanoborohydride, sodium borohydride, sodium cyanoborohydride, those of the reduction using metallic sodium, metallic magnesium in combination with alcohols, those of the reduction using the metals such as iron, zinc, etc. in combination with the acid such as hydrochloric acid, acetic acid, etc., those of the electrolytic reduction or those of the reduciton using the reduction-enzyme are mentioned.

The reduction reaction is usually conducted in the solvent used in the condensation reaction of the above-mentioned (IV) and (V). In some cases, the addition of the acid advantageously makes the reaction advance. The acids are exemplified by formic acid, acetic acid, propionic acid, trichloro-acetic acid, trifluoro-acetic acid, oxalic acid, methane-sulfonic acid, p-tolune-sulfonic acid, hydrogen chloride, sulfuric acid, phosphoric acid, boron trifluoride ethylether, alminum chloride etc. In some cases, in the presence of said acids, the compound (VIII), (VIII-1) or (VIII-2) is hydrolyzed to the compound (VI) or (VI-1) by the concomitant or by-produced water. In some cases, the dehydrating agents such as molecular-sieves and phosphorus pentoxide are used in the reaction for preventing the cases. Though the reaction temperature varies with the types of the reduction, it is preferably about −80° C. to 100° C. Though the reaction proceeds sufficiently at atmospheric pressure, it may be conducted under pressure or reduced pressure.

In the reduction reaction, when the compound represented by the formula (V) and of which A is the hydroxyl group which may be substituted, is used, it is advantageous to subject the dehydrated-condensate (VIII), (VIII-1) or (VIII-2) prepared beforehand to reduction reaction. In some cases, in the reduction, the compound representable by (VIII), (VIII-1) or (VIII-2) and of which A is hydrogen, is formed and then the reduction reaction proceed according to the types of the reducing agent.

The compound (VI) obtained by the reduction has a free-amino group as $R^4$. The compound may be isolated as it is, and also it may be isolated after protecting the formed amino group. Examples of the protecting group include the same ones of the protecting group shown by $R^8$. For the compound (VI), stereoisomers based on the asymmetric center which newly formed at the substituted position of the formed amino group, exist.

The formation ratio varies with the substituents of the compound (IV) used as starting material or the conditions of the reduction reaction.

The isomers are isolated as the mixture or the single isomer separated from the mixture by the known method such as chromatography, crystallization, recrystallization, etc., followed to be used in the production of the compound (I).

The compound (IV) or (IV-1) which is used as the starting material in the above method, is novel and can be produced by the reaction process shown below.

In the step 1, the carboxyl group is converted to the aldehyde group, and the aldehyde compound (X) is synthesized by the known method [for example, Y. Hamada and T. Shioiri, Chemical Pharmaceutical Bulletin, 30, 1921 (1982)] or an analogous one thereto.

In the step 2, the compound (X) is subjected to a condensed-ring-formation reaction with the equivalent compound for the acetoacetic acid ester to obtain the compound (IV-1). The examples of the equivalent compound for the acetoacetic acid ester include the known diene such as 1,3-bis(trimethylsilyloxy)-1-methoxybuta-1,3-diene [P. Brownbridge et al., Canadian Journal of Chemistry, 61, 688 (1982)], 1,1-dimethoxy-3-trimethylsilyloxybuta-1,3-diene [J. Branville et al., Journal of Chemical Society, Perkin I, 1976, 1852] and 1,3-dimethoxy-1-trimethylsilyloxybuta-1,3-diene [J. Savard et al., Tetrahedron Letters, 1979, 4911], etc. Among them, 1,3-bis(trimethylsilyloxy)-1-methoxybuta-1,3-diene is preferably used.

In this reaction, the equivalent compound for the acetoacetic acid ester is used in an amount of about 1 to 30 mol., preferably about 1 to 10 mol. relative to one mol. of the compound (X).

This reaction is usually subjected in a solvent. The solvent is exemplified by ethers such as dioxane, tetrahydrofuran, diethylether, diisopropylether, etc., esters such as ethyl acetate, ethyl formate, etc., halogenated hydrocarbons such as chloroform, dichloromethane, 1,2-dichloroethane, etc., hydrocarbons such as benzene, toluene, n-hexane, etc., amides such as N,N-dimethylformamide, N,N-dimethylacetamide, etc., nitriles such as acetonitrile, etc.

The above-enumerated organic solvent is used simply

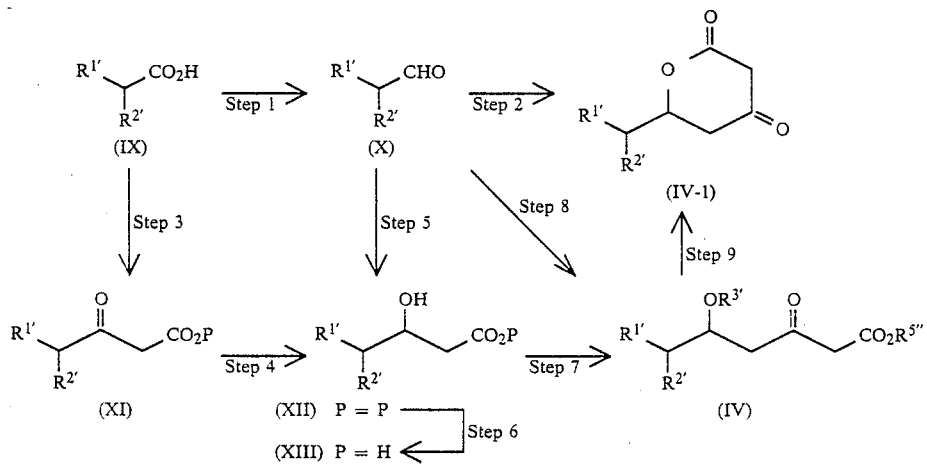

In the above chart, $R^{1'}$, $R^{2'}$, $R^{3'}$ and $R^{5''}$ are of the same meaning as defined above, and P is the protecting group of the carboxyl. As the protecting group shown by P, the same one as the above-mentioned protecting group of carboxyl is mentioned.

As the starting material, the compound (IX) is used, which is derived from the known d-, l- or dl-amino acids and of which each functional group other than the carboxyl group of the α-position is optionally protected.

Said amino acid is exemplified by glycine, alanine, 2-amino-butyric acid, valine, leucine, isoleucine, phenylalanine, tyrosine, serine, cysteine, threonine, methionine, aspartic acid, asparagine, glutamic acid, glutamine, arginine, lysine, histidine, proline, pyroglutamic acid, etc.

or in combination, usually under anhydrous condition. In the ring-formation reaction, Lewis acid is preferably used as a catalyst. The examples of the Lewis acid include salts of tin such as stannous chloride, stannic chloride, stannous fluoride, stannous iodide, stannous oxalate, stannous trifluoromethanesulfonate, etc., salts of zinc such as zinc chloride, zinc bromide, zinc iodide, zinc acetate, etc., salts of magnesium such as magnesium chloride, magnesium bromide, magnesium iodide, magnesium fluoride, etc., salts of titanium such as titanium tetrachloride, titanium tetrabromide, etc., salts of aluminum such as alaminum chlordie, etc., lanthanide compounds such as tris(6,6,7,7,8,8-hexafluoro-2,2-dimethyl-3,5-octanedionate) europium [Eu(fod)₃], tris-[3-(heptafluoropropylhydroxymethylene)-d-camphorato]europium[Eu(hfc)$_3$], tris(6,6,7,7,8,8,8-heptafluoro-2,2-dimethyl-3,5-octanedionate)ytterbium[Yb(fod)$_3$], etc., boron compound such as boron trifluoride ethyl acetate, etc.

The amount of the used catalyst is usually about 0.00001 mol. to 10 mol., preferably about 0.0001 mol. to 2 mol. relative to one mol. of the compound (X).

The reaction temperature is not limited so far as the reaction proceeds, however, it is usually about −50° C. to 100° C., preferably about −20° C. to 35° C. The reaction period varies with the types of the used starting materials and solvents, and the reaction period, however, the reaction usually proceeds within several 10 minutes to several 10 hours.

In the step 3, the carboxyl group of the compound (IX) is activated and then two carbon atoms are prolonged to obtain β-ketoester compound (XI) by the known production method, for example that described in T. Honori et al., European Journal of Medicinal Chemistry - Chimica Therapeutica, 13, 429 (1978); R. Steulmann et al., Liebigs Annalen der Chemie, 1975, 2245; B. D. Harris et al., Tetrahedron Letters, 28, 2837 (1987), etc.

In the step 4, the carbonyl group of the compound (XI) is reduced to obtain β-hydroxyester compound (XII). As the reaction conditions, the same ones mentioned in the production of the compound (VI) from the compound (VIII), are mentioned. And in this reaction, the known method which is mentioned in the above-mentioned references in the step 3 is employed.

In this reduction reaction, in some cases, the reduction proceeds with high stereoselectivity (enantio and/or diastereo) by using a microorganisms or reduction enzyme thereof. As the microorganism or reduction enzyme thereof used for the reaction, any one which are able to reduce the compound (XI) to obtain the compound (XII) are used; however, Baker's yeast is preferably used.

As the reaction solution used for the reduction, the aqueous solution (pH about 5 to 7) which may be buffer, containing about 1 to 30 g/l of the compound (XI) is preferable.

Said aqueous solution may contain about 0 to 100 ml/l of organic solvent such as alcohol, for example, methanol, ethanol, etc.

When the reduction enzyme being used, the reaction is carried out by using an excess of the reduction enzyme. In the case of using the Baker's yeast, 1 to 500 weight parts, preferably 1 to 50 weight parts of that is used relative to one weight part of the compound (XI). The reaction temperature is 15° to 40° C., preferably 20° to 35° C. and the reaction period is about one hour to two weeks. When the microorganisms other than the Baker's yeast being used, the reaction may be carried out analogously to the case using the Baker's yeast. In the asymmetric reduction using the microorganism, it is preferable to add sugar such as sucrose, glucose, etc. into the reaction solution as carbon sources.

And also, if necessary, bactotrypton, yeast extract, ammonium sulfate and so on, may be added into the reaction solution. After the reaction, the compound (XII) can be extracted with the solvent such as ethyl acetate, ether, alcohol, etc. after destroying the cell bodies using surface-active agents, bacteriolytic enzymes or glass beads or without destroying the cell bodies. The extraction of the compound (XII) from the reaction solution of the asymmetric reduction using the reduction enzyme, can be similarly carried out.

In the above-mentioned reduction using the microorganism or the enzyme, in the formula (XI), it is preferable that $R^{2'}$ is hydrogen or lower alkyl such as methyl, ethyl, etc., $R^{1'}$ is phenyl $C_{1-4}$ alkoxycarbonylamino such as benzyloxycarbonyl, etc., or $C_{1-4}$ alkoxycarbonylamino such as t-butyloxycarbonylamino and P is $C_{1-6}$ alkyl such as methyl, ethyl, etc. Said reduction reaction offers a novel production method of (R)-4-amino-3-hydroxybutyric acid or (3R,4S)- or (3S,4R)-4-amino-3-hydroxypentanoic acid and derivatives thereof, having a useful biological activity.

In the step 5, the acetic acid unit is added to the aldehyde group of the compound (X) to obtain the compound (XII) by the known method such as W. -S. Liu and G. I. Glover, Journal of Organic Chemistry, 43, 754 (1978); D. H. Lich, E. T. Sun, and A. S. Boparai, Journal of Organic Chemistry, 43, 3624 (1978); D. H. Lich, E. T. Sun, and E. Ulm, Journal of Medicinal Chemistry, 23, 27 (1980); K. E. Rittle, C. F. Hommick, G. S. Ponticello, and B. E. Evans, Journal of Organic Chemistry, 47, 3016 (1982); J. Boger, L. S. Payne, D. S. Perlow, N. S. Lohr, M. Poe, E. H. Blaine, E. H. Ulm, T. W. Schorn, B. I. LaMont, T. -Y. Lim, M. Kawai, D. H. Rich, and D. F. Veber, Journal of Medical Chemistry, 28, 1779 (1985); G. J. Hanson, J. S. Baran, and T. Lindberg, Tetrahedron Letters, 27, 3577 (1986); H. L. Sham, C. A. Rempel, H. Stein, adn J. Cohen, Journal of Chemical Society, Chemical Communication, 1987, 683; F. G. Salituro, N. Agarwal, T. Hofmann, and D. H. Rich, Journal of Medicinal Chemistry, 30, 286 (1987), etc.

In the step 6, the protecting group P of the carboxyl group of the compound (XII) is eliminated to obtain the compound (XIII).

In the deprotection reaction, according to the types of the protecting group, the one using a base or acid or the one by reduction is selected, which are mentioned as the deprotection method of the above protecting groups.

In the step 7, the carboxyl group of the compound (XIII) is activated and then two carbon atoms are prolonged to obtain β-ketoester compound (IV) by the method similar with that in the above-mentioned step 3. In the step, the compound (XIII) (1 mol.) is reacted with 1 to 2 mols. of the reagent such as 1,1'-carbonyldiimidazole, 1,1'-carbonylbis(2-methylimidazole), etc. in the solvent such as tetrahydrofuran, dimethoxyethane at 0° C. to 50° C. to a imidazolide compound. Then, without isolating the imidazolide compound, the resultant is reacted with one to 3 mols. of the magnesium salt of the malonic acid derivative of the formula (XIV)

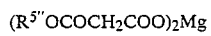    (XIV)

wherein $R^{5''}$ is of the same meaning as defined above at 0° C. to 50° C. for one to 48 hours.

In the step, the compound of which the hydroxyl group of the compound (XIII) is protected, may be used instead of the compound (XIII). Said compound is prepared by protecting the hydroxyl group of the compound (XII) obtained in the step 4 or 5 and then deprotecting the carboxyl group.

In the step 8, the acetoacetic unit is added to the aldehyde group of the compound (X) to obtain the compound (IV) wherein $R^{3'}$ is hydrogen. As the source of acetoacetic unit, acetoacetic acid ester, diketene, etc. are used. As the reaction condition, when using acetoacetic ester, the similar one used in the step 5 is adapted, and when using diketene, the similar one used in the step 2 is adopted.

In the step 9, the protecting group $R^{5''}$ of the carboxyl group of the compound (IV) wherein $R^{3'}$ is hydrogen, is eliminated to obtain the lactone compound (IV-1). The lactone-formation in the step readily proceeds and the dehydrative ring-formation usually occurs immediately after $R^{5''}$ is eliminated. Therefore, the same reaction condition in the step 6 is adopted.

For the compounds (IV), (IV-1), (XII) and (XIII) obtained in the above method, stereoisomers (optical isomer, diastereomer) referring to the carbon atom substituted by $R^{1'}$ and the oxygen atom, exist. The formation ratio varies with the types of the used starting compound, the reaction conditon, etc. The isomer may be isolated by the known means such as pH-change, phase transfer, solvent extraction, chromatography, crystallization recrystallization, etc. and may be used as the mixture.

TAN-749 to be used as the starting material for the present invention can be produced by the methods described later in Example.

A compound representable by the formula

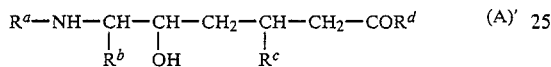
(A)' wherein $R^a$ is hydrogen, hexanoyl, or sorbyl, $R^b$ is hydrogen or methyl, $R^c$ is amino which may optionally be protected, and $R^d$ is hydroxyl or 2-amidino-ethylamino, with the proviso that when both $R^a$ and $R^b$ are hydrogen and $R^c$ is amino, $R^d$ is 2-amidino-ethylamino, or when $R^a$ is sorbyl and $R^d$ is 2-amidino-ethylamino, $R^c$ is a protected amino, can be used as a starting material to synthesize TAN-749, an antibiotic which can be used favorably as a therapeutic drug for bacterial infectious diseases.

TAN-749 can be synthesized from Compound (A)' using the following production method: For example, Compound (A)' is either dissolved or suspended in dimethylformamide; 1~2 equivalent triethylamine, 1~2 equivalent 1-hydroxybenzotriazole, and 1~2 equivalent dicyclohexylcarbodiimide are added while cooling the solution or suspension with ice. The mixture is then stirred for 2~16 hours either at normal temperature or under ice cooling conditions to yield TAN-749 whose amino group is protected by a t-butoxycarbonyl group (hereinafter referred to as N—BOC compound in some cases); the resulting N—BOC body is treated with trifluoroacetic acid at normal temperature for 5~30 minutes. The N—BOC compound of TAN-749 can also be obtained by dissolving Compound (A)' in a dilute alkali solution, adding sorbyl chloride, and then stirring the solution at normal temperature for 30 minutes to 2 hours.

The object compound (I) of this invention may form a salt with an acid or a base. When (I) is obtained in a free form, it may be derived into the salt by a conventional manner, and, when (I) is obtained in a form of salt, it may be converted into the free form by a conventional means.

Compound (I), in some cases, forms an internal salt, which is included in the present invention as well.

Stereoisomers of Compound (I), either singly or in an optional mixture thereof, can be used as medicines.

The object compound (I) thus obtained can be isolated and purified by per se known means such as concentration, liquid property conversion, phase transfer, solvent extraction, lyophilization, crystallization, recrystallization, fractional distillation, chromatography, etc.

The object compound (I) has, in its basic skeleton, two or more asymmetric carbons, thus existing theoretically four or more types of stereoisomers, and each of such isomers as well as a mixture thereof are included in the present invention. In case where the substituents of Compound (I) have asymmetric carbons, steric isomers occur likewise, and each isomer as well as a mxiture thereof are included in the present invention. When these isomers are mixedly produced by the above-mentioned reaction, the respective isomers can be isolated by conventional means such as various types of chromatography, recrystallization, etc. if necessary.

Thus obtained Compound (I) is useful as medicines, for example, antibiotics against certain types of gram-positive and gram-negative beacteria.

The biological characteristics of the compound are (I) described hereinafter.

Tables D and E show the antibacterial spectra of TAN-749A, B, C and D (dihydrochlorides) against various microorganisms.

TABLE D

| Test Organism | Minimal Inhibitory Concentration (Note 1) (μg/ml) | | | |
|---|---|---|---|---|
| | I | II | III | IV |
| Staphylococcus aureus FDA 209P | 50 | 12.5 | >100 | 50 |
| Escherichia coli NIHJ JC2 | >100 | >100 | >100 | >100 |
| Citrobacter freundii IFO 12681 | ≧100 | ≧100 | >100 | >100 |
| Klebsiella pneumoniae IFO 3317 | >100 | 100 | >100 | >100 |
| Proteus vulgaris IFO 3988 | 100 | 25 | 100 | 100 |
| Proteus morganii IFO 3168 | >100 | 100 | >100 | >100 |
| Pseudomonas aeruginosa IFO 3080 | 25 | 50 | 50 | 100 |
| Alcaligenes faecalis IFO 13111 | 3.13 | 6.25 | 12.5 | 6.25 |
| Acinetobacter calcoaceticus IFO 13006 | 25 | 50 | >100 | >100 |

(Note 1)
Medium composition

| | |
|---|---|
| Bacto-Antibiotic Medium 3 (Difco Laboratories, USA) | 17.5 g |
| Bacto-yeast extract (Difco Laboratories, USA) | 5.0 g |
| Bacto-agar (Difco Laboratories, USA) | 20 g |
| Distilled water (pH unadjusted) | 1,000 ml |
| Inoculum size | a loopful of approx. 10⁶ CFU/ml |

TABLE E

| Test Organism | Medium (Note 2) | Minimal Inhibitory Concentration (Note 1) (μg/ml) | | | |
|---|---|---|---|---|---|
| | | I | II | III | IV |
| Staphylococcus aureus 308A-1 | TSA | 12.5 | 3.13 | >100 | 25 |
| Escherichia coli T7 | TSA | 50 | 12.5 | >100 | 50 |
| Staphylococcus aureus FDA209P | B—TSA | 12.5 | 3.13 | >100 | 25 |
| Streptococcus pyogenes E-14 | B—TSA | 3.13 | 6.25 | 100 | 25 |
| Pseudomonas aeruginosa | B—TSA | 100 | 50 | 100 | 100 |

TABLE E-continued

| Test Organism | Medium (Note 2) | Minimal Inhibitory Concentration (Note 1) (μg/ml) | | | |
|---|---|---|---|---|---|
| | | I | II | III | IV |
| P9 | | | | | |

(Note 1) Determined by the agar dilution method. Inoculum size was a loopful of $10^8$ CFU/ml.
(Note 2) TSA (Tripticase Soy Agar; Baltimore Biological Laboratories, USA), B—TSA; 10% horse serum/TSA Table F shows the antibacterial activities of TAN-749A dihydrochloride against clinically isolated *Staphylococcus aureus* strains.

TABLE F

| Strain | Resistance Type | Minimal Inhibitory Concentration (Note 1) (μg/ml) |
|---|---|---|
| 1840 S | None | 12.5 |
| 1840-2 | Penicillin G | 12.5 |
| TN 2613 | Methicillin | 6.25 |
| TN 2648 | Methicillin | 3.13 |
| TN 2687 | Macrolide | 6.25 |
| TN 2684 | Macrolide | 6.25 |
| TN 2688 | Macrolide | 6.25 |

(Note 1) Determined by the agar dilution method. Medium: Mueller Hinton medium (Difco, USA) Inoculum size: a loopful of $10^6$ CFU/ml Table G shows the therapeutic effects of TAN-749A, B, C and D (dihydrochlorides) to infectious diseases in mice.

TABLE G

| Bacteria Infected Intraperitoneally | Route of Administration | ED$_{50}$ (mg/kg) | | | |
|---|---|---|---|---|---|
| | | I | II | III | IV |
| *Escherichia coli* O-111 | Subcutaneous | 67.2 | 27.3 | 50 | |
| *Escherichia coli* T7 | Subcutaneous | 50.8 | | | |
| *Pseudomonas aeruginosa* P-9 | Subcutaneous | 31.0 | 61.4 | | |
| *Staphylococcus aureus* 308A-1 | Subcutaneous | 1.31 | 0.351 | 12.5 | <6.25 |
| *Staphylococcus auresu* 308A-1 | Oral | 17.7 | 16.2 | | |

Table H shows the preliminary acute toxicities of TAN-749A and B (dihydrochlorides) in mice.

TABLE H

| Route | LD$_{50}$ (mg/kg) | |
|---|---|---|
| | I | II |
| Subcutaneous | Approx. 500 | 400~800 |
| Oral | 2000~4000 | |

The antibacterial activities against gram-positive bacteria (*S. aureus* 308A-1) of some compounds of the invention are as shown in Table 3.

TABLE 3

| Compound | (No.) | MIC(μg/ml)* | ED$_{50}$(mg/kg)** |
|---|---|---|---|
| 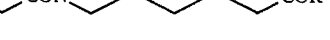 | (38b) | 100 | 6.25 |
| 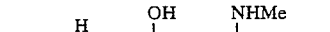 | (80) | >100 | 9.64 |
| 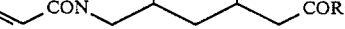 | (82) | >100 | 25 |
|  | (86b) | >100 | 25 |
| 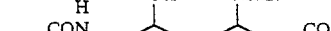 | (44b) | 100 | 21.5 |
|  | (101b) | >100 | *7.02 |
|  | (133b) | >100 | 8.41 |
|  | (124b) | >100 | 7.20 |

TABLE 3-continued

| Compound | (No.) | MIC(μg/ml)* | ED$_{50}$(mg/kg)** |
|---|---|---|---|
| 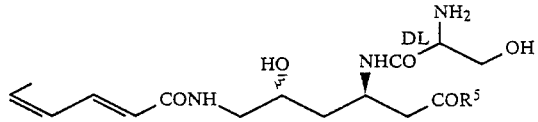 | (134b) | >100 | 7.79 |
| 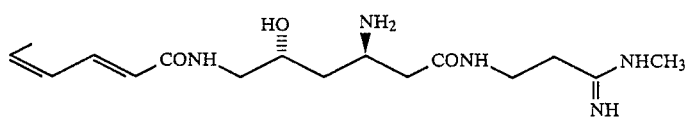 | (125b) | >100 | 19.2 |
| 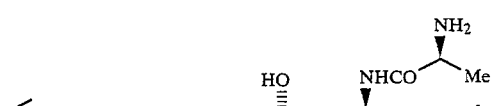 | (136b) | >100 | 8.16 |
| 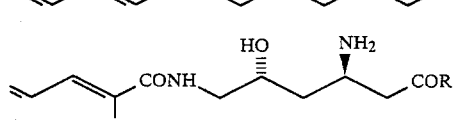 | (112b) | >100 | 6.25 |
| 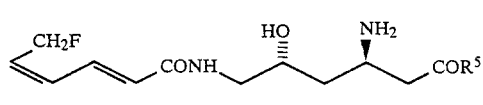 | (119b) | >100 | 4.42 |
| 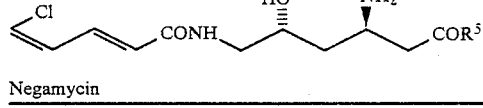 | (120b) | >100 | 8.61 |
| Negamycin | | >100 | 38.6 |

*Medium: Tripticase Soy Agar Inoculum size: 10⁸ cfu/ml
**mice, S.C.,

***$R^5$ = 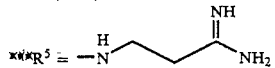

As is clear from the above data, Compound (I) or its salts of this invention have antibacterial activity and their toxicities are low, thus can be used as therapeutic agents or antibacterial agents for bacterial infections (e.g. respiratory infections, urinary tract infections, suppurative diseases, bile duct infections, intraintestinal infections, gynecological infections, surgical infections, etc.) in mammals (e.g. mice, rats, dogs, bovines, pigs and man).

The daily dosage of Compound (I) or a salt thereof is about 1 to 100 mg/kg, more preferably about 5 to 50 mg/kg, calculated on the basis of Compound (I).

Compound (I) or a pharmacologically acceptable salt thereof can be orally administered in combination with a suitable pharmacological allowable carrier, excipient and diluent in the dose form of, for example, tablet, granule, capsule, drop. etc. They can also be parenterally administered in the dose form of an injection prepared by a conventional method with the use of a sterile carrier prepared by a conventional means.

For producing the above-mentioned oral pharmaceutical preparations, for example, tablets, there may be incorporated properly a binder (e.g. hydroxypropyl cellulose, hydroxypropylmethyl cellulose, macrogol, etc.), a disintegrating agent (e.g. starch, carboxymethylcellulose calcium etc.), an excipient (e.g. lactose, starch, etc.), a lubricant (e.g. magnesium stearate, talc, etc.) and the like.

For producing the above-mentioned parenteral pharmaceutical preparations, for example, injections, there may be properly incorporated an isotonicity (e.g. glucose, D-sorbitol, D-mannitol, sodium chloride, etc.), a preservative (e.g. benzyl alcohol, chlorobutanol, methyl para-hydroxybenzoate, propyl para-hydroxybenzoate, etc.), a buffering agent (e.g. phosphate buffer solution, sodium acetate buffer solution, etc.) and the like. The compound (I) of the invention or salt thereof is given parenterally to said mammals via subcutaneous or intramuscular injection at a dose of approx. 1 to 50 mg/kg/day, preferably approx. 5 to 20 mg/kg/day. When the compound (I) or its salt is given orally, they can be given in the form of capsules at the compound (I) dose of approx. 1 to 100 mg/kg/day; it is recommended that the dose is between approx. 5 and 50 mg/kg/day.

The compound (I) or its salts can be used as bactericides. For example, hands, legs, faces, ears, etc. can be sterilized and disinfected by applying it over these portions as a liquid prepared by disslolving the compound (I) or its salts in distilled water at a concentration approx. 0.01 to 0.1 w/v % or an ointment containing approx. 0.2 to 20 mg, preferably approx. 1 to 10 mg, of the compound (I) per gram.

FIGS. 1 through 3 show the UV, IR and $^{13}$C NMR spectra of antibiotic TAN-749A dihydrochloride, respectively. FIGS. 4 through 6 show the UV, IR and $^{13}$C NMR spectra of antibiotic TAN-749B dihydrochloride, respectively. FIGS. 7 and 8 shows the UV and IR spectra of antibiotic TAN-749C dihydrocloride, respectively. FIGS. 9 and 10 show the UV and IR spectra of antibiotic TAN-749D dihydrochloride, respectively.

The present invention is hereinafter described in more detail with the following examples and reference examples but these examples are nothing more than mere practical examples and not to be construed as limitations of the present invention, and may be varied as long as they do not deviate from the scope of the present invention.

Unless specifically stated, elution in column chromatography in examples and reference examples was carried out while observing by means of TLC (Thin Layer Chromatography). In TLC observation, Merck 60F254 was used as the TLC plate, the solvent used as the elution solvent for column chromatography was used as the developing solvent, and a UV detector was used for detection of the desired products. The detection method based on the phenomenon that after a series of treatments of 48% HBr spraying, hydrolysis while heating, ninhydrin reagent spraying and re-heating, the color of TLC plate spots corresponding to eluted fractions containing the desired products changes to red to red-purple, was used in combination with the UV detection method to indentify the eluted fractions containing the desired products, which were then collected. When a mixture solvent was employed as the developing solvent, the mixing ratio was shown by volume.

Percentages used in the description of culture media show weight/volume %, unless otherwise specified.

In high performance liquid chromatography (hereinafter abbreviated as HPLC in some cases), YMC Packs S-30 and A312 (manufactured by Yamamura Chemical Laboratories) were used as the preparative carrier and the analytical carrier, respectively.

It should be noted that "room temperature" means usually 0° C. to 40° C.

The symbols used in examples and reference examples have the meanings shown below.

| | |
|---|---|
| TFA | trifluoroacetic acid |
| Boc | t-butoxycarbonyl |
| Cbz | benzyloxycarbonyl |
| MEM | methoxyethoxymethyl |
| MOM | methoxymethyl |
| THF | tetrahydrofuran |
| DMSO | dimethylsulfoxide |
| DMF | N,N—dimethylformamide |
| EEDQ | 1-ethoxycarbonyl-2-ethoxy-1,2-dihydroquinoline |
| DCC | 1,3-dicyclohexylcarbodiimide |
| WSC | 1-ethyl-3-(3-dimethylaminopropyl)carbodiimide |
| BOCON | 2-t-butoxycarbonyloxyimino-2-phenylacetonitrile |
| HOBT | 1-hydroxybenzotriazole |
| Hz | Herz |
| J | coupling constant |
| m | multiplet |
| d | doublet |
| s | singlet |
| br | broad |
| sh | shoulder |

EXAMPLE 1

*Pseudomonas fluorescens* YK-437 (IFO 14446, FERM BP-1005) grown on an enriched agar slant medium was inoculated into a 2 l Sakaguchi flask containing 500 ml of a medium prepared by adding 0.5% precipitating calcium carbonate to an aqueous solution (pH 7.0) containing 2% glucose, 3% soluble starch, 1% unprocessed soybean flour, 0.3% corn steep liquor, 0.5% Polypepton (Daigo Nutritive Chemical, Japan) and 0.3% sodium chloride, after which it was subjected to reciprocal shaking culture at 24° C. for 48 hours. The entire quantity of the resulting culture liquid was then inoculated into a 50 l fermentor containing 30 l of a medium prepared by adding 0.05% Actcol (Takeda Chemical Industries, Japan), an antifoaming agent, to said medium. and cultured at 24° C., with a 30 l/min. aeration rate and at 200 rpm for 48 hours. Six liters of the culture liquid was then inoculated into a 200 l fermentor containing 120 l of a medium containing 3% glycerol, 0.1% glucose, 0.5% Polypepton (Daigo Nutritive Chemicals, Japan), 0.5% meat extract (Wako Pure Chemical Industries, Japan), 0.5% sodium chloride, 0.05% sodium thiosulfate, 2 ppm cobalt chloride and 0.05% Actcol, after which it was incubated at 24° C., with a 120 l/min. aeration rate and at 170 rpm for 66 hours.

The culture liquid (105 l), after being adjusted to pH 6.5 with 2N hydrochloric acid, was added to a Hyflo super Cel (Jones Manville Product, USA) and subjected to filtration and water washing, yielding a filtrate (102 l). The filtrate, after adjustment to pH 6.5, was passed through a column packed with IRC-50 (Na+ type, 2 l). The column, after washing with water, was subjected to elution with a 2M saline solution (500 l). The eluate was passed through a column packed with activated charcoal (2 l), washed with water, and then subjected to elution using an 8% isobutanol water solution (15 l) as an eluent. The eluate, after adjusting to pH 6.2, was concentrated to 2 l and then passed through a column packed with CM-Sephadex C-25 (Na+ type, 0.5 l). Active fractions were then eluted using 0.1M brine (20 l) as an eluent.

A TAN-749B fraction appeared in the first half of the chromatogram and a TAN-749A fraction appeared in the last half of the chromatogram.

Each resulting fraction was subjected to chromatography using activated charcoal (1.0 l or 4.0 l) as the packing and then desalted, after which it was concentrated and lyophilized, yielding a crude TAN-749B product (4.0 g) or a crude TAN-749A product (8.9 g).

Crude product B (4.0 g) was then subjected to reversed-phase high performance liquid chromatography for separation [Mobile phase: 8% methanol/0.02M phosphate solution (pH 3)], yielding an active fraction. The active fraction was subjected to column chromatography using CM-Sephadex C-25 (Na+ type, 0.25 l) and then subjected to column chromatography using activated charcoal (0.3 l), yielding a purified fraction. The fraction was then concentrated and lyophilized, yielding TAN-749B dihydrochloride (0.66 g) in the form of a white powder. Crude product A (8.9 g) was treated with the same processes, yielding TAN-749A dihydrochloride in the form of a white powder (4.7 g).

EXAMPLE 2

*Pseudomonas fluorescens* YK-437 (IFO 14446, FERM BP-1005) grown on an enriched agar slant meidum was inoculated into a 2 l Sakaguchi flask containing 500 ml of a medium prepared by adding 0.5% precipitating calcium carbonate to an aqueous solution containing 2% glucose, 3% soluble starch, 1% unprocessed soybean powder, 0.3% corn steep liquor, 0.5% Polypepton, and 0.3% sodium chloride, after which it was subjected to reciprocal shaking culture at 24° C. for 48 hours. The entire quantity of the culture liquid was inoculated into a 200 l fermentor containing 120 l of a medium prepared by adding 0.05% Actcol, an antiforming agent, to the said medium, and then incubated at 24° C., with a 120 l/min. aeration rate and at 180 rpm for 48 hours. Fifty liters of the culture liquid was inoculated into a 2,000 l fermentor containing 1,200 l of a medium containing 3% glycerol, 0.1% glucose, 0.5% Polypepton, 0.5% meat extract, 0.5% sodium chloride, 0.05% sodium thiosulfate, 2 ppm cobalt chloride and 0.05% Actcol, after which it was incubated at 24° C., with a 1,200 l/min. aeration rate and at 150 rpm for 66 hours.

The culture liquid obtained (1,150 l), after adjusting to pH 6.5, was added to a Hyflo super cell and the subjected to filtration and water washing, yielding a filtrate (1,220 l). The filtrate, after adjustment to pH 6.2, was passed through a column packed with IRC-50 ($Na^+$ type, 20 l). The column, after washing with water, was subjected to elution using a 0.5M hydrochloric acid solution (200 l) as an eluent. The eluate, after adjusting to pH 5.6, was passed through a column packed with Diaion SP-207 (20 l) and then subjected to elution with water (120 l). The eluate was concentrated to 2 l; the concentrate was passed through a column packed with CG-50 ($NH_4^+$ type, 3 l). Active fractions were then eluted using a 0.4~0.6M brine (40 l) as an eluent.

TAN-749A, B, C and D fractions appeared in the first half of the chromatogram and a TAN-749A fraction appeared in the last half.

Each resulting fraction was subjected to chromatography using activated charcoal (1.2 l or 2.0 l) as the packing, and eluted with an 8% isobutanol water solution (4 l or 10 l). The fraction containing TAN-749A alone was concentrated and lyophilized, yielding TAN-749A (47.5 g).

Three separate lots (corresponding to 3,450 l of the initial culture liquid) or the fraction containing TAN-749A, B, C and D, obtained by the same process, were concentrated in a lump, yielding a concentrate. The concentrate (2 l) was then subjected to column chromatography using CG-50 ($NH_4^+$, 3 l) as the packing. The column, after washing with a 0.2M brine, was subjected to elution using a 0.5~0.8M brine (40 l). A fraction containing TAN-749B and D appeared in the first half of the chromatogram and one containing TAN-749A and C appeared in the last half. The fraction containing TAN-749A and C was subjected to chromatography using activated charcoal as the packing and desalted. The eluate was concentrated and lyophilized, yielding a TAN-749A powder (20 g) containing a small quantity of TAN-749C.

The fraction containing TAN-749B and D was subjected to chromatography using activated charcoal as the packing and desalted. The eluate was subjected to column chromatography using CM-Sephadex C-25 ($Na^+$ type, 1 l) as the packing and a 0.2M brine as an eluent. The eluate was concentrated, and the concentrate was subjected to reversed-phase HPLC for separation [Mobile phase: 5% methanol/0.02M phosphoric acid buffer solution (pH 3.0)], yielding two fractions, i.e. a fraction containing TAN-749B alone and one containing TAN-749B and D. The fraction containing TAN-749B alone was subjected to chromatography using CM-Sephadex and then activated charcoal as packings, yielding TAN-749B (3.05 g). The fraction containing TAN-749B and D was concentrated and then subjected to HPLC again. The fraction containing TAN-749D alone was then concentrated. The concentrate was passed through a column packed with IRA-402 ($Cl^-$ type, 10 ml) and the column was washed with water. The eluate and the wash solution were subjected to chromatography using activated charcoal for desalting, yielding TAN-749D (15.5 mg).

The TAN-749A powder (3 g) containing a small quantity of TAN-749C, obtained above, was subjected to chromatography using CM-Sephadex, Amberlite CG-50 (Rohm & Haas Co., U.S.A.) and then activated charcoal as packings to increase the ratio of TAN-749C content. The resulting powder with a high TAN-749C content was purified via two repetitions of HPLC under the conditions shown above, yielding TAN-749C (20.2 mg).

EXAMPLE 3

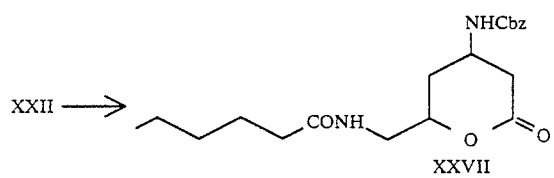

To a solution of Compound XXII(0.5 g) in water(10 ml) were added THF(10 ml), $NaHCO_3$(0.48 g) and benzyloxycarbonyl chloride(0.49 g), and the mixture was stirred at room temperature for 1.5 hours. To the reaction solution was added a small volume of pyridine to decompose excess amount of benzyloxycarbonyl chloride, followed by addition of 30 ml of ethyl acetate. With 2N HCl, the pH was adjusted to 2. The aqueous layer was separated, and the aqueous layer was subjected to extraction with ethyl acetate. The organic layers were combined, washed with a saturated brine, and then dried over magnesium sulfate, followed by concentration under reduced pressure. The concentrate was dissolved in 10 ml of methylene chloride. To the solution was added 0.57 g of WSC, then the reaction was allowed to proceed at room temperature for one hour. The reaction solution was washed with water, then dried over magnesium sulfate, followed by concentration. To the concentrate was added ether, then precipitating crystals were collected by filtration to afford Compound XXVII (0.51 g) as colorless needles, m.p. 111°–112° C.

IR$\nu_{max}^{KBr}$ cm$^{-1}$:1732, 1680, 1638, 1535.

Elemental Analysis for $C_{20}H_{28}N_2O_5$: Calcd.: C, 63.81; H, 7.50; N, 7.44, Found: C, 63.93; H, 7.44; N, 7.48.

EXAMPLE 4

The dihydrochloride of compound I (approx. 200 mg) was dissolved in water (20 ml) and sodium bicarbonate (0.73 g) and benzoyl chloride (0.175 ml) were added, after which the solution was stirred at room temperature. With the disappearance of benzoyl chloride and pH reduction in the reaction mixture, both benzoyl chloride and triethylamine were added properly so that the reaction mixture was maintained at a pH value of approx. 8.3. Some 5 hours later, the reaction liquid was washed twice with ethyl acetate (35 ml), adjusted to pH 2.0 with 2N HCl, and washed 3 times with ethyl acetate (30 ml). The washing, after adjusting to pH 6.7 with 3N sodium hydroxide, was concentrated and adsorbed to a column packed with Diaion HP-20 (50~100 mesh, 20 ml). The column was washed with water (120 ml), after which the adsorbed concentrate was eluted with a 5% methanol water solution, a 20% methanol water solution, a 50% methanol water solution and 50% methanol-0.008N HCl (each 60 ml) sequentially to fractionate into 20 ml portions of the eluate. Each fraction was subjected to high performance liquid chromatography [Mobile phase: 50% methanol/0.01M phosphoric acid solution (pH 3)]; the fractions exhibiting a single peak were combined together and concentrated, after which the concentrate was lyophilized, yielding the hydrochloride of compound V in the form of a white powder (167 mg).

Optical rotation: $[\alpha]_D^{23}$ −40.7° (c=0.46, water).

Elemental analysis ($C_{22}H_{31}N_5O_4 \cdot HCl \cdot 1.0H_2O$): Calcd.: C; 54.60, H; 7.08, N; 14.47, Cl; 7.33, Found: C; 54.52, H; 6.92, N; 14.41, Cl; 7.66.

EXAMPLE 5

The dihydrochloride of compound I (1.25 g, 83% purity) was dissolved in 50% dioxane-water (50 ml) and both triethylamine (0.5 ml) and BOC—ON (1.1 g) were added. The mixture was stirred at room temperature for 5.5 hours while adding triethylamine to maintain pH of the mixture at approx. 8.5. The reaction mixture, after adjustment to pH 7.2 with 2N HCl, was concentrated to remove dioxane. Water (200 ml) was added, after which the concentrate was washed with ethyl acetate-ethyl ether (1:1, 200 ml). The organic layer was separated and further extracted with water (150 ml). The extract was combined with the water layer and concentrated. The concentrate, after adjustment to pH 6.8, was passed through a column packed with Diaion HP-20 (50~100 mesh, 70 ml). Elution was then carried out with water (210 ml), 50% methanol-water (210 ml) and 50% methanol-1/200N HCl (280 ml) sequentially to fractionate into 70 ml portions of the eluate. Each fraction was analyzed by high performance liquid chromatography [Mobile phase: 50% methanol/0.01M phosphoric acid solution (pH 3)]. The fractions exhibiting a single peak were combined together and concentrated, after which the concentrate was lyophilized, yielding the hydrochloride of compound VI (834 mg).

Optical rotation: $[\alpha]_D^{25}$ −23.7° (c=0.52, water).

Elemental analysis ($C_{20}H_{35}N_5O_5 \cdot HCl \cdot 1.5H_2O$): Calcd.: C; 49.12, H; 8.04, N; 14.32, Cl; 7.25, Found: C; 49.08, H; 8.07, N; 14.44, Cl; 7.26.

EXAMPLE 6

The dihydrochloride of compound I (776 mg) was dissolved in 3% sodium bicarbonate water solution (40 ml) and carbobenzoxy chloride (798 μl) was added, after which the solution was stirred at room temperature for 5 hours. The reaction mixture, after adjustment to pH 2, was diluted with water (50 ml) and washed with ethyl acetate (100 ml×2). The aqueous layer, after adjustment to pH 4.5, was concentrated and subjected to column chromatography using Diaion HP-20 (50~100 mesh, 40 ml) as the packing. After washing with water (100 ml) and then with 10% methanol-water (100 ml), the concentrate was subjected to fractional elution using sequentially 50% methanol-water (100 ml) and 50% methanol-1/200N HCl (150 ml). Each fraction was analyzed by high performance liquid chromatography [Mobile phase: 60% methanol/0.01M phosphoric acid solution (pH 3)]. The fractions exhibiting a single peak were combined together and concentrated. The concentrate was then lyophilized, yielding the hydrochloride of compound VII (728 mg).

Optical rotation: $[\alpha]_D^{22}$ −41.7° (c=0.55, water).

Elemental analysis ($C_{23}H_{33}N_5O_5 \cdot HCl \cdot 0.5H_2O$): Calcd.: C; 54.70, H; 6.99, N; 13.87, Cl; 7.02. Found: C; 55.02, H; 6.85, N; 14.06, Cl; 7.29.

EXAMPLE 7

The dihydrochloride of compound I (20.0 g, approx. 97% purity) was dissolved in water (500 ml) and 10% palladium-carbon (2.0 g) was added, after which the solution was stirred at room temperature in hydrogen flow for some 4 hours. The reaction mixture was subjected to filtration to remove the catalyst; the filtrate was concentrated and lyophilized, yielding the dihydrochloride of compound XIII in the form of a white powder (19.0 g).

Optical rotation: $[\alpha]_D^{23.5}$ −5.2° (c=0.60, water).

Elemental analysis ($C_{15}H_{31}N_5O_3 \cdot 2HCl \cdot 1.0H_2O$): Calcd.: C; 42.86, H; 8.39, N; 16.66, Cl; 16.87, Found: C; 42.88, H; 8.84, N; 16.75, Cl; 17.26.

EXAMPLE 8

The dihydrochloride of compound II (1.04 g, 94% purity) was dissolved in water (100 ml) and 10% palladium-carbon (104 mg) was added, after which the solution was stirred at room temperature in hydrogen flow for some 80 minutes. The reaction mixture was subjected to filtration to remove the catalyst; the filtrate, after concentration, was passed through a column packed with activated charcoal (70 ml). Sequential elution was then carried out using water (350 ml) and then an 8% isobutanol water solution (500 ml) as eluents to fractionate into 70 ml portions of the eluate. Each fraction was analyzed by high performance liquid chromatography [Mobile phase: 25% methanol/0.01M phosphoric acid solution (pH 3)]. The fractions exhibiting a single peak were combined together and concentrated, after which the concentrate was lyophilized, yielding the dihydrochloride of compound IX in the form of a white powder (899 mg).

Optical rotation: $[\alpha]_D^{24}$ +28.9° (c=0.57, water).

Elemental analysis ($C_{16}H_{33}N_5O_3 \cdot 2HCl \cdot 0.5H_2O$): Calcd.: C; 45.18, H; 8.53, N; 16.46, Cl; 16.67, Found: C; 44.96, H; 8.82, N; 16.46, Cl; 17.10.

EXAMPLE 9

The dihydrochloride of compound VIII (19.3 g, 80% purity) was dissolved in 50% dioxane-water (400 ml) and both triethylamine (7.65 ml) and BOC—ON (13.5 g) were added. The mixture was stirred at room temperature for 5 hours, while triethylamine was added to maintain a pH value of approx. 8.5. The reaction mixture, after adjustment to pH 6.5 with 2N HCl, was concentrated to remove dioxane. The concentrate was diluted with water (900 ml) and washed with ethyl acetate-ethyl ether (1:1, 800 ml). The organic layer was separated and then further extracted with water (500 ml). The extract was combined with the water layer and concentrated, after which the concentrate was adjusted to pH 5.6 and then passed through a column packed with Diaion HP-20 (50~100 mesh, 450 ml). Sequential elution was then carried out using a series of water (1.35 l), 50% methanol-water (1.35 l) and 50% methanol-1/200N HCl (1.8 l) to fractionate into 450 ml portions of the eluate. Each fraction was analyzed by high performance liquid chromatography [Mobile phase: 60% methanol/0.01M phosphoric acid solution (pH 3)]. The fractions exhibiting a single peak were combined together and concentrated, after which the concentrate was lyophilized, yielding the hydrochloride of compound X (13.4 g).

Optical rotation: $[\alpha]_D^{25}$ −13.3° (c=0.67, water).

Elemental analysis ($C_{20}H_{39}N_5O_5 \cdot HCl$): Calcd.: C; 51.55, H; 8.65, N; 15.03, Cl; 7.61. Found: C; 51.22, H; 9.06, N; 14.82, Cl; 7.64.

EXAMPLE 10

The dihydrochloride of compound IX(700 mg) was dissolved in a 50% dioxane-water solution (28 ml) and both triethylamine (0.28 ml) and BOC—ON (455 mg) were added. The mixture was then stirred at room temperature for some 8 hours while a pH value of approx. 8.8 was maintained using triethylamine. The reaction mixture was concentrated to remove dioxane. The concentrate, after dilution with water (100 ml), was washed twice with ether-hexane (5:1, 100 ml). The organic layer was separated and extracted with water (150 ml). The extract was combined with the water layer; the mixture, after adjustment to pH 7, was concentrated and then adsorbed to Diaion HP-20 (50~100 mesh, 30 ml). Sequential elution was then carried out using a series of water, a 20% methanol water solution, a 50% methanol water solution and 50% methanol-0.005N dilute HCl water solution (each 120 ml) to fractionate into 20 ml portions of the eluate. Each fraction was analyzed by high performance liquid chromatography [Mobile phase: 60% methanol/0.01M pnosphoric acid solution (pH 3)]. The fractions exhibiting a single peak were combined together and concentrated. The concentrate was then lyophilized, yielding the hydrochloride of compound XI in the form of a white powder (487 mg).

Optical rotation: $[\alpha]_D^{23}$ +23.1° (c=0.38, water).

Elemental analysis ($C_{21}H_{41}N_5O_5 \cdot HCl \cdot H_2O$): Calcd.: C; 51.57, H; 8.86, N; 14.32, Cl; 7.25, Found: C; 51.40, H; 9.05, N; 14.21, Cl; 7.21.

EXAMPLE 11

The dihydrochloride of compound VIII(202 mg) was dissolved in a 0.03M phosphate buffer solution (pH 7.0, 100 ml). After the addition of bacterial cells (10 g) of *Pseudomonas acidovorans* IFO 13582, the solution was shaken at 37° C. for 15 hours. The reaction mixture was centrifuged; the resulting supernatant, after adjustment to pH 7.0, was passed through a column packed with Amberlite CG-50 (100~200 mesh, H+ type, Rohm & Hass, U.S.A, 40 ml). After washing the column with a series of water (200 ml) and 0.01N HCl (160 ml), fractional elution was carried out using 0.02N HCl as the eluent. Each fraction was analyzed by high performance liquid chromatography [Mobile phase: 30% acetonitrile/0.01M octanesulfonate-0.02M phosphoric acid solution (pH 3)]. The fractions whose main constituent was Compound 12, i.e. the desired product, were combined together and concentrated. The concentrate was then lyophilized, yielding a crude powder (147 mg). This crude powder was dissolved in a small amount of water and passed through a column packed with Diaion HP-20 (50~100 mesh, 40 ml). Fractional elution was then carried out. Each fraction was analyzed by high performance liquid chromatography [Mobile phase: 30% acetonitrile/0.01M octanesulfonate-0.02M phosphoric acid solution)pH 3)]. The fractions exhibiting a single peak were combined together and concentrated, after which the concentrate was lyophilized, yielding the trihydrochloride of compound XII(118 mg).

Optical rotation: $[\alpha]_D^{25}$ −7.6° (c=0.45, water).

Elemental analysis ($C_9H_{21}N_5O_2 \cdot 3HCl \cdot 2H_2O$): Calcd.: C; 28.70, H; 7.49, N; 18.59, Cl; 28.23, Found: C; 28.58, H; 7.19, N; 18.32, Cl; 28.41.

EXAMPLE 12

The hydrochloride of compound X (10.0 g) was dissolved in a 0.03M phosphate buffer solution (ph 7.0, 5.0 l). After the addition of bacterial cells (500 g) of *Pseudomonas acidovorance*, the solution was shaken at 37° C. for 15 hours. The reaction mixture was centrifuged; the supernatant, after adjusting to pH 7.3, was passed through a column packed with IRC-50 (Na+ type, 1 l). After washing the column with water (4 l), fractional elution was carried out using sequentially 0.5M brine (8 l) and 1.0M brine (5 l). Each fraction was analyzed by high performance liquid chromatography [Mobile phase: 15% methanol/0.01M phosphoric acid solution (pH 3)]. The fractions exhibiting a single peak were combined together and passed through a column packed with charcoal powder (0.8 l). After washing the column with water (2 l), elution was carried out using a series of 8% isobutanol-water (4 l) and 8% isobutanol-1/100N HCl (3 l). The eluate, after concentration, was lyophilized, yielding the dihydrochloride of compound XIII(6.82 g).

Optical rotation: $[\alpha]_D^{22}$ −1.6° (c=0.90, water).

Elemental analysis ($C_{14}H_{29}N_5O_4 \cdot 2HCl \cdot 0.5H_2O$): Calculated: C; 40.68, H; 7.80, N; 16.94, Cl; 17.15, Found: C; 40.62, H; 8.40, N; 17.04, Cl; 17.76.

EXAMPLE 13

The hydrochloride of compound XI (400 mg) was dissolved in a 0.03M phosphate buffer solution (pH 7.0, 200 ml). After adding bacterial cells (18 g) of *Pseudomonas acidovorans*, the solution was shaken at 37° C. for 25 hours. The reaction mixture was centrifuged and the supernatant was passed through a column packed with IRC-50 (NH4+ type, 30 ml). Elution was then carried out using water (100 ml), a 0.5M saline solution (150 ml) and 1.0M brine (100 ml) sequentially to fractionate into 20 ml portions of the eluate. Each resulting fraction was analyzed by high performance liquid chromatography [Mobile phase: 15% methanol/0.01M phosphoric acid solution (pH 3)]. The fractions exhibiting a single peak were combined together and concentrated. The concentrate was passed through a column packed with activated charcoal (20 ml), after which it was eluted with water (100 ml) and then with an 8% isobutanol-water solution (100 ml) to fractionate into 20 ml portions of the eluate. Each fraction was analyzed by high performance liquid chromatography [Mobile phase: 15% methanol/0.01M phosphoric acid solution (pH 3)]. The fractions exhibiting a single peak were combined together and concentrated. The concentrate was then lyophilized, yielding the dihydrochloride of compound XIV in the form of a white powder (271 mg).

Optical rotation: $[\alpha]_D^{21}$ +4.0° (c=0.55, water).

Elemental analysis ($C_{15}H_{31}N_5O_4 \cdot 2HCl \cdot 0.5H_2O$): Calcd.: C; 42.16, H; 8.02, N; 16.39, Cl; 16.59, Found: C; 42.23, H; 8.61, N; 16.33, Cl; 16.78.

EXAMPLE 14

The dihydrochloride of compound I (50.2 g, 83% purity) was dissolved in 2N hydrochloric acid (500 ml) and refluxed in an oil bath for 15 minutes under heating at 130° C. The refluxed solution was concentrated to evaporate hydrochloric acid and diluted with water (60 ml), after which it was adjusted to pH 6.8 with 1N aqueous sodium hydroxide and concentrated. The concentrate was then passed through a column packed with Diaion HP-20 (50~100 mesh, 10 l) and eluted with water (3 l) and then with a 10% methanol water solution (5 l) to fractionate 1 l portions of the eluate. Each fraction was analyzed by high performance liquid chromatography [Mobile phase: 20% methanol/0.01M phosphoric acid solution (pH 3)], after which the fractions exhibiting a single peak were combined together, concentrated, and lyophilized, yielding compound XV in the form of a powder (1.79 g).

Optical rotation: $[\alpha]_D^{21}$ −22.3° (c=0.52, water).

Elemental analysis ($C_{12}H_{20}N_2O_4 \cdot 0.5H_2O$): Calcd.: C; 54.33, H; 7.98, N; 10.56, Found: C; 53.81, H; 8.11, N; 10.46.

EXAMPLE 15

The dihydrochloride of compound II(1.25 g, 86% purity) was dissolved in 2N hydrochloric acid (125 ml) and refluxed in an oil bath for 18 hours under heating at 124° C. The reaction mixture was then cooled to room temperature and concentrated to evaporate hydrochloric acid. The concentrate, after diluting with water, was adjusted to pH 6.8 with 1N aqueous sodium hydroxide. The diluted solution, after concentration, was passed through a column packed with Diaion HP-20 (50~100 mesh, 150 ml) and eluted sequentially with water (500 ml), a 10% methanol water solution, a 20% methanol water solution and a 40% methanol water solution (each 450 ml) to fractionate into 150 ml portions of the eluate. Each fraction was analyzed by high performance liquid chromatography [Mobile phase: 25% methanol/0.01M phosphoric acid solution (pH 3)]. The fractions exhibiting a single peak were combined together and concentrated, after which the concentrate was lyophilized, yielding compound XVI in the form of a white powder (449 mg).

Optical rotation: $[\alpha]_D^{24}$ +84.7° (c=0.42, water).

Elemental analysis ($C_{13}H_{22}N_2O_4 \cdot 1.0H_2O$): Calcd.: C; 54.15, H; 8.39, N; 9.72, Found: C; 54.55, H; 8.15, N; 9.72.

EXAMPLE 16

Compound XV (3.4 g) was dissolved in a 50% acetone-water solution (114 ml) and both triethylamine (7.35 ml) and BOC—ON (3.92 g) were added, after which the solution was stirred at room temperature for about 5 hours. After evaporation of acetone, the reaction mixture was adjusted to pH approx. 8.8 by the addition of sodium bicarbonate (1.2 g) and then washed with ethyl ether (100 ml) 3 times. The water layer, after adjusting to pH 2.0 with 1N HCl, was extracted 4 times with ethyl acetate (100 ml). The extracts were combined together, washed twice with brine (100 ml), dried with anhydrous sodium sulfate, and then concentrated to dryness, yielding a colorless, oily substance, which was crystallized from an ethyl acetate-ethyl ether-hexane yielding compound XVII in the form of white crystals (4.12 g).

Melting point: 128.5° C.

Optical rotation: $[\alpha]_D^{26}$ −26.5° (c=0.50, methanol).

Elemental analysis ($C_{13}H_{28}N_2O_6$): Calcd.: C; 57.29, H; 7.92, N; 7.86, Found: C; 57.34, H; 7.72, N; 7.98.

EXAMPLE 17

Compound XV (600 mg) was dissolved in water (60 ml) and 10% palladium-carbon (60 mg) was added, after which the solution was stirred at room temperature in hydrogen flow for 3.5 hours. The reaction mixture was subjected to filtration, after which the filtrate was adjusted to pH 7.0 and concentrated. The concentrate was subjected to column chromatography using Diaion HP-20 (50~100 mesh, 180 ml) as the packing. After washing the column with water (720 ml), fractional elution was carried out using 15% methanol-water (540 ml) and then 25% methanol-water (540 ml) as eluents. Each fraction was analyzed by high performance liquid chromatography [Mobile phase: 40% methanol/0.01M phosphoric acid solution (pH 3)]. The fractions exhibiting a single peak were combined together and concentrated, after which the concentrate was lyophilized, yielding compound XVIII in the form of a powder (416 mg).

Optical rotation: $[\alpha]_D^{22}$ −13.9° (c=0.51, water).

Elemental analysis ($C_{12}H_{24}N_2O_4$): Calcd.: C; 55.36, H; 9.29, N; 10.76, Found: C; 55.22, H; 9.20, N; 10.87.

EXAMPLE 18

Compound XVII(383 mg) was dissolved in a solution of 0.1N NaOH (10.7 ml) in water (30 ml), and 10% palladiumcarbon (40 mg) was added. The mixture was stirred at room temperature in hydrogen atmosphere for 5 hours. The reaction mixture was subjected to filtration, after which the filtrate was adjusted to pH 7.0 and concentrated. The concentrate was subjected to column chromatography using Diaion HP-20 (50~100 mesh, 30 ml) as the packing. After washing the column with water (120 ml), fractional elution was carried out using 10% methanol-water (60 ml) and then 50% methanol-water (200 ml). Each fraction was analyzed by high performance liquid chromatography. [Mobile phase: 65% methanol/0.01M phosphoric acid solution (pH 3)]. The fractions exhibiting a single peak were combined together and concentrated, after which the concentrate was lyophilized, yielding the sodium salt of compound XX (356 mg).

Optical rotation: $[\alpha]_D^{23}$ −7.7° (c=0.48, water).

Elemental analysis ($C_{17}H_{31}N_2O_6Na$): Calcd.: C; 53.39, H; 8.17, N; 7.33, Found: C; 53.06, H; 8.01, N; 7.39.

EXAMPLE 19

Compound XVI (706 mg) was dissolved in water (70 ml) and 10% palladium-carbon (70 mg) was added. The mixture was then stirred at room temperature in a hydrogen flow for about 1 hour. The reaction liquid was subjected to filtration to separate the catalyst. The filtrate, after concentration, was crystallized from a water-acetone system, yielding compound XIX in the form of white crystals (647 mg).

Melting point: 204° C. (decomposition).

Optical rotation: $[\alpha]_D^{21}$ +31.8° (c=0.57, water).

Elemental analysis ($C_{13}H_{26}N_2O_4$): Calcd.: C; 56.91, H; 9.55, N; 10.21, Found: C; 56.80, H; 9.82, N; 10.13.

EXAMPLE 20

Compound XVIII (320 mg) was dissolved in a 3% sodium bicarbonate water solution (25 ml) and carbobenzoxy chloride (332 μl) was added, after which the mixture was stirred at room temperature for 6 hours. The reaction mixture, after adjusting to pH 2, was extracted with ethyl acetate. After washing with water, the organic layer was dried with anhydrous sodium sulfate and then concentrated. Ethyl etherhexane was added to the concentrate, yielding compound XXII in the form of a powder (389 mg).

Optical rotation: $[\alpha]_D^{22}$ 0° (c=0.49, methanol).

Elemental analysis ($C_{20}H_{30}N_2O_6$): Calcd.: C; 60.90, H; 7.67, N; 7.10, Found: C; 60.85, H; 7.53, N; 7.15.

EXAMPLE 21

Compound XIX(468 mg) was dissolved in a 50% acetone water solution (16 ml) and both triethylamine (0.95 ml) and BOC—ON (504 mg) were added, after which the mixture was stirred at room temperature for about 3 hours. After evaporating acetone and triethylamine by concentration, the reaction mixture was adjusted to pH 8.4 by adding sodium bicarbonate (160 ml) and water (20 ml). The diluted solution was washed 3 times with ethyl ether (30 ml), after which it was adjusted to pH 2.2 with 2N HCl and then extracted 3 times with ethyl acetate (40 ml). The ethyl acetate layers were combined, washed twice with saturated brine (20 ml), dried over anhydrous sodium sulfate, and then concentrated to dry, yielding a colorless, oily substance. This substance was then crystallized from an ether-hexane system, yielding compound XXI in the form of white crystals (423 mg).

Melting point: 102°~103° C.

Optical rotation: $[\alpha]_D^{23}$ +36.0° (c=0.45, methanol).

Elemental analysis ($C_{18}H_{34}N_2O_6$): Calcd.: C; 57.73, H; 9.15, N; 7.48, Found: C; 57.81, H; 9.21, N; 7.47.

EXAMPLE 22

The dihydrochloride of compound I (1.94 g) was dissolved in 2N HCl (193 ml) and refluxed for 6 hours under heating. After cooling, the reaction mixture was washed 3 times with chloroform (200 ml), concentrated to evaporate hydrochloric acid, and diluted with water (55 ml). The solution was passed through a column packed with Dowex 50W-X2 ($H^+$ type, 50~100 mesh, 100 ml) and eluted with a series of water (300 ml), 0.5N HCl, 0.8N HCl, 1.0N HCl, 1.2N HCl and 1.5N HCl (each 400 ml) to fractionate into 100 ml portions of the eluate. Each fraction was analyzed by thin-layer chromatography, after which the fractions containing the desired compound were combined together and concentrated. The concentrate was diluted with water to make 30 ml and again passed through a column packed with Dowex 50W-X2 ($H^+$ type, 50~100 mesh, 30 ml). The effluent was further eluted with a series of 0.8N HCl, 0.9N HCl and 1.0N HCl (each 150 ml) to fractionate into 30 ml tions of the eluate. Each fraction was analyzed in the same procedure as above. The fractions exhibiting a single spot were combined together, concentrated, and then lyophilized, yielding the dihydrochloride of compound XXIII in the form of a powder (301 mg).

Optical rotation: $[\alpha]_D^{25}$ −18.3° (c=0.85, water).

Elemental analysis ($C_6H_{14}N_2O_3.2HCl$): Calcd.: C; 30.65, H; 6.86, N; 11.92, Cl; 30.16, Found: C; 30.30, H; 7.13, N; 12.07, Cl; 30.57.

EXAMPLE 23

Compound XVI (310 mg) was dissolved in 2N HCl (31 ml) and refluxed for 6 hours under heating. After cooling, the reaction mixture was washed 3 times with chloroform (40 ml) and concentrated to evaporate hydrochloric acid. The concentrate, after diluting with water (18 ml), was passed through a column packed with Dowex 50W-X2 ($H^+$ type, 50~100 mesh, 17 ml) and eluted with a series of water (50 ml), a 0.2% aqueous ammonia (50 ml), a 0.3% aqueous ammonia (60 ml) and a 0.4% aqueous ammonia (60 ml) to fractionate into 17 ml portions of the eluate. Each fraction was analyzed by thin-layer chromatography. The fractions exhibiting a single spot were combined together, concentrated, and then lyophilized, yielding Compound 24 in the form of a powder (174 mg). 38 mg of the powder was dissolved in water (3.8 ml), adsorbed to Dowex 50W-X2 ($H^+$ type, 50~100 mesh, 5 ml), and eluted with a series of water (15 ml), 0.5N HCl, 0.8N HCl, 0.9N HCl and 1.0N HCl (each 20 ml) to fractionate into 5 ml portions of the eluate. Each fraction was analyzed by thin-layer chromatography. The fractions exhibiting a single spot were combined together, concentrated, and then lyophilized, yielding the dihydrochloride of compound XXIV(39 mg).

Optical rotation: $[\alpha]_D^{23}$ −2.7° (c=0.58, water),

Elemental analysis ($C_7H_{16}N_2O_3.2HCl$): Calcd.: C; 34.02, H; 6.53, N; 11.34, Cl; 28.69, Found: C; 33.81, H; 7.81, N; 11.20, Cl; 29.52.

EXAMPLE 24

The sodium salt of compound XX (280 mg) was dissolved in a 0.03M phosphate buffer solution (pH 7.0, 140 ml) and bacterial cells (14 g) of *Pseudomonas acidovorans* were added, after which the mixture was shaken at 37° C. for 20 hours. The reaction mixture was centrifuged; the supernatant, after adjusting to pH 7.0, was concentrated. The concentrate was subjected to column chromatography using Diaion HP-20 (50~100 mesh, 140 ml) as the packing and eluted with a series of water (900 ml) and 5% methanol-water (500 ml). Each fraction was analyzed by high performance liquid chromatography [Mobile phase: 25% methanol/0.01M phosphoric acid solution (pH 3)]. The fractions exhibiting a single peak were combined together and concentrated. The concentrate was then lyophilized, yielding compound XXV in the form of a white powder (145 mg).

Optical rotation: $[\alpha]_D^{23}$ +10.3° (c=0.48, water).

Elemental analysis ($C_{11}H_{22}N_2O_5$): Calcd.: C; 50.37, H; 8.45, N; 10.68, Found: C; 49.91, H; 8.54, N; 10.57.

EXAMPLE 25

Compound XXI (390 mg) was suspended in a 0.03M phosphate buffer solution (pH 7.0, 200 ml) and bacterial cells (40 g) of *Pseudomonas acidovorans* were added, after which the mixture was shaken at 37° C. for 18 hours. The reaction mixture was centrifuged; the supernatant, after adjusting to pH 7.0, was concentrated. The concentrate was subjected to column chromatography using Diaion HP-20 (50~100 mesh, 140 ml) as the packing and then eluted with a series of water (700 ml) and 5% methanol-water (700 ml) to fractionate into 140 ml portions of the eluate. Each fraction was analyzed by high performance liquid chromatography [Mobile phase: 25% methanol/0.01M phosphate solution (pH 6.3)]. The fractions exhibiting a single peak were combined together and concentrated. The concentrate was then lyophilized, yielding compound XXVI in the form of a white powder (94 mg).

Optical rotation: $[\alpha]_D^{21.5}$ +19.3° (c=0.45, water).

Elemental analysis ($C_{12}H_{24}N_2O_5.0.5H_2O$): Calcd.: C; 50.51, H; 8.83, N; 9.82, Found: C; 50.53, H; 8.71, N; 9.82.

EXAMPLE 26

The hydrochloride of compound VI (9.5 mg) was dissolved in 1N aqueous sodium hydroxide (0.95 ml) and stirred at room temperature for 60 hours. After the completion of the reaction, the reaction mixture was diluted and analyzed by high performance liquid chromatography [Mobile phase: 60% methanol/0.01M phosphoric acid solution (pH 3)]: it was found compound XVII was produced in an amount of 3.8 mg.

EXAMPLE 27

The hydrochloride of compound X (111 mg) was dissolved in water (3.7 ml) and sodium hydroxide (188 mg) was added, after which the mixture was stirred at 60° C. for about 16 hours. The reaction mixture, after adjusting to pH 6.7 with HCl, was diluted with water to make 13 ml and subjected to high performance liquid chromatography [Mobile phase: 70% methanol/0.01M phosphoric acid solution (pH 3)] for analysis and quantitative determination: it was found that compound XXV and compound XX were produced in amounts of 9 mg and 32 mg, respectively.

EXAMPLE 28

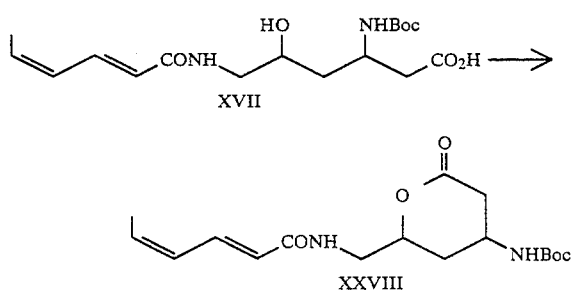

In 100 ml of $CH_2Cl_2$ was dissolved Compound XVII (10.7 g). To the solution was added WSC (6.0 g). One hour later, the reaction mixture was washed with water, and dried over $MgSO_4$. The solution was concentrated under reduced pressure, and the concentrate was subjected to a silica gel column chromatography ($SiO_2$,250 g) using ethyl acetate hexane=5:1 as an eluent to give Compound XXVIII (10 g) as colorless needles, m.p.156° to 157° C.

IR$\nu_{max}$ (KBr) cm$^{-1}$:3310, 1733, 1680, 1535.

Elemental Analysis: $C_{17}H_{26}N_2O_5$: Calcd.: C,60.34; H,7.74; N,8.28, Found: C,60.59; H,7.52; N,8.00.

REFERENCE EXAMPLE 1

A suspension of potassium salt of monomethyl malonate (23.4 g) and magnesium chloride(9.2 g) in anhydrous THF (150 ml) was stirred at 50° C. for 4 hours. On the other hand, to a solution of L-Boc-alanine(18.9 g) in anhydrous THF (200 ml) was added 1,1'-carbonyldimidazole(CDI) (19.4 g), and the mixture was stirred at room temperature for one hour. The solution was added to the above-mentioned suspension, and the mixture was stirred at room temperature for 14 hours, followed by distilling off the solvent. To the residue was added ethyl acetate, and the mixture was washed with 0.5N hydrochloric acid, water, a saturated aqueous solution of sodium hydrogencarbonate and water, successively, and dried ($Na_2SO_4$). The solvent was distilled off, and the residue was purified by means of a silica gel(150 g) column chromatography(hexane:ethyl acetate=3:1→1:1) to afford 16.6 g of methyl (4S)-t-butoxycarbonylamino-3-oxopentanoate (XXIX) as colorless crystals. Recrystallization from isopropylether-hexane afforded colorless needles, m.p.57°–58° C.

IR$\nu_{max}$ (Nujol) cm$^{-1}$:3350, 1750, 1720, 1680.

NMR(90 MHz,CDCl$_3$)ppm: 1.35(3H,d,J=7 Hz),1.43(9H,s),3.55(2H,s), 3.73(3H,s),4.35(1H,m),5.15(1H,b).

$[\alpha]_D^{26}$ −53.7° (c=0.99, methanol).

Elemental Analysis for $C_{11}H_{19}NO_5$: Calcd.: C,53.87; H,7.81; N,5.71, Found: C,53.78; H,7.78; N,5.71.

REFERENCE EXAMPLES 2-7 (TABLE 4)

By a process similar to that in Reference example 1 chain-elongation reaction was conducted using N-protected amino acid to afford compounds of Reference examples 2-7 The respective yields and some of their physico-chemical properties are shown in Table 4.

TABLE 4

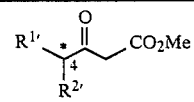

| Ref.Ex. No. | R$^{1'}$ (cpd. No.) | R$^{2'}$ | Steric Config. (C$_4$ Pos.) | Yield (%) | m.p. (°C.) | IR $\nu_{max}$ cm$^{-1}$ |
|---|---|---|---|---|---|---|
| 2 | NHCbz XXX | Me | S | 81 | oil | (Neat) 3340, 1750, 1720, 1690 |
| 3 | NHBoc XXXI | Me | R | 65 | 58–59 | (Nujol) 3350, 1750, 1720, 1680 |
| 4 | NHCbz XXXII | Me | R | 65 | oil | (Neat) 3340, 1750, 1720, 1690 |
| 5 | NHBoc XXXIII | Me | RS | 60 | 48–52 | (Nujol) 3350, 1750, 1720, 1680 |
| 6 | NHBoc XXXIV | II | — | 39 | oil | (Neat) 3400, 2980, 2940, 1770–1680 |
| 7 | NHCbz XXXV | II | — | 75 | 51–52 | (KBr) 3380, 2940, 1760, 1740, 1690 |

REFERENCE EXAMPLE 8

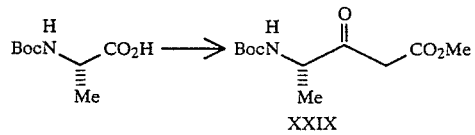

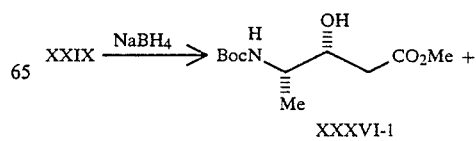

-continued

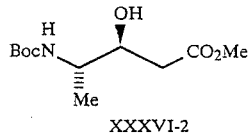
XXXVI-2

To a methanolic solution of Compound XXIX(250 mg) was added sodium borohydride(38 mg) at −78° C., and the mixture was stirred for 15 minutes. To the reaction mixture was added 1N hydrochloric acid to adjust the pH at 7, which was then concentrated. To the concentrate was added ethyl acetate, and the mixture was washed with water and was then dried(Na₂SO₄), followed by distilling off the solvent. The residue was purified by means of a silica gel (15 g) column chromatography(hexane→hexane:ethyl acetate=3:2) to afford a mixture of alcohol compounds (XXXVI-1, XXXVI-2) (the mixture ratio was confirmed to be about 4:1 by NMR spectrum) (240 mg) as colorless crystals.

NMR(90 MHz,CDCl₃)ppm: 1.14, 1.21(total 3H, each d (ca.4:1), J=7 Hz), 1.43(9H,s), 2.46, 250(total 2H, each d (ca.4:1), J=6 Hz), 3.4(1H,J=4 Hz), 3.70(3H,s), 3.7(1H,m), 4.0(1H,m), 4.85(1H,b).

This product was recrystallized twice from isopropyl ether to afford the main product(XXXVI-1) as colorless prisms, m.p.92°–93° C. $[\alpha]_D^{25}$ −9.3° (c=1.0, methanol).

IR and NMR spectra of this product were in grood agreement with those of the Compound (XXXVIII) obtained in Reference example 10.

REFERENCE EXAMPLE 9

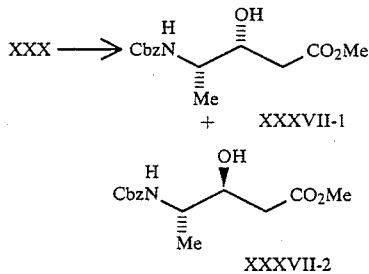

In a manner similar to that of Reference example 8 Compound(XXX) was subjected to reduction by using sodium borohydride to afford a mixture of alcohol compounds(XXXVII-1, XXXVII-2) (the mixture ratio was confirmed to be about 4:1 by NMR spectrum) as an oily product(95%).

NMR(90 MHz,CDCl₃)ppm: 1.15, 1.22(total 3H, each d (ca.4:1)), 2.46, 2.50(total 2H, each d, J=6 Hz), 3.16(1H,d,J=4 Hz), 3.70(3H,s), 3.7(1H,m), 4.05(1H,m), 5.0(1H,m), 5.10(2H,s), 7.36(5H,s).

REFERENCE EXAMPLE 10

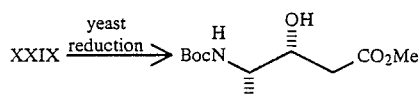
XXXVIII(≡XXXVI-1)

To a solution of saccharose(4 g) in water(50 ml) was added baker's yeast(dry yeast, Oriental Yeast Industry, K.K.) (2.0 g), and the mixture was stirred at room temperature for one hour. To this mixture were added the Compound XXIX(0.50 g) obtained in Reference example 1 and ethanol (1 ml), and the mixture was stirred at room temperature(15°–30° C.) for 5 days, to which was added celite, followed by filtration. The celite layer was washed with ethyl acetate. The filtrate was extracted with ethyl acetate. The extract and the washing were combined, washed with water and dried(Na₂SO₄), followed by distilling off the solvent. The residue was purified by means of a silica gel(20 g) column chromatography(hexane→hexane:ethyl acetate=3:2) to afford Compound XXXVIII(0.43 g) as colorless crystals, m.p.87°–89° C. $[\alpha]_D^{22}$ −9.0(c=0.80, methanol) Recrystallization of these crystals from isopropyl ether-hexane once afforded colorless prisms, showing the following physical constants. Melting point: 91°–92° C., IR$\nu_{max}$ (Nujol) cm⁻¹:3400, 3350, 1735, 1680.

NMR(90 MHz,CDCl₃)ppm: 1.14(3H,d,J=7 Hz), 1.43(9H,s), 2.46(2H,d,J=6 Hz), 3.30(1H,d,J=4 Hz), 3.70(3H,s), 3.7(1H,m), 4.0(1H,m), 4.7(1H,b).

$[\alpha]_D^{25}$ −9.5° (c=1.06, methanol).

Elemental Analysis for C₁₁H₂₁NO₅: Calcd.: C, 53.43; H, 8.56; N, 5.66, Found: C, 53.30; H, 8.52; N, 5.60.

Erythro:threo ratio in this product was found to be 99:1 from 400 MHz ¹H-NMR(judged from the signal of Me group). Reference Examples 11-16 (Table 5)

In a manner similar to that of Reference example 10 the Compounds XXX-XXXV obtained in Reference examples 2-7 were subjected to reduction using dry yeast to afford compounds of Reference examples 11-16. The reaction conditions, yields and some of the physico-chemical properties of the products are shown in Table 5.

TABLE 5

Reduction of 4-substituted amino-3-oxobutyric acid derivative by yeast

| Ref. Ex No. | Starting Material No. | Product No. | | Reaction time | Yield (%) (Recovery %) | m.p. (°C.) | $[\alpha]_D$ (Methanol °C., C%) | IR $\nu_{max}$ cm⁻¹ |
|---|---|---|---|---|---|---|---|---|
| 11 | XXX | CbzN-S-R-CO₂Me (Me) | XXXIX | 7 day | 13 (35) | 80–82 | −2.8° (26,0.5) | (Nujol) 3320 1740 1690 |
| 12 | XXXI | BocN-R-S-CO₂Me (Me) XL | | 5 day | 86 | 89–90 | +9.3° (22,0.75) | (Nujol) 3400 3350 1735 1680 |

TABLE 5-continued

Reduction of 4-substituted amino-3-oxobutyric acid derivative by yeast

| Ref. Ex No. | Starting Material No. | Product No. | Reaction time | Yield (%) (Recovery %) | m.p. (°C.) | $[\alpha]_D$ (Methanol °C., C%) | IR $\nu_{max}$ cm$^{-1}$ |
|---|---|---|---|---|---|---|---|
| 13 | XXXII | CbZN-H-R-OH(S)-Me-CO$_2$Me  XLI | 4 day | 23 (77) | 82–85 | +2.9° (25, 0.68) | (Nujol) 3320 1740 1690 |
| 14 | XXXIII | BocN-H-RS-OH-SR-Me-CO$_2$Me  XLII | 5 days | 82 | 65–67 | 0° (22, 0.715) | (Nujol) 3400 3350 1735 1680 |
| 15 | XXXIV | BocN-H-OH-R-CO$_2$Me  XLIII | 6 hours | 95 | 63–64 | −1.2° (26, 1.025) | (Nujol) 3420 1735 1670 |
| 16 | XXXV | CbZN-H-OH-R-CO$_2$Me  XLIV | 16 hours | 88 | 33–34 | −2.6° (23, 1.135) | (Liquid) 3350 1720 |

REFERENCE EXAMPLE 17

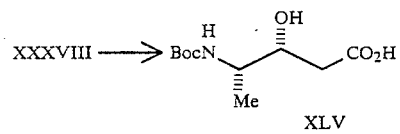

XXXVIII ⟶ BocN-H-OH-Me-CO$_2$H   XLV

To a solution of Compound XXXVIII(7.0 g) in a mixture of dioxane(40 ml) and water(20 ml) was added, while ice-cooling under stirring, 1N NaOH(35 ml) over a period of 1.5 hours. The whole mixture was stirred at room temperature for 3.5 hours. To the reaction mixture was added water, and the mixture was washed with ethyl acetate. Using a 10% aqueous solution of potassium hydrogensulfate, the aqueous layer was acidified under ice-cooling (pH 2–3), and extracted with ethyl acetate. The extract solution was dried (Na$_2$SO$_4$), followed by distilling off the solvent to afford Compound XLV as colorless crystals. Recrystallization from hexane - ethyl acetate afforded colorless prisms(6.2 g), m.p.103°–104° C.

IR$\nu_{max}$ (Nujol) cm$^{-1}$:3350, 1710, 1680.

NMR(90 MHz,CDCl$_3$)ppm: 1.15(3H,d,J=7 Hz), 1.43(9H,s), 2.50(2H,d,J=6 Hz), 3.73(1H,m), 4.0(1H,m), 4.90(1H,b), 6.33(1H,b).

$[\alpha]_D^{26}$ −9.8° (c=1.015, methanol).

Elemental Analysis for C$_{10}$H$_{19}$NO$_5$: Calcd.: C, 51.49; H, 8.21; N, 6.00, Found: C, 51.50; H, 8.15; N, 6.02.

REFERENCE EXAMPLES 18–20

In a manner similar to that of Reference example 17 Compounds XXXIX, XLIII and XLIV were subjected to alkaline hydrolysis to obtain compounds of Reference examples 18–20. The respective yields and some of the physico-chemical properties of the products are shown in Table 6.

TABLE 6

| Ref. Ex. No. | Compound No. | Yield (%) | m.p. (°C.) | $[\alpha]_D$ (Methanol °C. C%) | IR $\nu_{max}^{Nujol}$ cm$^{-1}$ |
|---|---|---|---|---|---|
| 18 | CbzN-H-OH-Me-CO$_2$H  XLVI | 91 | 83–84 | −4.2° (26, 1.025) | 3320 1720 1680 |
| 19 | BocN-H-OH-CO$_2$H  XLVII | 96 | 96–97 | −3.2° (23, 0.75) | 3490 3220 1690 |
| 20 | CbzN-H-OH-CO$_2$H  XLVIII | 90 | 81–82 | −5.4° (23, 0.67) | 3560 3340 1690 |

REFERENCE EXAMPLE 21

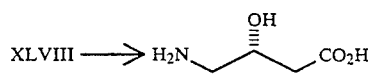

XLVIII ⟶ H$_2$N-OH-CO$_2$H

XLIX

A mixture of Compound XLVIII(0.25 g), 10% Pd-C(50 mg) and methanol(10 ml) was stirred under hydrogen at room temperature for 3 hours. The reaction mixture was filtrated, and the catalyst was washed with aqueous methanol(10%). The filtrate and the washing were combined, and the solvent was distilled off to afford 4-amino-3-hydroxybutyric acid (XLIX) (0.11 g) as colorless prisms, m.p.222°–223° C.(decomp.).

IR$\nu_{max}$ (Nujol) cm$^{-1}$:3125, 1650, 1570.

NMR(90 MHz, D$_2$O)ppm: 2.53(2H,d,J-7 Hz), 2.9–3.4(2H,m), 4.3(1H,m).

$[\alpha]_D^{26}$ −5.9° (c=1.035, methanol).

Elemental Analysis for C$_{13}$H$_{23}$NO$_6$: Calcd.: C, 53.97; H, 8.01; N, 4.84, Found: C, 54.05; H, 8.04; N, 4.85.

REFERENCE EXAMPLES 23–25 (TABLE 7)

In a manner similar to that in Reference example 22 compounds obtained in Reference examples 18–20 were subjected to chain-elongation reaction to obtain compounds of Reference examples 23–25. The respective yields and some of the physico-chemical properties of the prodcuts are shown in Table 7.

TABLE 7

| Ref. Ex. No. | Compound No. | Yield (%) | m.p. (°C.) | IR $\nu_{max}$ cm$^{-1}$ |
|---|---|---|---|---|
| 23 | CbzN–...–CO$_2$Me (Me, OH) L I | 60 | 104–105 | (Nujol) 3300 1750 1720 1690 |
| 24 | BocN–...–CO$_2$Me (OH) L II | 72 | oily product | (Liquid) 3400 1770– 1690 |
| 25 | CbzN–...–CO$_2$Me (OH) L III | 65 | oily product | (Liquid) 3400 1760– 1680 |

$[\alpha]_D^{23}$ −19.4° (c=0.635, water).

Elemental Analysis for C$_4$H$_9$NO$_3$: Calcd.: C, 40.33; H, 7.62; N, 11.76, Found: C, 40.26; H, 7.70; N, 11.66.

REFERENCE EXAMPLE 22

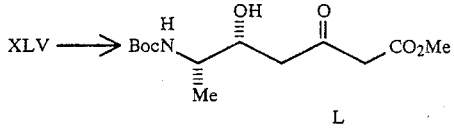

A suspension of potassium salt of monomethyl malonate (21.2 g) and magnesium chloride(8.4 g) in anhydrous THF (150 ml) was stirred at 50° C. for 16.5 hours. On the other hand, to a solution of Compound XLV(10.0 g) in anhydrous THF (120 ml) was added, while stirring under ice-cooling, a solution of CDI(7.7 g) in anhydrous THF(200 ml), over a period of one hour. The whole mixture was stirred for further 1.5 hours under ice-cooling. To the solution was added the above-mentioned suspension, and the mixture was stirred at room temperature for 16.5 hours, followed by distilling off the solvent. To the residue was added ethyl acetate, which was washed with water, a saturated aqueous solution of sodium hydrogencarbonate and water, successively, dried (Na$_2$SO$_4$) and the solvent was evaporated. The residue was purified by means of a silica gel (120 g) column chromatography(ethyl acetate) to afford methyl(5R,6S)-6-t-butoxycarbonylamino-5-hydroxy-3-oxopentanoate (L) as colorless crystals. Recrystallization from ether afforded colorless needles (7.0 g), m.p.83°–85° C.

IR$\nu_{max}$ (Nujol) cm$^{-1}$:3450, 1750, 1710, 1680.

NMR(90 MHz,CDCl$_3$)ppm: 1.13(3H,d,J=7 Hz), 1.43(9H,s), 2.67(2H,d,J=6 Hz), 3.50(2H,s), 3.73(3H,s), 4.05(1H,m), 4.76(1H,d,J=8 Hz).

REFERENCE EXAMPLE 26

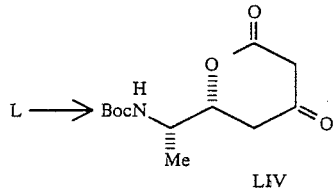

To a solution of Compound L(4.85 g) in THF(100 ml) was added 1N—NaOH(18.5 ml), while ice-cooling under stirring, over a period of 15 minutes. This mixture was stirred for 1.5 hours at room temperature, and concentrated. To the concentrate was added water, and the mixture was washed with ethyl acetate. The aqueous layer was acidified (pH about 2) with a 10% aqueous solution of potassium hydrogensulfate, and extracted with ethyl acetate. The extract was washed with water, then dried (Na$_2$SO$_4$), and the solvent was evaporated to afford (6R,1'S)-6-[(1'-t-butoxycarbonylamino)ethyl]-2,4-dioxotetrahydrofuran(LIV) (4.32 g) as colorless crystals, m.p.144°–145° C.

IR$\nu_{max}$ (Nujol) cm$^{-1}$:3380, 1750, 1735, 1720, 1685.

NMR(90 MHz,CDCl$_3$)ppm: 1.26(3H,d,J=7 Hz), 3.8(1H,m), 4.76(1H,m).

$[\alpha]_D^{23}$ +2.4° (c=0.63, methanol).

Elemental Analysis for C$_{12}$H$_{19}$NO$_5$: Calcd.: C, 56.02; H, 7.44; N, 5.44, Found: C, 56.23; H, 7.49; N, 5.44.

REFERENCE EXAMPLES 27–29 (TABLE 8)

In a manner similar to that of Reference example 26, the compounds obtained in Reference examples 23–25 were allowed to react with 1N—NaOH to afford compounds of Reference examples 27–29. The respective yeilds and some of the physico-chemical properties of the products are shown in Table 8.

TABLE 8

| Ref. No. | Compound No. | | yield (%) | 28 m.p. (°C.) | $[\alpha]_D$ (Solvent °C. C %) | IR $\nu_{max}^{Nujol}$ cm$^{-1}$ |
|---|---|---|---|---|---|---|
| 27 | ![LV structure: CbzNH-CH(Me)-CH2-C(=O)-CH2-C(=O)-O (ring)] | LV | 99 | 142–144 | +5.4° (Methanol 23,0.815) | 3370 1755 1720 1695 |
| 28 | ![LVI structure: BocNH-CH(H)-CH2-C(=O)-CH2-C(=O)-O (ring)] | LVI | 90 | 133–134 | +58.8° (Ethanol 24,0.495) | 3370 2630 1690 |
| 29 | ![LVII structure: CbzNH-CH(H)-CH2-C(=O)-CH2-C(=O)-O (ring)] | LVII | 92 | 102–103 | +49.3° (Methanol 26,0.56) | 3350 1725 1695 |

REFERENCE EXAMPLE 30

$$\text{Me-C(=O)-CH}_2\text{-CO}_2\text{Me} \longrightarrow \text{LVIIIa} \longrightarrow$$

LVIIIa: TMS-O-C(Me)=CH-CO2Me

LVIII: TMS-O-CH=CH-CH=C(OMe)-O-TMS

TMS = SiMe$_3$

A suspension of anhydrous zinc chloride(16 g) in triethylamine(226 g) was stirred at room temperature for 2 hours, to which was added a solution of methyl acetoacetate(416.5 g) in ether(1 ). To the mixture was then added, under ice-cooling and stirring, trimehtylsilylchloride(584 g). The reaction mixture was stirred at room temperature for 16 hours, then precipitating sediment was filtered off. The filtrate was purified by distillation to afford trimethylsilyloxy compound (LVIIIa) (b.p.50°–60° C./2.5 mmHg, 638 g) as a colorless liquid. A solution of LVIII(68.5 g) in anhydrous THF(70 ml) was added, at −78° C. under stirring, to a solution of LDA[prepared from n-BuLi(1.6M hexane solution, 250 ml) and diisopropylamine(40.5 g)] in anhydrous THF(500 ml), over a period of hour. The reaction mixture was stirred at −78° C. for 15 minutes and at room temperature for 2.5 hours, and, then, resulting precipitates were filtered off. The filtrate was concentrated under reduced pressure. To the concentrate was further added hexane, and the precipitates were filtered off, and the concentrate was again concentrated. The concentrate was purified by distillation to afford trimethylsilyloxydiene compound (LVIII) (b.p.65°–70° C./1 mmHg, 89.5 g) as a pale yellow liquid product.

REFERENCE EXAMPLE 31

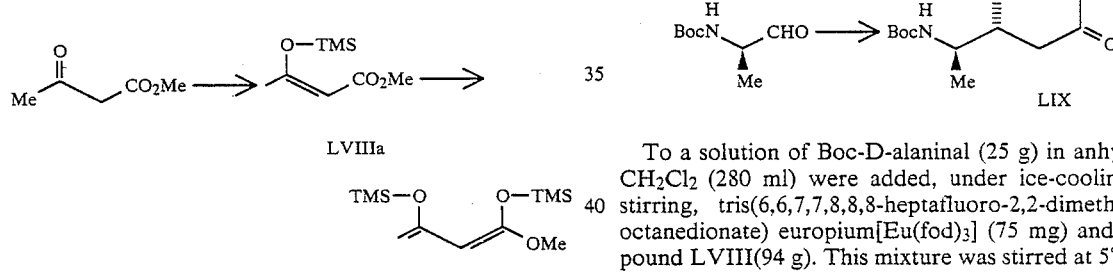

To a solution of Boc-D-alaninal (25 g) in anhydrous CH$_2$Cl$_2$ (280 ml) were added, under ice-cooling and stirring, tris(6,6,7,7,8,8,8-heptafluoro-2,2-dimethyl-3,5-octanedionate) europium[Eu(fod)$_3$] (75 mg) and Compound LVIII(94 g). This mixture was stirred at 5°–8° C. for 3 days, to which was added a saturated aqueous solution of potassium hydrogensulfate to suspend the reaction, followed by extraction with an aqueous solution of sodium carbonate. The extract was washed with CH$_2$Cl$_2$, to which was added potassium hydrogensulfate to render the solution acidic. The mixture was extracted with ethyl acetate. The extract was washed with water, dried(MgSO$_4$), and concentrated. The concentrate was crystallized from chloroform-carbon tetrachloride to afford (6R,1'R)-6-[('-t-butoxycarbonylamino)ethyl]-2,4-dioxotetrahydrofuran(LIX) (16.0 g) as colorless crystals, m.p. 146°–148° C.

IR$\nu_{max}$ (KBr) cm$^{-1}$:3360, 2980, 1675, 1615, 1580.

NMR(90 MHz,CDCl$_3$)ppm: 1.35(3H,d,J=7 Hz), 1.43(9H,s), 2.60(1H,d,J=4 Hz), 2.68(1H,s), 3.48(2H,q), 3.75–4.18(1H,m), 4.50–4.95(2H,m).

$[\alpha]_D^{23}$ +117.6° (c=0.25, chloroform).

Elemental Analysis for C$_{12}$H$_{19}$NO$_5$: Calcd.: C, 56.02; H, 7.44; N, 5.44, Found: C, 55.88; H, 7.47; N, 5.43.

REFERENCE EXAMPLES 32–39 (TABLE 9)

In a manner similar to that of Reference example 31 an aldehyde derivative of corresponding α-amino acid was allowed to react with trimethylsilyloxydiene(LVIII) in the presence of a catalyst to afford compounds of Reference Examples 32–39. The catalysts, yields and some of the physico-chemical properties of the products are shown in Table 9.

TABLE 9

| Ref. Ex. No. | Compound No. | | Catalyst | Yield (%) | m.p. (°C.) | $[\alpha]_D$ (Solvent, °C., C %) | IR $\nu_{max}$ cm$^{-1}$ |
|---|---|---|---|---|---|---|---|
| 32 | 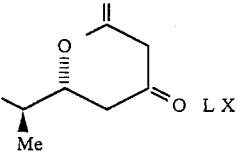 | L X | Eu(fod)$_3$ | 18[1] | 75–80 | +89.7° (DMSO, 27, 0.31) | (KBr) 3290, 1680, 1655, 1565, 1545 |
| 33 | 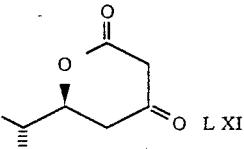 | L XI | Eu(fod)$_3$ | 41 | 147–149 | −114.1° (Chloroform, 23, 0.44) | (KBr) 3360, 2980, 1675, 1615, 1580 |
| 34 | 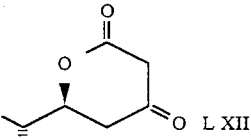 | L XII | Eu(fod)$_3$ | 20[1] | 70–85 | −81.1° (DMSO, 26, 0.355) | (KBr) 3290, 1680, 1655, 1565, 1545 |
| 35. | 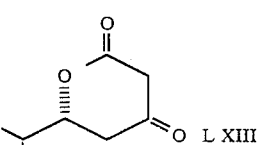 | L XIII | Eu(fod)$_3$ | 27[1] | oily product | —[2] | —[2] |
| 36 | 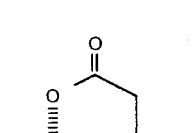 | L XIV | SnCl$_2$ | 17[1] | 155–159 | +106.2° (Chloroform, 24, 0.565) | (KBr) 3330, 2940, 1695, 1655, 1500 |
| 37 | 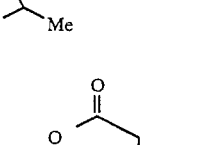 | L XV | Eu(fod)$^3$ | 21 | 146–148 | +3.9° (Chloroform, 23, 0.44) | (KBr) 3300, 2970, 1710, 1665, 1580 |
| 38 | 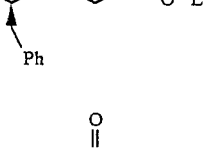 | L XVI | SnCl$_2$ | 10[1] | 140–142 | +79.3° (Chloroform, 24, 0.28) | (Neat) 3420, 1740–1650, 1615, 1500 |

TABLE 9-continued

| Ref. Ex. No. | Compound No. | | Catalyst | Yield (%) | m.p. (°C.) | $[\alpha]_D$ (Solvent °C. C %) | IR $\nu_{max}$ cm$^{-1}$ |
|---|---|---|---|---|---|---|---|
| 39 | 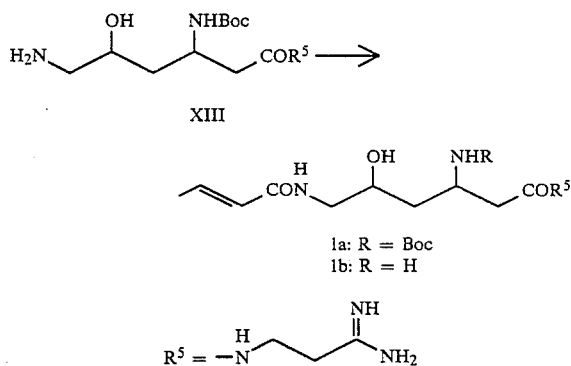 | LXVII | SnCl$_2$ | 20[(1)] | oily product | —[(2)] | (Neat) 3320 2920 1720– 1680 |

[(1)]Corresponding amino acid aldehyde was prepared by subjecting corresponding amino acid alcohol to oxidation with pyridine-SO$_3$/DMSO, and used in situ. Yields are shown in terms of the overall yields from alcohol.
[(2)]not determined

EXAMPLE 29

$$H_2N\diagup\underset{XIII}{\overset{OH}{\diagdown}}\diagup\underset{}{\overset{NHBoc}{\diagdown}}\diagup COR^5 \longrightarrow$$

$$\diagup\diagdown\underset{}{\overset{H}{CON}}\diagup\underset{}{\overset{OH}{\diagdown}}\diagup\underset{}{\overset{NHR}{\diagdown}}\diagup COR^5$$

1a: R = Boc
1b: R = H $$R^5 = -\underset{}{\overset{H}{N}}\diagup\diagdown\underset{}{\overset{NH}{\overset{\|}{C}}}NH_2$$

Step A (XIII→1a)

In DMF (3 ml) was suspended dihydrochloride of Compound XIII (250 mg). To the suspension were added under ice-cooling Et$_3$N (0.124 ml), crotonic acid (61 mg), HOBT (96 mg) and DCC (146 mg). The mixture was stirred for 30 minutes, then for six hours at room temperature. The reaction mixture was subjected to filtration. The filtrate was concentrated under reduced pressure. To the residue was added water (50 ml). The solution, after its pH being adjusted to 2.5 with 1N HCl, was washed with ethyl acetate (30 ml×3). The aqueous layer, after its pH being adjusted to 5.7 with 1N NaOH, was concentrated to a volume of about 30 ml. The concentrate was subjected to a column chromatography using Diaion HP-20 (50–100 mesh, 18 ml). The column was washed with water (50 ml), and then eluted with 10% methanol-water (70 ml), 50% methanol-water (50 ml)-N/200 hydrochloric acid (90 ml), successively to collect the respective fractions. Each fraction was subjected to analysis by means of high performance liquid chromatography [mobile phase: 40% methanol · 0.01M phosphoric acid solution (pH 3)]. Fractions showing single peak were collected, concentrated and then lyophilized to obtain hydrochloride of Compound 1a (228 mg) as white powder.

Elemental Analysis: C$_{18}$H$_{33}$N$_5$O$_5$.HCl.0.5H$_2$O. Calcd.: C,48.59; H,7.93; N,15.74; Cl,7.97, Found: C,48.91; H,7.97; N,16.06; Cl,8.01.

Step B (1a→1b)

In CF$_3$CO$_2$H(TFA) (1.8 ml) was dissolved hydrochloride of Compound 1a (180 mg), and the solution was left standing for 30 minutes at room temperature. The solvent was distilled off under reduced pressure, and the residue was treated with ether to obtain powder. The powder was dissolved in water (45 ml), and the solution was allowed to pass through Amberlite IRA-402 (Cl$^-$type) (15 ml). The resin was eluted with water (15 ml). The eluate was concentrated, followed by lyophilization to obtain dihydrochloride of Compound 1b (148 mg) as white powder.

IR$\nu_{max}$ (KBr) cm$^{-1}$:3250, 3070, 1660, 1550.

Elemental Analysis: C$_{13}$H$_{25}$N$_5$O$_3$.2HCl.0.5H$_2$O: Calcd.: C,40.95; H,7.40; N,18.37; Cl,18.60, Found: C,41.21; H,7.52; N,18.36; Cl,18.60.

EXAMPLES 30–73 (TABLE 10)

By the procedure similar to Example 29, dihydrochloride of Compound (XIII) was subjected to acylation (Step A) by using various carboxylic acid (R'CO$_2$H) or its derivatives, then to deprotection reaction (Step B) to obtain compounds of Examples 30–73. The reaction conditions, yields and some of the physico-chemical properties of the products are shown in Table 10.

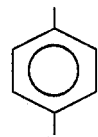

TABLE 10-continued

| | | R = | | | | |
|---|---|---|---|---|---|---|
| 35 | | 6b | evap. washing with Et₂O IRA-402(Cl⁻) lyophilization | 72 mg | | H 6.91 (6.76) N 15.67 (15.65) Cl 16.30 (15.85) |
| | | R = ―CH₂―C₆H₄―OH | | | | |
| 36 | A | XIII → 7a | R'CO₂H (97 mg) HOBT (115 mg) DCC (176 mg) Et₃N (148 μl) DMF (4 ml) 0° C. 0.5 hr. r.t. 7 h washing with EtOAc HP-20 lyophilization | 300 mg → 265 mg | —¹ | C₂₀H₃₇N₅O₅.HCl.0.5H₂O C 50.53 (50.79) H 8.49 (8.31) N 14.71 (14.81) |
| | | R' = ―CH₂CH₂CH=CHCH₂Me | | | | |
| | B | 7a → 7b | TFA (2 ml) r.t. 0.5 hr treatment with Et₂O IRA-402(Cl⁻) lyophilization | 248 mg → 208 mg | 3250 3060 1660 1545 | C₁₅H₂₈N₅O₃.2HCl.0.5H₂O C 43.69 (44.01) H 7.90 (7.88) N 16.68 (17.11) Cl 17.12 (17.32) |
| | | R = Me ¹not measured (hereinafter, same abbreviation is used hereinafter) | | | | |
| 37 | A | XIII → 8a | maleic anhydride (302 mg) NaHCO₃ (3.0 g) H₂O 100 ml r.t. 1 hr. pH 8 neutralization, HP-20 lyophilization | 588 mg (purity 69%) → 296 mg | — | C₁₈H₃₁N₅O₇.1.5H₂O C 47.06 (47.36) H 7.68 (7.51) N 15.18 (15.34) |
| | | R' = HO₂C―CH=CH― | | | | |
| | B | 8a → 8b | TFA (0.5 ml) r.t. 30 min evap. washing with Et₂O IRA-402(Cl⁻) lyophilization | 143 mg → 128 mg | — | C₁₃H₂₃N₅O₄.2HCl.1.3H₂O C 38.44 (38.30) H 6.27 (6.33) N 17.42 (17.18) Cl 17.00 (17.39) |
| | | R' = HO₂C―CH=CH― | | | | |
| | A | XIII → 9a | R'CO₂H 38 HOBT (115 mg) DCC (176 mg) Et₃N (148 μl) DMF (4 ml) 0° C. 0.5 h, r.t. 7 hr washing with EtOAc HP-20 lyophilization | 300 mg → 280 mg | — | C₂₀H₃₇N₅O₅.HCl.0.5H₂O C 50.84 (50.79) H 8.38 (8.31) N 14.61 (14.81) |
| | | R' = ―CH₂CH₂CH=CHCH₂Me | | | | |

TABLE 10-continued

| | | | | | | |
|---|---|---|---|---|---|---|
| | B | 9a → 9b<br>R = Me | TFA (2 ml)<br>r.t. 0.5 hr<br>treatment with Et$_2$O<br>IRA-402(Cl$^-$)<br>lyophilization | 264 mg<br>→<br>223 mg | 3270<br>3060<br>1640<br>1540 | C$_{15}$H$_{29}$N$_5$O$_3$.2HCl.0.5H$_2$O<br>C 43.95 (44.01)<br>H 8.20 (7.88)<br>N 17.18 (17.11)<br>Cl 16.89 (17.32) |
| 38 | A | XIII → 10a<br>R' = —(CH$_2$)$_{14}$CH$_3$ | R'CO$_2$H (218 mg)<br>HOBT (115 mg)<br>DCC (176 mg)<br>Et$_3$N (148 μl)<br>DMF (5 ml)<br>0° C. 1 hr, r.t. 25 h<br>Washing with EtOAc<br>HP-20<br>lyophilization | 300 mg<br>→<br>275 mg | — | C$_{30}$H$_{59}$N$_5$O$_5$.HCl.H$_2$O<br>C 57.66 (57.72)<br>H 10.19 (10.01)<br>N 11.08 (11.22) |
| | B | 10a → 10b<br>R = —(CH$_2$)$_{14}$CH$_3$ | TFA (2 ml)<br>r.t. 0.5 hr<br>treatment with Et$_2$O<br>IRA-402(Cl$^-$)<br>lyophilization | 258 mg<br>→<br>195 mg | 3270<br>3070<br>2920<br>2855<br>1640<br>1540 | C$_{26}$H$_{51}$N$_5$O$_3$.2HCl.H$_2$O<br>C 53.74 (53.56)<br>H 9.62 (9.89)<br>N 12.15 (12.49)<br>Cl 11.83 (12.65) |
| 39 | A | XIII → 11a<br>R' =  | R'CO$_2$H (338 mg)<br>HOBT (162 mg)<br>DCC (247 mg)<br>Et$_3$N (209 μl)<br>DMF (5 ml)<br>0° C. 0.5 hr, r.t. 7.5 h<br>washing with EtOAc—Et$_2$O<br>HP-20<br>lyophilization | 422 mg<br>→<br>552 mg | — | C$_{30}$H$_{41}$N$_5$O$_7$.HCl.H$_2$O<br>C 56.32 (56.46)<br>H 6.88 (6.95)<br>N 11.05 (10.97) |
| | B | 11a → 11b<br>R =  | 0.01N HCl (30 ml)<br>Concentration<br>to dryness (6 times)<br>HP-20<br>lyophilization | 300 mg<br>→<br>214 mg | 3250<br>3060<br>1710<br>1660<br>1540 | C$_{26}$H$_{33}$N$_5$O$_5$.2HCl.H$_2$O<br>C 52.93 (53.24)<br>H 6.37 (6.36)<br>N 12.16 (11.94)<br>Cl 13.17 (12.09) |
| 40 | B | 11a → 12b<br>R =  | TFA (2 ml)<br>r.t. 30 min<br>treatment with Et$_2$O<br>IRA-402(Cl$^-$)<br>lyophilization | 220 mg<br>→<br>129 mg | 3370<br>3060<br>1640<br>1550 | C$_{13}$H$_{23}$N$_5$O$_5$.HCl.H$_2$O<br>C 40.35 (40.68)<br>H 6.68 (6.83)<br>N 17.91 (18.25)<br>Cl 13.41 (9.24) |

TABLE 10-continued

| | | | | | | |
|---|---|---|---|---|---|---|
| 41 | A | XIII → 13a  R' = HO₂C— [cyclohexene with CO2H] | (Z,Z)—Muconic acid (226.5 mg) HOBT (172 mg) DCC (263 mg) Et₃N (0.22 ml) DMF (21 ml) r.t. 16 hr hereinafter same as 31A | 429.7 mg → 125 mg | — | C₂₀H₃₃N₅O₇·2H₂O C 48.99 (48.87) H 7.68 (7.59) N 14.03 (14.25) |
| | B | 13a → 13b  R = HO₂C— [cyclohexene with CO2H] | TFA (0.3 ml) r.t. 30 min evap. washing with Et₂O IRA-402(Cl⁻) lyophilization | 109 mg → 92 mg | 1750 1700– 1640 | C₁₅H₂₅N₅7₆·5.2HCl·2.0H₂O C 39.07 (38.80) H 6.76 (6.73) N 14.81 (15.08) Cl 15.99 (15.27) |
| 42 | A | XIII → 14a  R' = Ph₂CHOC(=O)— [cyclohexene] | RCO₂H (188 mg) HOBT (82.2 mg) DCC (125.5 mg) Et₃N (0.105 ml) DMF (6.8 ml) r.t. 15 hr Hereinafter same as 31A | 205 mg → 268 mg | — | C₃₃H₄₃N₅O₇·HCl·1.5H₂O C 57.93 (57.84) H 6.70 (6.91) N 10.28 (10.22) |
| | B | 14a → 14b  R = Ph₂CHOC(=O)— [cyclohexene] | 0.5N HCl (20 ml) i-BuOH (1.0 ml) EtOH (2.0 ml) r.t. 28 hr 0° C. 15 hr neutralization, HP-20 lyophilization | 208 mg → 104 mg | 1700 1660 | C₂₈H₃₆N₅O₅·2HCl·2.4H₂O C 52.75 (52.73) H 6.73 (6.61) N 11.09 (10.98) Cl 11.50 (11.12) |
| 43 | A | XIII → 15a  R' = ClCH₂CH(*D¹)— NHBoc | R'CO₂H (224 mg) EEDQ (281 mg) DMF (3 ml) r.t. 18 hr evaporation of DMF CHP-20P 50% MeOH—H₂O, lyophilization | 331 mg → 130 mg | 1690 1650 (sh) 1520 | C₂₂H₄₁N₆O₇·HCl·0.5H₂O C 48.11 (48.30) H 7.99 (7.92) N 15.08 (15.36) |
| | B | 15a → 15b  R = ClCH₂CH(*D)— NH₂ | TFA (5 μl) r.t. 40 min evap. washing with ET₂O IRA-402(Cl⁻) lyophilization | 120 mg → 102 mg | 1690 1645 1510 | C₁₂H₂₅ClN₆O₃·3HCl·0.5H₂O C 31.52 (31.66) H 6.21 (6.42) N 18.23 (18.46) |

[*D: D-compound (hereinafter the same applies)

TABLE 10-continued

| | | | | | | |
|---|---|---|---|---|---|---|
| 44 | A | XIII → 16a<br>R' = HO——CH(+l)—NHCbz | R'CO₂H (301 mg)<br>EEDQ (281 mg)<br>DMF (3 ml)<br>r.t. 18 hr<br>evap. washing with Et₂O<br>CHP-20P, 50% MeOH—H₂O<br>lyophilization | 331 mg<br>→<br>130 mg | 1715<br>(sh)<br>1690<br>1650<br>1515 | C₃₀H₄₂N₆O₈.HCl.H₂O<br>C 53.88 (53.85)<br>H 6.92 (6.78)<br>N 12.31 (12.56) |
| | B | 16a → 16b<br>R = HO—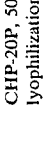—CH(+l)—NH₂ | ¹10% Pd—C (120 mg)<br>MeOH (5 ml), H₂<br>3 hr. evap.<br>²TFA (3 ml)<br>r.t. 40 min. evap.<br>IRA-402(Cl⁻)<br>lyophilization | 120 mg<br>→<br>23 mg | 1690<br>1645<br>1520 | C₁₇H₂₈N₈O₄.3HCl.H₂O<br>C 40.00 (40.21)<br>H 6.52 (6.55)<br>N 16.23 (16.55) |
| 45 | A | XIII → 17a<br>R' = H₂N—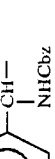 | R'CO₂H (402 mg)<br>HOBT (271 mg)<br>DDC (413 mg)<br>DMF (3 ml), 15 hr, r.t.<br>evap. CHP-20P column<br>50% MeOH—H₂O | 331 mg<br>→<br>500 mg | 1705<br>1680<br>1515 | C₂₀H₃₄O₆N₈S.HCl.1.5H₂O<br>C 41.25 (41.55)<br>H 6.70 (6.63)<br>N 19.09 (19.38) |
| | B | 17a → 17b<br>= H₂N— | TFA (3 ml)<br>r.t. 1 hr<br>evap. washing with Et₂O<br>CHP-20P, H₂O<br>lyophilization | 50 mg<br>→<br>200 mg | 1690<br>1520 | C₁₅H₂₀N₈O₄.3HCl.2H₂O<br>C 34.05 (34.13)<br>H 6.18 (6.30)<br>N 21.12 (21.23) |
| 46 | A,B | XIII → 18b<br>R = Ph₂CHO₂C— | R'CO₂H (185 mg)<br>HOBT (81 mg)<br>DCC (124 mg)<br>24 hr, r.t. evap. 50%<br>extraction with<br>50% EtOH<br>CHP-20P, 1/100N.HCl<br>50% EtOH,<br>lyophilization | 202 mg<br>→<br>237 mg | 1715<br>(sh)<br>1690<br>1650<br>1620<br>1550 | C₂₈H₃₅N₅O.2HCl.H₂O<br>C 61.20 (61.31)<br>H 7.05 (7.17)<br>N 12.63 (12.77) |
| 47 | B | 18b → 19b | TFA (2 ml)<br>r.t. 30 min. evap. | 138 mg<br>→ | 1730–<br>1610 | C₁₅H₂₆N₅O₅.2CF₃CO₂H.H₂O<br>C 38.07 (37.94) |

TABLE 10-continued

| | | | | | | | |
|---|---|---|---|---|---|---|---|
| 48 | A | XIII → 20a R' = MeO₂C | R = HO₂C ⁀⁀ | IRA-402(Cl⁻), H₂O lyophilization | 78 mg | 1550 | H 4.85 (4.86) N 11.86 (11.65) |
| | | | R' = MeO₂C ⁀⁀ | R'CO₂H (52 mg) EEDQ (89 mg) Et₃N (63 μl) DMF (3 ml) r.t. 20 hr, 60° C.,10 hr evap. 1N—HCl(pH 3.0) CHP-20P, 20% EtOH/H₂O lyophilization | 122 mg → 107 mg | 1720 1690 1655 1530 | C₂₁H₃₅N₅O₇.HCl.0.5H₂O C 49.11 (48.98) H 7.35 (7.24) N 13.39 (13.60) |
| | B | 20a → 20b R = MeO₂C | | TFA (2 ml) 0°C., 30 min evap. IRA-402(Cl⁻) H₂O, lyophilization | 106 mg → 93 mg | 1720 (sh) 1690 1650 | C₁₆H₂₇N₅O₇.HCl.0.5H₂O C 42.52 (42.58) H 6.56 (6.70) N 15.23 (15.52) |
| 49 | A | XIII → 21a R' = nC₈H₁₇O₂C | R = nC₈H₁₇O₂C ⁀⁀ | R'CO₂H (84 mg) EEDQ (89 mg) Et₃N (63 μl) DMF (3 ml) 60° C., 6 hr, evap. 1N—HCl(pH 3.0), CHP-20P 50% EtOH—H₂O lyophilization | 122 mg → 110 mg | 1710 (sh) 1690 1655 1535 | C₂₀H₄₉N₅O₅.HCl.1.5H₂O C 53.04 (53.28) H 8.70 (8.46) N 10.89 (11.10) |
| | B | 21a → 21b R = nC₈H₁₇O₂C | | TFA (2 ml) 0° C.,45 min evap. IRA-402(Cl⁻) H₂O lyophilization | 108 mg → 69 mg | 1720 (sh) 1690 1655 | C₂₃H₄₁N₅O₅.2HCl.2H₂O C 47.62 (47.91) H 7.97 (8.22) N 11.96 (12.15) |
| 50 | A | XIII → 22a R' = PhCH₂O₂C | R' = PhCH₂O₂C ⁀⁀ | R'CO₂H (77 mg) EEDQ (89 mg) Et₃N (63 μl) DMF (3 ml) 60° C., 4 hr, evap. 1N—HCl(pH 3.0),CHP-20P 40% EtOH—H₂O lyophilization | 122 mg → 124 mg | 1710 (sh) 1690 1655 1625 1520 | C₂₇H₃₀N₅O₇.HCl.H₂O C 54.22 (54.04) H 6.88 (7.05) N 11.73 (11.67) |
| | B | 22a → 22b R = PhCH₂O₂C | | TFA (2 ml) 0° C., 30 min, evap. IRA-402(Cl⁻),H₂O conc., CHP-20P, 20% EtOH—H₂O lyophilization | 123 mg → 100 mg | 1710 (sh) 1690 1650 1550 | C₂₂H₃₁N₅O₅.2HCl.1.5H₂O C 48.59 (48.44) H 6.22 (6.65) N 12.73 (12.84) |
| 51 | A | XIII → 23a | | R'CO₂H (62 mg) EEDQ (119 mg) Et₃N (84 μl) | 162 mg → 129 mg | 1710 (sh) 1690 | C₂₂H₃₀N₅O₅.HCl.H₂O C 52.13 (52.01) H 8.22 (8.33) |

TABLE 10-continued

| | | | | | | | |
|---|---|---|---|---|---|---|---|
| | | | | | | | N 13.80 (13.78) |
| 52 | B | 23a → 23b | R' = Me, Me (structure) | DMF (3 ml) 55° C., 5 hr, evap. 1N—HCl(pH 2.5),CHP-20P 50% EtOH—H₂O lyophilization | 128 mg → 85 mg | 1650 1535 | $C_{17}H_{31}N_5O_3 \cdot 2HCl \cdot 1.5H_2O$<br>C 45.13 (45.03)<br>H 8.09 (8.00)<br>N 15.25 (15.45) |
| | A | XIII → 24a | R' = Me (structure with Me) | R'CO₂H (62 mg) EEDQ (119 mg) Et₃N (84 μl) DMF (3 ml) 55° C., 5 hr, evap. 1N—HCl(pH 2.5), CHP-20P 50% EtOH—H₂O lyophilization | 162 mg → 127 mg | 1710 (sh) 1690 1650 1530 | $C_{22}H_{30}N_5O_5 \cdot HCl \cdot 12H_2O$<br>C 51.69 (51.64)<br>H 8.21 (8.35)<br>N 13.57 (13.69) |
| | B | 24a → 24b | R = Me (structure with Me) | TFA (2 ml) r.t. 50 min, evap. IRA-402(Cl⁻), H₂O conc., CHP-20P, 15% EtOH—H₂O lyophilization | 126 mg → 93 mg | 1690 1655 1545 | $C_{17}H_{31}N_5O_3 \cdot 2HCl \cdot 1.5H_2O$<br>C 44.92 (45.03)<br>H 8.50 (8.00)<br>N 15.33 (15.45) |
| 53 | A | XIII → 25a | R' = Ph (structure) | R'CO₂H (77 mg) EEDQ (119 mg) Et₃N (84 μl) DMF (3 ml) 60° C., 6 hr, evap. 1N—HCl(pH 3.0), CHP-20P 50% EtOH—H₂O lyophilization | 162 mg → 151 mg | 1710 (sh) 1690 1650 1610 1530 | $C_{25}H_{37}N_5O_5 \cdot 2HCl \cdot 1.5H_2O$<br>C 54.51 (54.49)<br>H 7.36 (7.50)<br>N 12.88 (12.71) |
| | B | 25a → 25b | R = Ph (structure) | TFA (2 ml) r.t. 1 hr, evap. IRA-402(Cl⁻), H₂O conc., CHP-20P 15% EtOH—H₂O lyophilization | 150 mg → 96 mg | 1690 1645 1610 1540 | $C_{20}H_{29}N_5O_3 \cdot 2HCl \cdot 1.5H_2O$<br>C 49.10 (49.28)<br>H 7.03 (7.03)<br>N 14.02 (14.37) |

TABLE 10-continued

| | | | | | |
|---|---|---|---|---|---|
| 54 | A | XIII<br>↓<br>26a<br>R' = ![structure with Ph]| R'CO$_2$H (77 mg)<br>EEDQ (119 mg)<br>Et$_3$N (84 μl)<br>DMF (3 ml)<br>55° C., 10 hr, evap.<br>1N—HCl(pH 2.5), CHP-20P<br>50% EtOH—H$_2$O<br>lyophilization | 162 mg<br>→<br>171 mg | 1690<br>1650<br>1530 | C$_{25}$H$_{37}$N$_5$O$_5$.HCl.H$_2$O<br>C 55.18 (55.39)<br>H 7.57 (7.44)<br>N 12.86 (12.92) |
| | B | 26a<br>↓<br>26b<br>R = ![structure with Ph] | TFA (2 ml)<br>r.t. 1 hr, evap.<br>IRA-402(Cl$^-$), H$_2$O<br>lyophilization | 170 mg<br>→<br>104 mg | 1690<br>1645<br>1605<br>1545 | C$_{20}$H$_{29}$N$_5$O$_3$.2HCl.1.5H$_2$O<br>C 49.05 (49.28)<br>H 7.15 (7.03)<br>N 14.20 (14.37) |
| 55 | A | XIII<br>↓<br>27a<br>R = F$_2$CHSCH$_2$— | R'CO$_2$H (213 mg)<br>HOBT (162 mg)<br>DCC (248 mg)<br>Et$_3$N (210 mg)<br>DMF (3 ml)<br>r.t. 24 hr, evap.<br>0.5N—HCl(pH 3.0),<br>CHP-20P, 30% EtOH—H$_2$O<br>lyophilization | 404 mg<br>→<br>600 mg | 1710<br>(sh)<br>1680<br>1530 | C$_{17}$H$_{31}$F$_2$N$_5$O$_3$S.HCl<br>C — (41.50)<br>H — (6.56)<br>N — (14.23) |
| | B | 27a<br>↓<br>27b<br>R = F$_2$CHSCH$_2$— | TFA (6 ml)<br>r.t. 1 hr, evap.<br>IRA-402(Cl$^-$), H$_2$O<br>conc., CHP-20P, H$_2$O<br>lyophilization | 580 mg<br>→<br>362 mg | 1690<br>1675<br>1520 | C$_{12}$H$_{23}$F$_2$N$_5$O$_3$S.2HCl.H$_2$O<br>C 32.64 (32.29)<br>H 6.21 (6.10)<br>N 16.00 (15.69) |
| 56 | A | XIII<br>↓<br>28a<br>R' = ![structure CH$_3$CH—CH—<br>\*S \*D$^1$<br>OH NHCON] | R'CO$_2$H (517 mg)<br>HOBT (243 mg)<br>DCC (372 mg)<br>Et$_3$N (310 mg)<br>DMF (5 ml)<br>r.t. 40 hr, evap.<br>ÅN—HCl (pH 3.0),<br>CHP-20P, 20% MeOH—H$_2$O<br>lyophilization | 606 mg<br>→<br>300 mg | 1710,<br>1670,<br>1515 | C$_{25}$H$_{44}$N$_8$O$_9$.HCl.1.5H$_2$O<br>C 45.04 (45.21)<br>H 7.40 (7.28)<br>N 16.74 (16.87) |

TABLE 10-continued

| | | | | | |
|---|---|---|---|---|---|
| B | 28a → 28b | R = CH$_3$CH—CH— OH NHCON 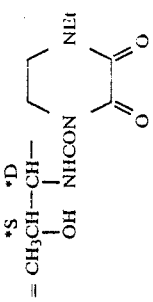 *S *D NEt O O | TFA (3 ml) r.t. 1 hr, evap IRA-402(Cl⁻), H$_2$O conc., CHP-20P 20% MeOH—H$_2$O lyophilization | 280 mg → 127 mg | 1690 1665 1520 | C$_{20}$H$_{36}$N$_6$O$_7$.2HCl.1.5H$_2$O C 40.23 (40.00) H 6.59 (6.86) N 18.42 (18.66) |

*S: steric configuration shown by R or S (The same shall apply hereinafter.)
*D: steric configuration shown by D or L (The same shall apply hereinafter.)

| 57 | A | XIII → 29a R' = CbzNHNCH$_2$— | Me | R'CO$_2$H (429 mg) HOBT (243 mg) DCC (371 mg) Et$_3$N (310 mg) DMF (5 ml) r.t. 72 hr, evap. 0.5N—HCl (pH 3.0), CHP-20P, 50% MeOH—H$_2$O lyophilization | 606 mg → 900 mg | 1710 (sh) 1670 1530 | C$_{25}$H$_{41}$N$_7$O$_7$.HCl.H$_2$O C 49.58 (49.54) H 7.6 (7.32) N 16.20 (16.18) |
| 58 | B | 29a → 29b R = CbzNHNCH$_2$— | Me | TFA (6 ml) r.t. 1 hr, evap IRA-402(Cl⁻), H$_2$O conc., CHP-20P 20% MeOH—H$_2$O lyophilization | 880 mg → 492 mg | 1700 1670 1520 | C$_{20}$H$_{33}$N$_7$O$_5$.2HCl.2H$_2$O C 43.10 (42.86) H 7.01 (7.01) N 17.53 (17.49) |
| | B | 29b → 30b R = H$_2$NNCH$_2$— | Me | H$_2$O (5 ml) 10% Pd—C (150 mg) H$_2$, 1 hr, filtration IRA-402(Cl⁻), H$_2$O lyophilization | 280 mg → 234 mg | 1690 1660 1530 | C$_{12}$H$_{27}$N$_7$O$_3$.3HCl.2H$_2$O C 31.10 (31.14) H 7.20 (7.40) N 21.11 (21.19) |
| 59 | A | XIII → 31a R' = Me \ Me / =NOCH$_2$CH— NHBoc*D | | R'CO$_2$H (580 mg) HOBT (270 mg) DCC (412 mg) Et$_3$N (310 mg) DMF (5 ml) r.t. 24 hr, evap. 1N—HCl(pH 3.0),CHP-20P 50% MeOH—H$_2$O lyophilization | 606 mg → 600 mg | 1710 (sh) 1690 1650 1520 | C$_{25}$H$_{47}$N$_7$O$_8$.HCl.H$_2$O C 47.84 (47.80) H 7.92 (8.02) N 15.66 (15.61) |

TABLE 10-continued

| | | | | | |
|---|---|---|---|---|---|
| | B | 31a → 31b<br>R = $\begin{array}{c}Me\\ \diagup\\ Me\end{array}$ =NOCH$_2$CH—*D<br>$\quad\quad\quad\quad\quad\quad\quad\quad$ NH$_2$ | TFA (6 ml)<br>r.t. 1 hr, evap.<br>IRA-402(Cl$^-$), H$_2$O<br>conc., CHP-20P, H$_2$O<br>lyophilization | 580 mg<br>→<br>348 mg | 1690<br>1645<br>1520 | C$_{15}$H$_{31}$N$_7$O$_4$.3HCl.H$_2$O<br>C 35.69 (35.97)<br>H 7.12 (7.24)<br>N 19.28 (19.58) |
| 60 | A | XIII → 32a<br>R' = ClCH$_2$COCH$_2$CH—*L'<br>$\quad\quad\quad\quad\quad$ ‖ $\quad$ NHBoc$^l$<br>$\quad\quad\quad\quad\quad$ O | R'CO$_2$H (447 mg)<br>HOBT (243 mg)<br>DCC (371 mg)<br>Et$_3$N (350 mg)<br>DMF (5 ml)<br>r.t. 4 days, evap.<br>0.5N—HCl(pH 3.0),<br>CHP-20P, 50% MeOH—H$_2$O<br>lyophilization | 606 mg<br>800 mg | 1705<br>1685<br>1520 | C$_{23}$H$_{43}$N$_7$O$_8$.HCl.0.5H$_2$O<br>C 45.39 (45.50)<br>H 7.52 (7.47)<br>N 16.01 (16.15) |
| | B | 32a → 32b<br>R = H$_2$NCOCH$_2$CH—*L<br>$\quad\quad\quad\quad$ ‖ $\quad$ NH$_2$<br>$\quad\quad\quad\quad$ O | TFA (6 ml)<br>r.t. 1 hr, evap.<br>IRA-402(Cl$^-$), H$_2$O<br>conc., CHP-20P, H$_2$O<br>lyophilization | 780 mg<br>→<br>490 mg | 1690<br>1650<br>1520 | C$_{13}$H$_{27}$N$_7$O$_5$.3HCl.2H$_2$O<br>C 30.64 (30.81)<br>H 6.59 (6.76)<br>N 19.26 (19.35) |
| 61 | A | XIII → 33a<br>R' = ClCH$_2$CONHCO—CH$_2$CH—*L<br>$\quad\quad\quad\quad\quad\quad\quad\quad$ ‖ $\quad\quad$ NHBoc$^l$<br>$\quad\quad\quad\quad\quad\quad\quad\quad$ O | R'CO$_2$H (535 mg)<br>HOBT (223 mg)<br>DCC (341 mg)<br>Et$_3$N (310 mg)<br>DMF (5 ml)<br>r.t. 3 days, evap.<br>0.5N—HCl(pH 3.0),<br>CHP-20P, 50% MeOH—H$_2$O<br>lyophilization | 606 mg<br>→<br>200 mg | 1710,<br>1680,<br>1520 | C$_{25}$H$_{44}$ClN$_7$O$_{10}$.HCl.0.5H$_2$O<br>C 43.82 (43.93)<br>H 6.90 (6.78)<br>N 14.18 (14.34) |
| | B | 33a → 33b<br>R = ClCH$_2$CONHCO—CH$_2$CH—*L<br>$\quad\quad\quad\quad\quad\quad\quad\quad$ ‖ $\quad\quad$ NH$_2$<br>$\quad\quad\quad\quad\quad\quad\quad\quad$ O | TFA (2 ml)<br>r.t. 1 hr, evap.<br>IRA-402(Cl$^-$), H$_2$O<br>conc., CHP-20P, H$_2$O | 198 mg<br>→<br>138 mg | 1690<br>1520 | C$_{15}$H$_{20}$ClN$_7$O$_8$.100.5 3HCl.0.5H$_2$O<br>C 32.09 (32.39)<br>H 5.95 (5.80)<br>N 17.43 (17.63) |
| 62 | A | XIII → 34a | R'CO$_2$H (340 mg)<br>HOBT (152 mg)<br>DCC (232 mg) | 404 mg<br>→<br>103 mg | 1710<br>(sh)<br>1680 | C$_{25}$H$_{40}$N$_7$O$_8$S.HCl.H$_2$O<br>C 44.93 (44.87)<br>H 6.63 (6.48) |

$^l$•L: L-compound (The same shall apply hereinafter.)

TABLE 10-continued

| | | L* | | | | |
|---|---|---|---|---|---|---|
| 63 | B | R' = H₂NSO₂CH₂CH—NHCbz | Et₃N (233 mg) DMF (5 ml) r.t. 4 days, evap. 0.5N—HCl(pH 3.0), CHP-20P, 50% MeOH—H₂O lyophilization | | 1520 | N 14.48 (14.65) |
| | | 34a → 34b R = H₂NSO₂CH₂CH—*L NHCbz | TFA (2 ml) r.t. 1 hr, evap. IRA-401(Cl⁻), H₂O conc., CHP-20P, 20% MeOH—H₂O lyophilization | 100 mg → 48 mg | 1690 1520 | $C_{20}H_{32}N_7O_7S.2HCl.H_2O$ C 39.82 (39.67) H 5.81 (5.99) N 16.40 (16.16) |
| 63 | A | XIII → 35a R' = Me | R'CO₂H (33 mg) Et₃N (50 μl) HOBT (37 mg) DCC (56 mg) DMF (2 ml) r.t. 20 hr, evap. 1N—HCl(pH 3.0), CHP-20P, 50% EtOH—H₂O lyophilization | 97 mg → 121 mg | 1710 1690 1650 1545 | $C_{22}H_{37}N_5O_5.HCl.H_2O$ C 52.10 (52.22) H 7.77 (7.97) N 13.91 (13.84) |
| | B | 35a → 35b R = Me | TFA (2 ml) r.t. 1.5 hr, evap CHP-20P, 30% EtOH—H₂O, conc., IRA-401(Cl⁻) H₂O lyophilization | 116 mg → 54 mg | 1690 1650 1600 1550 | $C_{17}H_{20}N_5O_3.2HCl.1.5H_2O$ C 46.14 (46.27) H 5.36 (5.48) N 15.90 (15.87) |
| 64 | A,B | XIII → 36b PhCH₂OCO R,R' = Me Me | R'CO₂H (202 mg) EEDQ (149 mg) Et₃N (105 μl) DMF (3 60° C., 6 hr, evap. CHP-20P, 1/100N—HCl— 50%, EtOH lyophilization | 202 mg → 140 mg | 1710 (sh) 1690 1640 1605 1530 | $C_{30}H_{39}N_5O_5.2HCl.1.5H_2O$ C 55.14 (55.47) H 6.75 (6.83) N 10.85 (10.78) |
| 65 | A | XIII → 37a R' = Me | R'CO₂H (61 mg) HOBT (65 mg) DCC (99 mg) Et₃N (84 μl) r.t., 24 hr, evap. 1N—HCl(pH 3.0), CHP-20P, 40% EtOH—H₂O lyophilization | 162 mg → 226 mg | 1710 (sh) 1650 1530 | $C_{21}H_{37}N_5O_3.HCl.0.5H_2O$ C 52.11 (52.00) H 8.01 (8.10) N 14.59 (14.44) |
| | B | 37a → | EtOH (10 ml) 1N—HCl (1 ml) | 226 mg → | 1685 1645 | $C_{18}H_{20}N_6O_3.2HCl.2.5H_2O$ C 42.27 (42.02) |

TABLE 10-continued

| | | R = | | | | |
|---|---|---|---|---|---|---|
| 66 | A | XIII → 38a<br>R' = H<br>R = Me | (structure: Me, Me alkenyl) | 138 mg | 1530 | H 7.98 (7.93)<br>N 15.49 (15.31) |
| | | | R'CO₂H (59 mg)<br>HOBT (41 mg)<br>DCC (124 mg)<br>Et₃N (105 μl)<br>DMF (2 ml)<br>r.t. 28 hr, evap.<br>1N—HCl(pH 2.5),<br>CHP-20P, 30% EtOH—H₂O<br>lyophilization | 202 mg<br>→<br>125 mg | 1710 (sh)<br>1690<br>1650<br>1630<br>1545 | C₁₈H₃₃N₅O₃.HCl.2H₂O<br>C 47.01 (47.15)<br>H 7.99 (7.91)<br>N 14.51 (14.47) |
| | B | 38a → R =<br>R' = H | (structure: alkenyl, H) | | | |
| | | | TFA (1.5 ml)<br>r.t., 1 hr, evap.<br>CHP-20P, H₂O<br>lyophilization | 124 mg<br>→<br>99 mg | 1670<br>1550 | C₁₄H₂₅N₅O₃.2CF₃CO₂H<br>C 37.62 (37.57)<br>H 5.80 (5.43)<br>N 12.09 (12.17) |
| 67 | A | XIII → 39a<br>R' = MeS<br>(O)ₙ<br>n = 0; n = 1 = 40:60 | (structure with MeS, alkenyl) | 303 mg<br>→<br>420 mg | 1710 (sh)<br>1695<br>1660<br>1640 | C₂₁H₃₇N₅O₅S.HCl(n = 0)<br>C₂₁H₃₇N₅O₆S.HCl(n = 1)<br>— |
| | | | R'CO₂H (160 mg)<br>HOBT (124 mg)<br>DCC (189 mg)<br>Et₃N (168 μl)<br>DMF (3 ml)<br>r.t. 20 hr, evap<br>1N—HCl(pH 2.5),<br>CHP-20P, 40% EtOH—H₂O<br>lyophilization | | | |
| | B | 39a → 39b<br>R = MeS | | | | |
| | | | TFA (2 ml)<br>r.t., 1 hr, evap.<br>CHP-20P, 5% EtOH—H₂O,<br>conc., IRA-402(Cl⁻),<br>H₂O, lyophilization | 420 mg<br>→<br>130 mg | 1695<br>1670<br>1655<br>1550 | C₁₀H₂₀N₅O₃S.2HCl.H₂O<br>(isolate only sulfide)<br>C 41.18 (41.56)<br>H 7.19 (7.19)<br>N 15.02 (15.14) |
| 68 | A | XIII → 40a<br>R' = MeSO₂ | (structure: MeSO₂, alkenyl) | 162 mg<br>→<br>225 mg | 1710 (sh)<br>1690<br>1660<br>1540 | C₂₁H₃₇N₅O₇S.HCl.1.5H₂O<br>C 44.53 (44.48)<br>H 7.16 (7.29)<br>N 12.18 (12.35) |
| | | | R'CO₂H (84 mg)<br>HOBT (27 mg)<br>DCC (91 mg)<br>Et₃N (84 μl)<br>DMF (2 ml)<br>r.t. 16 hr, evap.<br>1N—HCl(pH 2.5),<br>CHP-20P, 20% EtOH—H₂O<br>lyophilization | | | |
| | B | 40a → | (structure alkenyl) | 220 mg<br>→ | 1690<br>1660 | C₁₆H₂₀N₅O₅S.2HCl.1.5H₂O<br>C 38.11 (38.17) |
| | | | TFA (2 ml)<br>r.t., 1 hr, evap. | | | |

TABLE 10-continued

| | | | | | | | |
|---|---|---|---|---|---|---|---|
| | | | | | 176 mg | | H 6.66 (6.81) |
| | | 40b | | CHP-20P, H₂O, conc. | | | N 13.79 (13.91) |
| | | R = MeSO₂ | | IRA-402(Cl⁻),H₂O | | | |
| | | | | lyophilization | | | |
| 69 | A | XIII |  | R'CO₂H (76 mg) | 203 mg | 1710 | C₂₁H₃₇N₅O₅.HCl.H₂O |
| | | → | | HOBT (34 mg) | → | (sh) | C 50.89 (51.06) |
| | | 41a | | DCC (124 mg) | 231 mg | 1690 | H 8.03 (8.16) |
| | | | | Et₃N (105 μl) | | 1660 | N 14.26 (14.18) |
| | | R' = Me | | DMF (2 ml) | | 1530 | |
| | | | | r.t. 3 days,evap. | | | |
| | | | | 1N—HCl(pH 2.5), | | | |
| | | | | CHP-20P, 40% EtOH—H₂O | | | |
| | | | | lyophilization | | | |
| | B | 41a |  | TFA (2 ml) | 230 mg | 1690 | C₁₆H₂₀N₅O₃.2HCl.H₂O |
| | | → | | anisole (2 ml) | → | 1655 | C 44.41 (44.65) |
| | | 41b | | 0° C., 1.5 hr, evap. | 134 mg | 1545 | H 7.90 (7.73) |
| | | | | CHP-20P, H₂O, conc. | | | N 15.94 (16.27) |
| | | R = Me | | IRA-402(Cl⁻), H₂O | | | |
| | | | | lyophilization | | | |
| 70 | A | XIII |  | R'CO₂H (92 mg) | 162 mg | 1710 | C₂₀H₃₄BrN₅O₅.HCl.0.5H₂O |
| | | → | | HOBT (27 mg) | → | 1650 | C 43.49 (43.68) |
| | | 42a | | DCC (99 mg) | 215 mg | 1530 | H 6.52 (6.60) |
| | | R' = Me | | Et₃N (84 μl) | | | N 12.86 (12.74) |
| | | | | DMF (2 ml) | | | |
| | | | | r.t. 16 hr, evap. | | | |
| | | | | CHP-20P, 40% EtOH—H₂O | | | |
| | | | | lyophilization | | | |
| | B | 42a |  | TFA (2 ml) | 213 mg | 1690 | C₁₅H₂₆BrN₅O₃.2HCl.0.5H₂O |
| | | → | | r.t., 40 min,evap. | → | 1655 | C 36.92 (37.05) |
| | | 42b | | CHP-20P, 5% EtOH—H₂O, | 142 mg | 1550 | H 5.90 (6.01) |
| | | R = Me | | conc., IRA-402(Cl⁻), | | | N 14.21 (14.40) |
| | | | | H₂O, lyophilizaton | | | |
| 71 | A | XIII |  | R'CO₂H (61 mg) | 162 mg | 1710 | C₂₁H₃₇N₅O₅.HCl.H₂O |
| | | → | | HOBT (27 mg) | → | (sh) | C 51.14 (51.06) |
| | | 43a | | DCC (99 mg) | | 1690 | H 8.23 (8.16) |

TABLE 10-continued

| | | | | | | |
|---|---|---|---|---|---|---|
| | | R' = Me | Et$_3$N (84 μl)<br>DMF (2 ml)<br>r.t. 3 days, evap.<br>1N—HCl(pH 2.5),<br>CHP-20P, 30% EtOH—H$_2$O<br>lyophilization | 187 mg | 1640<br>1530 | N 14.13 (14.18) |
| 72 | B | 43a<br>→<br>44a<br>R = Me | TFA (2 ml)<br>r.t., 1 hr, evap.<br>CHP-20P, 5% EtOH—H$_2$O,<br>conc., IRA-402(Cl$^-$),<br>H$_2$O, lyophilization | 186 mg<br>→<br>71 mg | 1690<br>1650<br>1640 | C$_{10}$H$_{20}$N$_5$O$_3$S.2HCl.H$_2$O<br>C 36.60 (36.38)<br>H 6.01 (6.11)<br>N 14.19 (14.14) |
| | A | XIII<br>→<br>44a<br>R' = Me | R'CO$_2$H (61 mg)<br>HOBT (27 mg)<br>DCC (99 mg)<br>Et$_3$N (84 μl)<br>r.t. 16 hr, evap.<br>CHP-20P, 30% EtOH—H$_2$O<br>lyophilization | 162 mg<br>→<br>174 mg | 1710<br>(sh)<br>1690<br>1650<br>1530 | C$_{21}$H$_{37}$N$_5$O$_5$.HCl.1.5H$_2$O<br>C 50.00 (50.14)<br>H 8.13 (8.22)<br>N 14.02 (13.92) |
| | B | 44a<br>→<br>44b<br>R = Me | TFA (2 ml)<br>r.t., 1 hr, evap.<br>CHP-20P, 5% EtOH—H$_2$O,<br>conc., IRA-402(Cl$^-$),<br>H$_2$O, lyophilization | 172 mg<br>→<br>133 mg | 1690<br>1650<br>1590<br>1530 | C$_{16}$H$_{29}$N$_5$O$_3$.2HCl.H$_2$O<br>C 36.40 (36.38)<br>H 6.11 (6.11)<br>N 14.19 (14.14) |
| 73 | A | XIII.2HCl<br>→<br>IIIa<br>R' = Me | R'CO$_2$H (307 mg)<br>Et$_3$N (480 μl)<br>HOBT (369 mg)<br>DCC (563 mg)<br>DMF (10 ml)<br>0° C. 1 hr, r.t., 8 hr,<br>evapo. of DMF, HP-20,<br>lyophilization | 964 mg<br>→<br>999 mg | 3270<br>1660<br>1515 | C$_{20}$H$_{35}$N$_5$O$_5$.HCl.0.5H$_2$O<br>C 50.83 (51.00)<br>H 8.01 (7.92)<br>N 14.44 (14.87)<br>Cl 7.57 (7.53) |
| | B | IIIa<br>→ IIIb<br>R = Me | TFA (5 ml)<br>r.t., 0.5 hr<br>treatment with Et$_2$O<br>IRA-402(Cl$^-$),H$_2$O<br>lyophilization | 853 mg<br>→<br>725 mg | 3250<br>1660<br>1550 | C$_{15}$H$_{27}$N$_5$O$_3$.2HCl.0.5H$_2$O<br>C 44.35 (44.23)<br>H 7.83 (7.42)<br>N 17.28 (17.19)<br>Cl 17.59 (17.41) |

EXAMPLE 74

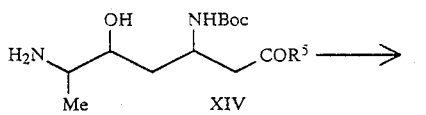

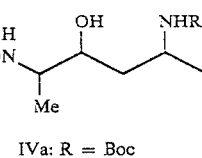

IVa: R = Boc
IV: R = H

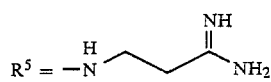

Step A (XIV→IVa)

To a suspension of dihydrochloride of Compound XIV (180 mg) in DMF (2 ml) were added under ice-cooling Et$_3$N (86 μl), sorbic acid (56 mg), HOBT (67 mg) and DCC (103 mg). The reaction was allowed to proceed in a manner similar to the Step A of Example 29 to obtain hydrochloride of Compound IVa (178 mg) as white powder.

IR$\nu_{max}$ (KBr) cm$^{-1}$:3260, 1660, 1510.

Elemental Analysis: $C_{20}H_{35}N_5O_5 \cdot HCl \cdot H_2O$: Calcd.: C,51.06; H,8.16; N,14.18; Cl,7.18, Found: C,51.00; H,8.27; N,14.27; Cl,7.36.

Step B (IVa→IV)

In TFA (1.5 ml) was dissolved hydrochloride of Compound IVa (145 mg). The reaction was allowed to proceed in a manner similar to the Step B of Example 29 to obtain dihydrochloride of Compound IV (126 mg) as white powder. This product was in complete agreement in the data of physicochemical properties with Compound IV of natural origin.

EXAMPLE 75

XIII ⟶

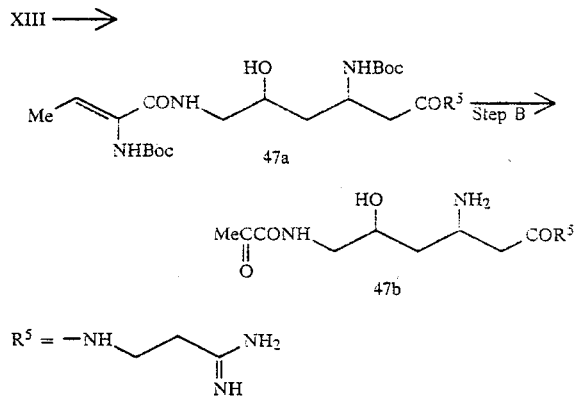

Step A (XIII→47a)

A mixture of N-Boc-L-vinylglycine (362 mg), HOBT (243 mg), DCC (372 mg) and CH$_2$Cl$_2$ (4 ml) was stirred at room temperature for one hour, followed by filtration. To the filtrate were added XIII (606 mg), Et$_3$N (310 mg) and DMF (3 ml), and the reaction was allowed to proceed at room temperature for 40 hours. The reaction mixture was concentrated under reduced pressure, followed by adjusting to pH 3.0 with 1N—HCl. The resultant was subjected to a CHP-20P column chromatography. Elution using 30% methanol-water, followed by freeze-drying afforded Compound 47a (600 mg) as white powder.

IR$\nu_{max}$ (KBr) cm$^{-1}$:1680, 1520.

Step B (47a→47b)

In TFA (3 ml) was dissolved Compound 47a (600 mg), and the solution was stirred at room temperature for one hour, followed by distilling off TFA under reduced pressure. The residue was dissolved in a small volume of water, and the solution was allowed to pass through Amberlite IRA-402 (Cl$^-$ type) resin (10 ml), followed by elution with 40 ml of water. The eluate was subjected to a CHP-20P column chromatography. Elution with water and lyophilization gave dihydrochloride of 47b (200 mg) as white powder.

IR$\nu_{max}$ (KBr) cm$^{-1}$:1700, 1640, 1525.

Elemental Analysis: $C_{13}H_{25}N_4O_4 \cdot 2HCl \cdot 3H_2O$: Calcd.: C,36.45; H,7.77; N,13.08, Found: C,36.40; H,7.62; N,12.94.

EXAMPLE 76

XIII ⟶

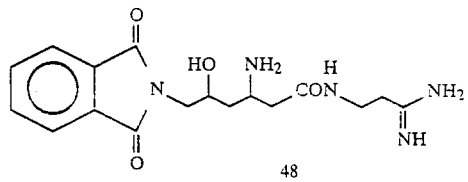

In DMF (2 ml) was dissolved dihydrochloride of Compound XIII (404 mg). To the solution were added Et$_3$N (250 mg) and N-carboethoxyphthalimide (219 mg), and the reaction was allowed to proceed at room temperature for 20 hours, followed by distilling off DMF under reduced pressure. To the residue was added TFA (3 ml), and the mixture was stirred at room temperature for one hour, followed by concentration under reduced pressure. To the concentrate was added water. Insolubles were removed by filtraiton. The filtrate was allowed to pass through Amberlite IRA-402 (Cl$^-$ type) (15 ml). The resin was eluted with water (15 ml), then the eluate was concentrated. The concentrate was subjected to a column chromatography using Diaion CHP-20P (50 to 100 mesh, 30 ml). Elution with 20% ethanol-water, followed by lyophilization gave dihydrochloride of Compound 48 (278 mg) as white powder.

IR$\nu_{max}$ (KBr) cm$^{-1}$:1710, 1690, 1650, 1540.

Elemental Analysis: $C_{17}H_{23}N_5O_4 \cdot 2HCl \cdot 2.5H_2O$: Calcd.: C,42.60; H,6.31; N,14.61, Found: C,42.60; H,6.24; N,14.42.

EXAMPLE 77

XXVII ⟶

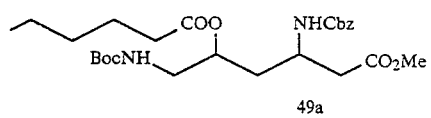

To a solution of Compound XXVII(3.8 g) in methylene chloride(100 ml)was added pyridine (3.2 g). To the mixture was added, while vigorously stirring under cooling with acetone-dry ice, pulverized phosphorus pentachloride(4.16 g), followed by stirring for 1.5 hours on an ice-water bath. To the resultant was added methanol(10 ml) under cooling with acetone-dry ice. The mixture was stirred for 45 minutes on an ice-water bath, to which was added water(20 ml), followed by stirring for 30 minutes. To the reaction mixture was added a saturated aqueous solution of sodium hydrogencarbonate to neutralize. The organic layer was then separated and dried over magnesium sulfate, which was concentrated to distill off pyridine. To the concentrate were added methylene chloride(4 ml) and di-tert-butyl bicarbonate(4.4 g), and the mixture was stirred at room temperature for 20 hours. To the reaction mixture were added ethyl acetate and water, and the mixture was shaken. The ethyl acetate layer was taken and dried over magnesium sulfate, followed by concentration under reduced pressure. The concentrate was subjected to a silica gel($SiO_2$ 100 g) column chromatography, eluting with n-hexane:ethyl acetate=2:1, to afford Compound 49a(3.6 g) as a pale yellow foamy product.

IR$\nu_{max}^{KBr}$ cm$^{-1}$:1680 to 1740, 1510.

Elemental Analysis for $C_{26}H_{40}N_2O_8$: Calcd.: C, 61.40; H, 7.93; N, 5.51, Found: C, 61.58; H, 8.13; N, 5.63.

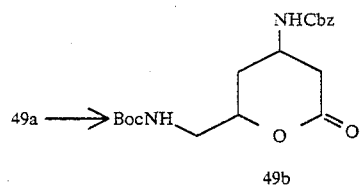

To a solution of Compound 49a(1.29 g) in methanol(16 ml) was added 1N NaOH (8 ml), and the mixture was stirred at room temperature for one hour. Methanol was distilled off under reduced pressure. To the residue was added a 5% aqueous solution of $KHSO_4$ to adjust the pH to 3, followed by saturation with sodium chloride. Then precipitating oily substance was extracted with methylene chloride, and the extract was dried over magnesium sulfate, followed by concentration to a volume of about 20 ml. To the concentrate was added WSC(0.72 g), and the reaction was allowed to proceed at room temperature for one hour. The reaction mixture was washed with water, dried over magnesium sulfate and concentrated under reduced pressure. The concentrate was purified by means of silica gel(-$SiO_2$ 30 g) column, eluting with ethyl acetate:n-hexane=1:1, to afford Compound 49b(0.65 g) as colorless needles, m.p. 136°–137° C.

IR$\nu_{max}^{KBr}$ cm$^{-1}$:1740, 1700, 1520.

Elemental Analysis for $C_{19}H_{26}N_2O_6$: Calcd.: C, 60.30; H, 6.93; N, 7.40, Found: C, 60.35; H, 6.38; N, 7.41.

EXAMPLE 78

XXVIII ⟶

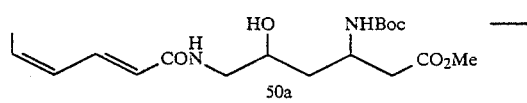

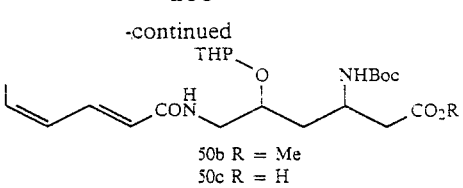

In methanol (70 ml) was dissolved Compound XXVIII (3.4 g). To the solution was added a 28% NaOMe-MeOH solution (0.3 ml), and the reaction was allowed to proceed at room temperature for one hour. The reaction mixture was neutralized with acetic acid, which was then concentrated under reduced pressure. The concentrate was dissolved in ethyl acetate, and the solution was washed with brine, and dried over $MgSO_4$. The resultant was concentrated under reduced pressure to give Compound 50a (3.5 g) as a white foamy substance.

IR$\nu_{max}$ (KBr) cm$^{-1}$:1740, 1715, 1670, 1540.

Elemental Analysis: $C_{18}H_{30}N_2O_6$: Calcd.: C,58.36; H,8.16; N,7.56, Found: C,58.60; H,8.10; N,7.26.

In dihydropyran (30 ml) was dissolved Compound 50a(6.2 g). To the solution was added under ice-cooling a catalytic amount of anhydrous p-TsOH, then the reaction was allowed to proceed at room temperature for 15 hours. To the reaction mixture was added ethyl acetate, and the mixture was washed with an aqueous solution of sodium hydrogencarbonate and a saturated brine, and dried over $MgSO_4$. The resultant was concentrated under reduced pressure, and the concentrate was subjected to a silica gel (60 g) column chromatography, followed by elution with ethyl acetate:hexane=3:1 to give Compound 50b (2.9 g) as a viscous oily substance.

IR$\nu_{max}$ (KBr) cm$^{-1}$:1740, 1715, 1665, 1520.

In DMSO (8 ml) was dissolved Compound 50b (2.4 g). To the solution was added 1N-NaOH (7 ml), and the reaction was allowed to proceed at room temperature for 24 hours. To the reaction mixture was added a 5% aqueous solution of $KHSO_4$ to adjust the pH to 3, and then extracted with $CH_2Cl_2$. The $CH_2Cl_2$ layer was washed with water, which was dried over $MgSO_4$, and then concentrated under reduced pressure to give Compound 50c (1.8 g) as a white foamy substance.

IR$\nu_{max}$ (KBr) cm$^{-1}$:1725(sh), 1715, 1660, 1530.

EXAMPLE 79

50a ⟶

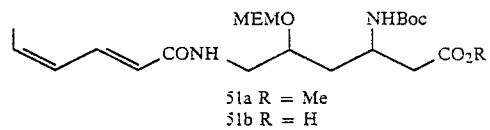

To a solution of Compound 50a (3.5 g) in $CH_2Cl_2$ (30 ml) were added iso-$Pr_2NEt$ (2 g) and methoxyethoxymethylchloride (1.9 g). The reaction was allowed to proceed at room temperature for 20 hours. The reaction mixture was washed with water, dried over $MgSO_4$ and concentrated under reduced pressure. The concentrate was subjected to a silica gel(50 g) column chromatography, followed by elution with ethyl acetate-hexane=5:1 to give Compound 51a (3.7 g) as a viscous oily substance.

IR$\nu_{max}$ (KBr) cm$^{-1}$:1740, 1715, 1665, 1530.

To a solution of Compound 51a (3.7 g) in a mixture of DMSO (4 ml) and MeOH (4 ml) was added under ice-cooling 1N-NaOH (14 ml), followed by stirring at room temperature for one hour. To the reaction mixture was added a 5% aqueous solution of KHSO₄ to bring its pH to 3.0 to allow an oily substance to precipitate, which was extracted with ether. The ether layer was washed with water, dried over MgSO₄, and concentrated under reduced pressure to give Compound 51b (3.4 g) as a white foamy substance.

IR$\nu_{max}$ (KBr) cm$^{-1}$: 1725(sh), 1715, 1665, 1535.

Elemental Analysis: $C_{21}H_{36}N_2O_8$: Calcd.: C,56.74; H,8.16; N,6.30, Found: C,56.40; H,8.42; N,6.11.

EXAMPLE 80

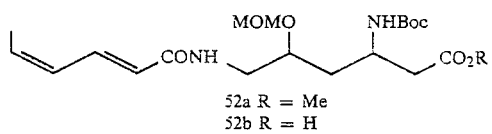

52a R = Me
52b R = H

To a solution of Compound XVII(1.43 g) in CH₂Cl₂(40 ml) were added under ice-cooling Et₃N(0.62 ml) and tBuPh₂SiCl (1.15 ml). The mixture was stirred at room temperature for 30 minutes, then concentrated under reduced pressure. The concentrate was dissolved in ethyl acetate, washed with water and dried over MgSO₄. The resultant was concentrated under reduced pressure to give silylester of carboxylic acid (2.6 g) as a white foamy substance.

This silylester(1.63 g) was dissolved in CH₂Cl₂(20 ml), to which were added under ice-cooling iso-Pr₂NEt(2.27 ml) and methoxymethylchloride (0.99 ml), followed by allowing the reaction to proceed at room temperature for 21 hours. The resultant was concentrated under reduced pressure, and the concentrate was dissolved in ethyl acetate, washed with water and dried over MgSO₄, followed by concentration under reduced pressure. The concentrate was subjected to a silica gel (35 g) column chromatography, followed by developing ethyl acetate:hexane=1:1 to give Compound 52a(1.4 g) as a colorless oily substance.

NMR (90 MHz, CDCl₃),ppm: 1.13(9H,s),1.43(9H,s),1.86(3H,d,6 Hz),3.38(3H,s),7.2~7.3(10H,m).

To a solution of Compound 52a(1.4 g) in MeOH(30 ml) was added KF(300 mg). The mixture was stirred at room temperature for 15 minutes, and concentrated under reduced pressure. The concentrate was dissolved in ether, and the solution was extracted with an aqueous solution of sodium hydrogencarbonate twice. The aqueous layer was adjusted to pH 3.5 with a 5% aqueous solution of KHSO₄ under ice-cooling, and extracted with ethyl acetate. The extract was washed with brine, dried over MgSO₄ and concentrated under reduced pressure to give Compound 52b(850 mg) as a white foamy substance.

NMR (90 MHz, CDCl₃)ppm: 1.41(9H,s),1.84(3H,d,J=6 Hz),3.38(3H,s),9.05(1H,br).

Elemental Analysis: $C_{19}H_{32}N_2O_8 \cdot 0.5H_2O$: Calcd.: C,53.64; H,7.82; N,6.58, Found: C,53.29; H,7.90; N,6.44.

EXAMPLE 81

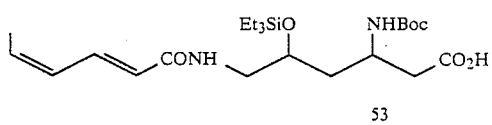

To a solution of Compound XVII(179 mg) in CH₂Cl₂(5 ml) were added with stirring under ice-cooling Et₃N(279 μl) and Et₃SiCl(335 μl), and the reaction was allowed to proceed at room temperature for 16 hours. The reaction mixture was concentrated under reduced pressure, and the concentrate was dissolved in ethyl acetate. The solution was washed once with each of water and brine, dried over MgSO₄, and concentrated under reduced pressure to give Compound 53(210 mg) as a colorless oily substance.

NMR (90 MHz, CDCl₃)ppm: 0.97(9H,t,J=7 Hz), 0.4~0.9(6H,m),1.43(9H,s),1.86(3H,d,J=6 Hz).

EXAMPLE 82

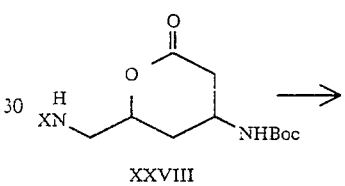

XXVIII

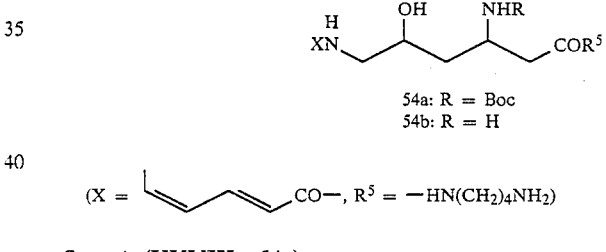

54a: R = Boc
54b: R = H (X = \~/\~CO—, R⁵ = —HN(CH₂)₄NH₂)

Step A (XXVIII→54a)

To a solution of Compound XXVIII (250 mg) in CH₂Cl₂(10 ml) was added tetramethylenediamine(0.7 ml), and the mixture was stirred at room temperature for one hour. The solvent was distilled off under reduced pressure. To the residue was was added water(50 ml), and the pH of the aqueous solution was adjusted to 2.0 with 1N HCl followed by washing with ethyl acetate(25 ml). To the aqueous layer was added 1N NaOH to adjust the pH to 5.5, followed by concentration to a volume of about 40 ml. The concentrate was subjected to a Diaion HP-20(50 to 100 mesh, 20 ml) column chromatography. The column was washed with water(80 ml), followed by fractional elution with 50% methanol-water(60 ml), and 50% methanol-N/200 hydrochloric acid (100 ml), successively. Each fraction was subjected to analysis by means of high performance liquid chromatography [mobile phase:55% methanol/0.01M phosphoric acid solution(pH 3)]. Fractions showing a single peak were collected and concentrated, followed by lyophilization to yield hydrochloride of Compound 54a(308 mg) as a white powdery product.

Elemental Analysis: $C_{21}H_{38}N_4O_5 \cdot HCl$: Calcd.: C,54.48; H,8.49; N,12.10; Cl,7.66, Found: C,54.00; H,8.71; N,12.11; Cl,7.59.

Step B (54a→54b)

A solution of Compound 54a hydrochloride(250 mg) in TFA (2 ml) was left standing at room temperature for 30 minutes. The solvent was distilled off under reduced pressure, and the residue was treated with ether to give a powdery substance, which was dissolved in water(60 ml), followed by allowing to pass through an Amberlite IRA-402($Cl^-$ type, 20 ml) column. The column was washed with water and eluted. The washing and eluate were combined and concentrated, followed by lyophilization to give Compound 54b dihydrochloride (218 mg) as a white powdery product.

IR:$\nu_{max}$ (KBr) $cm^{-1}$:3260, 2940, 1640, 1540.

Elemental Analysis: $C_{16}H_{30}N_4O_3 \cdot 2HCl \cdot 0.5H_2O$: Calcd.: C,47.06; H,8.15; N,13.72; Cl,17.36, Found: C,47.37; H,8.19; N,13.71; Cl,17.31.

EXAMPLES 83-94 (TABLE 11)

By the procedure similar to Example 82, Compound XXVIII was subjected to amidation by using various amines ($R'NH_2$) to obtain corresponding amido compounds (Step A), followed by deprotection reaction (Step B) to obtain compounds of Examples 83-94. The reaction conditions, yields and some of the physicochemical properties of the products are shown in Table 11.

TABLE II

XXVIII → (Step A, R'NH$_2$) → a → (Step B Deprotection) → b

X = CH=CH-CH=CH-CO—

| Example No. | Step | Starting Compd. → Product | Reaction Conditions | Yield Material → Product | IR $\nu_{max}^{KBr}$ cm$^{-1}$ | Molecular Formula Elemental Analysis (Calcd.) |
|---|---|---|---|---|---|---|
| 83 | A | XXVIII → 55a R' = —(CH$_2$)$_3$NH$_2$ | R'NH$_2$ (0.6 ml) CH$_2$Cl$_2$ (10 ml) r.t. 1 hr HP-20 lyophilization | 250 mg → 278 mg | — | $C_{20}H_{36}N_4O_5 \cdot HCl \cdot 0.5H_2O$ C 52.73 (52.45) H 8.38 (8.36) N 12.47 (12.23) Cl 7.76 (7.74) |
|  | B | 55a → 55b R = —(CH$_2$)$_3$NH$_2$ | TFA (2 ml) r.t. 0.5 hr treatment with Et$_2$O IRA-402 (Cl$^-$) lyophilization | 240 mg → 207 mg | 3260 2930 1645 1550 | $C_{15}H_{20}N_4O_3 \cdot 2HCl \cdot 0.5H_2O$ C 46.18 (45.69) H 8.07 (7.92) N 14.39 (14.21) Cl 18.17 (17.98) |
| 84 | A | XXVIII → 56a R' = —(CH$_2$)$_2$NH$_2$ | R'NH$_2$ (1.6 ml) CH$_2$Cl$_2$ (40 ml) r.t. 1 hr HP-20 lyophilization | 800 mg → 898 mg | — | $C_{19}H_{34}N_4O_5 \cdot HCl$ C 52.23 (52.47) H 8.21 (8.11) N 12.51 (12.88) Cl 8.07 (8.15) |
|  | B | 56a → 56b R = —(CH$_2$)$_2$NH$_2$ | TFA (2 ml) r.t. 0.5 hr treatment with Et$_2$O IRA-402(Cl$^-$) lyophilization | 200 mg → 177 mg | 3250 3000 1640 1540 | $C_{14}H_{28}N_4O_3 \cdot 2HCl \cdot 0.5H_2O$ C 44.47 (44.21) H 7.57 (7.69) N 14.99 (14.73) Cl 18.63 (18.64) |
| 85 | A | XXVIII → 57a R' = —CH$_2$CHCO$_2$H \| NH$_2$ | R'NH$_2$·HCl (156 mg) Et$_3$N (1.5 ml) MeOH (15 ml) 50° C., 20 hr HP-20 lyophilization | 250 mg → 271 mg | — | $C_{20}H_{34}N_4O_7 \cdot H_2O$ C 52.00 (52.16) H 8.02 (7.88) N 12.02 (12.17) |
|  | B | 57a → 57b R = —CH$_2$CHCO$_2$H \| NH$_2$ | TFA (1.5 ml) r.t. 0.5 hr treatment with Et$_2$O IRA-402 (Cl$^-$) lyophilization | 142 mg → 121 mg | 3250 2930 1620 1530 | $C_{15}H_{20}N_4O_5 \cdot HCl \cdot H_2O$ C 45.62 (45.40) H 7.33 (7.36) N 14.20 (14.12) Cl 10.06 (8.93) |
| 86 | A | XXVIII → 58a R' = —(CH$_2$)$_2$—N⌐O⌐ (morpholine) | R'NH$_2$ (110 μl) CH$_2$Cl$_2$ (15 ml) treatment with MeOH—Et$_2$O | 250 mg → 311 mg | 3300 2940 1650 | $C_{23}H_{40}N_4O_6 \cdot HCl$ C — (54.70) H — (8.18) N — (11.09) |

TABLE II-continued

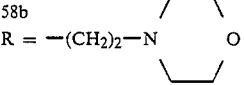

| Example No. | Step | Starting Compd. → Product | Reaction Conditions | Yield Material → Product | IR $\nu_{max}^{KBr}$ cm$^{-1}$ | Molecular Formula Elemental Analysis (Calcd.) |
|---|---|---|---|---|---|---|
| | B | 58a → 58b R = —(CH$_2$)$_2$—N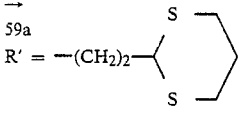O | TFA (2 ml) r.t. 0.5 hr treatment with Et$_2$O IRA-402 (Cl$^-$) lyophilization | 282 mg → 270 mg | 3260 2930 1650 1535 | C$_{18}$H$_{32}$N$_4$O$_4$.2HCl.0.5H$_2$O C 48.19 (48.00) H 8.01 (7.83) N 12.35 (12.44) Cl 15.62 (15.74) |
| 87 | A | XVIIII → 59a R' = —(CH$_2$)$_2$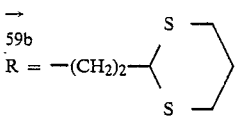 | R'NH$_2$ (~40 mg) MeOH (3.0 ml) Et$_3$N (0.44 ml) r.t. 62 hr 50° C. 5 hr evap. crystallization (MeOH—EtOAc) | 100 mg → 41 mg | — | C$_{23}$H$_{30}$N$_3$O$_5$S$_2$ C 54.86 (55.06) H 7.80 (7.84) N 8.29 (8.38) |
| | B | 59a → 59b R = —(CH$_2$)$_2$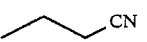 | TFA (0.5 ml) r.t. 30 min evap, washing with Et$_2$O IRA-402 (Cl$^-$) HP-20 lyophilization | 33 mg → 18 mg | 3300 1650 | C$_{18}$H$_{31}$N$_3$O$_3$S$_2$.HCl.2H$_2$O C 42.20 (42.43) H 7.19 (7.12) N 8.15 (8.25) |
| 88 | A | XXVIII → 60a R' = 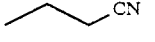 | R'NH$_2$ (214 μl) Et$_3$N (213 μl) MeOH (2 ml) r.t. 24 hr 50° C., 12 hr evap. SiO$_2$ column (CHCl$_3$: EtOAc:MeOH = 4:5:1) | 196 mg → 236 mg | 3330 2250 1705(sh) 1690 1665(sh) 1650 1550 | C$_{20}$H$_{32}$N$_4$O$_5$ C — (58.81) H — (7.90) N — (13.72) |
| | B | 60a → 60b R = 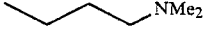 | TFA (1 ml) r.t. 30 min. evap. IRA-402 (Cl$^-$), H$_2$O conc., CHP-20P 20% EtOH—H$_2$O, lyophilization | 70 mg → 50 mg | 2250 1655 1610 1550 | C$_{15}$H$_{24}$N$_4$O$_3$.HCl.H$_2$O C 49.35 (49.65) H 7.80 (7.50) N 15.23 (15.44) |
| 89 | A,B | XXVIII → 61b R = 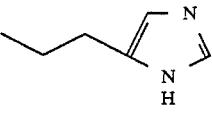NMe$_2$ | R'NH$_2$ (95 μl) MeOH (1 ml) r.t. 24 hr, evap. TFA (1 ml) r.t. 40 min evap. IRA-401 (Cl$^-$), H$_2$O concentration CHP-20P, H$_2$O lyophilization | 51 mg → 62 mg | 1650 1610(sh) 1550 1470 | C$_{17}$H$_{32}$N$_4$O$_3$.2HCl.1.5H$_2$O C 46.16 (46.36) H 8.62 (8.47) N 12.43 (12.72) |
| 90 | A | XXVIII → 62a R' = (propyl-imidazole structure) | R'NH$_2$.2HCl (166 mg) 1.36M MeOLi/MeOH (1.32 ml), MeOH (2 ml) reflux, 7 hr, evap. 1N—HCl (pH 3.0) CHP-20P 30% EtOH—H$_2$O lyophilization | 102 mg → 139 mg | 1690 1650 1615 1540 | C$_{23}$H$_{35}$N$_5$O$_5$.HCl.1.5H$_2$O C 55.41 (55.47) H 7.20 (7.29) N 14.00 (14.06) |

TABLE II-continued

XN(H)—CH₂—CH(OH)—CH₂—CH(NHBoc)—...—C(=O)—O (XXVIII) →Step A R'NH₂→ XN(H)—...—CH(OH)—CH(NHBoc)—CONHR' (a) →Step B Deprotection→ XN(H)—...—CH(OH)—CH(NH₂)—CONHR (b)

X = CH₂=CH—CH=CH—CO—

| Example No. | Step | Starting Compd. → Product | Reaction Conditions | Yield Material → Product | IR $\nu_{max}^{KBr}$ cm⁻¹ | Molecular Formula Elemental Analysis (Calcd.) |
|---|---|---|---|---|---|---|
| | B | 62a → 62b  R = (propyl-imidazole) | TFA (2 ml) 0 °C. 30 min evap, IRA-402 (Cl⁻), H₂O conc., CHP-20P 5% EtOH—H₂O lyophilization | 139 mg → 143 mg | 1670 1540 | C₁₇H₂₇N₅O₃·2HCl C 48.24 (48.34) H 6.90 (6.92) N 16.41 (16.58) |
| 91 | A | XXVIII → 63a  R' = (propyl-imidazoline-N-Boc) | R'NHCbz(174 mg) 5% Pd—C (174 mg) MeOH (5 ml) H₂, 40 min, evap. MeOH (2 ml) 60° C., 20 hr, evap. SiO₂column (CHCl₃: AcOEt:MeOH = 3:3:1) | 102 mg → 67 mg | 1705 1650 1530 | C₂₇H₄₅N₅O₇ C — (58.78) H — (8.22) N — (12.69) |
| | B | 63a → 63b  R = (propyl-imidazoline) | TFA (2 ml) r.t. 1.5 hr evap. IRA-402 (Cl⁻), H₂O conc., CHP-20P H₂O lyophilization | 89 mg → 54 mg | 1655 1605 1545 | C₁₇H₂₀N₅O₃·2HCl C 44.39 (44.35) H 7.82 (7.66) N 15.49 (15.21) |
| 92 | A,B | XXVIII → 64a  R' = —(CH₂)₃—NMe₂  64a → 64b  R = —(CH₂)₃—N⁺Me₃Cl⁻ | R'NH₂ (189 μl) MeOH (2 ml) r.t. 16 hr, evap. MeOH (2 ml) MeI (38 μl) r.t. 6 hr, evap. TFA (2 ml) r.t. 1.5 hr, evap. CHP-20P, H₂O,conc. IRA-402(Cl⁻), H₂O lyophilization | 102 mg → 139 mg | 1670 1655 1545 | C₁₈H₃₅ClN₄O₃·HCl·H₂O C 48.40 (48.54) H 8.19 (8.60) N 12.40 (12.58) |
| 93 | A | XXVIII → 65a  R' = —CH(CO₂Me)—(CH₂)₄—CO₂Me | R'NH₂ (204 mg) DMF (3 ml) Et₃N (70 μl) 110 °C., 28 hr extn. with EtOAc, SiO₂ column (CHCl₃:EtOAc:MeOH = 40:55:5) | 170 mg → 176 mg | 1740 1655 1545 1530 | C₂₆H₄₃N₃O₈ C — (57.66) H — (8.00) N — ( 7.76) |
| | B | 65a → 65b  R = —CH(CO₂Me)—(CH₂)₄—CO₂Me | TFA (2 ml) r.t. 1 hr, evap. IRA-402(Cl⁻), 50% MeOH—H₂O lyophilization | 287 mg → 276 mg | 1740 1670 1650 1550 | C₂₁H₃₅N₃O₇·HCl C 52.38 (52.77) H 7.69 (7.59) N 8.61 (8.79) |
| 94 | B' | 65a → 66b  R' = —CH(CO₂H)—(CH₂)₄—CO₂H | MeOH (10 ml) 1N—NaOH (2.82 ml) r.t. 4.5 hr, evap. 1N—HCl (pH 3.5) CHP-20P 15% EtOH—H₂O lyophilization | 245 mg → 153 mg | 1710 1665 1655 1550 | C₁₉H₃₁N₃O₇ C 55.40 (55.19) H 7.80 (7.56) N 10.31 (10.16) |

EXAMPLE 95

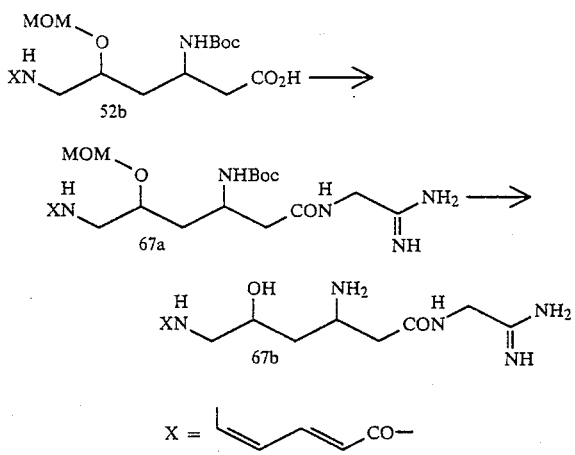

Step A (52b→67a)

To a solution of 52b(260 mg) in anhydrous THF(2 ml) were added HOBT(97 mg) and DCC(148 mg), and the mixture was stirred at room temperature for one hour. This reaction mixture was added, while stirring vigorously, to a mixture of 2 ml of $H_2O$ solution of 2-aminoacetoamidine.dihydrochloride(143 mg) and sodium hydrogencarbonate(123 mg). The whole mixture was stirred at room temperature for 16 hours. Insolubles were filtered off, followed by distilling off THF under reduced pressure. To the residue was added 1N—HCl to adjust its pH to 4.0, which was subjected to a CHP-20P(wet 70 ml) column chromatography, followed by elution with 30% ethanol-water. The eluate was concentrated and lyophilized to give Compound 67a(291 mg) as a pale yellow powdery product.

IR$\nu_{max}$ (KBr) cm$^{-1}$:1710(sh), 1685, 1650, 1530.

Step B (67a→67b)

To a suspension of 67a(290 mg) in anisole(2 ml) was added, under ice-cooling, TFA(3 ml). The mixture was stirred at room temperature for one hour, followed by concentration under reduced pressure. The concentrate was subjected to a CHP-20P(wet 20 ml) column chromatogrpahy. The column was eluted with water, and the objective fractions were combined, and concentrated under reduced pressure. The concentrate was allowed to pass through an Amberlite IRA-402 (Cl$^-$ type) (20 ml) column, and the column was washed with water(100 ml). The eluate was concentrated and lyophilized to give Compound 67b(133 mg) as a pale yellow foamy product.

IR$\nu_{max}$ (KBr) cm$^{-1}$:1690, 1650, 1540.

Elemental Analysis: $C_{14}H_{25}N_5O_3.2HCl.0.5H_2O$: Calcd.: C,42.75; H,7.18; N,17.81, Found: C,42.45; H,7.30; N,17.61.

EXAMPLES 96–101 (TABLE 12)

Instead of Compound 52b were employed Compounds 50c, 51b and 53, and corresponding amido-compounds were obtained by procedures similar to Example 95 (Step A), followed by deprotection reaction (Step B) to obtain compounds of Examples 96–101. The reaction conditions, yields and some of the physicochemical properties of the products are shown in Table 12.

TABLE 12

| Example No. | Step | Starting Compd. → Product | Reaction Conditions | Yield Material → Product | IR $\nu_{max}^{KBr}$ cm$^{-1}$ | Molecular Formula Elemental Analysis (Calcd.) |
|---|---|---|---|---|---|---|
| 96-1 | A | 50c → 68-1a<br>R' = —NCH$_2$CO$_2$CH$_2$Ph (Me)<br>P = THP | R'NH$_3$·P—Tso$^-$(183 mg)<br>HOBT(68 mg), DCC(103 mg)<br>Et$_3$N(0.07 ml)<br>CH$_2$Cl$_2$ (3 ml), r.t. 4 hr<br>evap. SiO$_2$ column<br>(EtOAc:MeOH = 5:1) | 220 mg →<br>193 mg | 1735<br>1710<br>1660<br>1530 | C$_{32}$H$_{48}$N$_4$O$_8$<br>C — (62.32)<br>H — (7.84)<br>N — (9.08) |
| | B | 68-1a → 68b<br>R = —NCH$_2$CO$_2$Na (Me) | TFA (3 ml)<br>r.t. 40 min, evap.<br>MeOH(2 ml), 1 N—NaOH<br>(0.6 ml), r.t. 1 hr, evap.<br>CHP—20P,H$_2$O, lyophilization | 247 mg →<br>110 mg | 1690(sh)<br>1655<br>1590<br>1450 | C$_{15}$H$_{25}$N$_4$O$_5$Na.H$_2$O<br>C 47.00 (47.12)<br>H 7.01 (7.12)<br>N 14.65 (14.65) |
| 96-2 | A | 51b → 60-2a<br>R' = —NCH$_2$CO$_2$CH$_2$Ph (Me)<br>P = MEM | R'NH$_3$·P—Tso$^-$(145 mg)<br>HOBT(49 mg), DCC(75 mg)<br>Et$_3$N(50 mg), THF(3 ml)<br>r.t. 20 hr, evap.<br>SiO$_2$ column<br>(EtOAc:MeOH = 5:1) | 155 mg →<br>83 mg | 1740<br>1710<br>1665<br>1523 | C$_{31}$H$_{48}$N$_4$O$_9$<br>C — (59.98)<br>H — (7.79)<br>N — (9.03) |
| 97-1 | A | 50c → 69-1a<br>R' = —CH$_2$CO$_2$Me<br>P = THP | R'NH$_3$Cl$^-$(251 mg)<br>HOBT(135 mg), DCC(206 mg)<br>Et$_3$N(220 mg)<br>DMF (3 ml), r.t. 2 day,<br>evap. SiO$_2$ column<br>(EtOAc:MeOH = 10:1) | 440 mg →<br>220 mg | 1740<br>1705<br>1680<br>1530 | C$_{25}$H$_{41}$N$_3$O$_8$<br>C — (58.69)<br>H — (8.08)<br>N — (8.21) |
| 97-2 | A | 51b → 69-2a<br>R' = —CH$_2$CO$_2$Me<br>P = THP | R'NH$_3$Cl$^-$(172 mg)<br>Et$_3$N(0.234 ml)<br>DCC (145 mg)<br>CH$_2$Cl$_2$(3 ml), r.t. 20 hr | 305 mg →<br>200 mg | 1745<br>1710(sh)<br>1690<br>1660 | C$_{24}$H$_{41}$N$_3$O$_9$<br>C — (55.91)<br>H — (8.01)<br>N — (8.15) |

50c: P = THP
51b: P = MEM
53: P = Et$_3$Si

TABLE 12-continued $$\underset{a}{\overset{P}{\underset{XN}{\overset{|}{\text{H}}}}\overset{O}{\underset{}{}}\overset{NHBoc}{\underset{}{}}\text{CO}_2\text{H}} \xrightarrow[\text{R'NH}_2]{\text{Step A}} \underset{a}{\overset{P}{\underset{XN}{\overset{|}{\text{H}}}}\overset{O}{\underset{}{}}\overset{NHBoc}{\underset{}{}}\overset{H}{\underset{}{}}\text{CONR'}} \xrightarrow[\text{Deprotection}]{\text{Step B}} \underset{b}{\overset{}{\underset{XN}{\overset{|}{\text{H}}}}\overset{OH}{\underset{}{}}\overset{NH_2}{\underset{}{}}\text{CONHR}}$$

50c: P = THP
51b: P = MEM
53: P = Et₃Si

X = (dienoyl)—CO—

| Example No. | Step | Starting Compd. → Product | Reaction Conditions | Yield Material → Product | IR $\nu_{max}^{KBr}$ cm⁻¹ | Molecular Formula Elemental Analysis (Calcd.) |
|---|---|---|---|---|---|---|
| | | | conc., SiO₂ column (EtOAc) | | 1530 | |
| | B | 69-2a → 69b  R = —CH₂CO₂Na | TFA (2 ml) r.t. 40 min, evap. MeOH(2 ml), 1 N—NaOH (0.6 ml),r.t. 1 hr,evap. CHP—20P,H₂O,lyophilization | 198 mg → 70 mg | 1690(sh) 1660 1610 1400 | C₁₄H₂₂N₃O₆Na.0.5H₂O C 46.29 (46.67) H 6.60 (6.43) N 11.38 (11.66) |
| 98 | A | 51b → 70a  *DL⁽¹⁾ R' = —CH(CH₃)—P(O)(OMe)₂  P = MEM | R'—NHCbz.HCl(396 mg) 10% Pd—C (300 mg) CH₂Cl₂(15 ml),H₂,20 min filtn.conc.,addn. of THF (5 ml) HOBT (96 mg),DCC(147 mg) Et₃N (300 mg) r.t. 24 hr conc., SiO₂ column (EtOAc:MeOH = 5:1) | 305 mg → 242 mg | 1710 1665 1530 1030 | C₂₅H₄₈N₃O₁₀P C — (51.80) H — (8.00) N — (7.25) |
| | B | 70a → 70b  R = *DL —CH(CH₃)—P(O)(ONa)(OH) | CH₃CN (3 ml) NaI (276 mg) Me₃SiCl (0.22 ml) r.t. 3.5 hr, evap. 1N—NaOH (pH 9.0) CHP—20P,20% MeOH.H₂O lyophilization | 240 mg → 36 mg | 1650 1540 1070 | C₁₄H₂₅N₃O₆NaP.H₂O C 41.40 (41.69) H 6.75 (6.75) N 10.23 (10.42) |
| 99 | A | 51b → 71a  R' = *L —CH(CH₃)—CONH— *DL —CH(CH₃)—P(O)(OMe)₂  P = MEM | R'—NHCbz (294 mg) Pd-black (200 mg) THF (10 ml) H₂,r.t. 40 min, filtn. HOBT (101 mg) DCC (154 mg) r.t. 24 hr,filtn.,evap. SiO₂ column (EtOAc:MeOH = 5:1) | 321 mg → 250 mg | 1710(sh) 1690(sh) 1655 1530 1030 | C₂₈H₅₁N₄O₁₁P C — (51.68) H — (7.90) N — (8.61) |
| | B | 71a → 71b  R = *L —CH(CH₃)—CONH— *DL —CH(CH₃)—P(O)(ONa)(OH) | CH₃CN (3 ml) NaI (254 mg) Me₃SiCl (0.20 ml) r.t. 3.5 hr, evap. 1N—NaOH (pH 9.0) CHP—20P, 20% MeOH—H₂O lyophilization | 248 mg → 45 mg | 1650 1545 1060 | C₁₇H₃₀N₄O₇NaP.1.5H₂O C 42.14 (42.24) H 6.76 (6.88) N 11.49 (11.59) |
| 100 | A | 53 → 72a  R' = —CH₂CH₂—C(=NH)—N(piperidine)  P = Et₃Si | 1 R'—NHCbz.HCl(165 mg) H₂O (3 ml),1N—HCl (0.54 ml),5% Pd—C (150 mg),H₂r.t. 50 min. filtn.,NaHCO₃(pH 8.0) 2 53, THF(5 ml),HOBT (102 mg),DCC(165 mg) r.t. 2 hr 1 + 2 (0° C., pH 8(NaHCO₃) r.t.2 hr,1N—HCl(pH 4.0), evap. washing with EtOAc conc. of aq. layer, CHP—20P 30% EtOH—H₂O, lyophil. | 353 mg → 113 mg | 1710(sh) 1690 1660 1630 1550 | C₂₅H₄₃N₅O₅S₂O C 54.58 (54.78) H 8.14 (8.46) N 12.70 (12.78) |
| | B | 72a → 72b  R = —CH₂CH₂—C(=NH)—N(piperidine) | TFA (1.5 ml) r.t. 1 hr, evap. CHP—20P twice 10% EtOH conc.,IRA-402(Cl⁻),H₂O lyophilization | 112 mg → 81 mg | 1665 1620 1540 | C₂₀H₃₅N₅O₃.2HCl.H₂O C 49.40 (49.58) H 8.01 (8.11) N 4.40 (14.46) |

TABLE 12-continued

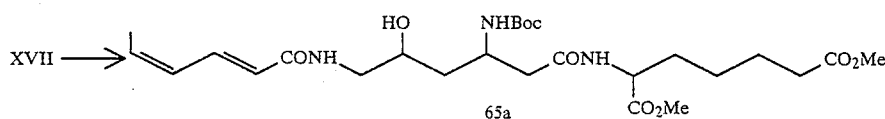

50c: P = THP
51b: P = MEM
53: P = Et₃Si

X = (structure) CO—

| Example No. | Step | Starting Compd. → Product | Reaction Conditions | Yield Material → Product | IR $\nu_{max}^{KBr}$ cm$^{-1}$ | Molecular Formula Elemental Analysis (Calcd.) |
|---|---|---|---|---|---|---|
| 101 | A | 53 → 73a<br>R' = (structure with piperidine-morpholine)<br>P = Et₃Si | 1 R'—NHCbz.HCl(213 mg)<br>H₂O (5 ml)<br>1N—HCl(0.64 ml)<br>5% Pd—C(200 mg)<br>H₂,r.t. 50 min,filtn.<br>NaHCO₃(pH 8)<br>2 53, THF (7 ml)<br>HOBT(135 mg)<br>DCC(227 mg),r.t., 2 hr<br>1 + 2 (0° C., pH 8(NaHCO₃))<br>r.t. 2 hr,1N—HCl(pH 3.0),<br>filtn., conc.<br>EtOAc(10 ml)<br>extraction twice with H₂O<br>CHP—20P,30% EtOH—H₂O<br>lyophilization | 471 mg →<br>172 mg | 1710(sh)<br>1690<br>1660<br>1630<br>1530 | $C_{24}H_{41}N_5O_6 \cdot HCl$<br>C — (54.20)<br>H — (7.64)<br>N — (14.44) |
| | B | 73a → 73b<br>R' = (structure with piperidine-morpholine) | TFA (2 ml)<br>r.t. 1 hr, evap.<br>CHP—20P,10% EtOH—H₂O<br>conc.,IRA-402(Cl⁻), H₂O<br>lyophilization | 171 mg →<br>95 mg | 1670<br>1615<br>1545 | $C_{19}H_{33}N_5O_4 \cdot 2HCl \cdot H_2O$<br>C 47.00 (46.91)<br>H 7.35 (7.67)<br>N 14.26 (14.40) |

(1)*DL: Racemic compounds (hereinafter the same apples)

EXAMPLE 102

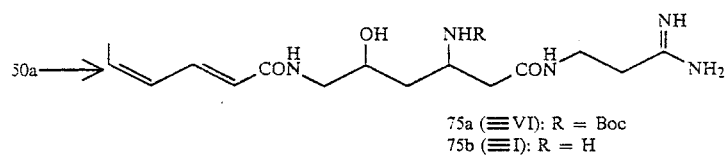

To a solution of Compound XVII(179 mg) in CH₂Cl₂(5 ml) were added, under ice-cooling, Et₃N(279 μl) and Me₃SiCl(253 μl). The mixture was stirred at room temperature for 20 hours. To the reaction mixture was added ice-water. The mixture was extracted twice with CH₂Cl₂ quickly, the extract was dried over MgSO₄, and concentrated under reduced pressure. To the concentrate were added CH₂Cl₂ (10 ml), HOBT(68 mg) and DCC(124 mg). The mixture was stirred at room temperature for 30 minutes, to which was then added DL-α-aminopimelic acid methyl ester(122 mg). The reaction was allowed to proceed for 20 hours. The reaction mixture was subjected to filtration to remove insolubles. The filtrate was concentrated under reduced pressure. The concentrate was subjected to a silica gel(18 g) column chromatography, followed by elution with chloroform:ethyl acetate:methanol=40:55:5 to obtain Compound 65a(112 mg) as a white powdery product. This product was in agreement with the compound obtained in Example 93A in the physico-chemical data.

EXAMPLE 103

50a → (structure)

75a (≡VI): R = Boc
75b (≡I): R = H

Step A (50a→75a)

In methanol(2.0 ml) were dissolved Compound 50a(57.8 mg) and 2-aminoethylamidine·dihydrochloride(30 mg). To the solution was added at room temperature t-butoxypotassium (29 mg, 90% purity). The mixture was stirred for 19 hours, to which was poured a saturated aqueous solution of ammonium chloride(10 ml), then the aqueous layer was washed with ether and ethyl acetate. The aqueous layer, after adjusting the pH thereof to 5 to 6, was concentrated. The concentrate was allowed to adsorb onto a column of Diaion HP-20(50 to 100 mesh, 5 ml). The column was washed with water followed by elution with 20% aqueous methanol, 50% aqueous methanol and 50% methanol-0.01N hydrochloric acid (each 25 ml), successively to fractionate into 5 ml each portions. Each fraction was subjected to analysis by means of high performance liquid chromatography[mobile phase: 25% acetonitrile-0.01M phosphoric acid buffer(pH 3.0)]. Fractions showing a single peak were combined and concentrated, followed by lyophilization to obtain hydrochloride of Compound 75a (53 mg). Comparison of this product with N—Boc compound (VI) of I of natural origin by means of a high performance liquid chromatography [mobile phase; the same as above] for analysis revealed that both were in complete agreement with each other.

Step B (75a→75b)

A solution of Compound 75a hydrochloride(50 mg) in TFA (0.5 ml) was subjected to a reaction similar to that of Step B in Example 68 to yield Compound 75b dihydrochloride (38 mg) as a white powdery product. Which was in agreement with Compound I of natural origin in the physico-chemical properties.

EXAMPLE 104

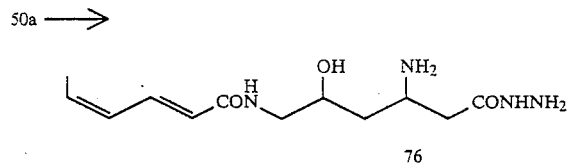

To a solution of Compound 50a(251 mg) in methanol(8.0 ml) was added hydrazine-hydrate(0.325 ml), and the mixture was stirred at room temperature for 40 minutes. The solvent was distilled off under reduced pressure. To the residue was added water, whose pH was adjusted to 3 to 4 with dilute hydrochloric acid, followed by washing twice with ether. To the aqueous layer was added 1N—NaOH to adjust the pH to 8 to 9, followed by extraction three times with ethyl acetate-isobutanol (3:1). Organic layers were combined and washed with saturated brine, and concentrated under reduced pressure. To the concentrate was further added water, then isobutanol was distilled off azeotropically, followed by lyophilization to obtain N—Boc compound of Compound 76 as a white powdery product(177 mg). This compound(122.8 mg) was dissolved in TFA(0.5 ml), and the solution was left standing at room temperature for 30 minutes, followed by removing TFA under reduced pressure. To the residue was added ether. The resultant solid material was washed with ether, and dissolved in water (15 ml). The aqueous solution was allowed to pass through the resin of Amberlite IRA-402(Cl⁻ type, 50 to 100 mesh, 10 ml), which was eluted with water(30 ml). The solution which was passed through the resin and the eluate were combined and concentrated and lyophilized to obtain dihydrochloride of Compound 76 as a white powdery product(105 mg).

IR$\nu_{max}$ (KBr) cm$^{-1}$:1700 to 1500.

Elemental Analysis: $C_{12}H_{22}N_4O_3 \cdot 2HCl$: Calcd.: C,41.99; H,7.05; N,16.32; Cl,20.66, Found: C,42.23; H,7.23; N,16.07; Cl,18.31.

EXAMPLE 105

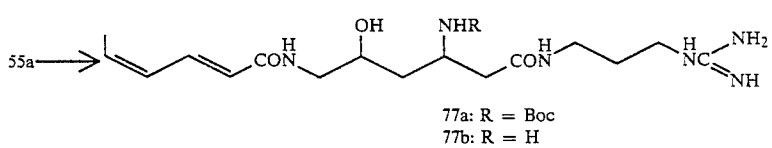

Step A (55a→77a)

In water(0.6 ml) was dissolved sulfuric acid S-methyl isothiourea(117 mg), to which was added, under ice-cooling, 1N—KOH(0.255 ml). To this solution was added Compound 55a (70 mg), and the reaction was allowed to proceed at room temperature for 20 hours, followed by purification by means of a CHP-20P column chromatography. Fractions eluted with 40% ethanol-water were combined, concentrated, and lyophilized to yield Compound 77a(55 mg) as a white powdery product.

IR$\nu_{max}$ (KBr) cm$^{-1}$:1710 to 1610, 1550.

Step B (77a→77b)

In TFA(1 ml) was dissolved Compound 77a(55 mg). The solution was stirred at room temperature for 30 minutes, and concentrated under reduced pressure. The concentrate was dissolved in a small volume of water, which was allowed to pass through Amberlite IRA-402(Cl⁻ type) (5 ml), followed by elution with water(40 ml). The eluate was concentrated and subjected to a CHP-20P column chromatography, using water as an eluent. The eluate was concentrated and then lyophilized to obtain dihydrochloride of Compound 77b (30 mg) as a pale yellow resinous powdery product.

IR$\nu_{max}$ (KBr) cm$^{-1}$:1690 to 1610, 1550.

Elemental Analysis: $C_{16}H_{30}N_6O_3 \cdot 2HCl \cdot 0.5H_2O$: Calcd.: C,44.04; H,7.62; N,19.26, Found: C,44.00; H,7.82; N,19.01.

EXAMPLE 106

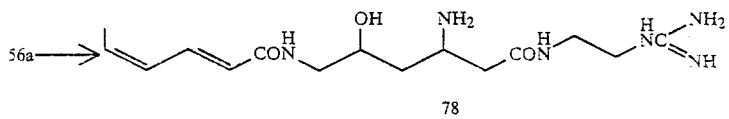

Employing Compound 56a(500 mg) and sulfuric acid S-methylisothiourea(450 mg), a similar reaction to that in Step A of Example 105 was conducted to obtain N—Boc compound of Compound 78a(291 mg) as a white powdery product. This compound(275 mg) was dissolved in TFA(2 ml), which was subjected to a reaction similar to that in Step B of Example 105 to obtain dihydrochloride of Compound 78(241 mg) as a white powdery product.

IR$\nu_{max}$ (KBr) cm$^{-1}$:3270, 1645, 1530.

Elemental Analysis: $C_{15}H_{28}N_6O_3 \cdot 2HCl \cdot 0.5H_2O$: Calcd.: C,42.66; H,7.40; N,19.90; Cl,16.79, Found: C,42.79; H,7.56; N,19.78; Cl,16.45.

EXAMPLE 107

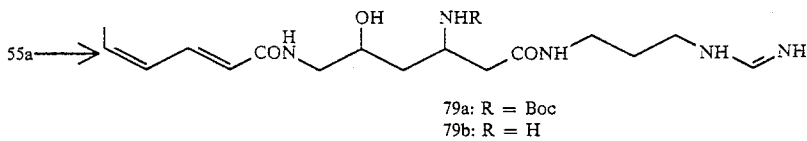

79a: R = Boc
79b: R = H

Step A (55a→79a)

Compound 55a (103 mg) obtained in Example 83 was dissolved in water(2 ml). To the solution were added, under ice-cooling, benzylformimidate hydrochloride(129 mg) and 1N—KOH(0.75 ml), followed by stirring at room temperature for 3 hours. To the resultant was added, under ice-cooling, 1N—HCl to adjust the pH to 2.0. The resultant was shaken together with ethyl acetate. The aqueous layer was concentrated under reduced pressure, and the residue was subjected to a CHP-20P column chromatography. The fraction eluted with 20% ethanol-water was lyophilized to obtain Compound 79a(60 mg) as a white powdery product.

IR$\nu_{max}$ (KBr) cm$^{-1}$:1715, 1665, 1650, 1545.

Step B (79a→79b)

In TFA(1 ml) was dissolved Compound 79a(60 mg). The reaction was allowed to proceed at room temperature for 30 minutes, and concentrated under reduced pressure. The concentrate was dissolved in water, and the aqueous solution was allowed to pass through a column of Amberlite IRA-402(Cl$^-$ type) resin(6 ml), followed by elution with water(25 ml). The eluate was concentrated under reduced pressure, and the concentrate was subjected to a CHP-20P column chromatography. The fraction eluted with water was lyophilized to obtain Compound 79b(48 mg) as a pale yellow resinous powdery product.

IR$\nu_{max}$ (KBr) cm$^{-1}$:3270, 1710, 1670 to 1610, 1550.

Elemental Analysis: $C_{16}H_{29}N_5O_3.2HCl.H_2O$: Calcd.: C,44.65; H,7.73; N,16.27, Found: C,44.65; H,7.61; N,16.00.

EXAMPLE 108

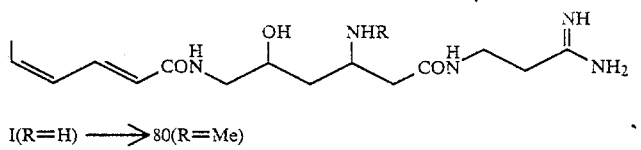

I(R=H) ——→80(R=Me)

To a solution of dihydrochloride of Compound I (443 mg) in methanol(5 ml) was added 37% formaline(86 μl), and the mixture was stirred for one hour, to which were added acetic acid(0.5 ml) and sodium cyanoborohydride(95 mg). The whole mixture was stirred for 5 hours, which was left standing overnight. The resultant was concentrated under reduced pressure, and the concentrate was dissolved in water, followed by purification by means of an Amberlite XAD-2 column. Fractions eluted with water were combined and allowed to pass through activated charcoal and Amberlite IRA-401(Cl$^-$ type), and the aqueous solution was concentrated. The concentrate was lyophilized to obtain dihydrochloride of Compound 80(101 mg) as a white powdery product.

IR$\nu_{max}$ (KBr) cm$^{-1}$:1690, 1650, 1545, 1435.

Elemental Analysis: $C_{16}H_{29}N_5O_3.2HCl$: Calcd.: C,46.60; H,7.58; N,16.98, Found: C,46.60; H,7.29; N,16.78.

EXAMPLE 109

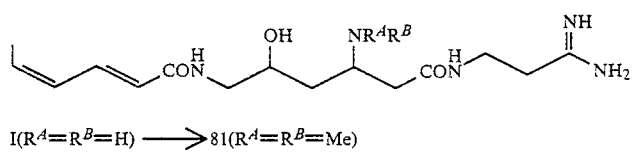

I(R$^A$=R$^B$=H) ——→81(R$^A$=R$^B$=Me)

To a solution of dihydrochloride of Compound I(443 mg) in methanol(5 ml) was added Et$_3$N(154 μl), followed by adding 37% formalin(150 μl) and stirring for 30 minutes. To the resultant were added acetic acid(0.5 ml) and sodium cyanoborohydride(126 mg) and the mixture was stirred for 2 hours. To the resultant was further added sodium cyanoborohydride (63 mg), and the mixture was stirred for one hour, which was left standing overnight. The same work-up of reaction mixture as that in Example 108 afforded dihydrochloride of Compound 81(342 mg).

IR$\nu_{max}$ (KBr) cm$^{-1}$:1690, 1650, 1545.

Elemental Analysis: $C_{17}H_{31}N_5O_3.2HCl.0.5H_2O$: Calcd.: C,46.90; H,7.87; N,16.09, Found: C,46.80; H,7.90; N,16.05.

EXAMPLE 110

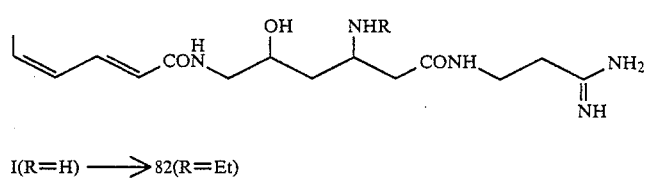

I(R=H) ——→82(R=Et)

To a solution of dihydrochloride of Compound I(222 mg) in methanol(5 ml) was added a 80% aqueous solution of acetaldehyde(60 μl). The mixture was stirred for 30 minutes, to which were added, under ice-cooling, acetic acid(0.25 ml) and sodium cyanoborohydride(63 μg). The temperature of the mixture was allowed to revert to room temperature. The mixture was stirred for 4 hours, left standing overnight, and concentrated under reduced pressure. The concentrate was allowed to pass through Amberlite IRA-401(Cl⁻ type), followed by purification by means of an Amberlite XAD-2 column chromatography. Fractions eluted with water were combined and concentrated, and the concentrate was lyophilized to obtain dihydrochloride of Compound 82(190 mg) as a white powdery product.

IR$\nu_{max}$ (KBr) cm$^{-1}$:1690, 1650, 1545.

Elemental Analysis: $C_{17}H_{31}N_5O_3 \cdot 2HCl \cdot 0.5H_2O$: Calcd.: C,46.90; H,7.87; N,16.09, Found: C,46.75; H,7.99; N,15.85.

EXAMPLE 111

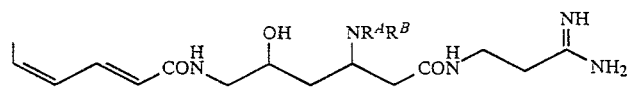

I($R^A=R^B=H$) ⟶ 83($R^A=R^B=Et$)

To a solution of dihydrochloride of Compound I(443 mg) in methanol(8 ml) was added a 80% aqueous solution of acetaldehyde(175 μl), and the mixture was stirred for 30 minutes. To the resultant were added, under ice-cooling, acetic acid (0.5 ml) and sodium cyanoborohydride(157 mg). The temperature of the mixture was allowed to revert to room temperature. The mixture was then stirred for 2 hours. To the mixture were further added twice every two hours a 80% aqueous solution of acetaldehyde(105 μl each) and sodium cyanoborohydride(95 mg each). The whole mixture was left standing overnight, and concentrated under reduced pressure. The concentrate was dissolved in a small volume of water. The pH of the solution was adjusted to 1.5 with 1N hydrochloric acid. The solution was subjected to an activated charcoal column chromatography for purification. Fractions eluted with a 30% aqueous solution of ethanol and with a 50% aqueous solution of ethanol were combined, concentrated, and lyophilized to obtain dihydrochloride of Compound 83 (276 mg) as a white powdery product.

IR$\nu_{max}$ (KBr) cm$^{-1}$:1690, 1670, 1650, 1440, 1190.

Elemental Analysis: $C_{19}H_{35}N_5O_3 \cdot 2HCl \cdot 3H_2O$: Calcd.: C,44.88; H,8.52; N,13.77, Found: C,44.80; H,8.32; N,13.89.

EXAMPLE 112

81 ⟶

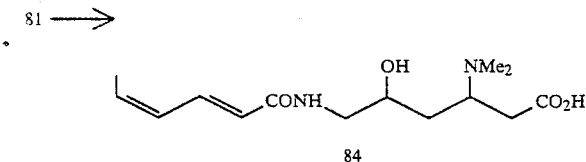

84

A solution of dihydrochloride of Compound 81(220 mg) in 2N hydrochloric acid(20 ml) was stirred for 10 minutes on an oil bath(bath temperature: 120° C.), and concentrated under reduced pressure. The concentrate was dissolved in water, to which was added sodium hydrogen-carbonate to adjust the pH to 7.0, followed by purification by means of an Amberlite XAD-2 column chromatography. Fractions eluted with 15% ethanol-water were combined, concentrated, and lyophilized to obtain Compound 84(63 mg) as a white powdery product.

IR$\nu_{max}$ (KBr) cm$^{-1}$:1650, 1600, 1390.

Elemental Analysis: $C_{14}H_{24}N_2O_4 \cdot 1.2H_2O$: Calcd.: C,54.96; H,8.70; N,9.15, Found: C,54.77; H,8.72; N,9.37.

EXAMPLE 113A

83 ⟶

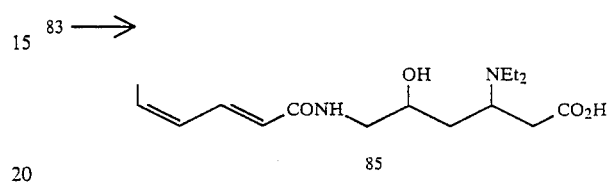

85

A solution of dihydrochloride of Compound 83(196 mg) in 2N hydrochloric acid(20 ml) was stirred for 20 minutes on an oil bath(bath temperature: 120° C.), and work-up in a manner similar to that in Example 112 afforded Compound 85(29 mg).

IR$\nu_{max}$ (KBr) cm$^{-1}$:1670, 1610, 1540, 1430, 1390, 1270.

Elemental Analysis: $C_{16}H_{28}N_2O_4 \cdot H_2O$: Calcd.: C,58.16; H,9.15; N,8.48, Found: C,58.00; H,9.10; N,8.19.

EXAMPLE 113B

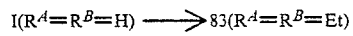

XV($R^A=R^B=H$) ⟶ 85($R^A=R^B=Et$)

To a solution of sodium salt of Compound xv(195 mg) in methanol(5 ml) was added a 80% aqueous solution of acetaldehyde, and the mixture was stirred for 15 minutes. To the mixture were added, while stirring under ice-cooling, acetic acid(0.5 ml) and sodium cyanoborohydride(116 mg). The whole mixture was, after reverting to room temperature, stirred for 1.5 hour. To the mixture were added each poriton of a 80% aqueous solution of acetaldehyde(100 μl) and sodium cyanoborohydride(88 mg) five times at an interval of one hour. The mixture was left standing overnight and concentrated under reduced pressure. The concentrate was dissolved in a small volume of water. To the solution was added sodium hydrogencarbonate to adjust the pH to 6.5, followed by purification by means of an Amberlite XAD-2 column chromatography. Fractions eluted with 15% ethanol-water were combined, concentrated, and lyophilized to obtain Compound 85(192 mg) as a white powdery product. This product was in agreement with the compound obtained in Example 113A in physico-chemical data.

EXAMPLE 114

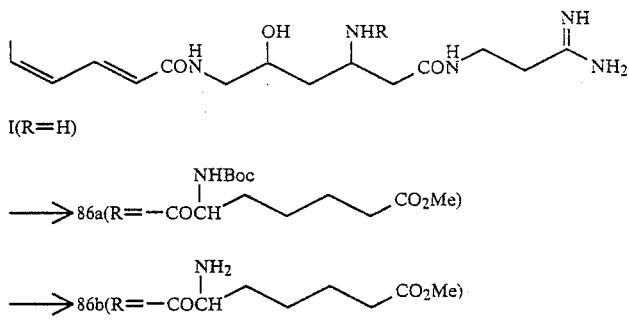

I(R=H)

⟶ 86a(R= —COCH(NHBoc)CH₂CH₂CH₂CH₂CO₂Me)

⟶ 86b(R= —COCH(NH₂)CH₂CH₂CH₂CH₂CO₂Me)

To a suspension of dihydrochloride of Compound I(399 mg) in DMF(5 ml) were added monomethylester of 2-t-butyloxycarbonylaminopimelic acid(290 mg), HOBT(61 mg), DCC(227 mg) and Et₃N(250 μl). The mixture was stirred at room temperature for 16 hours and at 40° C. for 3 hours. DMF was distilled off under reduced pressure, and the residue was suspended in water, to which was added 1N HCl to adjust the pH to 2.5, followed by purificaiton by means of an Amberlite XAD-2 column chromatography. Fractions eluted with 30% ethanol-water were combined, concentrated and lyophilized to give hydrochloride of Compound 86a(570 mg).

The hydrochloride of Compound 86a(569 mg) was suspended in TFA(3 ml), which was stirred at room temperature for one hour. The solvent was distilled off under reduced pressure. The residue was dissolved in water, followed by purification by means of an Amberlite XAD-2 column chromatography. Fractions eluted with water and 5% ethanol were combined, concentrated and lyophilized to obtain ditrifluoroacetic acid salt of Compound 86b(390 mg).

IR$\nu_{max}$ (KBr) cm$^{-1}$:3290, 1670, 1545, 1200.

Elemental Analysis: $C_{23}H_{40}N_6O_6F_6 \cdot 2CF_3CO_2H \cdot H_2O$: Calcd.: C,43.67; H,5.97; N,11.32, Found: C,43.25; H,6.21; N,11.02.

EXAMPLE 115

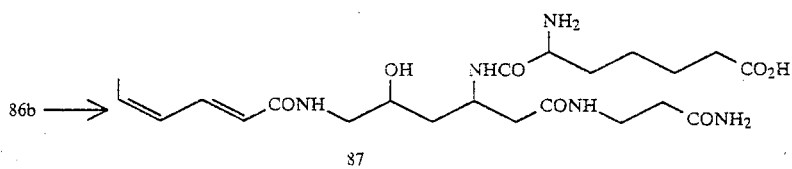

87

To a solution of 2TFA salt of Compound 86b(288 mg) in water(2 ml) was added 1N NaOH(1.59 ml), and the mixture was stirred for 3 hours. To the mixture was added, under ice-cooling, 1N HCl to adjust the pH to 5.0, followed by purification by means of an Amberlite XAD-2 column chromatography. Fractions eluted with 5% ethanol-water were combined, concentrated and lyophilized to obtain Compound 87 (158 mg).

IR$\nu_{max}$ (KBr) cm$^{-1}$:1670, 1545, 1410, 1275, 1200.

Elemental Analysis: $C_{22}H_{37}N_5O_7 \cdot 2H_2O$: Calcd.: C,50.86; H,7.95; N,13.48, C,50.70; H,7.78; N,13.62.

EXAMPLE 116

XVII ⟶

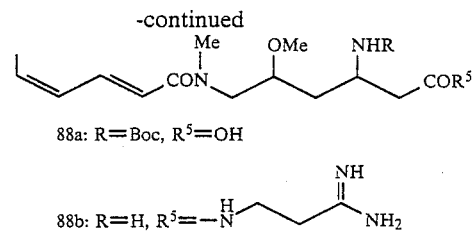

88a: R=Boc, R⁵=OH

88b: R=H, R⁵= —NHCH₂CH₂C(=NH)NH₂

To a suspension of 60% oily sodium hydride (200 mg) in anhydrous THF(5 ml) was added, under ice-cooling in argon streams, a solution of Compound XVII(356 mg) in anhydrous THF. The mixture was stirred for 15 minutes, to which was added methyl iodide(374 μl). The mixture was, after reverting the temperature thereof to room temperature, stirred for 4 hours. The solvent was distilled off under reduced pressure. To the residue were added a small volume of methanol and the ice-water, followed by washing with ethyl acetate. To the aqueous layer thus obtained was added 1N HCl to render its pH to 3.0. The mixture was extracted with ethyl acetate three times, and the extract was washed with brine, dried (MgSO₄), and evaporated under reduced pressure. The residue was prurified by means of a silica gel column chromatography. Fractions eluted with ethyl acetate:acetic acid=100:1 were combined and concentrated to obtain Compound 88a(132 mg).

NMR (90 MHz, CDCl₃)ppm: 1.43(9H,s),1.5–2.0(2H,m),1.87(3H,d,J=6 Hz),2.55(2H,d,J=5 Hz),3.04,3.16(3H,s),3.2–3.7(3H,m),3.41(3H,s),3-.8–4.3(1H,m),5.5(1H,br.),5.7–7.9(4H,m).

To a solution of Compound 88a(132 mg) in anhydrous THF (2 ml) were added HOBT(51 mg) and DCC(78 mg), and the mixture was stirred for 1.5 hour. To a solution of dihydrochloride of 3-aminopropioamidine(111 mg) in water(2 ml) was added sodium hydrogencarbonate(102 mg), and the mixture was stirred. To the mixture was added the above-mentioned active ester solution. The mixture was stirred at room temperature for 15 hours, and insolubles were removed by filtration, followed by concentration of the filtrate. The concentrate was dissolved in ethanol. To the concentrate was then added, under ice-cooling, TFA(3 ml).

The temperature of the mixture was reverted to room temperature, and the mixture was stirred for one hour. The solvent was distilled off under reduced pressure, and the residue was purified by means of an Amberlite XAD-2 column chromatography. Fractions eluted with water and 5% ethanol-water were combined and concentrated. The concentrate was allowed to pass through a column of Amberlite IRA-401(Cl⁻ type). The column was subjected to elution with water. The eluate was concentrated and lyophilized to obtain dihydrochloride of Compound 88b(82 mg) as a white powdery product.

IR$\nu_{max}$ (KBr) cm⁻¹:1690, 1635, 1560, 1480, 1435, 1100.

Elemental Analysis: $C_{17}H_{31}N_5O_3 \cdot 2HCl \cdot 0.5H_2O$: Calcd.: C,46.90; H,7.87; N,16.09, Found: C,46.60; H,7.99; N,16.00.

EXAMPLE 117

XVII ⟶

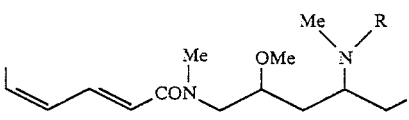

89a: R=Boc, R⁵=OH

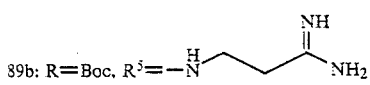

89b: R=Boc, R⁵=

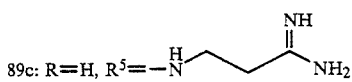

89c: R=H, R⁵=

To a solution of Compound XVII(282 mg) in anhydrous THF (10 ml) was added, in argon streams, 60% sodium hydride in oil(221 mg), and the mixture was stirred for 5 hours. To the mixture was then added methyl iodide(345 μl), and the mixture was left standing at room temperature for 3 days. To the reaction mixture was added methanol(2 ml), and the mixture was concentrated under reduced pressure. The concentrate was dissolved in cold water, followed by washing with ethyl acetate. To the aqueous layer was added a 5% aqueous solution of potassium hydrogensulfate to adjust the pH to 3.0, followed by extracting with ethyl acetate three times, washing with brine and drying (over MgSO₄). The solvent was distilled off under reduced pressure. The residue was purified by means of a silica gel column chromatography. Fractions eluted with ethyl acetate-acetic acid=100:1 were combined and concentrated to obtain Compound 89a(235 mg).

NMR (90 MHz, CDCl₃)ppm: 1.47(9H,s),1.5-2.0(2H,m),1.88(3H,d,J=6 Hz),2.3-2.8(2H,m), 2.75(3H,s),3.06,3.17(3H,s),3.2-3.7(3H,m), 3.39(3H,s),4.3-4.8(1H,m),5.7-7.9(4H,m).

To a solution of Compound 89a(176 mg) in anhydrous THF (2 ml) were added HOBT(68 mg) and DCC(104 mg), and the mixture was stirred at room temperature for one hour. To a solution of dihydrochloride of 3-aminopropioamidine(147 mg) in water(2 ml) was added sodium hydrogencarbonate(115 mg), and the mixture was stirred, to which was added the above-mentioned active ester solution. The mixture was stirred at room temperature for 19 hours. Insolubles were filtered off, and the filtrate was concentrated. To the concentrate was added 1N HCl to adjust the pH to 3.0, followed by purication by means of an Amberlite XAD-2 column chromatography. Fractions eluted with 30% ethanol-water were combined, concentrated and lyophilized to obtain hydrochloride of Compound 89b(135 mg) as a white powdery product.

IR$\nu_{max}$ (KBr) cm⁻¹:1690, 1650, 1400.

To hydrochloride of Compound 89b(134 mg) was added, while stirring under ice-cooling, TFA(2 ml). The temperature of the mixture was reverted to room temperature, and the mixture was stirred for 40 minutes. The solvent was distilled off under reduced pressure. The residue was dissolved in cold water, followed by purification by means of an Amberlite XAD-2 column chromatography. Fractions eluted with water and 5% ethanol were combined and concentrated. The concentrate was allowed to pass through Amberlite IRA-401(Cl⁻ type). Elution was conducted with water, and the eluate was concentrated, followed by lyophilization to obtain dihydrochloride of Compound 89c(83 mg) as a white powdery product.

IR$\nu_{max}$ (KBr) cm⁻¹:1690, 1645, 1570, 1415, 1100.

Elemental Analysis: $C_{18}H_{33}N_5O_3 \cdot 2HCl \cdot 1.3H_2O$: Calcd.: C,46.61; H,8.17; N,15.10, Found: C,46.41; H,8.07; N,14.81.

EXAMPLE 118

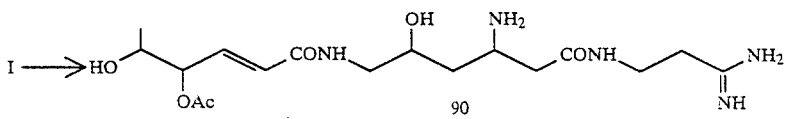

To a suspension of dihydrochloride of Compound I(223 mg) in acetic acid(3 ml) was added, while stirring under ice-cooling, m-chloroperbenzoic acid(148 mg). The mixture was stirred at room temperature for 3 hours, which was then left standing for 3 days. The solvent was distilled off under reduced pressure, and the residue was dissolved in water, followed by purification by means of an Amberlite XAD-2 column. Fractions eluted with water were combined and concentrated. The concentrate was allowed to pass through Amberlite IRA-401(Cl⁻ type). The eluate was concentrated, followed by lyophilization to obtain dihydrochloride of Compound 90(109 mg) as a white powdery product.

IR$\nu_{max}$ (KBr) cm⁻¹:1735, 1690, 1670(sh), 1650, 1550, 1235.

Elemental Analysis: $C_{17}H_{31}N_5O_6 \cdot 2HCl \cdot 1.5H_2O$: Calcd.: C,40.72; H,7.24; N,13.97, Found: C,40.61; H,7.10; N,13.86.

EXAMPLE 119

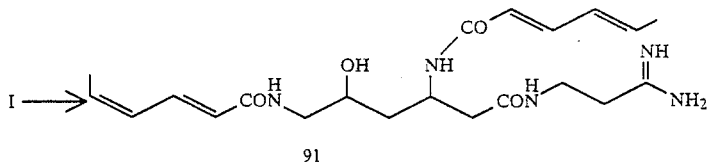

91

To a solution of Compound I(295 mg) in DMF(8.0 ml) were added sorbic acid(97 mg) and Et₃N(0.149 ml). To the mixture were added, under ice-cooling, HOBT(116 mg) and DCC(178 mg), followed by stirring for 30 minutes. The mixture was stirred at room temperature for 20 hours, followed by distilling off DMF under reduced pressure. To the residue was added water(20 ml), to which was added 1N HCl to adjust the pH to 1.9. The mixture was washed with ethyl acetate (12 ml) three times. To the aqueous layer was added 1N NaOH to adjust the pH to 6.4, followed by concentration under reduced pressure to a volume of about 1 ml. The concentrate was subjected to a Diaion HP-20(50–100 mesh, 20 ml) column chromatography. Elution was conducted using water(100 ml), 20% methanol-water(60 ml), 50% methanol-water(100 ml) and 50% methanol-0.01N HCl(100 ml), successively, followed by fractionating at 20 ml each portion. Each fraction was subjected to analysis by means of a high performance liquid chromatography [mobile phase: 25% acetonitrile/0.01M phosphate buffer(pH 3.0)]. Fractions showing single peak were combined and concentrated, followed by lyophilization to obtain hydrochloride of Compound 91(190 mg) as a white powdery product.

Elemental Analysis: $C_{21}H_{33}N_5O_4 \cdot HCl \cdot 3.0H_2O$: Calcd.: C,49.45; H,7.90; N,13.73; Cl,6.95, Found: C,49.44; H,7.33; N,14.14; Cl,6.95.

EXAMPLE 120

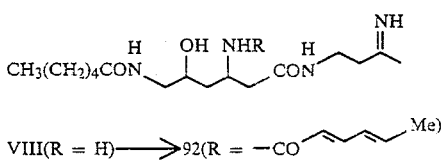

In DMF were dissolved Compound VIII(307.3 mg), sorbic acid (103 mg) and Et₃N(0.16 ml). To the mixture were added, under ice-cooling, HOBT(124 mg) and DCC(189 mg), successively. The mixture was stirred for 30 minutes, then for 16 hours at room temperature. The reaction mixture was concentrated, to which was added dilute hydrochloric acid (25 ml) to adjust the pH to 1.8, followed by washing with ethyl acetate(13 ml) three times. To the mixture was added 1N-NaOH to adjust the pH to 6.7. The mixture was concentrated, and the concentrate was subjected to a Diaion HP-20(50 to 100 mesh, 20 ml) column chromatography, followed by elution with water(100 ml), 10%, 20%, 50%, aqueous methanol(each 60 ml) and 50% methanol-0.01N HCl(60 ml), successively to fractionate into 20 ml each portion. Each fraction was subjected to analysis by means of a high performance liquid chromatography[mobile phase: 26% acetonitrile/0.01M phosphate buffer(pH 3.0)]. Fractions exhibiting single peak were combined and concentrated, followed by lyophilization to obtain hydrochloride of Compound 92(302 mg) as a white powdery product.

Elemental Analysis: $C_{21}H_{37}N_5O_4 \cdot HCl \cdot 1.5H_2O$: Calcd.: C,51.79; H,8.49; N,14.38; Cl,7.28, Found: C,51.58; H,8.51; N,14.10; Cl,7.48.

EXAMPLE 121

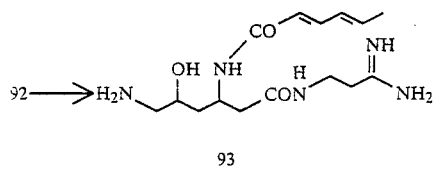

In a 0.03M phosphate buffer solution(pH 7.0, 100 ml) was dissolved monohydrochloride of Compound 92(186 mg). To the solution were added cells of Pseudomonas.acidovorans IFO 13582(10 g), and the mixture was shaken at 37° C. for 14 hours. The reaction solution was subjected to centrifugation. The supernatant was allowed to pass through a column of IRC-50 (NH₄⁺,14 ml), followed by elution with water, 0.5M, 1.0M, 1.5M and 0.2M brine (each 70 ml), successively, fractionating into 14 ml each portion. Each fraction was subjected to analysis by means of a high performance liquid chromatography[mobile phase: 6% acetonitrile/0.01M phosphate buffer solution(pH 3.0)]. Fractions exhibiting single peak were combined and concentrated. The concentrate was allowed to pass through a column of activated charcoal (10 ml), followed by elution with water(50 ml) and 8% isobutanol water(60 ml), fractionating into 10 ml each portion. Each fraction was subjected to a high performance liquid chromatography[mobile phase: the same as above]. Fractions exhibiting single peak were combined and concentrated under reduced pressure, followed by lyophilization to obtain dihydrochloride of Compound 93(99 mg) as a white powdery product.

Elemental Analysis: $C_{15}H_{27}N_5O_3 \cdot 2HCl \cdot 1.0H_2O$: Calcd.: C,43.27; H,7.50; N,16.82; Cl,17.03, Found: C,43.27; H,8.23; N,16.85; Cl,17.03.

EXAMPLE 122

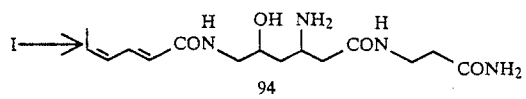

A solution of dihydrochloride of Compound I(170 mg) in water(30 ml) was subjected to a Dowex 1×2(OH⁻ type, 50 to 100 mesh, 15 ml) column chromatography. The column was washed with water. The solution which passed through the column and the washing were combined and concentrated, followed by lyophilization to obtain Compound 94 as a crude powdery product(141 mg). The crude powder was dissolved in water (30 ml), and the solution was subjected

135 to an Amberlite CG-50(H+ type, 100 to 200 mesh, 15 ml) column chromatography. The column was wahsed with water(45 ml) and 0.5% aqueous ammonia(75 ml), successively, followed by elution with 2% aqueous ammonia(45 ml). The eluate was concentrated and then lyophilized to obtain Compound 94 as a white powdery product(100 mg).

IR$\nu_{max}$ (KBr) cm$^{-1}$:3320, 1660, 1550.

Elemental Analysis: $C_{15}H_{26}N_4O_4 \cdot H_2O$: Calcd.: C,52.31; H,8.19; N,16.27, Found: C,52.62; H,7.36; N,15.60.

EXAMPLE 123

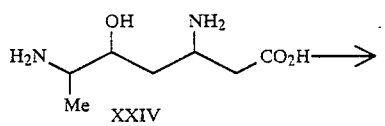

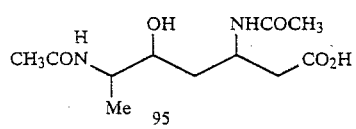

To a solution of Compound XXIV(108 mg) in a 3% aqueous solution of sodium hydrogencarbonate(15 ml) was added acetic anhydride(0.17 ml). The mixture was stirred at room temperature for 3 hours, followed by addition of Dowex 50W-X2(H+,10 ml). The mixture was stirred for further 30 minutes. The resin was separated by filtration and washed with water(40 ml). The filtrate and the washing were combined and concentrated under reduced pressure, followed by lyophilization to obtain Compound 95 as a crude powdery product(123 mg). This crude product was subjected to a silica gel column chromatography, using as eluents ethyl acetate:methanol=7:1,5:1,4:1 and 3:1(each 60 ml) successively, to fractionate into 12 ml each portion. Each fraction was subjected to analysis by means of a silica gel thin layer chromatography(mobile phase: ethyl acetate:methanol=3:1). Fractions exhibiting single spot were combined and concentrated to dryness to obtain Compound 95 as a white powdery product(69 mg), which was crystallized from acetone to obtain Compound 95 as colourless crystals(44 mg).

136

Elemental Analysis: $C_{11}H_{20}N_2O_5$: Calcd.: C,50.76; H,7.74; N,10.76, Found: C,50.68; H,7.80; N,10.50.

EXAMPLE 124

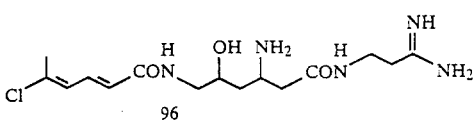

To a solution of dihydrochloride of Compound I(196 mg) in water(1.8 ml) and dioxane(5.2 ml) was added at room temperature N-bromosuccinimide(87 mg), and the mixture was stirred for 60 minutes. Dioxane was distilled off under reduced pressure, and the reaction mixture was allowed to pass through Amberlite CG-50(type I,+ NH$_4$,20 ml), elution being conducted with water, 0.1M, 0.2M, 0.3M, 0.4M, 0.5M, 0.6M and 0.8M brine (each 60 ml) and 1.0M and 1.5M brine (each 200 ml), fractionating into 20 ml each portion. Each fraction was subjected to analysis by means of high performance liquid chromatography[mobile phase: 25% methanol/0.01M phosphate buffer(pH 3.0)]. Fractions exhibiting substantially single peak were combined and concentrated under reduced pressure. The concentrate was subjected to a Diaion HP-20(50 to 100 mesh, 15 ml) column chromatography, eluting with water(100 ml) to fractionate into 15 ml each portion. Each fraction was subjected to analysis by means of high performance liquid chromatography[mobile phase: the same as above]. Fractions exhibiting single peak were combined and concentrated under reduced pressure, followed by lyophilization to obtain dihydrochloride of Compound 96(45 mg) as a white powdery product.

Elemental Analysis: $C_{15}H_{26}N_5O_3Cl \cdot 2HCl \cdot 8.0H_2O$: Calcd.: C,31.23; H,7.69; N,12.14, Found: C,31.32; H,5.97; N,12.06.

EXAMPLE 125-148 (TABLE 13)

By the procedure similar to Example 29, dihydrochloride of Compound (XIII) was subjected to acylation (Step A) by using various carboxylic acid (R'CO$_2$H) or its derivatives, then to deprotection reaction (Step B) to obtain compounds some of the physicochemical properties of the products are shown in Table 13.

TABLE 13

$$\underset{XIII}{H_2N \diagup \overset{OH}{\diagdown} \diagup \overset{\overset{Boc}{|}}{\underset{NH}{\diagdown}} \diagup CO-R^5} \xrightarrow[\text{(Acylation)}]{\text{Step A}} R'CONH \diagup \overset{HO}{\diagdown} \diagup \overset{\overset{Boc}{|}}{\underset{NH}{\diagdown}} \diagup CO-R^5 \xrightarrow[\text{(Deprotection)}]{\text{Step B}} RCON \diagup \overset{H}{\diagdown} \diagup \overset{HO}{\diagdown} \diagup \overset{NH_2}{\diagdown} \diagup CO-R^5$$

$$R^5 = -\underset{a}{N} \diagdown \underset{H}{\diagup} \diagdown \underset{b}{\overset{NH}{\diagup \diagdown NH_2}}$$

| Ex. No. | Step | Starting Compound → Product Compd. | Reaction Conditions | Yield Material → Product | IR $\nu_{max}^{KBr}$ cm$^{-1}$ | Molecular Formula Analysis (Calcd.) |
|---|---|---|---|---|---|---|
| 125 | A | XIII → 97a; R' = Me (trans-Ph alkene) | R'CO$_2$H (113 mg) HOBT (34 mg) DCC (124 mg) Et$_3$N (105 μl) DMF (3 ml) r.t. 20 hr (hereafter same as 31A) | 202 mg → 252 mg | 1710 (sh) 1690 1650 1540 | C$_{26}$H$_{39}$N$_5$O$_5$.HCl.H$_2$O C 55.86 (56.16) H 7.88 (7.61) N 12.31 (12.59) |
|  | B | 97a → 97b; R = Me (trans-Ph alkene) | TFA (2 ml) r.t. 30 min evap. Et$_2$O washing IRA-402(Cl$^-$), HP-20 Lyophilization | 240 mg → 181 mg | 1690 1650 1530 | C$_{21}$H$_{31}$N$_5$O$_3$.2HCl.1.5H$_2$O C 50.02 (50.30) H 7.44 (7.24) N 13.67 (13.97) |
| 126 | A | XIII → 98a; R' = Me (alkyne) | R'CO$_2$H (6.6 mg) HOBT (34 mg) DCC (124 mg) Et$_3$N (105 μl) DMF (3 ml) r.t. 15 hr (hereafter same as 31A) | 202 mg → 235 mg | 1710 (sh) 1690 1650 1610 1540 | C$_{26}$H$_{33}$N$_5$O$_5$.HCl.0.5H$_2$O C 57.65 (57.72) H 6.74 (6.52) N 12.88 (12.94) |
|  | B | 98a → 98b; R = Me (alkyne) | TFA (2 ml) anisole (2 ml) r.t. 1 hr (hereafter same as 125B) | 235 mg → 180 mg | 1690 1650 1610 1545 | C$_{15}$H$_{25}$N$_5$O$_3$.2HCl.H$_2$O C 43.19 (43.48) H 7.32 (7.05) N 16.68 (16.90) |
| 127 | A | XIII → 99a; R' = Me (ene-yne) | R'CO$_2$H (16 mg) HOBT (34 mg) DCC (124 mg) Et$_3$N (105 μl) DMF (3 ml) r.t. 20 hr (hereafter same as 31A) | 202 mg → 225 mg | 1710 (sh) 1690 1650 1530 | C$_{26}$H$_{33}$N$_5$O$_5$.HCl.H$_2$O C 56.51 (56.77) H 6.88 (6.60) N 12.49 (12.73) |

TABLE 13-continued

| | | | | | | | |
|---|---|---|---|---|---|---|---|
| 128 | B | 99a → 99b<br>R = Me | TFA (2 ml)<br>anisole (2 ml)<br>0° C. → r.t. 1 hr<br>(hereafter same as 125B) | 224 mg → 169 mg | 1690<br>1645<br>1545 | $C_{15}H_{25}N_5O_3\cdot 2HCl\cdot 1.5H_2O$<br>C 42.28 (42.56)<br>H 7.41 (7.14)<br>N 16.27 (16.54) |
| | A | XIII → 100a<br>R' = Me | R'CO$_2$H (60 mg)<br>HOBT (27 mg)<br>DCC (100 mg)<br>Et$_3$N (84 μl)<br>DMF (2 ml)<br>r.t. 3 days<br>(hereafter same as 31A) | 162 mg → 165 mg | 1710 (sh)<br>1695<br>1650<br>1535 | $C_{21}H_{35}N_5O_5\cdot HCl\cdot 0.5H_2O$<br>C 51.95 (52.22)<br>H 7.96 (7.72)<br>N 14.23 (14.50) |
| | B | 100a → 100b<br>R = Me | TFA (2 ml)<br>anisole (2 ml)<br>0° C. → r.t. 1 hr<br>(hereafter same as 125B) | 164 mg → 116 mg | 1690<br>1640<br>1600<br>1535 | $C_{16}H_{27}N_5O_3\cdot 2HCl\cdot H_2O$<br>C 44.59 (44.86)<br>H 7.56 (7.29)<br>N 16.09 (16.35) |
| 129 | A | XIII → 101a<br>R' = Me | R'CO$_2$H (61 mg)<br>HOBT (27 mg)<br>DCC (100 mg)<br>Et$_3$N (84 μl)<br>DMF (2 ml)<br>r.t. 3 days<br>(hereafter same as 31A) | 162 mg → 158 mg | 1710 (sh)<br>1690<br>1650<br>1530 | $C_{21}H_{37}N_5O_5\cdot 2HCl\cdot 0.5H_2O$<br>C 51.72 (52.00)<br>H 8.34 (8.10)<br>N 14.21 (14.44) |
| | B | 101a → 101b<br>R = Me | TFA (2 ml)<br>anisole (2 ml)<br>0° C. → r.t. 75 min<br>(hereafter same as 125B) | 157 mg → 106 mg | 1690<br>1650<br>1540 | $C_{16}H_{29}N_5O_3\cdot 2HCl\cdot H_2O$<br>C 44.39 (44.65)<br>H 8.31 (8.05)<br>N 14.48 (14.71) |
| 130 | A | XIII → 102a<br>R' = Me | R'CO$_2$H (61 mg)<br>HOBT (27 mg)<br>DCC (100 mg)<br>Et$_3$N (84 μl)<br>DMF (2 ml)<br>r.t. 3 days<br>(hereafter same as 31A) | 162 mg → 184 mg | 1710 (sh)<br>1690<br>1650<br>1530 | $C_{21}H_{37}N_5O_5\cdot HCl\cdot H_2O$<br>C 50.79 (51.06)<br>H 8.44 (8.16)<br>N 14.00 (14.18) |

TABLE 13-continued

| | | | | | | |
|---|---|---|---|---|---|---|
| 131 | B | 102a → 102b<br><br>R = Me—/=/—Me (with Me branch) | TFA (2 ml)<br>0° C. → r.t. 1 hr<br>(hereafter same as 125B) | 183 mg → 72 mg | 1690<br>1650<br>1540 | $C_{16}H_{29}N_5O_3 \cdot 2HCl \cdot 1.5H_2O$<br>C 43.49 (43.74)<br>H 8.09 (7.80)<br>N 15.68 (15.94) |
| | A | XIII → 103a<br><br>R' = Me—/=/—Me | R'CO$_2$H (61 mg)<br>HOBT (27 mg)<br>DCC (100 mg)<br>Et$_3$N (84 μl)<br>DMF (2 ml)<br>r.t. 15 hr<br>(hereafter same as 31A) | 162 mg → 197 mg | 1710 (sh)<br>1690<br>1650<br>1605<br>1540 | $C_{21}H_{37}N_5O_5 \cdot HCl \cdot 0.5H_2O$<br>C 51.74 (52.00)<br>H 8.32 (8.10)<br>N 14.18 (14.44) |
| | B | 103a → 103b<br><br>R = Me—/=/—Me | TFA (2 ml)<br>(hereafter same as 125B) | 196 mg → 147 mg | 1690<br>1650<br>1600<br>1550 | $C_{16}H_{29}N_5O_3 \cdot 2HCl \cdot H_2O$<br>C 44.39 (44.65)<br>H 7.93 (7.73)<br>N 16.03 (16.27) |
| 132 | A | XIII → 104a<br><br>R' = Me—C≡C—CH=CH— | R'CO$_2$H (39 mg)<br>HOBT (27 mg)<br>DCC (87 mg)<br>Et$_3$N (73 μl)<br>DMF (2 ml)<br>r.t. 23 hr<br>(hereafter same as 31A) | 142 mg → 164 mg | 1710 (sh)<br>1690<br>1630<br>1530 | $C_{20}H_{33}N_5O_5 \cdot HCl \cdot H_2O$<br>C 50.01 (50.26)<br>H 7.81 (7.59)<br>N 14.42 (14.65) |
| | B | 104a → 104b<br><br>R = Me—C≡C—CH=CH— | TFA (2 ml)<br>0° C. → 1.5 hr<br>(hereafter same as 125B) | 164 mg → 119 mg | 1680<br>1630<br>1610<br>1540 | $C_{15}H_{25}N_5O_3 \cdot 2HCl \cdot 1.5H_2O$<br>C 42.29 (42.56)<br>H 7.36 (7.14)<br>N 16.28 (16.54) |
| 133 | A | XIII → 105a<br><br>R' = cyclohexenyl-methylene | R'CO$_2$H (53 mg)<br>HOBT (27 mg)<br>DCC (89 mg)<br>Et$_3$N (81 μl)<br>DMF (2 ml)<br>r.t. 3 days<br>(hereafter same as 31A) | 154 mg → 173 mg | 1710(sh)<br>1690<br>1640<br>1530 | $C_{22}H_{37}N_5O_5 \cdot HCl \cdot 0.5H_2O$<br>C 52.96 (53.16)<br>H 8.05 (7.91)<br>N 13.88 (14.09) |

TABLE 13-continued

| | | | | | | |
|---|---|---|---|---|---|---|
| | B | 108a → 108b  R = [cyclopentenyl-methylene] | 169 mg → 101 mg | THF (2 ml) r.t. 1 hr (hereafter same as 125B) | 1690 1650 1545 | $C_{16}H_{27}N_5O_3.2HCl.H_2O$ C 44.63 (44.86) H 7.47 (7.29) N 16.21 (16.35) |
| 137 | A | XII → 109a  R = [dithiolane-CH$_2$CH$_2$-] | 100 mg → 130 mg | R'CO$_2$H (80 mg) HOBT (45 mg) DCC (85 mg) Et$_3$N (0.35 ml) DMF (2 ml) r.t. 24 hr (hereafter same as 31A) | 1690 1640 1540 | $C_{22}H_{41}N_5O_5S_2.HCl.0.5H_2O$ C 46.48 (46.75) H 7.89 (7.67) N 12.11 (12.39) |
| 138 | A | XIII → 110a  R' = MeS[CH=CH-] | 200 mg → 200 mg | R'CO$_2$H (90 mg) HOBT (90 mg) DCC (150 mg) Et$_3$N (0.06 ml) DMF (3 ml) r.t. 24 hr (hereafter same as 31A) | 1680 1590 1450 | $C_{18}H_{33}N_5O_3S.HCl.H_2O$ C 44.22 (44.48) H 7.69 (7.47) N 14.21 (14.41) |
| | B | 110a → 110b  R = MeS[CH=CH-] | 100 mg → 60 mg | TFA (2 ml) r.t. 20 min Distn. off TFA, activ. chrom Eltn. with 10% MeOH—H$_2$O Lyophilization | 1680 1580 1440 | $C_{13}H_{25}N_5O_3S.2CF_3CO_2H.H_2O$ C 35.22 (35.36) H 5.26 (5.06) N 12.01 (12.13) |
| 139 | A | XIII → 111a  R' = CH$_3$CH$_2$O[CH=CH-] | 200 mg → 200 mg | R'CO$_2$H (90 mg) HOBT (90 mg) DCC (150 mg) Et$_3$N (0.06 ml) DMF (3 ml) r.t. 24 hr (hereafter same as 31A) | 1690 1660 1600 1550 | $C_{19}H_{35}N_5O_6.HCl.0.5H_2O$ C 47.85 (48.05) H 8.03 (7.85) N 14.51 (14.74) |
| 140 | A | XIII → 112a  R' = [Me$_2$C=CH-CH=CH-] | 162 mg → 177 mg | R'CO$_2$H (50 mg) HOBt (27 mg) DCC (100 mg) Et$_3$N (84 μl) DMF (2 ml) r.t. 3 days (hereafter same as 31A) | 1710(sh) 1690 1650 1530 | $C_{20}H_{35}N_5O_5.HCl.0.5H_2O$ C 50.74 (51.00) H 8.19 (7.92) N 14.72 (14.87) |

TABLE 13-continued

| # | Step | Reaction / R group | Amounts | IR | Formula / Analysis |
|---|---|---|---|---|---|
| | B | 112a → 112b; TFA (2 ml), 0° C. → r.t. 1.5 hr (hereafter same as 125B); R = CH=CH-C(Me)=CH-Me (prenyl-type) | 176 mg → 161 mg | 1690, 1650, 1530 | $C_{15}H_{27}N_5O_3 \cdot 2HCl \cdot H_2O$<br>C 43.08 (43.27)<br>H 7.66 (7.50)<br>N 16.68 (16.82) |
| 141 | A | XIII → 113a; R'CO₂H (318 mg), HOBT (180 mg), DCC (300 mg), Et₃N (0.1 ml), DMF (6 ml), r.t. 24 hr (hereafter same as 31A); R' = 3,4,5-tri-MeO-C₆H₂ | 400 mg → 490 mg | 1690, 1650, 1550 | $C_{24}H_{39}N_5O_8 \cdot HCl \cdot H_2O$<br>C 49.47 (49.69)<br>H 7.51 (7.30)<br>N 11.92 (12.07) |
| | B | 113a → 113b; 2N-HCl (5 ml), r.t. 3 hr, Activ.-C chrom., Eltn. with 10% MeOH, Lyophilization; R = 3,4,5-tri-MeO-C₆H₂ | 490 mg → 200 mg | 1690, 1650, 1540 | $C_{19}H_{31}N_5O_6 \cdot 2HCl \cdot H_2O$<br>C 44.01 (44.19)<br>H 6.99 (6.83)<br>N 13.33 (13.56) |
| 142 | A | XIII → 114a; R'CO₂H (408 mg), HOBT (350 mg), DCC (615 mg), Et₃N (0.2 ml), DMF (10 ml), r.t. 24 hr (hereafter same as 31A); R' = PhCH₂- | 800 mg → 900 mg | 1690, 1650, 1620, 1540 | $C_{22}H_{35}N_5O_5 \cdot HCl \cdot 0.5H_2O$<br>C 53.13 (53.38)<br>H 7.69 (7.53)<br>N 14.00 (14.15) |
| | B | 114a → 114b; 1N-HCl (20 ml), Activ.-C chromato. Eltn. with 10% MeOH, Lyophilization; R = PhCH₂- | 900 mg → 550 mg | 1690, 1650, 1630, 1540, 1480 | $C_{17}H_{27}N_5O_3 \cdot 2HCl \cdot H_2O$<br>C 46.18 (46.37)<br>H 7.24 (7.10)<br>N 15.77 (15.90) |

TABLE 13-continued

| | | | | | | |
|---|---|---|---|---|---|---|
| 143 | A | XIII → 115a  R' = (diphenylmethyl) | 800 mg → 1020 mg | R'CO₂H (635 mg)  HOBT (350 mg)  DCC (617 mg)  Et₃N (0.28 ml)  DMF (10 ml)  r.t. 24 hr  (hereafter same as 31A) | 1690  1650  1550 | C₂₈H₃₉N₅O₅·HCl·H₂O  C 57.76 (57.97)  H 7.48 (7.30)  N 11.92 (12.07) |
| | B | 115a → 115b  R = (diphenylmethyl) | 1020 mg → 650 mg | 1N—HCl (20 ml)  r.t. 4 hr  Activ.-C Chromato.  Eltn. with 10% MeOH  Lyophilization | 1690  1640  1550  1495 | C₂₃H₃₁N₅O₃·2HCl·1.5H₂O  C 45.17 (45.44)  H 7.40 (7.18)  N 15.30 (15.58) |
| 144 | A | XIII → 116a  R' = (2-naphthylmethyl) | 1000 mg → 1000 mg | R'CO₂H (650 mg)  HOBT (440 mg)  DCC (760 mg)  Et₃N (0.34 ml)  DMF (15 ml)  r.t. 24 hr  (hereafter same as 31A) | 1690  1630  1550 | C₂₅H₃₅N₅O₅·HCl·0.5H₂O  C 56.25 (56.54)  H 7.21 (7.02)  N 13.03 (13.19) |
| | B | 116a → 116b  R = (2-naphthylmethyl) | 1000 mg → 500 mg | 1N—HCl (20 ml)  Activ.-C chromato.  Eltn. with 10% MeOH  Lyophilization | 1690  1630  1540 | C₂₀H₂₇N₅O₃·2HCl·H₂O  C 50.19 (50.42)  H 6.80 (6.56)  N 14.54 (14.70) |
| 145 | A | XIII → 117a  R' = CF₃CH=CH— | 162 mg → 228 mg | R'CO₂H (67 mg)  HOBT (54 mg)  DCC (99 mg)  Et₃N (84 µl)  DMF (2 ml)  r.t. 16 hr  (hereafter same as 31A) | 1710(sh)  1690  1675  1640  1530 | C₂₀H₃₂F₃N₅O₅·HCl·H₂O  C 44.77 (44.99)  H 6.87 (6.61)  N 13.01 (13.12) |

TABLE 13-continued

| | | | | | |
|---|---|---|---|---|---|
| B | 117a → 117b  R = [structure with CF$_3$] | 228 mg → 16.3 mg | TFA (2 ml) 0° C. → r.t. 1 hr (hereafter same as 125B) | 1690 1635 1550 | C$_{15}$H$_{24}$F$_3$N$_5$O$_3$.2HCl.1.5H$_2$O C 37.28 (37.59) H 6.32 (6.10) N 14.39 (14.61) |
| 146 A | XIII → 118a  R' = Me [structure with Et] | 162 mg → 161 mg | R'CO$_2$H (67 mg) HOBT (27 mg) DCC (99 mg) Et$_3$N (84 μl) DMF (2 ml) r.t. 16 hr (hereafter same as 31A) | 1710(sh) 1685 1650 1520 | C$_{22}$H$_{39}$N$_5$O$_5$.HCl.0.5H$_2$O C 52.71 (52.95) H 8.40 (8.28) N 13.88 (14.03) |
| B | 118a → 118b  R = Me [structure with Et] | 160 mg → 101 mg | TFA (2 ml) 0° C. → r.t. 1 hr (hereafter same as 125B) | 1690 1645 1530 | C$_{17}$H$_{31}$N$_5$O$_3$.2HCl.H$_2$O C 45.87 (46.05) H 7.89 (7.73) N 15.70 (15.79) |
| 147 A | XIII → 119a  R' = [structure with CH$_2$F] | 203 mg → 234 mg | R'CO$_2$H (83 mg) HOBT (34 mg) DCC (130 mg) Et$_3$N (105 μl) DMF (3 ml) r.t. 16 hr (hereafter same as 31A) | 1710(sh) 1690 1660 1530 | C$_{20}$H$_{34}$FN$_5$O$_5$.HCl.H$_2$O C 47.98 (48.24) H 7.64 (7.49) N 13.87 (14.06) |
| B | 119a → 119b  R = [structure with CH$_2$F] | 233 mg → 153 mg | TFA (2 ml) 0° C. → r.t. 1 hr (hereafter same as 125B) | 1690 1655 1540 | C$_{15}$H$_{26}$FN$_5$O$_3$.2HCl.H$_2$O C 41.25 (41.48) H 7.17 (6.96) N 16.01 (16.12) |
| 148 A | XIII → 120a  R' = [structure with Cl] | 162 mg → 201 mg | R'CO$_2$H (106 mg) HOBT (108 mg) DCC (206 mg) THF (3 ml) r.t. 1.5 hr XIII, NaHCO$_3$ (51 mg) H$_2$O (3 ml) soln. + above active ester 0° C. → r.t. 1.5 hr 1N—HCl 3 drops, HP-20 column purifcn. | 1710(sh) 1690 1655 1530 | C$_{19}$H$_{32}$ClN$_5$O$_5$.HCl.0.5H$_2$O C 46.23 (46.44) H 7.11 (6.97) N 14.08 (14.25) |

TABLE 13-continued

| B | | | |
|---|---|---|---|
| | 120a → 120b | TFA (2 ml)<br>0° C. —→ r.t. 1 hr  201 mg —→ 147 mg<br>(hereafter same as 125B) | 1690<br>1655<br>1610<br>1545 | C$_{14}$H$_{24}$ClN$_5$O$_3$.2HCl.H$_2$O<br>C 41.82 (41.90)<br>H 7.21 (7.03)<br>N 17.38 (17.45) |
| R = (structure: Cl-CH=CH-CH₂-CH=CH-) | | | |

EXAMPLES 149-151 (TABLE 14)

By the procedure similar to Example 82, Compound (XXVIII) was subjected to amidation by using various amines (R'NH$_2$) to obtain corresponding amido compounds (Step A), followed by deprotection reaction (Step B) to obtain compounds of Examples 149-151. The reaction conditions, yields and some of the physico-chemical properties of the products are shown in Table 14.

EXAMPLES 152-158 (TABLE 15)

By the procedure similar to Example 95, Compound 52b was subjected to amidation (Step A) by using various amines (R'NH$_2$) or its derivatives, then to deprotection reaction (Step B) to obtain compounds of Examples 152-158. The reaction conditions, yields and some of the physico-chemical properties of the products are shown in Table 15.

TABLE 14

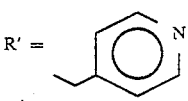

| Ex. No. | Step | Starting Compd. → Product Compds. | Reaction Conditions | Yield Material → Product | IR $\nu_{max}^{KBr}$ cm$^{-1}$ | Molecular Formula Analysis (Calcd.) |
|---|---|---|---|---|---|---|
| 149 | A | XXVIII → 121a<br>R' = 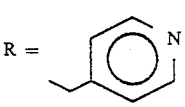 | R'NH$_2$ (275 mg)<br>MeOH (10 ml)<br>r.t. 7 days conc.,<br>SiO$_2$ column chromato<br>CHCl$_3$:EtoAc:MeOH = 3:3:1 elution | 576 mg → 758 mg | 1710(sh)<br>1690<br>1655 | C$_{23}$H$_{34}$N$_4$O$_5$<br>C 61.88 (61.86)<br>H 7.65 (7.67)<br>N 12.62 (12.55) |
|  | B | 121a → 121b<br>R = 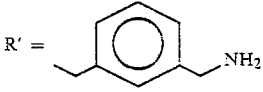 | TFA (3 ml)<br>0° C.→r.t. 1 hr<br>hereafter same as 125B | 358 mg → 322 mg | 1665<br>1650<br>1630<br>1600<br>1540 | C$_{18}$H$_{26}$N$_4$O$_3$.2HCl.H$_2$O<br>C 49.38 (49.43)<br>H 7.13 (6.91)<br>N 12.65 (12.81) |
| 150 | A | XXVIII → 122a<br>R' = 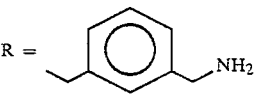 | R'NH$_2$ (2270 mg)<br>MeOH (20 ml)<br>r.t. 18 hr conc.,<br>SiO$_2$ column chromato<br>EtoAc:MeOH = 5:1 eltn. | 1128 mg → 700 mg | 1710(sh)<br>1695<br>1655<br>1525 | C$_{25}$H$_{38}$N$_4$O$_5$<br>C 63.11 (63.27)<br>H 8.18 (8.07)<br>N 11.74 (11.81) |
|  | B | 122a → 122b<br>R = 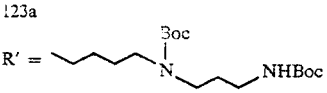 | Conc. HCl (1 ml)<br>MeOH (4 ml)<br>0° C.→r.t. 1 hr<br>HP-20 column chromato.<br>Eltn. with H$_2$O,<br>lyophilization | 500 mg → 334 mg | 1655<br>1610<br>1540 | C$_{20}$H$_{30}$N$_4$O$_3$.2HCl.H$_2$O<br>C 51.49 (51.61)<br>H 7.51 (7.36)<br>N 12.00 (12.04) |
| 151 | A | XXVIII → 123a<br>R' = 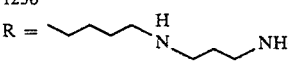 | R'NH$_2$ (1036 mg)<br>MeOH (5 ml)<br>r.t. 3 days<br>conc., silica gel<br>column chromato.<br>Eltn. with EtOAc | 677 mg → 900 mg | 1710(sh)<br>1690<br>1655<br>1540 | C$_{34}$H$_{61}$N$_5$O$_9$<br>C 59.67 (59.71)<br>H 8.29 (8.99)<br>N 10.09 (10.24) |
|  | B | 123a → 123b<br>R = ~~~N(H)~~~NH$_2$ | TFA (4 ml)<br>0° C.→r.t. 1 hr<br>(hereafter same as 125B) | 800 mg → 400 mg | 1655<br>1620<br>1530 | C$_{19}$H$_{37}$N$_5$O$_3$.3HCl.2H$_2$O<br>C 42.96 (43.14)<br>H 8.52 (8.38)<br>N 13.08 (13.24) |

TABLE 15

Scheme:
XN(H)–C(O)–CH(NHBoc)–CO$_2$H  (52b, P = MOM)
— Step A, R'NH$_2$ → XN(H)–C(O)–CH(NHBoc)–CONHR'  (a)
— Step B, Deprotection → XN(H)–CH(OH)–CH(NH$_2$)–CONHR  (b)

| Ex. No. | Step | Starting Compd. → Product Compd. | Reaction Conditions | Yield Material → Product | IR $\nu_{max}^{KBr}$ cm$^{-1}$ | Molecular Formula Analysis (Calcd.) |
|---|---|---|---|---|---|---|
| 152 | A | 52b → 124a; R' = –CH(Me)CH$_2$–C(=NH)NH$_2$ | R'NH$_2$.2HCl (130 mg), NaHCO$_3$ (95 mg), H$_2$O (3 ml), 52b, HOBT (75 mg), DCC (114 mg), THF (2 ml), 0° C.→r.t. 15 hr stir. pH 3.0 (1N—HCl), HP-20 Lyophilization | 220 mg → 253 mg | 1710 (sh), 1690, 1660, 1650, 1540 | C$_{23}$H$_{41}$N$_5$O$_6$.HCl.0.5H$_2$O<br>C 52.20 (52.21)<br>H 8.40 (8.19)<br>N 13.03 (13.24) |
| | B | 124a → 124b; R = –CH(Me)CH$_2$–C(=NH)NH$_2$ | TFA (3 ml), 0° C.→r.t. 1.5 Hr (hereafter same as 125B) | 252 mg → 135 mg | 1690, 1660, 1650, 1540 | C$_{16}$H$_{29}$N$_5$O$_3$.2HCl.H$_2$O<br>C 44.45 (44.65)<br>H 7.88 (7.73)<br>N 16.09 (16.27) |
| 153 | A | 52b → 125a; R' = –CH$_2$CH$_2$CH$_2$–C(=NH)NHMe | R'NH$_2$.2HCl (130 mg), NaHCO$_3$ (95 mg), H$_2$O (3 ml), 52b, HOBT (75 mg), DCC (114 mg), THF (2 ml), 0° C.→r.t. 20 hr, pH 3.0 (1N—HCl), HP-20 Lyophilization | 220 mg → 270 mg | 1710, 1690, 1650, 1535 | C$_{23}$H$_{41}$N$_5$O$_6$.HCl.H$_2$O<br>C 51.17 (51.34)<br>H 8.41 (8.24)<br>N 12.89 (13.02) |
| | B | 125a → 125b; R = –CH$_2$CH$_2$CH$_2$–C(=NH)NHMe | TFA (3 ml), 0° C.→r.t. 1.5 Hr (hereafter same as 125B) | 270 mg → 139 mg | 1680, 1650, 1540 | C$_{16}$H$_{29}$N$_5$O$_3$.2HCl.1.5H$_2$O<br>C 43.60 (43.74)<br>H 7.91 (7.80)<br>N 15.77 (15.94) |
| 154 | A | 52b → 126a; R' = –CH$_2$CH(Me)–C(=NH)NH$_2$ | R'NH$_2$.2HCl (105 mg), NaHCO$_3$ (101 mg), H$_2$O (3 ml), 52h, HOBT (60 mg), DCC (91 mg), THF (2 ml), 0° C.→r.t. 2 hr, pH 3.0 (1N—HCl), HP-20 Lyophilization | 176 mg → 184 mg | 1710 (sh), 1690, 1650, 1530 | C$_{23}$H$_{41}$N$_5$O$_6$.HCl.H$_2$O<br>C 51.09 (51.34)<br>H 8.48 (8.24)<br>N 12.88 (13.02) |
| | B | 126a → 126b; R = –CH$_2$CH(Me)–C(=NH)NH$_2$ | TFA (2 ml), 0° C.→r.t. 1 hr (hereafter same as 125B) | 183 mg → 96 mg | 1685, 1650, 1540 | C$_{16}$H$_{29}$N$_5$O$_3$.2HCl.H$_2$O<br>C 44.39 (44.65)<br>H 7.91 (7.73)<br>N 16.07 (16.27) |
| 155 | A | 52b → 127b; R' = –CH(Ph)–C(=NH)NH$_2$ | R'NH$_2$.2 HCl (142 mg), NaHCO$_3$ (76 mg), H$_2$O (2 ml), 52b, HOBT (60 mg), DCC (91 mg), THF (2 ml), 0° C.→r.t. 2 hr, EtOAc:THF (1:1) extn. Concn. TFA (2 ml), 0° C.→r.t. 1.5 hr (hereafter same as 125B) | 176 mg → 138 mg | 1690, 1650, 1540 | C$_{21}$H$_{31}$N$_5$O$_3$.2HCl.1.5H$_2$O<br>C 50.12 (50.30)<br>H 7.38 (7.24)<br>N 13.79 (13.97) |
| 156 | A | 52b → 128a; R' = –N(Me)–C(=NH)NH–CH$_2$–NH$_2$ | R'NH$_2$.2 HCl (105 mg), NaHCO$_3$ (101 mg), H$_2$O (2 ml), 52b, HOBt (60 mg), DCC (91 mg), THF (2 ml), 0° C.→r.t. 20 hr, pH 3.5 (1N—HCl), HP-20 Lyophilization | 176 mg → 91 mg | 1710, 1690, 1530 | C$_{22}$H$_{40}$N$_6$O$_6$.HCl.0.5H$_2$O<br>C 49.70 (49.85)<br>H 8.17 (7.99)<br>N 15.66 (15.85) |

TABLE 15-continued $$\underset{52b\ P=MOM}{\overset{H}{\underset{\times N}{\vphantom{|}}}\!\!\!\!\!\!\underset{}{\overset{O}{\vphantom{|}}}\!\!\!\!\!\!\underset{}{\overset{NHBoc}{\vphantom{|}}}\!\!\!CO_2H} \xrightarrow[R'NH_2]{Step\ A} \underset{a}{\overset{H}{\underset{\times N}{\vphantom{|}}}\!\!\!\!\!\!\underset{}{\overset{O}{\vphantom{|}}}\!\!\!\!\!\!\underset{}{\overset{NHBoc}{\vphantom{|}}}\!\!\!CONHR'} \xrightarrow[Deprotection]{Step\ B} \underset{b}{\overset{H}{\underset{\times N}{\vphantom{|}}}\!\!\!\!\!\!\underset{}{\overset{HO}{\vphantom{|}}}\!\!\!\!\!\!\underset{}{\overset{NH_2}{\vphantom{|}}}\!\!\!CONHR}$$

| Ex. No. | Step | Starting Compd. → Product Compd. | Reaction Conditions | Yield Material → Product | IR $\nu_{max}^{KBr}$ cm$^{-1}$ | Molecular Formula Analysis (Calcd.) |
|---|---|---|---|---|---|---|
| | B | 128a → 128b<br>R = —N(Me)—C(=NH)NH₂ | TFA (2 ml)<br>0° C. → r.t. 1 hr<br>concn., HP-20<br>Lyophilization | 91 mg<br>→<br>51 mg | 1685<br>1200<br>1130 | C₁₅H₂₈N₆O₃·2CF₃CO₂H·H₂O<br>C 38.70 (38.91)<br>H 5.69 (5.50)<br>N 14.13 (14.33) |
| 157 | A | 52b → 129a<br>R' = —CH₂CH₂CH₂—C(=NH)NHNH₂ | R'NH₂·2 HCl (176 mg)<br>NaHCO₃ (84 mg), H₂O (3 ml)<br>52b, HOBT (81 mg), DCC<br>(124 mg), THF (3 ml)<br>0° C. → r.t. 2 hr<br>pH 3.5 (1N—HCl), HP-20<br>Lyophilization | 220 mg<br>→<br>254 mg | 1710<br>1690<br>1650<br>1530 | C₂₂H₄₀N₆O₆·HCl·H₂O<br>C 48.89 (49.02)<br>H 8.19 (8.04)<br>N 15.44 (15.59) |
| | B | 129a → 129b<br>R = —CH₂CH₂CH₂—C(=NH)NHNH₂ | TFA (3 ml)<br>0° C. → r.t. 75 min<br>(hereafter same as 125B) | 253 mg<br>→<br>108 mg | 1690 (sh)<br>1675<br>1650<br>1610<br>1540 | C₁₅H₂₈N₆O₃·2HCl·H₂O<br>C 41.59 (41.77)<br>H 7.69 (7.48)<br>N 19.32 (19.48) |
| 158 | A | 52b → 130a<br>R' = —O—CH₂—C(=NH)NH₂ | R'NH₂·2 HBr (151 mg)<br>NaHCO₃ (84 mg), H₂O (3 ml)<br>52b, HOBT (75 mg), DCC<br>(114 mg), THF (3 ml)<br>r.t. 20 hr<br>pH 3.0 (1N—HCl), HP-20<br>Lyophilization | 220 mg<br>→<br>91.5 mg | 1710 (sh)<br>1690<br>1520<br>1360 | C₂₁H₃₇N₅O₇·0.5 H₂O₂<br>C 48.57 (48.79)<br>H 7.82 (7.60)<br>N 13.39 (13.55) |
| | B | 130a → 130b<br>R = —O—CH₂—C(=NH)NH₂ | TFA (2 ml)<br>0° C. → r.t. 1 hr<br>(hereafter same as 125B) | 91 mg<br>→<br>17 mg | 1690<br>1650<br>1610 | C₁₄H₂₅N₅O₄·2HCl·H₂O<br>C 40.01 (40.20)<br>H 7.12 (6.99)<br>N 16.58 (16.74) |

EXAMPLE 159

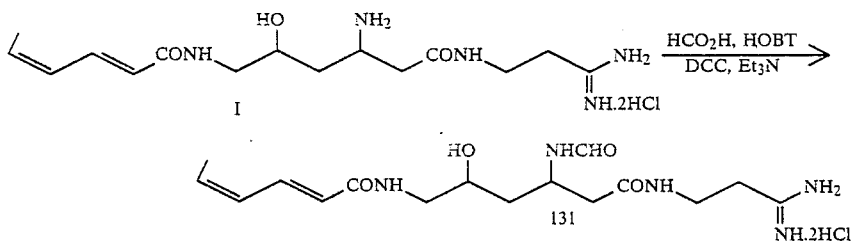

To a solution of Compound I (222 mg) in DMF (2 ml) was added Et₃N (105 μl). To the mixture were added, 5 minutes later, HCO₂H (35 mg), HOBT (102 mg) and DCC (155 mg), followed by allowing the reaction to proceed at room temperature for 4 days. The reaction mixture was concentrated under reduced pressure. The concentrate was passed through an IRA-401 (Cl⁻) resin column (20 ml), followed by elution with water (100 ml). The eluate was concentrated and purified by means of an HP-20 column and eluted with 5% EtOH—H₂O. The eluate was lyophilized to afford Compound 131 (38 mg) as a pale yellow powdery product.

IR$\nu_{max}^{KBr}$ cm$^{-1}$: 1690, 1650, 1540.
Elemental analysis for: C₁₆H₂₇N₅O₄·HCl·1.5 H₂O:
Calcd.: C, 46.10; H, 7.49; N, 16.80, Found: C, 45.88; H, 7.62; N, 16.63.

EXAMPLE 160

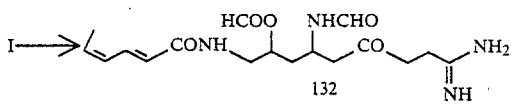

To a solution of Compound I (222 mg) in HCO₂H (4 ml) was added AC₂O (2 ml) under ice-cooling, and the mixture was stirred at room temperature for 2.5 hours, followed by concentration under reduced pressure. The concentrate was dissolved in water, which was passed through an IRA-401 (Cl⁻) column (20 ml), then eluted with water (150 ml). The eluate was concentrated, followed by purification by means of an HP-20(70 ml) column chromatography, eluting with 5% EtOH—H₂O. The eluate was lyophilized to afford Compound 132 as colorless powder.

IR$\nu_{max}^{KBr}$ cm⁻¹:1720, 1690, 1660, 1540.

Elemental analysis for: $C_{17}H_{27}N_5O_5 \cdot HCl \cdot H_2O$: Calcd.: C, 46.84; H, 6.94; N, 16.07, Found: C, 46.66; H, 7.19; N, 15.89.

EXAMPLE 161

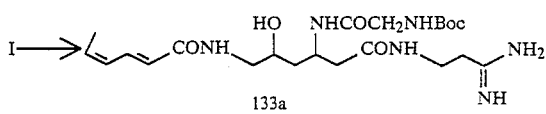

To a suspension of Compound I (177 mg) in DMF (2 ml) was added Et₃N (84 μl), and the mixture was stirred for 5 minutes. To the reaction mixture were added N-Boc.glycine (84 mg), HOBT (27 mg) and DCC (100 mg), and the reaction was allowed to proceed at room temperature for 3 days. DMF was distilled off under reduced pressure, then the residue was dissolved in a small volume of water, to which was added 1N—HCl to adjust the pH at 3, followed by purification by means of an HP-20 (70 ml) column chromatography, eluting with 30% EtOH—H₂O. The eluate was lyophilized to afford Compound 133a (194 mg) as colorless powder.

IR$\nu_{max}^{KBr}$ cm⁻¹:1710(sh), 1690, 1660, 1550.

Elemental analysis for: $C_{22}H_{38}N_6O_6 \cdot HCl \cdot 0.5H_2O$: Calcd.: C, 50.04; H, 7.64; N, 15.92, Found: C, 49.88; H, 7.77; N, 15.81.

133a⟶

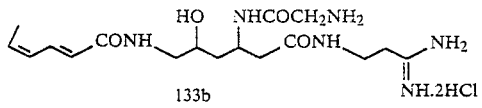

To Compound 133a (193 mg) was added, under ice-cooling, TFA (2 ml), and the mixture was stirred at room temperature for one hour, followed by concentration under reduced pressure. The residue was dissolved in a small volume of water, which was purified by means of an HP-20 (70 ml) column, eluting with 5% EtOH—H₂O. Eluate fractions containing the desired compound were combined and concentrated. The concentrate was passed through an IRA-401 (Cl⁻) (20 ml) column, followed by elution with water (60 ml). The eluate was lyophilized to afford Compound 133b (129 mg) as pale yellow powder.

IR$\nu_{max}^{KBr}$ cm⁻¹:1690, 1655, 1545.

Elemental analysis for: $C_{17}H_{30}N_6O_4 \cdot 2HCl \cdot H_2O$: Calcd.: C, 43.13; H, 7.24; N, 17.75, Found: C, 42.96; H, 7.48; N, 17.52.

EXAMPLE 162

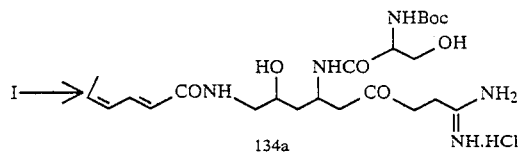

To a solution of Compound I (177 mg) and DL-N-Boc.serine (99 mg) in DMF (2 ml) were added Et₃N(84 μl), HOBT (27 mg) and/DCC (100 mg), followed by allowing the reaction to proceed for 20 hours. DMF was distilled off under reduced pressure, and the residue was purified by means of an HP-20 (70 ml) column, eluting with 30% EtOH—H₂O. The eluate was lyophilized to afford Compound 134a (240 mg) as colorless powder.

IR$\nu_{max}^{KBr}$ cm⁻¹:1710(sh), 1690, 1660, 1650, 1540.

Elemental analysis for: $C_{23}H_{40}N_6O_7 \cdot HCl \cdot H_2O$: Calcd.: C, 48.71; H, 7.64; N, 14.82, Found: C, 48.50; H, 7.78; N, 14.73.

134a⟶

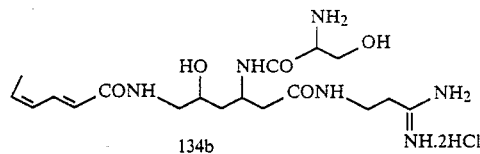

To Compound 134a (240 mg) was added, under ice-cooling, TFA (2 ml), and the mixture was stirred at room temperature for one hour. The mixture was concentrated under reduced pressure, then the concentrate was subjected to an HP-20 (70 ml) column chromatography, eluting with 5% EtOH—H₂O. The eluate was concentrated, which was passed through an IRA-401 (Cl⁻) (20 ml) column, followed by elution with water (60 ml). The eluate was lyophilized to afford Compound 134b (123 mg) as colorless powder.

IR$\nu_{max}^{KBr}$ cm⁻¹:1690, 1650, 1545.

Elemental analysis for: $C_{18}H_{32}N_6O_5 \cdot 2HCl \cdot 1.5H_2O$: Calcd.: C, 42.19; H, 7.28; N, 16.40, Found: C, 42.00; H, 7.43; N, 16.21.

EXAMPLE 163

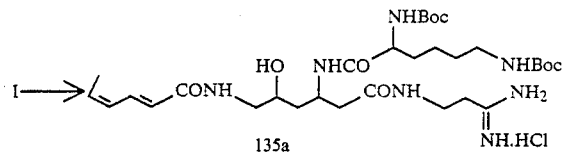

To a solution of DL-N², N⁶-diBoc-lysine (167 mg) in THF (2 ml) were added HOBT (65 mg) and DCC (99 mg), and the mixture was stirred at room temperature for 1.5 hours. On the other hand, Compound I (177 mg) was dissolved in H₂O (3 ml), to which was added sodium hydrogencarbonate (51 mg). To the mixture was added, while stirring under ice-cooling, the above-mentioned THF solution of active ester, followed by allowing the reaction to proceed at room temperature for 3 hours. To the reaction mixture was added under ice-cooling 1N—HCl to adjust the pH at 3.0, followed by distilling off THF under reduced pressure. The residue was subjected to an HP-20 (60 ml) column chromatography, eluting with 40% EtOH—H₂O. The eluate was lyophilized to afford Compound 135a (245 mg) as colorless powder.

IR$\nu_{max}^{KBr}$ cm$^{-1}$:1710(sh), 1690, 1660, 1525.

Elemental analysis for: C₃₁H₅₅N₇O₈.HCl.0.5H₂O: Calcd.: C, 53.25; H, 8.22; N, 14.02, Found: C, 53.19; H, 8.29; N, 13.82.

135a ⟶

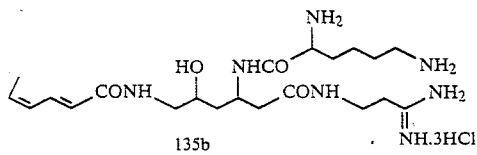

To Compound 135a (244 mg) was added, under ice-cooling, TFA (3 ml), and the mixture was stirred for 1.5 hours, followed by concentration under reduced pressure. The concentrate was subjected to an HP-20 (60 ml) column chromatography, eluting with 5% EtOH—H₂O. The eluate was concentrated and passed through an IRA-401 (Cl⁻) (20 ml) column, followed by elution with 60 ml of water. The eluate was lyophilized to afford Compound 135b (144 mg) as pale yellow powder.

IR$\nu_{max}^{KBr}$ cm$^{-1}$:1685, 1650, 1540.

Elemental analysis for: C₂₁H₃₉N₇O₄.3HCl.1.5H₂O: Calcd.: C, 42.75; H, 7.69; N, 16.62, Found: C, 42.64; H, 7.81; N, 16.49.

EXAMPLE 164 solution of active ester as prepared above, followed by allowing the reaction to proceed at room temperature for 1.5 hours. The reaction mixture was adjusted to pH 3.0 with 1N—HCl, from which was distilled off THF under reduced pressure, followed by filtering off insolubles. The filtrate was subjected to an HP-20 (60 ml) column chromatography. Fractions eluted with 30% EtOH—H₂O were combined and lyophilized to afford Compound 136a (246 mg) as colorless powder.

IR$\nu_{max}^{KBr}$ cm$^{-1}$:1710(sh), 1690, 1655, 1540.

Elemental analysis for: C₂₃H₄₀N₆O₆.HCl.H₂O: Calcd.: C, 50.13; H, 7.86; N, 15.25, Found: C, 49.85; H, 7.97; N, 15.04.

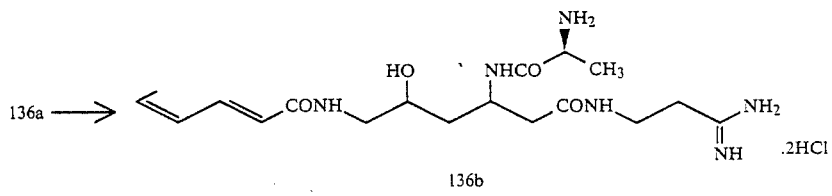

To Compound 136a (201 mg) was added, under ice-cooling, TFA (2 ml), and the mixture was stirred at room temperature for one hour. The reaction mixture was concentrated under reduced pressure. The concentrate was subjected to an HP-20 (60 ml) column chromatography, eluting with 5% EtOH—H₂O. The eluate was concentrated and passed through an IRA-401 (Cl⁻) column, eluting with water (60 ml), followed by lyophilization to afford Compound 136b (145 mg) as pale yellow powder.

IR$\nu_{max}^{KBr}$ cm$^{-1}$:1690, 1655, 1550.

Elemental analysis for: C₁₈H₃₂N₆O₄.2HCl.H₂O: Calcd.: C, 44.36; H, 7.44; N, 17.24, Found: C, 44.29; H, 7.61; N, 17.11.

EXAMPLE 165

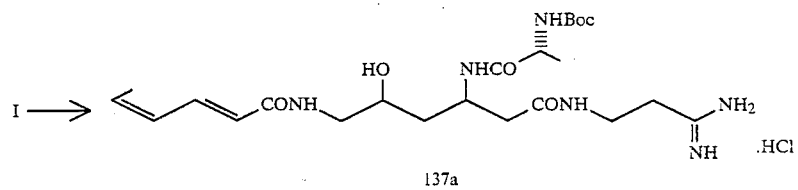

To the solution of D-Boc-Ala(114 mg) in THF (2 ml) were added HOBT (81 mg) and DCC (124 mg), and the reaction was allowed to proceed at room temperature for one hour. On the other hand, Compound I (221 mg) was dissolved in water (2 ml), to which was added sodium hydrogencarbonate (84 mg). To the mixture

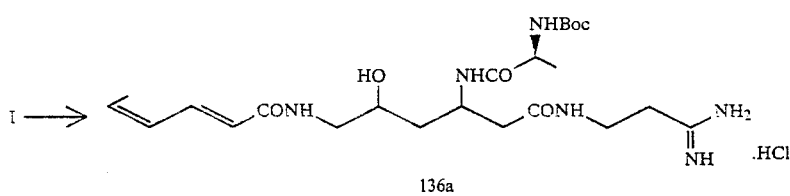

To a solution of L-Boc-Ala (114 mg) in THF (2 ml) were added HOBT (81 mg) and DCC (124 mg), and the mixture was stirred at room temperature for one hour. On the other hand, Compound I (221 mg) was dissolved in H₂O (2 ml). To the solution was added the THF was added, under ice-cooling, the THF solution of active ester prepared as above, followed by stirring at room temperature for 1.5 hours. The reaction mixture was adjusted to pH 3.0 with 1N—HCl under ice-cooling, followed by distilling off THF under reduced pressure. Insolubles were then filtered off. The filtrate was subjected to an HP-20 (60 ml) column chromatography. Fractions eluted with 30% EtOH—H₂O were combined and lyophilized to afford Compound 137a (235 mg) as colorless powder.

IR$\nu_{max}^{KBr}$ cm$^{-1}$:1710(sh), 1690, 1665, 1650, 1530.

Elemental analysis for: $C_{23}H_{40}N_6O_6 \cdot HCl \cdot 0.5H_2O$: Calcd.: C, 50.96 H, 7.81; N, 15.50, Found: C, 50.71 H, 7.98; N, 15.35.

lized to afford Compound 138 (667 mg) as colorless powder.

IR$\nu_{max}^{KBr}$ cm$^{-1}$:1680, 1640, 1530.

Elemental analysis for: $C_{22}H_{33}N_5O_3 \cdot 2HCl \cdot H_2O$: Calcd.: C, 52.17; H, 7.36; N, 13.83, Found: C, 52.02; H, 7.49; N, 13.69.

EXAMPLE 167

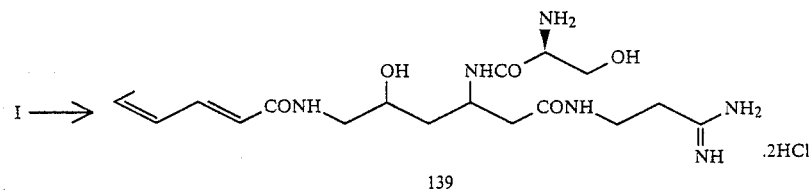

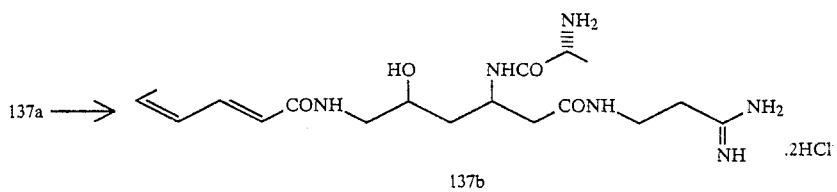

Compound 137a (230 mg) was dissolved in THF (2 ml) under ice-cooling, and the reaction was allowed to proceed at room temperature for one hour, followed by concentration under reduced pressure. The concentrate was subjected to an HP-20 (60 ml) column chromatography, eluting with 5% EtOH—H₂O. The eluate was concentrated, passed through an IRA-40 (Cl⁻) (20 ml) column, eluted with water (60 ml) and lyophilized to afford Compound 137b (143 mg) as colorless powder.

IR$\nu_{max}^{KBr}$ cm$^{-1}$:1690–1640, 1545.

Elemental analysis for: $C_{18}H_{32}N_6O_4 \cdot 2HCl \cdot H_2O$: Calcd.: C, 44.36 H, 7.44; N, 17.24, Found: C, 44.18; H, 7.58; N, 17.13.

EXAMPLE 166

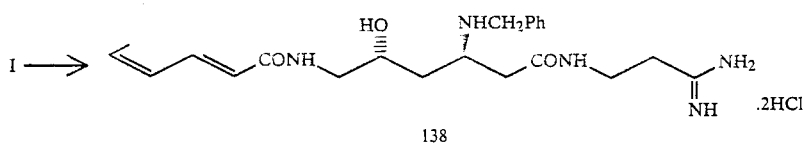

To a solution of Compound I (844 mg) in MeOH (18 ml) was added benzaldehyde (0.485 ml), and the mixture was stirred at room temperature for 30 minutes. To the reaction mixture were added NaBH₃CN (283 mg) and acetic acid (0.7 ml), and the mixture was stirred at room temperature for 3 hours, followed by further addition of benzaldehyde (0.254 ml) and NaBH₃CN (157 mg). The whole mixture was stirred for further one hour, which was concentrated under reduced pressure. The concentrate was dissolved in water, which was adjusted to pH 3 with 1n HCl. The mixture was subjected to an HP-20 (350 ml) column chromatography, eluting with 20% EtOH—H₂O. The eluate was lyophi- To a solution of L-Boc-Ser (154 mg) in THF (3 ml) were added DCC (155 mg) and HOBT (102 mg), and the mixture was stirred at room temperature for one hour. On the other hand, Compound I (234 mg) was dissolved in water (3 ml), to which was added sodium hydrogencarbonate (42 mg). To the solution was added the above-mentioned THF solution of active ester under ice-cooling, followed by stirring at room temperature for 2.5 hours. Insolubles were filtered off, and the filtrate was adjusted to pH 3.0, which was then purified by means of an HP-20 (60 ml) column, eluting with 5% H₂O—EtOH. Eluate fractions were combined and lyophilized to afford a BOC derivative (261 mg) as colorless powder. To the Boc derivative was added under ice-cooling, TFA (2 ml), and the mixture was stirred at room temperature for one hour, followed by concentration under reduced pressure. The concentrate was subjected to an HP-20 (60 ml) column chromatography, eluting with 5% EtOH.H₂O. The eluate was concentrated and passed through an IRA-40 (Cl⁻) (20 ml) column, eluting with H₂O (60 ml), followed by lyophilization to afford Compound 139 (200 mg) as pale yellow powder.

IR$\nu_{max}^{KBr}$ cm$^{-1}$:1690, 1650, 1550.

Elemental analysis for: $C_{18}H_{32}N_6O_5 \cdot 2HCl \cdot 1.5H_2O$: Calcd.: C, 42.19; H, 7.28; N, 16.40, Found: C, 42.04; H, 7.44; N, 16.27.

EXAMPLE 168

I → 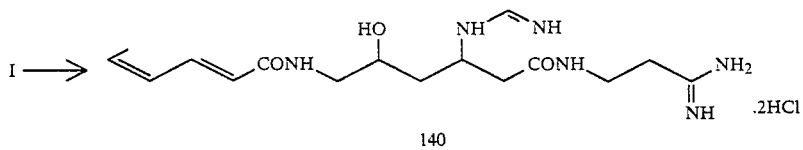

140

To a solution of Compound I (188 mg) in H₂O (3 ml) were added, under stirring at room temperature, benzylformimidate.hydrochloride (103 mg) and sodium hydrogencarbonate (101 mg), then the reaction was allowed to proceed at room temperature for 3 hours. To the reaction mixture were further added benzylformimidate hydrochloride (138 mg) and NaHCO₃ (101 mg). Benzylformimidate hydrochloride (each 206 mg) and NaHCO₃ (each 101 mg) were further added to the mixture after 18 hours and 26 hours thereafter. Then, the reaction was further allowed to proceed for 15 hours. The reaction mixture was adjusted to pH 3 by the addition of 1N HCl under ice-cooling, followed by subjecting to an HP-20 (120 ml) column chromatography, eluting with 5% EtOH—H₂O. The eluate was lyophilized to afford Compound 140 (77 mg) as colorless powder.

IR$\nu_{max}^{KBr}$ cm$^{-1}$:1690, 1650, 1540.

Elemental analysis for: $C_{16}H_{28}N_6O_3 \cdot 2HCl \cdot H_2O$: Calcd.: C, 43.34; H, 7.27; N, 18.95, Found: C, 43.15; H, 7.48; N, 18.69.

EXAMPLE 169

I → 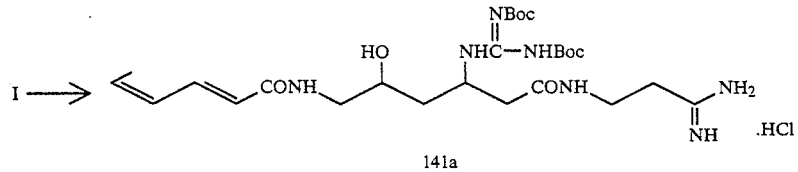

141a

To a solution of Compound I (600 mg) in DMF (5 ml) and water (1 ml) were added Et₃N (300 mg) and N,N'-bis(tert-butoxycarbonyl)-S'-methylisothiourea (450 mg), and the mixture was stirred at 50° C. for 8 hours. DMF was distilled off under reduced pressure, and the residue was adjusted to pH 3 with 1N HCl, which was subjected to an HP-20 (350 ml) column chromatography. Fractions eluted with 20% MeOH—H₂O were combined and lyophilized to afford Compound 141a (400 mg) as colorless powder.

IR$\nu_{max}^{KBr}$ cm$^{-1}$:1710(sh), 1690, 1655, 1540.

Elemental analysis for: $C_{26}H_{45}N_7O_5 \cdot HCl \cdot 0.5H_2O$: Calcd.: C, 53.74; H, 8.15; N, 16.87, Found: C, 53.69; H, 8.09; N, 16.93.

141a → 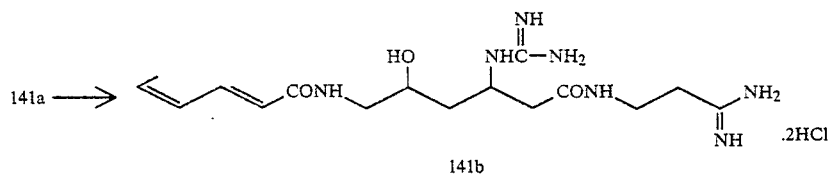

141b

Compound 141a (400 mg) was dissolved in 2N HCl (14 ml), and the reaction was allowed to proceed at room temperature for 3 hours. The reaction mixture was purified by means of an HP-20 (350 ml) column chromatography. Fractions eluted with 10% MeO-H—H₂O were combined and lyophilized to afford Compound 141b (250 mg) as colorless powder.

IR$\nu_{max}^{KBr}$ cm$^{-1}$:1690, 1650, 1530.

Elemental analysis for: $C_{16}H_{29}N_7O_3 \cdot 2HCl \cdot H_2O$: Calcd.: C, 41.73; H, 7.26; N, 21.39, Found: C, 41.73; H, 7.49; N, 21.13.

EXAMPLE 170

I → 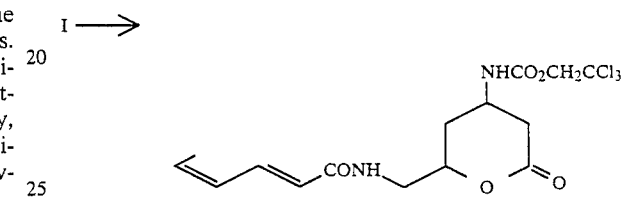

142

A solution of Compound I (2.35 g) in 2N—HCl (200 ml) was heated under reflux for 40 minutes, followed by concentration to dryness under reduced pressure. The concentrate was dissolved in H₂O:THF (1:1) (100 ml), whose pH was adjusted to 9.0 with 2N—NaOH under ice-cooling, to which was added 2,2,2-trichloroethoxycarbonyl chloride (2.07 ml). The mixture was stirred at room temperature for one hour while keeping the pH of the reaction mixture within the range of from 8.0 to 9.0. The reaction mixture was extracted with ethyl acetate, washed with saturated brine, followed by drying over anhydrous magnesium sulfate. The mixture was concentrated under reduced pressure, to which was added ether. Then precipitating crystals were collected by filtration to afford Compound 142 (1.31 g).

IR$\nu_{max}^{KBr}$ cm$^{-1}$:1745, 1725, 1665, 1540.

Elemental analysis for: $C_{15}H_{19}Cl_3N_2O_5$: Calcd.: C, 47.63; H, 5.06; N, 7.41, Found: C, 47.58; H, 5.11; N, 7.38.

EXAMPLE 171

142 → 

-continued

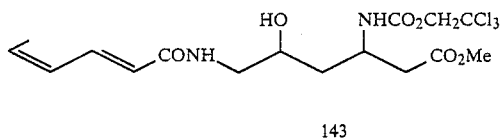

143

To a suspension of Compound 142 (743 mg) in MeOH (20 ml) was added a 28% MeONa/MeOH solution (0.3 ml), and the mixture was stirred at room temperature for 2 hours, to which was added acetic acid (0.3 ml), followed by concentration under reduced pressure. To the concentrate was added saturated brine, and the mixture was subjected to extraction with AcOEt-THF (2:1), followed by drying over magnesium sulfate. The mixture was concentrated under reduced pressure, and the concentrate was subjected to a silica gel (40 g) column chloromatography, eluting with EtoAc:CHCl$_3$=3:1, to afford Compound 143 (462 mg) as a colorless foamy product.

IR$\nu_{max}^{KBr}$ cm$^{-1}$:1740, 1720(sh), 1640, 1540.

Elemental analysis for: C$_{16}$H$_{23}$Cl$_3$N$_2$O$_6$: Calcd.: C, 43.12; H, 5.20; N, 6.28, Found: C, 43.30; H, 5.14; N, 6.37.

EXAMPLE 172

142 ⟶

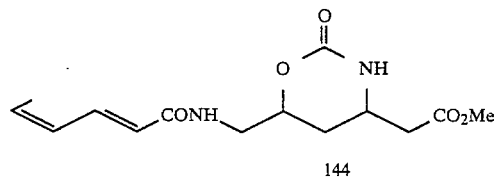

144

To a suspension of Compound 142 (414 mg) in MeOH (10 ml) was added a 28% NaOME/MeOH solution (0.3 ml), and the reaction was allowed to proceed at room temperature for 18 hours. To the mixture was added acetic acid (0.3 ml), which was concentrated under reduced pressure. The concentrate was subjected to a silica gel (35 g) column chromatography, eluting with EtoAc:CHCl$_3$:MeOH 10:10:1, to afford Compound 144 (220 mg) as colorless cyrstals.

IR$\nu_{max}^{KBr}$ cm$^{-1}$:1730, 1710, 1675, 1550.

m.p.: 141°–143° C.

Elemental analysis for: C$_{14}$H$_{20}$N$_2$O$_5$: Calcd.: C, 56.75; H, 6.80; N, 9.45, Found: C, 56.62; H, 6.93; N, 9.32.

EXAMPLE 173

143 ⟶

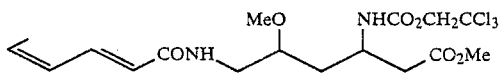

145

To a solution of Compound 143 (360 mg) in CH$_2$Cl$_2$ (10 ml) was added BF$_3$Et$_2$O/ClCH$_2$CH$_2$Cl (0.5 mmol/ml) solution (0.34 ml). To the mixture was then added an excess of CH$_2$N$_2$/ether solution, followed by stirring for 15 minutes. The mixture was concentrated under reduced pressure, and the concentrate was dissolved in ethyl acetate. The solution was washed with an aqueous solution of sodium hydrogencarbonate and saturated brine in that order, followed by drying over MgSO$_4$. The mixture was concentrated under reduced pressure, which was then subjected to a silica gel (30 g) column chromatography, eluting with Hexane:EtOAc=1:3, to afford Compound 145 as a colorless oily product.

IR$\nu_{max}^{KBr}$ cm$^{-1}$:1740, 1720, 1650, 1550.

Elemental analysis for: C$_{17}$H$_{25}$Cl$_3$N$_2$O$_6$: Calcd.: C, 44.41; H, 5.48; N, 6.09, Found: C, 44.32; H, 5.37; N, 6.17.

EXAMPLE 174

145 ⟶

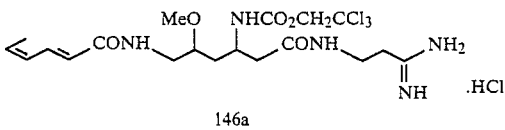

146a

To a solution of Compound 145 (175 mg) in EtOH (2 ml) was added 1N—KOH (0.76 ml), and the reaction was allowed to proceed at room temperature for 2.5 hours. The reaction mixture was concentrated under reduced pressure, whose pH was adjusted to 2.0 with 1N—HCl, followed by extraction with ethyl acetate. The ethyl acetate layer was washed with saturated brine, which was dried over MgSO$_4$, followed by concentration under reduced pressure. The concentrate was dissolved in THF (2 ml), to which were added HOBT (61 mg) and DCC (93 mg), and the mixture was stirred at room temperature for one hour.

On the other hand, 3-aminopropioamidine.2HCl(92 mg) was dissolved in water (2m). To the solution was added NaHCO$_3$ (73 mg). To the mixture was added, while stirring under ice-cooling, the active ester solution prepared as above. The mixture was stirred at room temperature for 16 hours, which was concentrated under reduced pressure. To the concentrate was added 1N—HCl to adjust the pH to 2.0. The mixture was subjected to an HP-20 (70 ml) column chromatography. The fractions eluted with 30% EtOH—H$_2$O were combined and lyophilized to afford Compound 146a (79 mg) as colorless powder.

IR$\nu_{max}^{KBr}$ cm$^{-1}$:1720, 1695, 1550, 1390.

Elemental analysis for: C$_{19}$H$_{30}$Cl$_3$N$_5$O$_5$HCl.0.5H$_2$O: Calcd.: C, 40.73; H, 5.76; N, 12.50, Found: C, 40.58; H, 5.99; N, 12.38.

146a ⟶

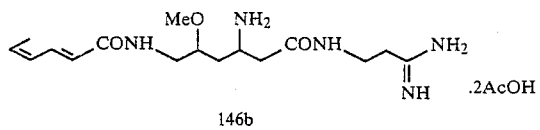

146b

To a solution of Compound 146a (78 mg) in AcOH (2 ml) was added zinc powder (100 mg), and the mixture was stirred at room temperature. In every 30 minutes, 100 mg each portion of zinc powder was added three times, followed by stirring for one hour. The reaction mixture was subjected to filtration and washed with water. The filtrate was concentrated under reduced pressure, followed by subjecting to an HP-20 (70 ml) column chromatography. The fractions eluted with 5%

EtOH were combined and lyophilized to afford Compound 146b as pale yellow powder.

IR$\nu_{max}^{KBr}$ cm$^{-1}$:1665, 1630–1550, 1400.

Elemental analysis for: C$_{16}$H$_{29}$N$_5$O$_3$2AcOH.H$_2$O: Calcd.: C, 50.30; H, 8.23; N, 14.66, Found: C, 50.09; H, 8.48; N, 14.40.

EXAMPLE 175

144⟶

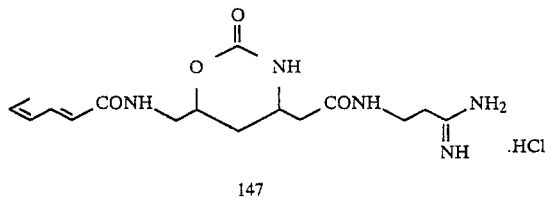

147

To a suspension of Compound 144 (163 mg) in EtOH (3 ml) was added 1N—KOH (1.1 ml), and mixture was stirred at room temperature for 30 minutes, followed by concentration under reduced pressure. To the concentrate was added 1N—HCl to adjust the pH to 2.0, followed by saturation with sodium chloride. The mixture was extracted with AcOEt:THF (1:1) and dried over MgSO$_4$. The extract was concentrated under reduced pressure. The concentrate was dissolved in THF (2 ml), to which were added HOBT (81 mg) and DCC (124 g). The mixture was stirred at room temperature for 1.5 hours.

To a solution of 3-aminopropioamidine.2HCl salt (132 mg) in water (2 ml) was added NaHCO$_3$ (105 mg), and the mixture was cooled with ice. To this mixture was added, while stirring, the active ester solution prepared as above, and the mixture was stirred at room temperature for 6 hours, followed by allowing the reaction to proceed overnight. To the reaction mixture was added 1N—HC to adjust the pH to 3.0, which was then subjected to filtration. The filtrate was concentrated under reduced pressure, and the concentrate was subjected to an HP-20 (70 ml) column chromatography. Elution was conducted with water, and eluate fractions were combined and lyophilized to afford Compound 147 (111 mg) as pale yellow powder.

IR$\nu_{max}^{KBr}$ cm$^{-1}$:1710(sh), 1690, 1655, 1545.

Elemental analysis for: C$_{16}$H$_{25}$N$_5$O$_4$HCl.H$_2$O: Calcd.: C, 47.35; H, 6.95; N, 17.25, Found: C, 47.11; H, 7.20; N, 17.00.

EXAMPLE 176

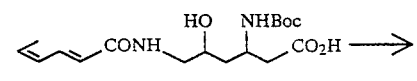

XVII

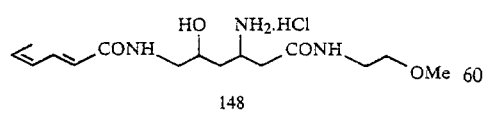

148

To a solution of Compound XVII (180 mg) in dry DMF were added Et$_3$N (0.28 ml) and Me$_3$SiCl (0.1 ml). The mixture was stirred for 10 minutes, to which was then added ethyl chlorocarbonate (0.1 ml). The mixture was stirred for 10 minutes, to which was further added 2-methoxyethylamine (0.075 ml), followed by stirring at room temperature for 30 minutes. The mixture was concentrated under reduced pressure, and the concentrate was dissolved in EtOAc. The solution was washed with an aqueous solution of sodium hydrogencarbonate and saturated brine, successively, followed by drying over anhydrous sodium sulfate. The solvent was distilled off. The residue was subjected to a silica gel (5 g) column chromatography, eluting with CHCl$_3$:MeOH:AcOEt=85:10:5, to afford an N—Boc derivative of Compound 148 (70 mg). To this compound was added 2N—HCl (3 ml), and the reaction was allowed to proceed for 4 hours. The mixture was subjected to an activated charcoal (Shirasagi A, Takeda Chemical Industries, Ltd., Japan, 3 g) column chromatography. The fractions eluted with 60% EtOH—H$_2$O to 80% EtOH—H$_2$O were combined and lyophilized to afford Compound 148 (50 mg) as colorless powder.

IR$\nu_{max}^{KBr}$ cm$^{-1}$:1690, 1660, 1650.

Elemental analysis for: C$_{15}$H$_{27}$N$_3$O$_4$HCl.0.5H$_2$O: Calcd.: C, 50.20; H, 8.15; N, 11.71, Found: C, 50.04; H, 8.30; N, 11.62.

EXAMPLE 177

52b ⟶

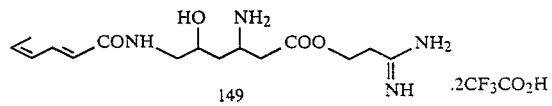

149

To a solution of Compound 52b (167 mg) in DMF (2 ml) was added 1,1'-carbonyldiimidazole (81 mg), and the mixture was stirred for 80 minutes in argon streams, followed by addition of 3-hydroxypropioamidine (78 mg). The reaction was allowed to proceed at room temperature for 18 hours. DMF was distilled off under reduced pressure. To the residue were added anisole (2 ml) and TFA (2 ml), and the mixture was stirred at room temperature for 1.5 hours. The mixture was concentrated under reduced pressure, and the concentrate was subjected to an HP-20 (70 ml) column chromatography, eluting with water. Eluate fractions were combined and lyophilized to afford Compound 149 (44 mg) as colorless powder.

IR$\nu_{max}^{KBr}$ cm$^{-1}$:1675, 1540.

Elemental analysis for: C$_{15}$H$_{26}$N$_4$O$_4$.2CF$_3$CO$_2$H: Calcd.: C, 40.50; H, 5.19; N, 9.94, Found: C, 40.27; H, 5.31; N, 9.77.

EXAMPLE 178

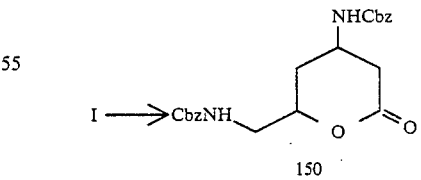

150

I ⟶

A mixture of Compound I (5.0 g) and 2N HCl (400 ml) was heated under reflux for 6 hours. The mixture was concentrated under reduced pressure, and the concentrate was dissolved in H$_2$O:THF (1:1) (100 ml). To the solution were added, while stirring under ice-cooling, carbobenzoxychloride (9.075 m) and 2N NaOH alternatively so that the pH was kept within the range of from 8.0 to 9.0. The mixture was stirred at room temperature for one hour, followed by extraction with EtOAc, and the EtOAc layer was washed with 1N HCl then with saturated brine, followed by drying over MgSO₄. The extract was concentrated under reduced pressure, and the concentrate was subjected to a silica gel (160 g) column chromatography, eluting with hexane:EtOAc=3:2 to afford Compound 150 (3.302 g) as crystals.

IR$\nu_{max}^{KBr}$ cm$^{-1}$:1760, 1730–1690, 1540.

Elemental analysis for: C₂₂H₂₄N₂O₆: Calcd.: C, 60.07; H, 5.87; N, 6.79, Found: C, 63.88; H, 6.02; N, 6.91.

EXAMPLE 179

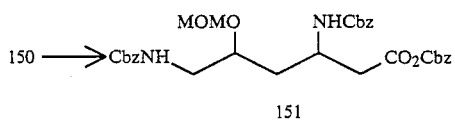

To a suspension of Compound 150 (1.65 g) in MeOH (30 ml) was added 28% NaOMe/MeOH solution (0.4 ml), and the reaction was allowed to proceed at room temperature for 30 minutes. To the reaction mixture was added acetic acid (0.4 ml), and the mixture was concentrated under reduced pressure. The concentrate was dissolved in EtOAc, and the solution was washed with water, then dried over MgSO₄. The solution was concentrated under reduced pressure, and the concentrate was dissolved in dry CH₂Cl₂ (25 ml). To the solution were added, under ice-cooling, diisopropylethylamine (2.79 ml) and methoxymethyl chloride (1.22 ml), and the reaction was allowed to proceed at room temperature for 3 days. The mixture was concentrated under reduced pressure, and the concentrate was dissolved in EtOAc. The solution was washed with water, dried over MgSO₄ and concentrated, followed by subjecting to a silica gel (30 g) column chromatography, eluting with EtOAc:hexane=1:1 to afford Compound 151 (1.90 g) as a colorless oily product.

IR$\nu_{max}^{KBr}$ cm$^{-1}$:1730–1660, 1520.

Elemental analysis for: C₂₅H₃₂N₂O₈: Calcd.: C, 61.46; H, 6.60; N, 5.73, Found: C, 61.57; H, 6.55; N, 5.84.

EXAMPLE 180

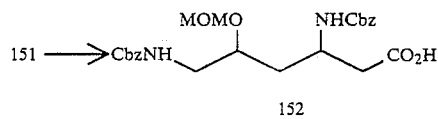

To a solution of Compound 151 (1.9 g) in EtOH (30 ml) was added 2N NaOH (4 ml), and the reaction was allowed to proveed at room temperature for one hour. The reaction mixture was concentrated under reduced pressure, and the concentrate was dissolved in a small volume of water, whose pH was adjusted to 3.0 with 1N HCl, followed by extraction with EtOAc. The ethyl acetate layer was washed with saturated brine, followed by drying over MgSO₄. The solvent was distilled off under reduced pressure to afford Compound 152 (1.58 g) as a colorless oily product.

IR$\nu_{max}^{KBr}$ cm$^{-1}$:1730, 1680, 1520.

Elemental analysis for: C₂₄H₃₀N₂O₈: Calcd.: C, 60.75; H, 6.37; N, 5.90, Found: C, 60.88; H, 6.39; N, 5.78.

EXAMPLE 181

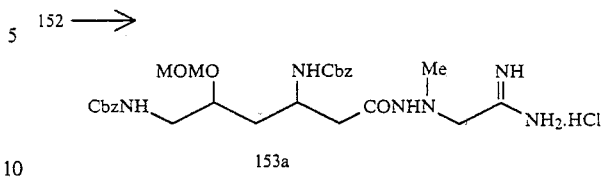

To a solution of Compound 152 (285 mg) in THF (3 ml) were added HOBT (90 mg) and DCC (137 mg), and the mixture was stirred at room temperature for one hour. On the other hand, 2-(1-methylhydrazino)acetoamidine.2HCl salt (158 mg) was dissolved in water (3 ml), to which was added NaHCO₃ (152 mg). To the mixture was added the active ester solution prepared as above, followed by stirring vigorously at room temperature for 6 hours. To the mixture was added, under ice-cooling, 1N HCl to adjust the pH to 3.0, followed by filtration. The filtrate was, after distilling off THF, subjected to an HP-20 (60 ml) column chromatography. The fraction eluted with 40% EtOH—H₂O was lyophilized to afford Compound 153a (162 mg) as yellow powder.

IR$\nu_{max}^{KBr}$ cm$^{-1}$:1725, 1700, 1525, 1450.

Elemental analysis for: C₂₇H₃₈N₆O₇HCl.0.5H₂O: Calcd.: C, 53.68; H, 6.67; N, 13.91, Found: C, 53.60; H, 6.84; N, 13.78.

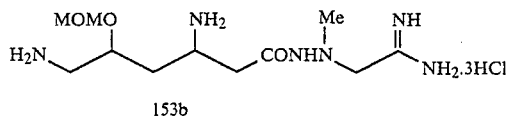

To a solution of Compound 153a (161 mg) in water (3 ml) were added 10% Pd-C (100 mg), 1N HCl (0.54 ml) and H₂O (3 ml), and the mixture was stirred for 30 minutes under hydrogen. The catalyst was filtered off, and the filtrate was concentrated. The concentrate was subjected to an HP-20 (60 ml) column chromatography. The fraction eluted with H₂O was lyophilized to afford Compound 153b (58 mg) as pale yellow powder.

IR$\nu_{max}^{KBr}$ cm$^{-1}$:1690, 1660(sh), 1480.

Elemental analysis for: C₁₁H₂₆N₆O₃3HCl.1.5H₂O: Calcd.: C, 30.96; H, 7.56; N, 19.69, Found: C, 30.76; H, 7.84; N, 19.42.

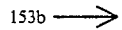
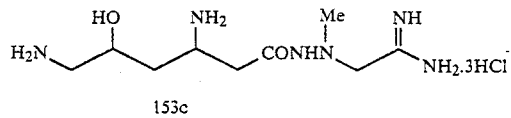

To Compound 153b (84 mg) was added, under ice-cooling, TFA (2 ml), and the mixture was stirred at room temperature for one hour. TFA was distilled off, and the residue was dissolved in a small volume of water. The solution was to pass through an IRA-401 (Cl⁻) (20 ml), eluting with water (50 ml), followed by lyophilization to afford Compound 153c (83 mg) as pale yellow powder.

IR$\nu_{max}^{KBr}$ cm$^{-1}$:1690, 1490, 1400.

Elemental analysis for: C$_9$H$_{22}$N$_6$O$_3$3HCl.1.5H$_2$O: Calcd.: C, 28.25; H, 7.37; N, 21.96, Found: C, 28.04; H, 7.55; N, 21.76.

EXAMPLE 182

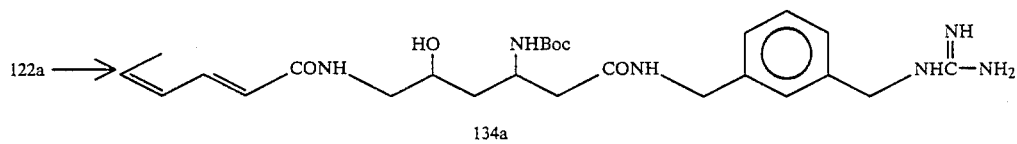

134a

To a solution of Compound 122a (700 mg) in EtOH (13 ml) was added S'-methyl isothiourea.½H$_2$SO$_4$ (1.4 g). To the mixture was added, under ice-cooling, 1N NaOH (10 ml), followed by allowing the reaction to proceed at room temperature for 15 hours. EtOH was distilled off, and the residue was subjected to an HP-20 (350 ml) column chromatography. The fraction eluted with 50% MeOH—H$_2$O was concentrated to afford Compound 154a (256 mg) as a colorless oily product.

IR$\nu_{max}^{KBr}$ cm$^{-1}$:1710(sh), 1690, 1655, 1530.

Elemental analysis for: C$_{26}$H$_{40}$N$_6$O$_5$: Calcd.: C, 60.45; H, 7.80; N, 16.27, Found: C, 60.36; H, 7.89; N, 16.42.

154a ⟶

HO NH$_2$
CONH ... CONH ... NHC—NH$_2$
                                    ‖
                                    NH
.2HCl

154b

To Compound 154a (256 mg) was aded, under ice-cooling, TFA (2 ml), and the mixture was stirred at room temperature for one hour, followed by distilling off TFA under reduced pressure. The residue was dissolved in a small volume of water, and the solution was allowed to pass through an IRA-401 (Cl$^-$) (20 ml) column, followed by elution with water (60 ml). The eluate was lyophilized to afford Compound 154b (243 mg) as colorless powder.

IR$\nu_{max}^{KBr}$ cm$^{-1}$:1660, 1610, 1540.

Elemental analysis for: C$_{21}$H$_{32}$N$_6$O$_3$2HCl.1.5H$_2$O: Calcd.: C, 48.84; H, 7.22; N, 16.27, Found: C, 48.62; H, 7.38; N, 16.28.

EXAMPLE 183

XIII ⟶

MeO
MeO—⟨ ⟩—CH$_2$NH ... CONH ... NH$_2$ .2HCl
MeO            155              ‖
                                NH

To a solution of Compound XIII (600 mg) in MeOH (15 ml) was added 3,4,5-trimethoxybenzaldehyde (600 mg), and the mixture was stirred at room temperature for 30 minutes. To the mixture were added, under ice-cooling, NaBH$_4$CN (201 mg) and acetic acid (0.7 ml), and the mixture was stirred at room temperature for 15 hours. MeOH was distilled off under reduced pressure. To the residue was added 1N HCl to adjust the pH to 2.5, which was shaken with ethyl acetate. The aqueous layer was separated and concentrated. To the concentrate was added 2N HCl (3 ml), and the reaction was allowed to proceed at room temperature for 3 hours, followed by purification by means of an activated charcoal (Shirasagi A, 10 g) column chromatography. The fraction eluted with 10% MeOH—H$_2$O was lyophilized to afford Compound 155 (150 mg) as colorless powder.

IR$\nu_{max}^{KBr}$ cm$^{-1}$:1680, 1635, 1520.

Elemental analysis for: C$_{19}$H$_{33}$N$_5$O$_5$3HCl.H$_2$O: Calcd.: C, 42.35; H, 7.11; N, 13.00, Found: C, 42.21; H, 7.24; N, 12.89.

EXAMPLE 184

49b ⟶ BocNH⟵HO NHCbz⟶CO$_2$Me

156

To a solution of Compound 49b (2.0 g) in methanol (50 ml) was added 28% NaOMe/MeOH solution (0.3 ml). The reaction was allowed to proceed for one hour. To the mixture was added acetic acid (0.3 ml), followed by concentration under reduced pressure. The concentrate was dissolved in ethyl acetate, washed with saturated brine and dried over magnesium sulfate. The resultant was concentrated under reduced pressure to afford Compound 156 (2.2 g) as colorless needles, m.p. 83°–84° C.

IR$\nu_{max}^{KBr}$ cm$^{-1}$:1730, 1705, 1670, 1550, 1520.

Elemental analysis for: C$_{20}$H$_{30}$N$_2$O$_7$: Calcd.: C, 58.52; H, 7.37; N, 6.82, Found: C, 58.49; H, 7.33; N, 6.87.

EXAMPLE 185

L ⟶ BocN⟵H OH NHBoc⟶CO$_2$Me
         Me
         157

To a solution of Compound L(100 mg) in methanol(4 ml) were added molecular sieves 3A(manufactured by Wako Pure Chemicals Industreis, Ltd., Japan) (excess) and ammonium acetate(0.2 g). To the mixture was added a solution of sodium cyanoborohydride (70 mg) in methanol (0.7 ml) at room temperature under stirring, over a period of 2 hours. The mixture was stirred at room temperature for further one hour, followed by filtration using celite. The filtrate was concentrated. To the concentrate were added water and ethyl acetate, and the mixture was acidified (pH 3) under ice-cooling with a 10% aqueous solution of potassium hydrogensulfate, followed by making the mixture alkaline with an aqueous solution of potassium carbonate. To this mixture was added di-t-butyl dicarbonate(0.1 ml), and the whole mixture was stirred at room temperature for 4 hours. Then, the ethyl acetate layer was separated, and the aqueous layer was extracted with ethyl acetate. Organic layers were combined, washed with water and dried($Na_2SO_4$), followed by distilling off the solvent. The residue was purified by means of a silica gel(20 g) column chromatography (hexane→hexane:ethyl acetate=2:1) to obtain methyl (3S,5R,6S)-3,6-di(t-butoxycarbonylamino)-5-hydroxyheptanoate(157) (35 mg) as colorless crystals, which were recrystallized from isopropyl ether to afford colorless prisms, m.p.126°–127° C.

IR$\nu_{max}$ (Nujol) cm$^{-1}$:3490, 3380, 3360, 1725, 1690, 1660.

NMR(90 MHz,CDCl$_3$)ppm: 1.08(3H,d,J=7 Hz), 1.43(18H,s), 1.75(2H,m), 2.60(2H,d,J=5 Hz), 3.45(1H,m), 3.68(3H,s), 4.05(1H,m), 4.83(1H,d,J=8 Hz), 5.35(1H,d,J=8 Hz).

Elemental Analysis for $C_{18}H_{33}N_2O_7$: Calcd.: C, 55.51; H, 8.54; N, 7.19, Found: C, 55.37; H, 8.68; N, 7.25.

EXAMPLE 186

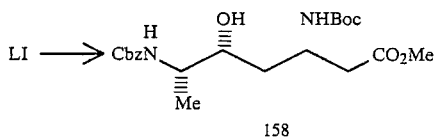

158

The Compound LI obtained in Example 79 was subjected to a reaction and treatment in a manner similar to those of Example 185 to obtain Compound 158 as colorless crystals, m.p.102.5°–103.5° C.

NMR(90 MHz,CDCl$_3$)ppm: 1.08(3H,d,7 Hz), 1.43(9H,s), 1.75(2H,m), 2.55(2H,d,J=7 Hz), 3.45(1H,m), 3.68(3H,s), 4.05(1H,m), 5.05(2H,s), 5.25(1H,m), 7.30(5H,s).

EXAMPLE 187

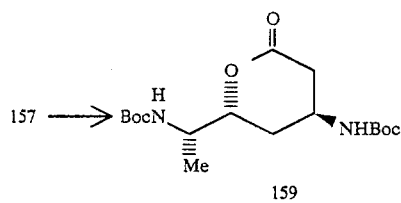

159

To a solution of Compound 157(30 mg) in THF(1ml) was added 1N NaOH(0.1 ml), and the mixture was stirred at room temperature for 2.5 hours. The solvent was distilled off, and the residue was dissolved in water. The solution was acidified with a 10% aqueous solution of potassium hydrogensulfate, followed by extraction with ethyl acetate. The extract was washed with water, dried ($Na_2SO_4$), and the solvent was evaporated. The residue was dissolved in chloroform(2 ml). To the solution was added 1-ethyl-3-(3-dimethylaminopropyl)carbodiimide.hydrochloride(40 mg), and the mixture was stirred at room temperature for 30 minutes. The reaction mixture was washed with water, dried($Na_2SO_4$), followed by distilling off the solvent to give (4S,6R,1′S)-4-t-butoxycarbonylamino-6-[(1′-t-butoxycarbonylamino)ethyl]-2-oxotetrahydropyran(159) (24 mg) as colorless crystals. Recrystallization from ethyl acetate-isopropyl ether gave colorless prisms, m.p.143°–145° C.

IR$\nu_{max}$ (KBr) cm$^{-1}$:3380, 2980, 2930, 1710, 1695, 1520,

NMR(90 MHz,CDCl$_3$)ppm: 1.17(3H,d,J=6 Hz), 1.43(18H,s), 1.7–2.2(3H,m), 2.7(1H,m), 3.7(1H,m), 4.1(1H,m), 4.5(1H,m), 5.0(2H,m).

Mass Spectrum: m/e 385(M$^+$) $[\alpha]_D^{22.5°}$ $-40.62°$(c=0.485, CHCl$_3$).

EXAMPLE 188

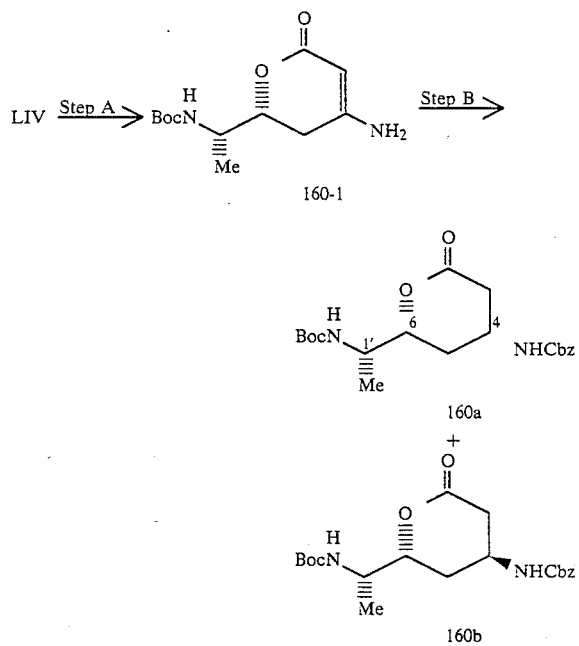

Step A

To a solution of Compound XIV(1.00 g) in acetic acid(10 ml) was added ammonium acetate(5.99 g), and the mixture was stirred at room temperature for 4 hours. To the reaction mixture was further added ammonium acetate(12.58 g), and the mixture was stirred at room temperature for 16.5 hours, followed by adding water and extracting with ethyl acetate. The aqueous layer was made alkaline with a saturated aqueous solution of sodium hydrogencarbonate, which was subjected to extraction with ethyl acetate. The extracts were combined, washed with an aqueous solution of sodium chloride, dried($Na_2SO_4$), followed by distilling off the solvent to leave a pale yellow oily product. To the oily product was added CH$_2$Cl$_2$-isoPr$_2$O to obtain Compound 160-1(553 mg) as colorless crystals, m.p.170°–172° C.

IR$\nu_{max}$ (KBr) cm$^{-1}$:3360, 3140, 2960, 1670, 1640, 1570.

NMR(90 MHz, CDCl₃)ppm: 1.22(3H,d,J=7 Hz), 1.43(9H,s), 2.00-2.76(2H,m), 3.83(1H,m), 4.23(1H,m), 4.60(1H,b), 4.93(1H,s).

Elemental Analysis: C₁₂H₂₀N₂O₄: Calcd.: C,56.24; H,7.86; N,10.93, Found: C,56.00; H,7.59; N,10.70.

Step B (method 1)

To a solution of Compound 160-1(80 mg) in THF(4 ml) were added acetic acid(4 ml) and a solution of sodium cyanoborohydride(59 mg) in THF(0.5 ml), and the mixture was stirred at room temperature for 3 hours. The reaction mixture was made alkaline(pH 11) with a saturated aqueous solution of sodium hydrogencarbonate and 1N—NaOH, followed by addition of ethyl acetate(30 ml) and benzyloxycarbonyl chloride(0.3 ml). The mixture was stirred at room temperature for 14.5 hours The ethyl acetate was separated dried (NA₂SO₄), and the solvent was distilled off. The residue was purified by means of silica gel (15 g) column chromatography-(hexane:ethyl acetate=1:1) to obtain a colorless oily product(49 mg) (this product was confirmed by the NMR spectrum as a mixture (about 1:1 ratio) of two isomers of 4-benzyloxycarbonylamino-6-[1'-t-butoxycarbonylamino)ethyl]-2-oxotetrahydropyrans, i.e. (4R,6R,1'S)isomer(160a) and (4S,6R,1'S)isomer(160b)). Recrystallization of this product from ether afforded Compound 160a(11mg) as colorless crystals. m.p. 133°-134° C.

IRν_{max} (KBr) cm⁻¹:3350, 2900, 1750, 1690, 1520.

NMR(90 MHz, CDCl₃)ppm: 1.14(3H,d,J=6 Hz), 1.43(9H,s), 2.06-2.53(3H,m), 2.80-3.15(1H,m), 3.8(1H,m), 4.1(1H,m), 4.4(1H,m), 5.0(1H,m), 5.10(2H,s), 7.36(5H,s), [α]_D²² −34.0°(c=0.65, ethanol).

Elemental Analysis for C₂₀H₂₈N₂O₆: Calcd.: C,61.21; H,7.19; N,7.13, Found: C,61.01; H,7.30; N,7.40.

Step B (method 2)

To a solution of phosphoric acid(0.32 ml) in anhydrous THF(20 ml) were added phosphorus pentoxide(0.28 g), 5% Pt-C (0.8 g) and Compound 160-1(0.52 g), and the mixture was stirred at room temperature in hydrogen streams for 2 hours. The reaction solution was filtrated and washed with THF(about 20 ml). The filtrate and the washing were combined, to which were added a saturated aqueous solution of sodium hydrogencarbonate(about 25 ml) and benzyloxycarbonyl chloride(1 ml), The mixture was stirred at room temperature for 3.5 hours, and THF was distilled off. The residue was subjected to extraction with ethyl acetate, and the extract was washed with water and dried(Na₂SO₄), followed by distilling off the solvent. The residue was purified by means of a silica gel (25 g) column chromatography(hexane:ethyl acetate=1:1→2:3) to afford a colorless oily product(0.80 g) (this product is confirmed from the NMR data as mixture of Compound 160a and Compound 160b at a ratio of about 3:1). This product was recrystallized twice from CHCl₃-isoPro₂O to afford Compound 160a(0.35 g) as colorless crystals. The physico-chemical properties of this product were in agreement with those of Compound 160a obtained in the method 1 described above.

EXAMPLE 189

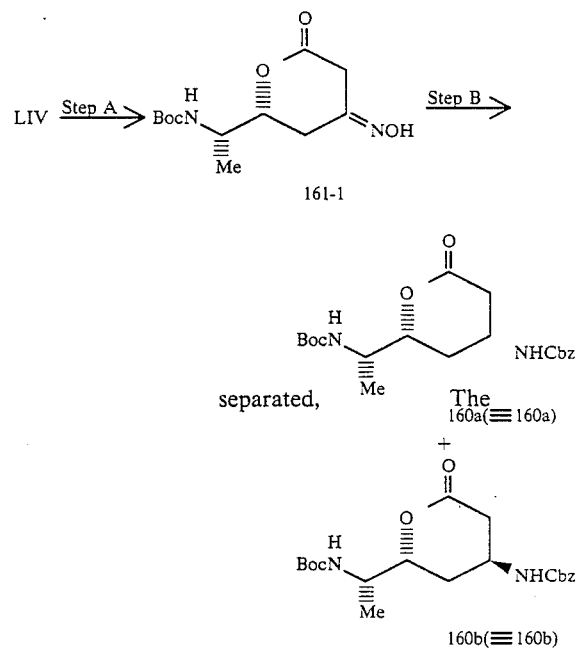

Step A

To a solution of Compound LIV(2.50 g) in methanol(30 ml) were added pyridine(1.05 ml) and hydroxylamine hydrochloride (1.01 g). The mixture was stirred at room temperature for 2.5 hours and concentrated. To the concentrate was added water, and precipitating colorless crystals were collected by filtration, washed with water and dried to afford (6R,1'S)-6-[(1'-t-butoxycarbonylamino)ethyl]-2,4-dioxotetrahydropyran 4-oxime(161-1) (2.26 g), m.p.187°-189° C.

IRν_{max} (KBr) cm⁻¹:3300, 2950, 1720, 1680, 1515.

NMR(90 MHz,CDCl₃)ppm: 1.21(3H,d,J=7 Hz), 1.43(9H,s), 2.33-2.95(2H,m), 3.36-3.65(2H,m), 3.93(1H,m), 4.50(1H,m), 5.0(1H,m).

Elemental Analysis for C₁₂H₂₀N₂O₅: Calcd.: C,52.93; H,7.40; N,10.29, Found: C,52.89; H.7.43; N,10.11.

Step B

Using Compound 161-1(0.67 g), reduction was conducted in a manner similar to that of Step B (Method 2) in Example 188 to thereby afford a mixture of Compound 161a and Compound 161b (about 3:1), which was recrystallized to give Compound 161a (0.39 g). (The physico-chemical properties of this product were in agreement with those of Compound 160a obtained in Example 188.

EXAMPLE 190

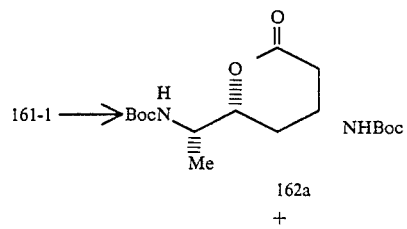

+

181

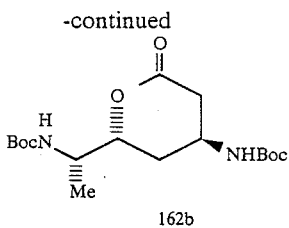

162b

Using the Compound 161-1 obtained by Step A of Example 189, reduction was conducted in a manner similar to Step B (method 2) of Example 188 using Pt-C, and using di-t-butyl dicarbonate instead of benzyloxycarbonyl chloride, a mixture of 162a and 162b (about 3:1 composition ratio). Recrystallization afforded Compound 162a(40%), m.p.163°–164.5° C.

IR$\nu_{max}$ (KBr) cm$^{-1}$:3375, 2990, 1720, 1680, 1520,

182

NMR(90 MHz,CDCl$_3$)ppm: 1.14(3H,d,J=6 Hz), 1.43(18H,s), 2.06–2.53(3H,m), 2.85–3.15(1H,m), 3.8(1H,m), 4.1(1H,m), 4.4(1H,m), 4.63(1H,m), 4.86(1H,m).

$[\alpha]_D^{22.5}$ −32.37° (c=0.519, chloroform).

Elemental Analysis for C$_{17}$H$_{30}$N$_2$O$_6$: Calcd.: C,56.97; H,8.44; N,7.82, Found: C,56.75; H,8.21; N,7.90.

EXAMPLES 191–201 (TABLE 16)

By manners similar to those of Examples 189–190, using Compounds LVI and LIX–LXVII, compounds of Examples 191–201 were obtained via (1) enamination employing ammonium acetate or oximation employing hydroxylamine (Step A, A'), (2) catalytic reduction employing Pt-C or reduction employing sodium cyanoborohydride (Step B,B') and (3) reaction of protecting the resulting amino group with Boc group or cbz group (Step C,C'). Yields of isolated products and physicochemical properties thereof are shown in Table 16.

TABLE 16

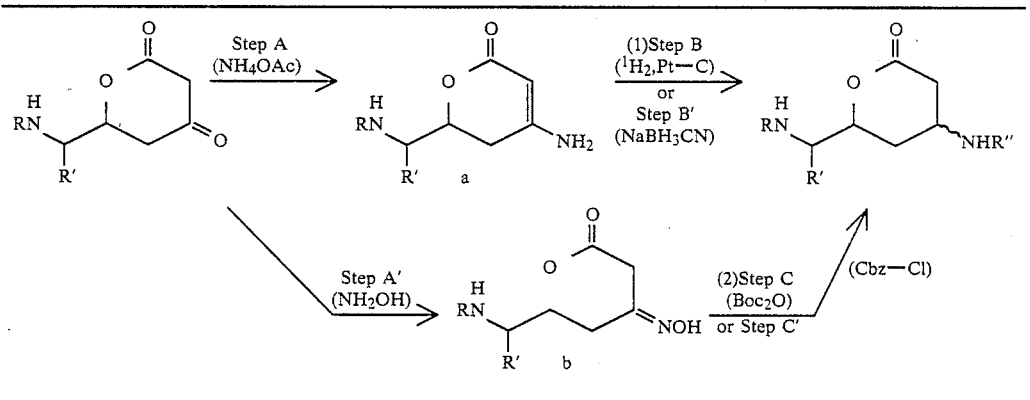

| Ex. No. | Step | Starting Compd. No. | Isolated Compound No. | Yield (%) | m.p. (°C.) |
|---|---|---|---|---|---|
| 191 | A' | LVI | 163-1 | 87 | 165–167 |
|  | B' → C' | 163-1 | 163a(≡49b) (1) | 41 | 135–137 |
| 192 | A | LIX | 164-1 | 51 | 169–171 |
|  | B → C' | 164-1 | 164a | 35 | 121–123 |

TABLE 16-continued

| | | | | | |
|---|---|---|---|---|---|
| 193 | B → C | 164-1 | *structure 165a*: BocNH-CH(Me)-[pyranone ring]-NHBoc | 38 | 164–165 |
| 194 | A | LX | *structure 166-1*: CbzNH-CH(Me)-[dihydropyranone]-NH$_2$ | 62 | 190–193 |
| | B' → C | 166-1 | *structure 166a*: CbzNH-CH(Me)-[pyranone]-NHBoc | 13 | 151–152 |
| | | | *structure 166b*: CbzNH-CH(Me)-[pyranone]-NHBoc | 1 | 129–130 |
| 195 | A | LXI | *structure 167-1*: BocNH-CH(Me)-[dihydropyranone]-NH$_2$ | 60 | 172–174 |
| | B → C' | 167-1 | *structure 167a*: BocNH-CH(Me)-[pyranone]-NHCbz | 32 | 123–124 |
| 196 | A | LXII | *structure 168-1*: CbzNH-CH(Me)-[dihydropyranone]-NH$_2$ | 43 | 194–196 |
| | B → C | 168a | *structure 168a*: CbzNH-CH(Me)-[pyranone]-NHBoc | 19 | 150–151 |
| 197 | A → B → C' | LXIII | *structure 169*: BocNH-C(Me)$_2$-[pyranone]-NCbz, 4R-4S (ca. 3:1) | 63 | oily[2] product |

TABLE 16-continued

| | | | | | |
|---|---|---|---|---|---|
| 198 | A'→B→C' | LXIV | (structure 170a: CbzN-H, Me, Me, NCbz) | 46 | 74–76 |
| 199 | A'→B''[(3)]→C' | LXV | (structure 171a: BocN-H, Ph, NCBz) | 20 | Powder (not de-[(4)] termined yet) |
| | | | (structure 171b: BocN-H, Ph, NCbz) | 9 | 156–158 |
| 200 | A'→B→C' | LXVI | (structure 172: BocN-H, CO$_2^t$Bu, NCbz) 4R-4S(ca. 3:1) | 29 | oily[(5)] product |
| 201 | A'→B→C' | LXVII | (structure 173: BocN-H, (CH$_2$)$_4$NCO$_2$Me, NCbz) 4R-4S(ca. 4:1) | 22 | oily[(6)] product |

[(1)] The physico-chemical data of this product were in agreement with those of Compound 49b obtained in Example 77.
[(2)] NMR(90MHz,CDCl$_3$)ppm:0.97(6H,d,J = 7Hz),1.43(9H,s),1.60–2.30(2H,m),2.31(1H,dd,J = 10,18Hz),2.95(1H,dd,J = 6,18Hz),3.35(1H,t,J = 10Hz),3.90–4.60(3H,m),4.76(1H,d,J = 11Hz),5.10(2H,s),5.32(1H,d,J = 8Hz),7.35(5H,s)
[(3)] After oximination, reduction using 10% Pd-C was conducted in MeOH in the presence of HCO$_2$NH$_4$ was conducted to give an enamine compound, which was then reduced by using sodium cyanoborohydride.
[(4)] NMR(90MHz,CDCl$_3$)ppm:1.35(9H,s),1.48–2.25(2H,m),2.31(1H,dd,J = 9,18Hz),2.92(1H,dd,J = 6,18Hz),2.90(H,d,J = 8Hz),3.60–4.30(3H,m),4.79(1H,d,J = 10Hz),5.00–5.20(1H,m),5.09(2H,s),7.25,7.34(5H × 2,s)
[(5)] NMR(90MHz,CDCl$_3$)ppm:1.43(18H,s),1.60–2.35(2H,m),2.35(1H,dd,J = 9,15Hz),2.42–2.74(2H,m),2.92(1H,dd,J = 6,15Hz),3.50–4.51(3H,m),5.00(1H,d,7Hz),5.40(1H,d,J = 8Hz),5.08(2H,s),7.34(5H,s)
[(6)] NMR(90MHz,CDCl$_3$)ppm:1.42(9H,s),1.20–1.74(6H,m),1.74–2.35(2H,m),2.33(1H,dd,J = 10,18Hz),2.96(1H,dd,J = 6,18Hz),2.96–3.31(2H,m),3.64(3H,s),3.45–4.40(2H,m),4.65–5.32(3H,m),5.10(2H,s),7.34(5H,s)

EXAMPLE 202

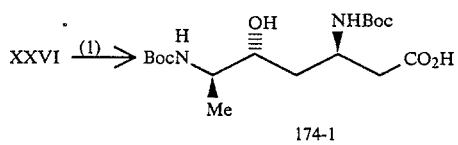

174-1

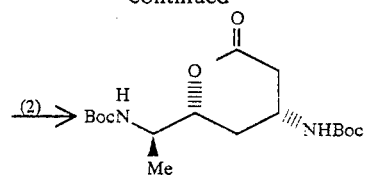

174(≡165a)

(1) Compound XXVI(40 mg) was dissolved in a mixture of dioxane(0.8 ml) and methanol(0.5 ml). To the solution were added at room temperature triethylamine(24 μl) and BOC.ON(44 mg), successively. The mixture was stirred at room temperature for further 8 hours, to which was added a 10% aqueous solution of sodium hydrogencarbonate, followed by washing with ether. To the aqueous layer was added 2N hydrochloric acid to adjust the pH at 2, which was then extracted with ethyl acetate. The extract was washed with water, which was passed through a column($\phi$15×100 mm) of anhydrous sodium sulfate. The effuluent was concentrated to afford Compound 174-1(53 mg) as an oily prodcut.

NMR(90 MHz,CDCl$_3$)ppm: 1.20(3H,d,J=7 Hz), 1.43(18H,s), 1.60(2H,n), 2.60(2H,d,J=5 Hz), 3.60(2H,m), 4.20(1H,m), 5.60(2H,d,J=10 Hz).

(2) Compound 174-1(52 mg) was dissolved in dichloromethane (1.7 ml), to which was added 10-camphor sulfonic acid(3 mg). The mixture was stirred at room temperature for 50 minutes. To the reaction solution was added water, which was extracted with ethyl acetate. The extract solutions were combined, washed with water, then allowed to pass through a column of anhydrous sodium sulfate ($\phi$15×80 mm), and the effluent was concentrated to obtain an oily product, which was crystallized from ether to afford Compound 174(29 mg) as colorless crystals, m.p.163°–164° C.

IR$\nu_{max}$ (KBr) cm$^{-1}$:3370, 2970, 1715, 1690, 1530.

NMR(90 MHz,CDCl$_3$)ppm: 1.28(3H,d,J=7 Hz), 1.45(18H,s), 1.35–1.70, 2.05–2.35(2H,m), 2.30(1H,dd,J=9,18 Hz), 2.95(1H,dd, J=7,18 Hz), 3.67–4.72(5H,m).

$[\alpha]_D^{22.5}$ +19.6°(c=0.49, chloroform).

Elemental Analysis for C$_{17}$H$_{30}$N$_2$O$_6$: Calcd.: C,56.97; H,8.44; N,7.82, Found: C,57.14; H,8.38; N,7.78.

IR and NMR spectra of this product are in agreement with those of the Compound (165a) obtained in Example 193.

EXAMPLE 203

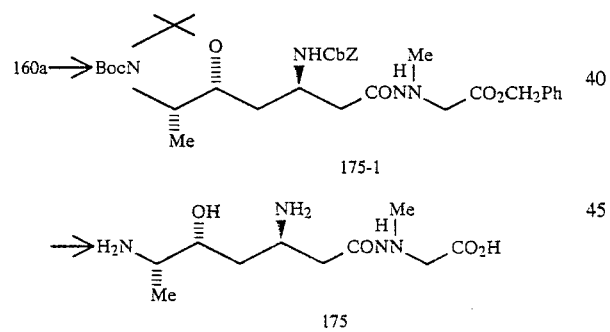

To a solution of Compound 160a(185 mg) in methanol(20 ml) was added NaOMe(3 mg), and the mixture was stirred at room temperature for 5 hours, then the solvent was distilled off. To the residue were added CH$_2$Cl$_2$(5 ml), pyridinium p-toluene sulfonate(5 mg), 2-methoxypropene(0.5 ml) and 2,2-dimethoxypropane(2 ml), and the mixture was stirred at room temperature for one hour. The solvent was distilled off. To the residue was added ethyl acetate, and the mixture was washed with water, dried(Na$_2$SO$_4$), followed by distilling off the solvent. To the residue were added methanol(15 ml), THF (5 ml), water(5 ml) and 1N—NaOH(5 ml), and the mixture was stirred at room temperature for 2 hours, then the solvent was distilled off. To the residue was added water, and the mixture was washed with ether. The aqueous layer was acidified with a 10% aqueous solution of potassium hydrogensulfate, followed by extraction with ethyl acetate. The extract was dried(Na$_2$SO$_4$), then the solvent was distilled off. To the residue were added anhydrous THF(10 ml), DCC(117 mg) and HOBT(87 mg), and the mixture was stirred for 3.5 hours. To the mixture was added a solution of 1-methylhydrazinoacetic acid(154 mg) in anhydrous THF(5 ml), and the mixture was stirred at room temperature for 15 hours, then the solvent was distilled off. To the residue was added ethyl acetate, and the mxture was washed with a saturated aqueous solution of sodium hydrogencarbonate and dried(Na$_2$SO$_4$), followed by distilling off the solvent. The residue was purified by means of a silica gel(20 g) column chromatography(hexane-ethyl acetate=1:1→ethyl acetate) to afford Compound 175-1(170 mg) as a colorless oily product.

[NMR(90 MHz,CDCl$_3$)ppm: 1.05(3H,d,J=6 Hz), 1.43(15H,b), 1.83(b), 2.45(b), 2.73(b), 3.57(b), 3.70(s), 4.10(b), 5.08(2H,s), 5.16(2H,s), 5.96(b), 7.36(10H,s)]

To a solution of Compound 175-1(170 mg) in methanol(5 ml) and acetic acid(2.5 ml) was added 10%Pd-C(170 mg), and the mixture was stirred at room temperature for 6 hours in hydrogen streams. The solvent was filtered off and washed with methanol. The filtrate and the washing were combined, from which was distilled off the solvent. To the residue was added TFA(5 ml), and the mixture was stirred at room temperature for one hour, then the solvent was distilled off. To the residue was added water(0.5 ml), which was purified by means of a CG-50(50 ml) column chromatography(water→0.5% aqueous ammonia). The eluate was concentrated and lyophilized to afford Compound(175) (65 mg) as a white powdery product.

IR$\nu_{max}$ (KBr) cm$^{-1}$:3700–2400, 1650, 1580, 1400, 1310.

NMR(90 MHz,D$_2$O)ppm: 1.30(3H,d,J=7 Hz), 1.70(2H,m), 2.51(2H,d,J=6 Hz), 2.72(3H,6s), 3.36–3.66(4H,m), 4.1(1H,m).

SIMS:m/e 263(M+).

EXAMPLE 204

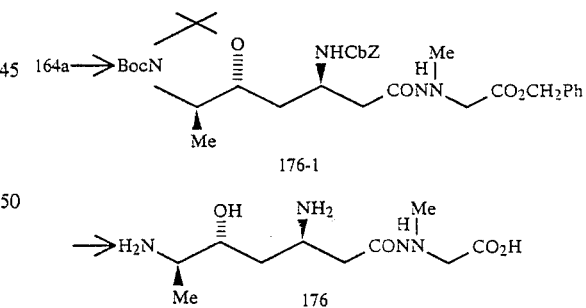

By a process similar to that of Example 203, Compound 176 was obtained from Compound 164a via Compound 176-1.

176-1: colorless oily product, yield 75%.

IR$\nu_{max}$ (Neat) cm$^{-1}$:3260, 2960, 1680(b), 1390.

NMR(90 MHz,CDCl$_3$)ppm: 1.25(3H,d,J=7 Hz), 1.44(9H,s), 1.53, 1.58(3Hx2,sx2), 1.60–2.20(2H,m), 2.41(2H,d,J=6 Hz), 2.75(3H,s), 3.20–3.88(2H,m), 3.70(2H,s), 3.90–4.38(1H,m), 5.10,5.18(2Hx2,sx2), 7.34,7.37(5Hx2,sx2).

SIMS:m/e 627(M+).

176: white powder, yield 85%.

IR$\nu_{max}$ (KBr) cm$^{-1}$:3400–2900, 1655, 1580, 1400.

NMR(90 MHz,D$_2$O)ppm: 1.33(3H,d,J=7 Hz), 1.60–1.95(2H,m), 2.47(2H,d,J=7 Hz), 2.72(3H,s), 2.95–40(3H,m), 2.49(2H,s).

$[\alpha]_D^{22}$ +14.0°(c=0.25, H$_2$O).

Elemental Analysis for C$_{10}$H$_{22}$N$_4$O$_4$·1.2H$_2$O: Calcd.: C,42.30; H,8.66; N,19.73, Found: C,42.43; H,8.38; N,19.83.

EXAMPLE 205

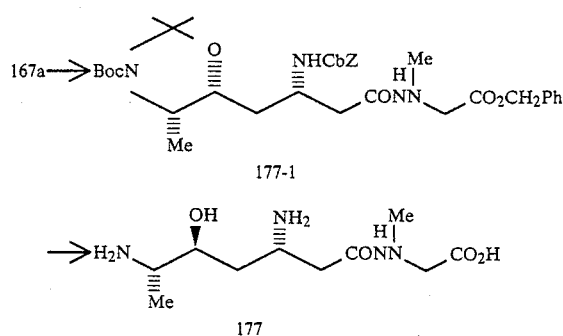

By a process similar to that of Example 203, Compound 177 was obtained from Compound 167a via 177-1.

177-1: colorless oily product, yield 64%.

NMR(90 MHz,CDCl$_3$)ppm: 1.24(3H,d,J=7 Hz), 1.43(9H,s), 1.53,1.56(3Hx2,sx2), 1.61–2.20(2H,m), 2.42(2H,d,J=6 Hz), 2.75(3H,s), 3.24–3.90(2H,m), 3.70(2H,s), 3.92–4.34(1H,m), 5.09,5.15(2Hx2,sx2), 7.31,7.33(5Hx2,sx2).

177: white powder, yield 81%.

IR$\nu_{max}$ (KBr) cm$^{-1}$:3450–2950, 1660–1630, 1580, 1395.

NMR(90 MHz,D$_2$O)ppm: 1.35(3H,d,J=7 Hz), 1.60–2.05(2H,m), 2.46(2H,d,J=7 Hz), 2.71(3H,s), 2.85–4.00(3H,m), 3.48(2H,s).

$[\alpha]_D^{22}$ −14.6° (c=0.185, water).

Elemental Analysis: C$_{10}$H$_{22}$N$_4$O$_4$·1.4H$_2$O: Calcd.: C,41.77; H,8.69; N,19.49, Found: C,42.03; H,8.48; N,19.17.

EXAMPLE 206 and stirring, pyridine(0.3 ml) and sorbyl chloride (80 mg). This mixture was stirred for 30 minutes under ice-cooling, and the solvent was distilled off. The residue was dissolved in ethyl acetate. The solution was washed with water, a saturated aqueous solution of potassium hydrogensulfate, a saturated aqueous solution of sodium hydrogencarbonate and an aqueous saline solution, successively, which was dried (Na$_2$SO$_4$), followed by distilling off the solvent. To the residue was ether, whereupon Compound 178-1(110 mg) was obtained as white powder, m.p.148°–150° C.

IR$\nu_{max}$ (KBr) cm$^{-1}$:3300, 1725, 1695, 1665, 1650, 1605.

NMR(90 MHz,CDCl$_3$)ppm: 1.10(3H,d,J=7 Hz), 1.40–1.73(2H,m), 1.86(3H,d,J=5 Hz), 2.58(2H,d,J=5 Hz), 3.63(3H,s), 3.50–4.45(3H,m), 5.10(2H,s), 5.60–6.21, 7.00–7.60(4H,m), 7.32(5H,s).

Step B

To a solution of Compound 178-1(150 mg) in CH$_2$Cl$_2$(20 ml) were added 2-methoxypropene(1 ml) and p-toluenesulfonic acid. anhydride(catalytic amount), and the mixture was stirred at room temperature for 2 hours, then the solvent was distilled off. To the residue were added 5N—NaOH(1 ml), methanol(10 ml) and water(5 ml), and the mixture was stirred at room temperature for 2 hours, followed by distilling off the solvent. To the residue was added water, and the mixture was washed with ether. To the mixture was added a saturated aqueous solution of potassium hydrogensulfate to acidify, which was extracted with ethyl acetate. The extract solution was dried(MgSO$_4$) and concentrated. To the concentrate were added anhydrous THF(10 ml), HOBT(48 mg) and DCC(81 mg), successively, then the mixture was stirred at room temperature for 1.5 hours. Precipitating crystals were filtered off, and, to the filtrate was added a solution of 3-aminopropioamidine.hydrobromide (89 mg) and a solution of sodium hydrogencarbonate(60 mg) in water(10 ml), and the mixture was stirred at room temperature for 18 hours. The solvent was distilled off, and the residue was dissolved in chloroform-ethanol(5:1), then the solution was dried(MgSO$_4$). The solvent was distilled off, and the residue was dissolved in acetonitrile(20 ml). To the solution were added sodium

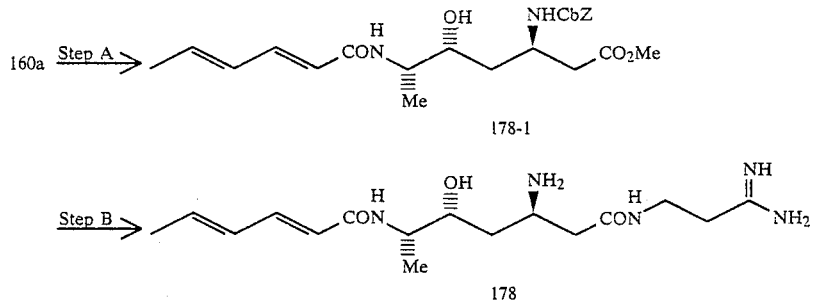

Step A

To a solution of Compound 160a(200 mg) in methanol(10 ml) was added diisopropyl ethylamine (one drop), and the mixture was stirred at room temperature for 10 hours, then the solvent was distilled off. To the residue was added, under ice-cooling and stirring, methanol(8 ml) saturated with hydrogen chloride, and the mixture was stirred for 2 hours, followed by distilling off the solvent. To the residue was added CH$_2$Cl$_2$(20 ml), and to the mixture were added, under ice-cooling iodide(3 g) and trimethylchlorosilane(2.17 g), and the mixture was stirred at room temperature for 1.5 hours. To the reaction mixture was added an aqueous solution of sodium phosphate to suspend the reaction, and the reaction solution was washed with ether. The aqueous layer was concentrated and purified by means of an Amberlite XAD-2(50 ml) column chromatography(water→20% ethanol) and of an Amberlite IRA-401(Cl$^-$-type, 30 ml), followed by lyophilization to afford dihydrochloride of Compound 178(145 mg) as white powder.

IR$\nu_{max}$ (KBr) cm$^{-1}$:3420, 1690, 1650, 1340.

NMR(90 MHz,D$_2$O)ppm: 1.25(3H,d,J=7 Hz), 1.75-2.20(5H,m), 2.81(2H,d,J=7 Hz), 2.68-3.02(2H,m), 3.65(2H,t,J=7 Hz), 3.50-4.43(3H,m), 5.93-6.64, 7.10-7.45(4H,m).

$[\alpha]_D^{26}$ −33.3° (c=0.15, water).

SIMS: m/e 340(M$^+$).

EXAMPLES 207-211 (TABLE 17)

By processes similar to Step A and B of Example 206, the compounds of Examples 207-211 were obtained. The respective yields and some of the physico-chemical properties of those compounds are shown in the table 17.

TABLE 17

| Ex. No. | Starting Compound No. | Isolated Compound No. | Yield (%) | Melting Point (°C.) | [α]_D solvent (°C., C %) |
|---|---|---|---|---|---|
| 207 | 167a | 179-1 | 58 | 136—140 | −10.4° (chloroform, 23, 0.135) |
| | 179-1 | 179 | 17 | lyophilized product (not determined)(1) | (not determined)(1) |
| 208 | 169 | 180 | 25 | lyophilized product (not determined) | +40.0° (water, 25, 0.15) |
| 209 | 170a | 181 | 21 | lyophilized product (not determined) | +24.8° (water, 24, 0.125) |
| 210 | 171a | 182-1 | 70 | 152—155 | +21.5° (chloroform, 24, 0.2) |

TABLE 17-continued

| Ex. No. | Starting Compound No. | Isolated Compound No. | Yield (%) | Melting Point (°C.) | $[\alpha]_D$solvent (°C., C %) |
|---|---|---|---|---|---|
| | 182-1 | 182 | 50 | lyophilized product (not determined) | +46.9° (water, 24, 0.30) |
| 211 | 171b | 183-1 | 66 | 138—141 | +59.5° (chloroform, 24, 0.185) |
| | 183-1 | 183 | 38 | lyophilized product (not determined) | +4.6° (water, 26, 1.375) |

(1)179-1; IR $\nu_{max}$(KBr)cm$^{-1}$: 3260, 1685, 1650, 1630
NMR(90MHz,D$_2$O)ppm: 1.28(3H,d,J=7Hz),1.68–2.12(2H,m),1.90(3H,d,J=5Hz),2.77(2H,t,J=9Hz),2.80(2H,d,J=7Hz),3.53–4.35(5H,m),5.96–6.48,7.10–7.40(4H,m)

EXAMPLE 212

|   | Capsule |   |
|---|---|---|
| (1) | TAN-749A | 300 mg |
| (2) | Lactose | 28 mg |
| (3) | Corn starch | 58 mg |
| (4) | Hydroxy propyl cellulose | 12 mg |
| (5) | Magnesium stearate | 2 mg |
|   |   | 400 mg/capsule |

The above ingredients (1), (2), (3) and (4) are mixed and granulated by the conventional method. To the granules is added the ingredient (5). The mixture is packed into a gelatin capsule No. 1 (according to the Pharmacopoeia of Japan, Tenth Edition).

EXAMPLE 213

20 g of TAN-749B is dissolved into one liter of distilled water. After adding and solving 50 g of mannitol, each 2 ml of the solution is poured into an ample after filtration for sterilization. This is lyophilized, and sealed to prepare amples.

When it is used, the said ample is opened and dissolved into 2 ml of physiological saline to prepare a subcutaneous or intramuscular injection.

What we claimed is:

1. A compound of the formula

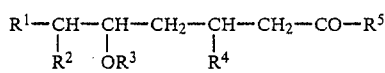

wherein $R^1$ and $R^4$ are independently amino or an organic residue bonded through nitrogen, $R^2$ is hydrogen or alkyl which may be substituted, $R^3$ is hydrogen or a protecting group and $R^5$ is hydroxyl which may be substituted or amino which may be substituted; with the proviso that when $R^1$ is amino, leucylamino, acetylamino or benzyloxycarbonylamino, $R^3$ is hydrogen, methyl or 2-tetrahydropyranyl, $R^4$ is amino, acetylamino or benzyloxycarbonylamino and $R^5$ is hydroxyl which may be substituted or amino which may be substituted, $R^2$ is alkyl which may be substituted, or a pharmaceutically acceptable salt thereof.

2. A compound of the formula

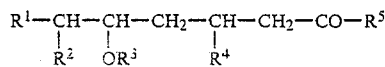

wherein $R^1$ and $R^4$ are independently amino or an organic residue bonded through nitrogen, $R^2$ is hydrogen or alkyl which may be substituted, $R^3$ is hydrogen or a protecting group and $R^5$ is hydroxyl which may be substituted or amino which may be substituted; with the proviso that when $R^1$ is amino, sorbylamino or hexanoylamino, $R^2$ is hydrogen or methyl, $R^4$ is amino which may be protected and $R^5$ is hydroxyl or 2-amidinoethylamino, $R^3$ is a protecting group, and that when $R^1$ is amino, leucylamino, acetylamino or benzyloxycarbonylamino, $R^3$ is hydrogen, methyl or 2-tetrahydropyranyl, $R^4$ is amino, acetylamino or benzyloxycarbonylamino and $R^5$ is hydroxyl which may be substituted or amino which may be substituted, $R^2$ is alkyl which may be substituted, or a pharmaceutically acceptable salt thereof.

3. A compound of the formula

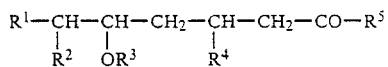

wherein $R^1$ is amino, hexanoylamino or 2,4-hexadienoylamino, $R^2$ is hydrogen or methyl, $R^3$ is hydrogen, $R^4$ is an amino which may optionally be protected and $R^5$ is hydroxyl or 2-amidinoethylamino, with the proviso that when $R^1$ is amino, $R^2$ is hydrogen, $R^3$ is hydrogen and $R^4$ is amino, $R^5$ is 2-amidinoethylamino, or a pharmaceutically acceptable salt thereof.

4. The compound according to claim 2, wherein the organic residue bonded through nitrogen is (A) acylamino represented by the formula (a) 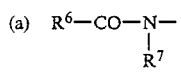

wherein $R^6$ is hydrogen, alkyl*, alkenyl*, cycloalkyl*, aryl*, heterocyclic ring*, alkoxy*, aryloxy*, or alkynyl*, $R^7$ is hydrogen, alkyl* or acyl*, and $R^6$ and $R^7$ may form a ring, (b) 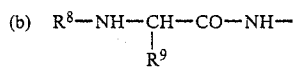

wherein $R^8$ is hydrogen, amino acid residue*, an amino-protecting group or groups represented by the formula $R^{10}$—$(CH_2)_n$—$C(=Z)$— wherein $R^{10}$ is heterocyclic ring*, alkoxy* or amino*, n is an integer of 0 to 2 and Z is O or S, $R^9$ is hydrogen, alkyl*, aryl*, cycloalkenyl or heterocyclic ring*, (c) $R^{11}$—$R^{12}$—CO—NH— wherein $R^{11}$ is groups represented by the formula

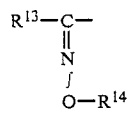

$R^{13}$ is alkyl*, heterocyclic ring* or aryl*, $R^{14}$ is hydrogen, alkyl*, alkenyl*, arylcarbonyl*, cycloalkyl*, heterocyclic ring* or groups represented by the formula —$R^{15}$—$R^{16}$ wherein $R^{15}$ is alkylene*, cycloalkylene or alkenylene, $R^{16}$ is aryl*, carboxyl* or its ester or mono-or di-alkylamide and $R^{12}$ is a chemical bond or groups represented by the formula

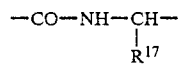

wherein $R^{17}$ is alkyl*, aryl* or heterocyclic ring*, (d) 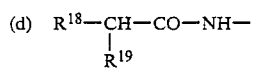

wherein $R^{18}$ is aryl*, heterocyclic ring* or cycloalkenyl and $R^{19}$ is hydroxy, carboxy*, sulfamoyl, sulfo, sulfoxy, aryloxycarbonyl* or acyloxy* groups (e) $R^{20}$—$R^{21}$—$CH_2$—CO—NH— wherein $R^{20}$ is alkyl*, alkynyl*, cyano, aryl*, aryloxy*, alkenylene*, heterocyclic ring*, amino* or groups represented by the formula $R^{20'}$—C(=S)— wherein $R^{20'}$ is alkoxy and $R^{21}$ is a chemical bond or —S—
(f) $R^{22}$—CO—CO—NH— wherein $R^{22}$ is hydrogen, alkyl*, alkoxy*, aryl*, aryloxy*, heterocyclic ring* or amino*, or (g) 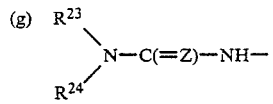

wherein $R^{23}$ and $R^{24}$ are independently hydrogen, alkyl*, aryl*, heterocyclic ring* or cycloalkyl, and Z is O, S or NH
(B) amino substituted through carbon represented by the formula
(a) $R^{25}$—NH— wherein $R^{25}$ is alkyl* or alkenyl*, (b) 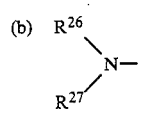

wherein $R^{26}$ and $R^{27}$ are independently alkyl*, aryl* ooralkenyl*, including the case where $R^{26}$ and $R^{27}$ form heterocyclic ring* together with the adjacent nitrogen atom or (c) 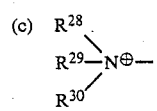

wherein $R^{28}$, $R^{29}$ and $R^{30}$ are independently alkyl*, aryl* or alkenyl*, including the case where $R^{28}$ and $R^{29}$ or $R^{30}$ form a heterocyclic ring* together with the adjacent nitrogen atom,
(C) alkenylamino represented by the formula

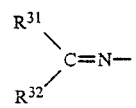

wherein $R^{31}$ and $R^{32}$ are independently hydrogen, alkyl*, aryl*, cycloalkyl*, amino* or heterocyclic ring*, including the case where $R^{31}$ and $R^{32}$ form cycloalkyl* or heterocyclic ring* together with the adjacent carbon atom,
(D) thioamino represented by the formula $R^{33}$—SO-n—NH— wherein $R^{33}$ is alkyl* or aryl* and n is an integer of 0 to 2,
(E) phosphorylamino represented by the formula

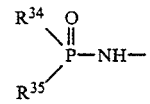

wherein $R^{34}$ and $R^{35}$ are independently alkyl*, aryl*, alkoxy* or aryloxy*, including the case where $R^{34}$ and $R^{35}$ form heterocyclic ring*;
the alkyl which may be substituted is $C_{1-20}$ alkyl*, the protecting group is $C_{1-20}$ alkyl, ester residue, esterified carboxyl group, ether residue, silylether residue or acetal residue;
the hydroxyl which may be substituted is hydroxyl or hydroxyl substituted by alkyl*, cycloalkyl*, aryl* or alkenyl*, and the amino which may be substituted is represented by the formula
(a) $R^{36}$—NH— wherein $R^{36}$ is hydrogen, alkyl*, cycloalkyl*, aryl*, alkenyl*, heterocyclic ring*, hydroxy, alkoxy* or amino* or (b) 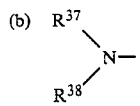

wherein $R^{37}$ and $R^{38}$ are independently alkyl*, aryl* or alkenyl*, including the case where $R^{37}$ and $R^{38}$ form heterocyclic ring* together with the adjacent nitrogen atom, and the superscript asterisk "*" represents the group which may have 1 to 3 substituent(s).

5. The compound according to claim 2, wherein $R^1$ is the group of the formula

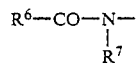

wherein $R^6$ is $C_{2-10}$ alkenyl which may be substituted by $C_{1-10}$ alkyl, $C_{2-10}$ alkenyl, $C_{2-6}$ alkynyl, phenyl, benzyl, $C_{1-5}$ alkyl-thio, $C_{1-5}$ alkyl-sulfonyl, halogen, fluorinated $C_{1-10}$ alkyl, $C_{1-4}$ alkoxy, carboxy which may be substituted by $C_{1-5}$ alkyl which may be substituted by phenyl, $C_{3-6}$ cycloalkyl which may be substituted by $C_{1-5}$ alkyl, or furyl; phenyl which may be sustituted by $C_{1-5}$ alkoxy or amino which may be substituted by $C_{1-5}$ alkyl; pyridyl; 4-oxo-thiopyranyl, $C_{1-20}$ alkyl which may be substituted by hydroxyl, phenyl or 1,2-dithioran; or $C_{2-6}$ alkynyl which may be substituted by $C_{2-10}$ alkenyl and $R^7$ is hydrogen or $C_{1-10}$ alkyl.

6. The compound according to claim 2, wherein $R^1$ is the group of the formula

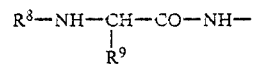

wherein $R^8$ is hydrogen or benzyloxycarbonyl and $R^9$ is $C_{1-20}$ alkyl which may be substituted by halogen, hydroxyl, aminosulfonyl or carboxyl which may be substituted by amino, or phenyl which may be substituted by hydroxyl.

7. The compound according to claim 2, wherein $R^1$ is the group of the formula

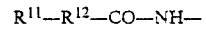

wherein $R^{11}$ is the group represented by the formula

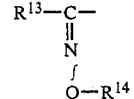

wherein $R^{13}$ is thiazolyl which may be substituted by amino and $R^{14}$ is $C_{1-5}$ alkyl and $R^{12}$ is a chemical bond.

8. The compound according to claim 2, wherein $R^1$ is the group of the formula $$R^{22}-CO-CO-NH-$$

wherein $R^{22}$ is $C_{1-10}$ alkyl.

9. The compound according to claim 2, wherein $R^2$ is hydrogen or $C_{1-10}$ alkyl which may be substituted by phenyl, t-butoxycarbonyl or methoxycarbonylamino.

10. The compound according to claim 2, wherein $R^1$ is the group of the formula $$R^6-CO-N-\underset{R^7}{|}$$

wherein $R^6$ is $C_{4-10}$ alkenyl which may be substituted by $C_{1-5}$ alkyl or halogen and $R^7$ is hydrogen or $C_{1-5}$ alkyl.

11. The compound according to claim 2, wherein $R^1$ is 2,4-pentadienoylamino, 2,4-hexadienoylamino, 2-methyl-2,4-hexadienoylamino, 6-fluoro-2,4-hexadienoylamino or 5-chloro-2,4-pentadienoylamino.

12. The compound according to claim 2, wherein $R^2$ is hydrogen or $C_{1-6}$ alkyl.

13. The compound according to claim 2, wherein $R^2$ is methyl, isopropyl or isobutyl.

14. The compound according to claim 2, wherein $R^3$ is hydrogen.

15. The compound according to claim 2, wherein $R^4$ is amino which may be substituted by $C_{1-5}$ alkyl or amino acid having 2 to 10 carbon atoms.

16. The compound according to claim 2, wherein $R^4$ is amino, methylamino, ethylamino, glycylamino, serylamino, alanylamino, 2-amino-0-methylpimelylamino.

17. The compound according to claim 2, wherein $R^5$ is the group of the formula $R^{36}$—NH— wherein $R^{36}$ is $C_{1-5}$ alkyl which may be substituted by amidino which may be substituted by $C_{1-5}$ alkyl.

18. The compound according to claim 2, wherein $R^5$ is 2-amidinoethylamino, 2-amidinopropylamino or 2-(N-methyl)amidinoethylamino.

19. The compound according to claim 2, wherein $R^1$ is 2,4-pentadienoylamino, $R^2$ and $R^3$ are hydrogen, $R^4$ is amino and $R^5$ is 2-amidinoethylamino.

20. The compound according to claim 2, wherein $R^1$ is 2,4-hexadienoylamino, $R^2$ and $R^3$ are hydrogen, $R^4$ is methylamino and $R^5$ is 2-amidinoethylamino.

21. The compound according to claim 2, wherein $R^1$ is 2,4-hexadienoylamino, $R^2$ and $R^3$ are hydrogen, $R^4$ is ethylamino and $R^5$ is 2-amidinoethylamino.

22. The compound according to claim 2, wherein $R^1$ is 2,4-hexadienoylamino, $R^2$ and $R^3$ are hydrogen, $R^4$ is 2-amino-0-methylpimelylamino and $R^5$ is 2-amidinoethylamino.

23. The compound according to claim 2, wherein $R^1$ is 2-methyl-2,4-hexadienoylamino, $R^2$ and $R^3$ are hydrogen, $R^4$ is amino and $R^5$ is 2-amidinoethylamino.

24. The compound according to claim 2, wherein $R^1$ is 2,4-hexadienoylamino, $R^2$ and $R^3$ are hydrogen, $R^4$ is glycylamino and $R^5$ is 2-amidinoethylamino.

25. The compound according to claim 2, wherein $R^1$ is 2,4-hexadienoylamino, $R^2$ and $R^3$ are hydrogen, $R^4$ is amino and $R^5$ is 2-amidinopropylamino.

26. The compound according to claim 2, wherein $R^1$ is 2,4-hexadienoylamino, $R^2$ and $R^3$ are hydrogen, $R^4$ is serylamino and $R^5$ is 2-amidinopropylamino.

27. The compound according to claim 2, wherein $R^1$ is 2,4-hexadienoylamino, $R^2$ and $R^3$ are hydrogen, $R^4$ is amino and $R^5$ is 2-(N-methyl)amidinoethylamino.

28. The compound according to claim 2, wherein $R^1$ is 2,4-hexadienoylamino, $R^2$ and $R^3$ are hydrogen, $R^4$ is alanylamino and $R^5$ is 2-amidinopropylamino.

29. The compound according to claim 2, wherein $R^1$ is 2-methyl-2,4-pentadienoylamino, $R^2$ and $R^3$ are hydrogen, $R^4$ is amino and $R^5$ is 2-amidinoethylamino.

30. The compound according to claim 2, wherein $R^1$ is 6-fluoro-2,4-hexadienoylamino, $R^2$ and $R^3$ are hydrogen, $R^4$ is amino and $R^5$ is 2-amidinoethylamino.

31. The compound according to calim 2, wherein $R^1$ is 5-chloro-2,4-pentadienoylamino, $R^2$ and $R^3$ are hydrogen, $R^4$ is amino and $R^5$ is 2-amidinoethylamino.

32. The compound according to claim 3, wherein $R^1$ is 2,4-hexadienoylamino.

33. The compound according to claim 3, wherein $R^2$ is hydrogen or methyl.

34. The compound according to claim 3, wherein $R^3$ is hydrogen.

35. The compound according to claim 3, wherein $R^4$ is amino.

36. The compound according to calim 3, wherein $R^5$ is 2-amidinoethylamino.

37. The compound according to claim 3, wherein $R^1$ is 2,4-hexadienoylamino, $R^2$ and $R^3$ are hydrogen, $R^4$ is amino and $R^5$ is 2-amidinoethylamino.

38. The compound according to claim 3, wherein $R^1$ is 2,4-hexadienoylamino, $R^2$ is methyl, $R^3$ is hydrogen, $R^4$ is amino and $R^5$ is 2-amidinoethylamino.

39. The compound according to claim 3, wherein $R^1$ is 2,4-hexadienoylamino, $R^2$ and $R^3$ are hydrogen, $R^4$ is t-butoxycarbonylamino and $R^5$ is 2-amidinoethylamino.

40. The compound according to claim 3, wherein $R^1$ is amino, $R^2$ and $R^3$ are hydrogen, $R^4$ is t-butoxycarbonylamino and $R^5$ is 2-amidinoethylamino.

41. The compound according to claim 3, wherein $R^1$ is 2,4-hexadienoylamino, $R^2$ and $R^3$ are hydrogen, $R^4$ is amino and $R^5$ is 2-amidinoethylamino.

42. The compound according to claim 3, wherein $R^1$ is 2,4-hexadienoylamino, $R^2$ is methyl, $R^3$ is hydrogen, $R^4$ is amino and $R^5$ is 2-amidinoethylamino.

43. The compound according to claim 3, wherein $R^1$ is 2,4-hexadienoylamino, $R^2$ and $R^3$ are hydrogen, $R^4$ is t-butoxycarbonylamino and $R^5$ is 2-amidinoethylamino.

44. The compound according to claim 3, wherein $R^1$ is amino, $R^2$ is methyl, $R^3$ is hydrogen, $R^4$ is t-butoxycarbonylamino and $R^5$ is 2-amidinoethylamino.

45. The compound according to claim 3, wherein $R^1$ is 2,4-hexadienoylamino, $R^2$ and $R^3$ are hydrogen, $R^4$ is amino and $R^5$ is hydroxyl.

46. The compound according to claim 3, wherein $R^1$ is 2,4-hexadienoylamino, $R^2$ and $R^3$ are hydrogen, $R^4$ is t-butoxycarbonylamino and $R^5$ is hydroxyl.

47. The compound according to claim 3, wherein $R^1$ and $R^4$ are amino, $R^2$ is methyl, $R^3$ is hydrogen and $R^5$ is hydroxyl.

48. The compound according to claim 3, wherein $R^1$ is 2,4-hexadienoylamino, $R^2$ and $R^3$ are hydrogen, $R^4$ is amino and $R^5$ is hydroxyl.

49. The compound according to claim 3, wherein $R^1$ is amino, $R^2$ is methyl, $R^3$ is hydrogen, $R^4$ is t-butoxycarbonylamino and $R^5$ is hydroxyl.

50. A pharmaceutical composition which comprises an amount effective for treating bacterial infections of a compound according to claim 1 or a pharmaceutically acceptable salt thereof and a carrier.

* * * * *